(12) United States Patent
Myers et al.

(10) Patent No.: US 10,011,875 B2
(45) Date of Patent: Jul. 3, 2018

(54) METHODS AND ASSAYS RELATING TO HUNTINGTONS DISEASE AND PARKINSON'S DISEASE

(71) Applicant: TRUSTEES OF BOSTON UNIVERSITY, Boston, MA (US)

(72) Inventors: Richard H. Myers, Boston, MA (US); Andrew Hoss, Boston, MA (US); Vinay Krishna Kartha, Boston, MA (US)

(73) Assignee: Trustees of Boston University, Boston, MA (US)

(*) Notice: Subject to any disclaimer, the term of this patent is extended or adjusted under 35 U.S.C. 154(b) by 0 days.

(21) Appl. No.: 15/411,329

(22) Filed: Jan. 20, 2017

(65) Prior Publication Data

US 2017/0145511 A1   May 25, 2017

Related U.S. Application Data

(63) Continuation-in-part of application No. 14/595,783, filed on Jan. 13, 2015, now abandoned.

(60) Provisional application No. 61/926,652, filed on Jan. 13, 2014, provisional application No. 62/069,003, filed on Oct. 27, 2014.

(51) Int. Cl.
*C12Q 1/68* (2018.01)
*C12Q 1/6883* (2018.01)

(52) U.S. Cl.
CPC ...... *C12Q 1/6883* (2013.01); *C12Q 2600/118* (2013.01); *C12Q 2600/158* (2013.01); *C12Q 2600/16* (2013.01); *C12Q 2600/178* (2013.01)

(58) Field of Classification Search
CPC ........ C12Q 2600/178; C12Q 2600/158; C12Q 1/6883; C12Q 2600/118; C12Q 2525/207; C12Q 2600/16
See application file for complete search history.

(56) References Cited

U.S. PATENT DOCUMENTS

| | | |
|---|---|---|
| 2007/0092889 A1 | 4/2007 | Cox et al. |
| 2007/0292403 A1 | 12/2007 | Nivaggiol |
| 2008/0176793 A1 | 7/2008 | Simons et al. |
| 2012/0025693 A1 | 2/2012 | Wang et al. |
| 2013/0317083 A1 | 11/2013 | Rigoutsos |
| 2014/0272993 A1 | 9/2014 | Van Keuren-Jensen et al. |
| 2014/0303025 A1 | 10/2014 | Van Keuren-Jensen et al. |

OTHER PUBLICATIONS

Ortega et al. Profiling of circulating microRNAs reveals common microRNAs linked to type 2 diabetes that change with insulin sensitization. Diabetes Care. 2014;37(5):1375-83. doi: 10.2337/dc13-1847. Epub Jan. 29, 2014.*
Xu et al. Differential expression of PDGFRB and EGFR in microvascular proliferation in glioblastoma. Tumour Biol. Aug. 2016;37(8): 10577-86. doi: 10.1007/s13277-016-4968-3. Epub Feb. 2016.*
Wang et al. A ten-microRNA signature identified from a genome-wide microRNA expression profiling in human epithelial ovarian cancer. PLoS One. May 9, 2014;9(5):e96472. doi: 10.1371/journal.pone.0096472. eCollection 2014.*
Sand et al. Comparative microarray analysis of microRNA expression profiles in primary cutaneous malignant melanoma, cutaneous malignant melanoma metastases, and benign melanocytic nevi. Cell Tissue Res. Jan. 2013;351(1):85-98. doi: 10.1007/ s00441-012-1514-5. Epub Oct. 31, 2012.*
Wang et al. Characterization and Identification of novel serum microRNAs in sepsis patients with different outcomes. Shock. Jun. 2013;39(6):480-7. doi: 10.1097/SHK.0b013e3182940cb8.*
"Homo sapiens microRNA 8082 (MIR8082), microRNA", NCBI Reference Sequence: NR_107049.1, https://www.ncbi.nlm.nih.gov/nuccore/NR_107049, retrieved Feb. 7, 2018.*
Creighton et al. Discovery of novel microRNAs in female reproductive tract using next generation sequencing. PLoS One. Mar. 10, 2010;5(3):e9637. doi: 10.1371/journal.pone.0009637.*
"Homo sapiens microRNA 3928 (MIR3928), microRNA", NCBI Reference Sequence: NR_037496.1, https://www.ncbi.nlm.nih.gov/nuccore/312147097/, retrieved Feb. 7, 2018.*
Burgos et al., "Profiles of Extracellular miRNA in Cerebrospinal Fluid and Serum from Patients with Alzheimer's and Parkinson's Diseases Correlate with Disease Dtatus and Features of Pathology." PloS One 9(5):1-20 (2014).
Gui et al., "Altered microRNA profiles in cerebrospinal fluid exosome in Parkinson disease and Alzheimer disease." Oncotarget 6(35):37043-37053 (2015).
Gaughwin et al., Hum Mol Genet.20(11):2225-37 (2011). "Hsa-miR-34b is a plasma-stable microRNA that is elevated in premanifest Huntington's disease."
Johnson et al., Neurobiology of Disease, 29(3):438-445 (2008). "A microRNA-based gene dysregulation pathway in Huntington's diesease."
Kozlowska et al., International Journal of Molecular Science, 14:16999-17016 (2013). "Regulation of Huntingtin Gene Expression by miRNA-137, -214, -148a, and their respective isomiRs."
Lagos-Quintana et al., Current Biology 12:735-739 (2002). "Identification of Tissue-Specific MicroRNAs from Mouse."
Lau et al., "Alteration of the microRNA network during the progression of Alzheimer's disease", EMBO Mol Med. 5 (10)1613-1634 (2013).
Lee et al., Experimental Neurology, 227(1):172-179 (2011). "Altered microRNA regulation in Huntington's disease models."
Li et al., PNAS 109(38):15491-15496 (2012). "Conditional ablation of brain-derived neurotrophic factor-TrkB signaling impairs striatal neuron development."
Meseguer et al., Journal of Biological Chemistry, 286:4150-4164 (2011). "MicroRNAs-10a and -10b contribute to retinoic acid-induced differentiation of neuroblastoma cells and target the alternative splicing regulatory factor SFRS1 (SF2/ASF)."

(Continued)

*Primary Examiner* — Gregory S Emch
(74) *Attorney, Agent, or Firm* — Nixon Peabody LLP

(57) ABSTRACT

Described herein are methods for the diagnosis, prognosis, and treatment of neurological conditions, e.g. Huntington's Disease, relating to the misregulation of miRNAs in such conditions.

14 Claims, 35 Drawing Sheets

(56) References Cited

OTHER PUBLICATIONS

Mir-132, See Mirbase; [Retrieved on May 26, 2015] from http://www.mirbase.org/cgi-bin/mature.pl?mature_acc=MIMAT0000426].

miRBASE, Mature sequence has-miR-196a-5p. Obtained from the Internet on Mar. 15, 2015 from http://www.mirbase.org/cgi-bin/mature.pl?mature_acc=MIMAT0000226.

Miska et al., Genome Biology 5(9):R68 (2004). "Microarray analysis of microRNA expression in the developing mammalian brain."

Packer et al., The Journal of Neuroscience, 28(53):14341-14346 (2008). "The Bifunctional microRNA miR-9/miR-9 Regulates REST and CoREST and Is Downregulated in Huntington's Disease."

Pardo et al., Neurobiol Aging. 34(7):1825-36 (2013). "Regional differences in gene expression and promoter usage in aged human brains".

Schmittgen et al., "Real-time PCR quantification of precursor and mature microRNA", Methods 44(1):31-38 (2008).

Shaked, Immunity 31(6):966-73 (2009). "MicroRNA-132 potentiates cholinergic anti-inflammatory signaling by targeting acetylcholinesterase."

Sinha et al., RNA Biology 8(6):1005-1021 (2011). "Micro RNA -214, -150, -146a and -125b target Huntingtin gene."

Vo et al., PNAS 102(45):16426-16431 (2005). "A cAMP-response element binding protein-induced microRNA regulates neuronal morphogenesis."

Zhao et al., A Journal of Human Genetics, 58(3):135-41 (2013). "Single-nucleotide polymorphisms inside microRNA target sites influence the susceptibility to type 2 diabetes."

Zuccato et al., Proress in Neurobiology 81(506):294-330 (2008). "Role of brain-derived neurotrophic factor in Huntington's Disease."

\* cited by examiner

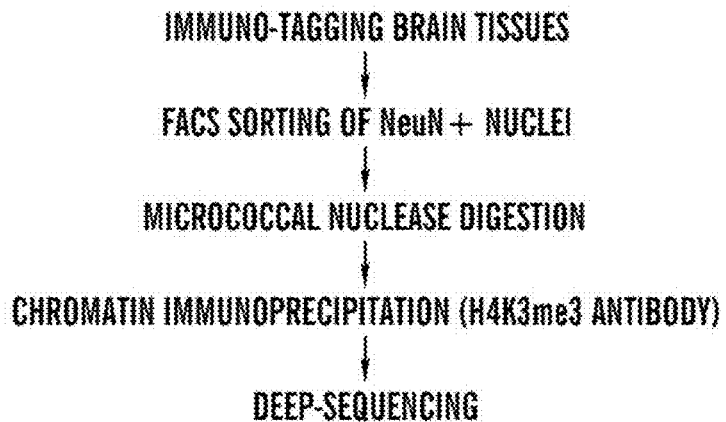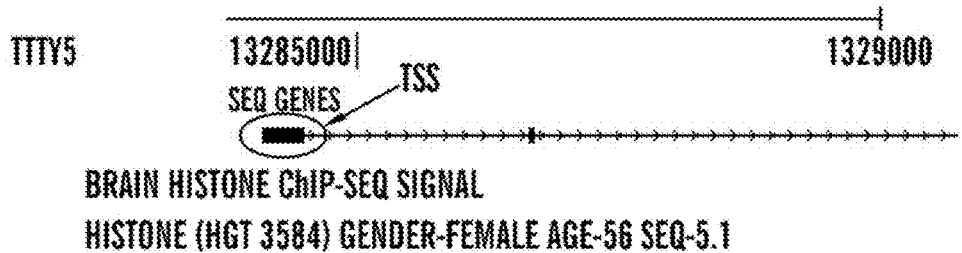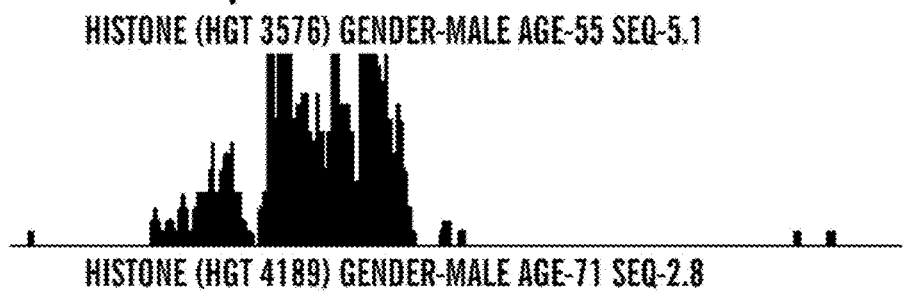
FIG. 1A

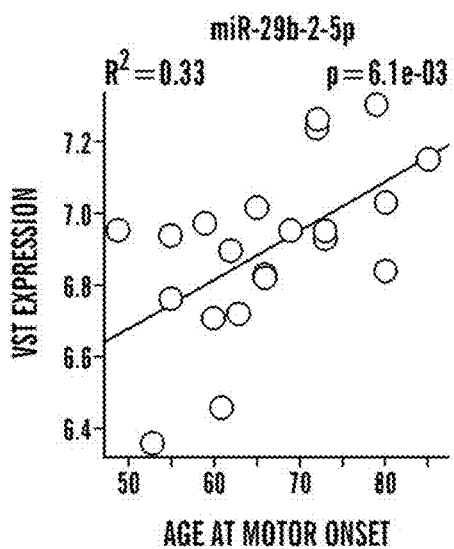
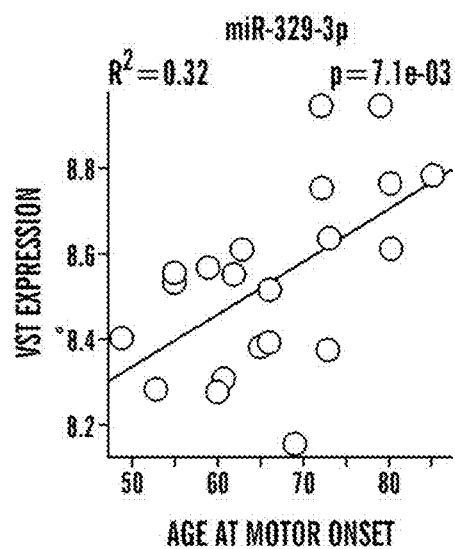
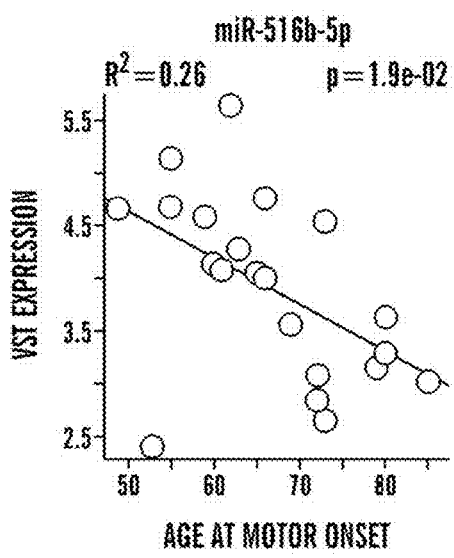
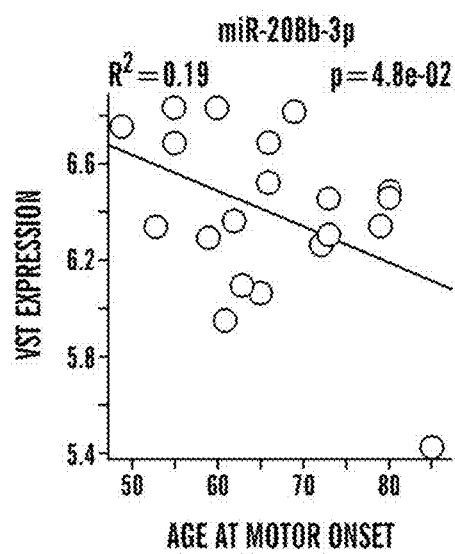
*FIG. 13 (cont.)*

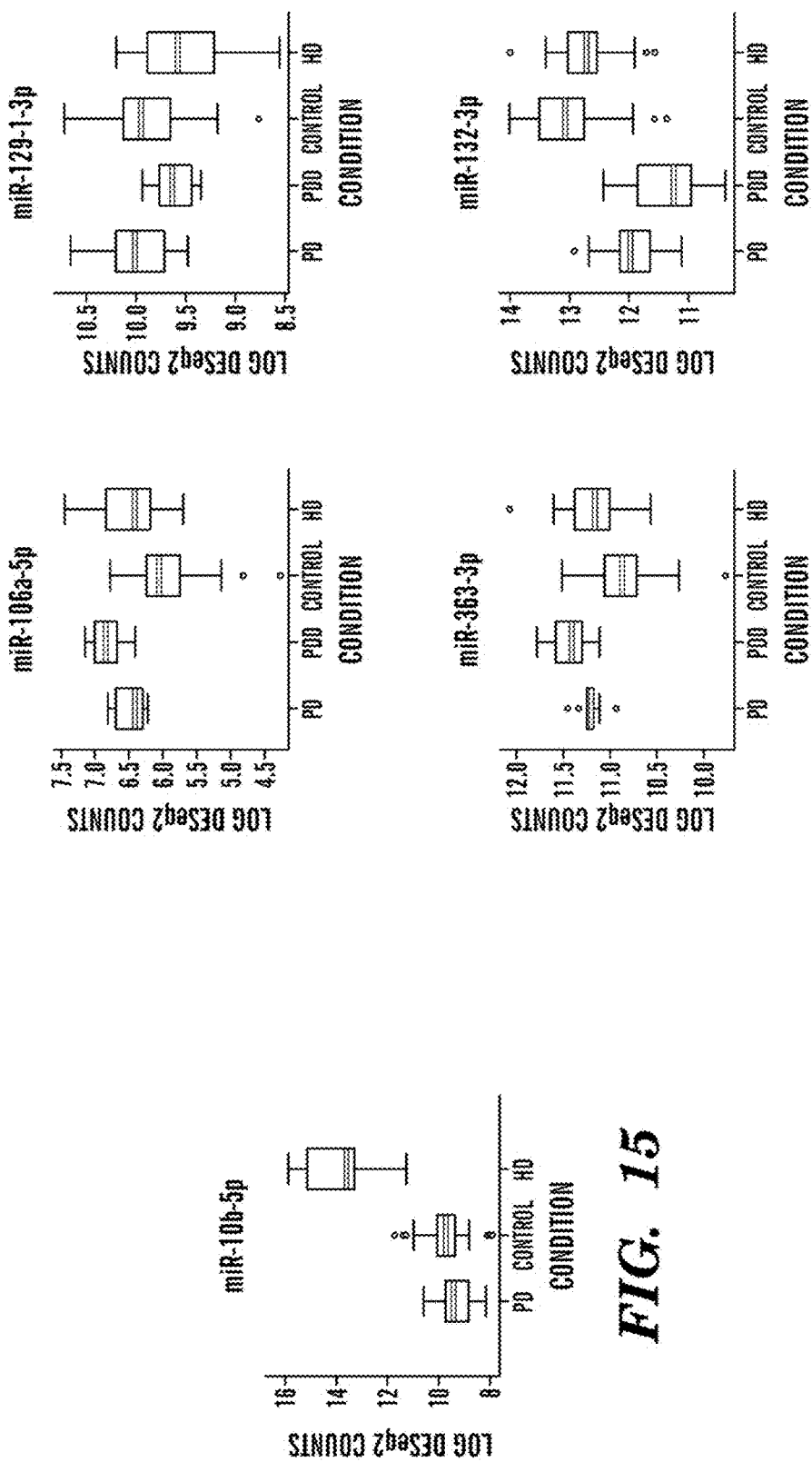

METHODS AND ASSAYS RELATING TO HUNTINGTONS DISEASE AND PARKINSON'S DISEASE

CROSS-REFERENCE TO RELATED APPLICATIONS

This application is a continuation-in-part of co-pending U.S. application Ser. No. 14/595,783 filed Jan. 13, 2015, and which claims benefit under 35 U.S.C. § 119(e) of U.S. Provisional Application Nos. 61/926,652 filed Jan. 13, 2014 and 62/069,003 filed Oct. 27, 2014, the contents of which are incorporated herein by reference in their entirety.

GOVERNMENT SUPPORT

This invention was made with Government Support under Contract Nos. NS073947 NS041083, and NS076958 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Jan. 11, 2017, is named 701586-078853-CIP_SL.txt and is 63,704 bytes in size.

TECHNICAL FIELD

The technology described herein relates to the diagnosis, prognosis, and treatment of Huntington's Disease and Parkinson's Disease.

BACKGROUND

Huntington's disease (HD) is a devastating and progressive neurodegenerative disorder characterized by chorea, dystonia, cognitive impairment, and behavioral changes. There is no effective treatment available. At the present time, it is possible to determine if a subject will develop Huntington's Disease, e.g. by determining whether or not the subject has a particular mutation at the huntingtin (htt) gene 3.

It is important for subjects with the Huntington's disease mutation to be able to predict the age of onset in their particular case, as knowing this information provides crucial information relevant to major life decisions such as education, healthcare, and family planning. While the severity of the mutation at the htt3 gene can provide some guidance as to the age of onset, current predictors are not reliable. At least one third of the variation of the age of onset of HD is not currently predictable, nor is the etiological source understood.

This gap in the understanding of the mechanisms of HD is also a hinderance to drug development, as none of the known mutations present in HD subjects is correlated with HD pathogenesis and striatal degeneration.

SUMMARY

As described herein, the inventors have discovered that the level of certain miRNAs is highly correlated with Huntington's Disease and/or Parkinson's Disease (e.g. the age of onset and/or certain clinical symptoms). In particular, there is a significant correlation between these markers and the age of onset and the development of dementia.

In some aspects, described herein is an assay comprising: measuring, in a sample obtained from a subject, the level of a gene of Table 9, 10, or 11 and/or an miRNA selected from the group consisting of: miR-10b-5p; miR196a-5p; miR196b-5p; miR615-3p; and miR1247-5p; determining that the subject is at increased risk of developing Huntington's Disease if the level of the gene or miRNA is increased relative to a reference, and determining that the subject is at decreased risk of developing Huntington's Disease if the level of the gene or miRNA is not increased relative to a reference.

In some embodiments, the subject is a Huntington's Disease carrier. In some embodiments, increased risk of developing Huntington's Disease comprises developing Huntington's Disease at a younger age; death due to Huntington's Disease at a younger age, and/or increased CAG repeat size.

In some aspects, described herein is an assay comprising (a) measuring, in a sample obtained from a subject, the level of a gene of Table 9, 10, or 11 and/or an miRNA selected from the group consisting of: miR-10b-5p; miR196a-5p; miR196b-5p; miR615-3p; and miR1247-5p; (b) administering a potential treatment for Huntingon's Disease; (c) measuring, in a sample obtained from a subject, the level of the gene and/or miRNA; (d) determining that the potential treatment is efficacious in reducing the risk and/or severity of Huntington's Disease if the level of the gene and/or miRNA measured in step (c) is not decreased relative to the level measured in step (a) and determining that the potential treatment is not efficacious in reducing the risk and/or severity of Huntington's Disease if the level of the gene and/or miRNA measured in step (c) is decreased relative to the level measured in step (a). In some embodiments, the sample is selected from the group consisting of: a blood sample and a brain sample.

In some aspects, described herein is a method of increasing axonal projections, the method comprising; administering an effective amount of an agonist of expression of a gene of Table 9, 10, or 11 and/or an miRNA selected from the group consisting of: miR-10b-5p; miR196a-5p; miR196b-5p; miR615-3p; and miR1247-5p. In some aspects, described herein is a method of treating a neuronal disease, the method comprising; administering a therapeutically effective amount of an agonist of expression of a gene of Table 9, 10, or 11 and/or an miRNA selected from the group consisting of: miR-10b-5p; miR196a-5p; miR196b-5p; miR615-3p; and miR1247-5p. In some embodiments, the neuronal disease is selected from the group consisting of: Huntington's Disease; spinal cord injury; and stroke.

In some embodiments, the subject is a Huntington's Disease carrier. In some embodiments, increased risk of developing Huntington's Disease comprises developing Huntington's Disease at a younger age. In some embodiments, increased risk of developing Huntington's Disease comprises greater striatal degeneration.

BRIEF DESCRIPTION OF THE DRAWINGS

FIGS. 1A-1C demonstrate the detection and distribution of H3K4me3 peaks surrounding the HES4 and HES1 genes in HD and control subjects. FIG. 1A depicts a flow chart of the FACS-ChIP-seq procedure as described in Example 2 for detecting genome-wide distribution of H3K4me3 marks from NeuN+ cortical nuclei of 6 HD and 5 control subjects. Bottom panel: detection of H3K4me3 peak signal for Y chromosome gene TTTY5 by FACS-ChIP-seq H3K4me3 peaks are distributed in punctuated pattern and highly enriched in TSS of TTTY5 gene (as indicated by circle). H3K4me3 peaks surround TTS of TTTY5 were absent in a female subject (first line) but present in a male sample (second line), confirming specificity of the H3K4me3 peaks detected by FACS-ChIP-seq. FIG. 1B depicts graphs of H3K4me3 peaks detected by FACS-ChIP-seq in NeuN+ cortical nuclei from 6 HD and 5 control subjects as described in Example 2. H3K4me3 peaks are clustered around TSS of the HES4 gene (as indicated by circle). Moreover, the H3K4me3 peak (tag) densities (ad indicated by long square/box) in HD were lower, compared to controls. FIG. 1C depicts peak densities around HES1. The H3K4me3 peak densities around HES1 gene were indistinguishable between HD and control subjects.

FIGS. 2A-2B depict graphs of examples of qPCR curves of all four reactions in one control (FIG. 2A) and in one HD (FIG. 2B) for the HES4 gene. DNA methylation status for HES4 gene promoter was expressed as fractions of unmethylated (UM), intermediate-methylated (IM) or fully methylated (FM) DNA. FIG. 2C depicts a schematic of HES4. FIGS. 2D-2E depicts graphs of % of type of methylation. IM was robustly increased from 5% of total input DNA in control to 49% in HD while UM fraction in HES4 gene promoter was reduced in HD. In contrast, FM of the HES4 gene did not exhibit significant change.

FIG. 4A depicts graphs demonstrating that HES4 mRNA is enriched in human neuronal nuclei. Bar graph showing relative HES4 mRNA level in NeuN− and NeuN+ nuclei FACS sorted from human brains using two different primer sets (primer #2, primer #3). 18s rRNA was used as the normalizer gene. *=p<0.05 (n=3, Mann-Whitney, one-tailed). FIGS. 4B and 4C depicts graphs of mRNA levels for HES4 (FIG. 4B) and its down-stream targets Mash1 and p21 (FIG. 4C) in cortex as detected by qPCR analysis as described in Example 2. FIG. 4B demonstrates that that HES4 mRNA is reduced ~40% in HD cortex compared to control. FIG. 4C demonstrates that Mash1 mRNA in HD cortex compared to the control while p21 mRNA was increased in the cortex of HD compared to control. *=p<0.05 (n=14, t-test).

FIG. 15 depicts miR-10b-5p expression in PD, control and HD. Expression of miR-10b-5p is altered in both PD (decreased expression) and HD (increased expression).

FIG. 16 depicts miRNA expression of four important miRNAs in PD and HD. The differences in expression between HD and control brains resembles the differences in expression between PD and PDD (PD with dementia). miRNAs that are decreased in HD relative to controls are also decreased in PDD relative to PD. miRNAs that are increased in HD relative to controls are also increased in PDD relative to PD.

FIG. 23A illustrates the overlap in GO Biological Processes between targets of increased miRNA (in orange) and decreased miRNA (in blue) in HD. The x-axis shows the number of gene ontology terms that fall within a given semantic term set, and the y-axis lists the top twenty enriched terms for each set of miRNA targets. Dark colored points represent terms with higher significance and the size of the points represents the union of all genes that fall within a given the term. The similarity targets of up-regulated miRNA (in orange) and down-regulated miRNA (in blue) for GO Molecular Function are seen in FIG. 23B and for GO Cellular Component in FIG. 23C.

DETAILED DESCRIPTION

Figure 1B:
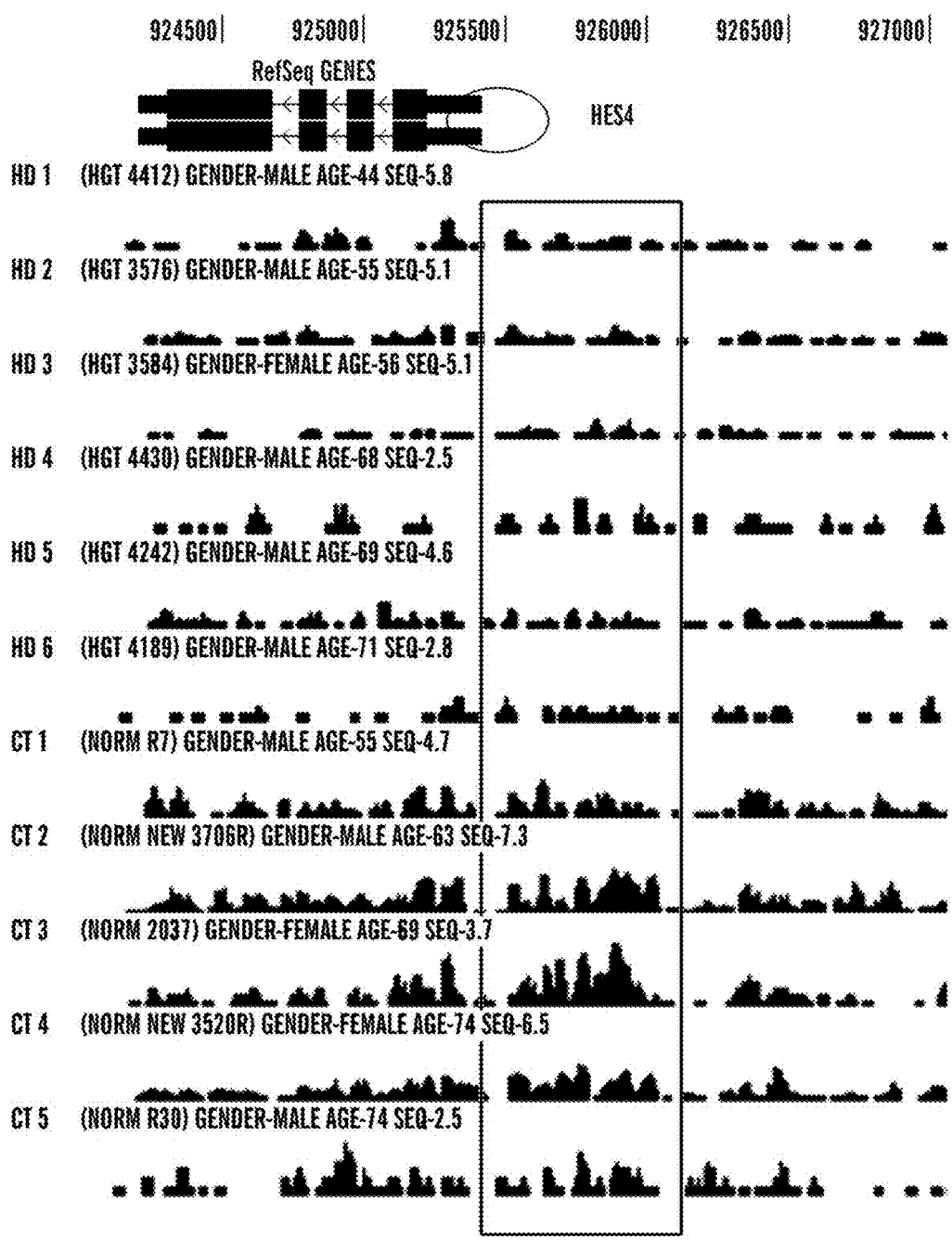

As described herein, the inventors have found that an increase in the level of certain miRNAs (see, e.g. Table 8) and their target genes (see e.g. Table 9) is correlated with the risk of developing Huntington's Disease, e.g. developing Huntington's Disease at a younger age, dying of Huntington's Disease at a younger age, and/or the level of CAG repeats, as compared to a reference subject not having an increase in the miRNA or target gene.

In some embodiments, the miRNA is one or more of miR-10b-5p, miR196a-5p, miR196b-5p, 615-3p, and/or miR-1247-5p, e.g. one of the miRNAs, two of the miRNAs, three of the miRNAs, four of the miRNAs, or all five of the miRNAs. Any combination of the foregoing miRNAs is specifically contemplated. In some embodiments, the miRNA is one or more of miR-10b-5p, miR196a-5p, miR196b-5p, and/or 615-3p. In some embodiments, the miRNA is one or more of miR-10b-5p, miR196b-5p, 615-

3p, and/or miR-1247-5p. In some embodiments, the miRNA is one or more of miR-10b-5p, 615-3p, and/or miR-1247-5p. In some embodiments, the miRNA is one or more of miR-10b-5p and 615-3p. In some embodiments, the miRNA is miR-10b-5p. In some embodiments, the miRNA is miR-615-3p.

As used herein, "miR-10b-5p" refers to a mature miRNA derived from miR-10. The sequences for the precursor and mature form are known for a variety of species, e.g. human miR-10 (NCBI Gene ID NO: 406903; NCBI transcript accession number NR_029609; SEQ ID NO: 14) and human miR-10b-5p (SEQ ID NO: 15). A "miR-10b-5p oligonucleotide" can be a miR-10b-5p oligonucleotide (e.g., SEQ ID NO: 15) or a sequence encoding such an oligonucleotide, e.g. SEQ ID NO: 14.

As used herein, "miR-196a-5p" refers to a mature miRNA derived from miR-196. The sequences for the precursor and mature form are known for a variety of species, e.g. human miR-196a (NCBI Gene ID NOs: 406973 and 406972; NCBI transcript accession number NR_029617 and NR_029582) and human miR-196a-5p (SEQ ID NO: 19).

As used herein, "miR-196b-5p" refers to a mature miRNA derived from miR-196b. The sequences for the precursor and mature form are known for a variety of species, e.g. human miR-196b (NCBI Gene ID NO: 442920; NCBI transcript accession number NR_029911) and human miR-196b-5p (SEQ ID NO: 20).

As used herein, "miR-615-3p" refers to a mature miRNA derived from miR-615. The sequences for the precursor and mature form are known for a variety of species, e.g. human miR-615 (NCBI Gene ID NO: 693200; NCBI transcript accession number NR_030753) and human miR-615-3p (SEQ ID NO: 21).

As used herein, "miR-1247-5p" refers to a mature miRNA derived from miR-1247. The sequences for the precursor and mature form are known for a variety of species, e.g. human miR-1247 (NCBI Gene ID NO: 100302145; NCBI transcript accession number NR_031649) and human miR-1247-59 (SEQ ID NO: 22).

In some embodiments, the miRNA is one or more of miR520f-3p, miR-135b-3p, miR-4317, miR-3928-5p, miR-8082, and mir-140-5p, e.g. one of the miRNAs, two of the miRNAs, three of the miRNAs, four of the miRNAs, five of the miRNAs, or all six of the miRNAs. Any combination of the foregoing miRNAs is specifically contemplated.

In some embodiments, the miRNA is one or more of miR520f-3p, miR-135b-3p, miR-4317, miR-3928-5p, miR-8082, and mir-140-5p, e.g. one of the miRNAs, two of the miRNAs, three of the miRNAs, four of the miRNAs, five of the miRNAs, or all six of the miRNAs. Any combination of the foregoing miRNAs is specifically contemplated.

As used herein, "miR520f-3p" refers to a mature miRNA derived from miR-520f. The sequences for the precursor and mature form are known for a variety of species, e.g. human miR-520f (NCBI Gene ID NO: 574464; NCBI transcript accession number NR_030186.1) and human miR-520f-3p (mirBASE Accession No: MIMAT0002830; SEQ ID NO: 45).

As used herein, "miR-135b-3p" refers to a mature miRNA derived from miR-135b. The sequences for the precursor and mature form are known for a variety of species, e.g. human miR-135b (NCBI Gene ID NO: 442891; NCBI transcript accession number NR_029893.1) and human miR-135b-3p (mirBASE Accession No: MIMAT0004698; SEQ ID NO: 46).

As used herein, "miR-3928-5p" refers to a mature miRNA derived from miR-3928. The sequences for the precursor and mature form are known for a variety of species, e.g. human miR-3928 (NCBI Gene ID NO: 100500901; NCBI transcript accession number NR_037496.1) and human miR-3928-5p (mirBASE Accession No: MIMAT0027037; SEQ ID NO: 47).

As used herein, "miR-140-5p" refers to a mature miRNA derived from miR-140. The sequences for the precursor and mature form are known for a variety of species, e.g. human miR-140 (NCBI Gene ID NO: 406932; NCBI transcript accession number NR_029681.1) and human miR-140-5p (mirBASE Accession No: MIMAT0000431; SEQ ID NO: 48).

As used herein, "miR-4317" refers to a mature miRNA derived from precursor miR-4317. The sequences for the precursor and mature form are known for a variety of species, e.g. human miR-4317 precursor (NCBI Gene ID NO: 100422840; NCBI transcript accession number NR_036205.1); and human miR-4317 (mirBASE Accession No: MIMAT0016872; SEQ ID NO: 49).

As used herein, "miR-8082" refers to a mature miRNA derived from precursor miR-8082. The sequences for the precursor and mature form are known for a variety of species, e.g. human miR-8082 precursor (NCBI Gene ID NO: 102465878; NCBI transcript accession number NR_107049.1); and human miR-4317 (mirBASE Accession No: MIMAT0031009; SEQ ID NO: 50).

The gene names listed herein, including the miRNA names, are common names. NCBI Gene ID numbers and/or sequences for each of the genes given herein can be obtained by searching the "Gene" Database of the NCBI (available on the World Wide Web at http://www.ncbi.nlm.nih.gov/) using the common name as the query and selecting the first returned Homo sapiens gene. Alternatively, sequences for each of the miRNAs given herein can be obtained by searching the miRbase (available on the world wide web at mirbase.org) using the common name as the query and selecting the first returned Homo sapiens miRNA.

In some embodiments, the level of a target of one of the miRNAs described herein is correlated with an increased risk of developing Huntington's Disease. Targets of the five miRNAs described herein are known in the art, see, e.g., miRWalk (available on the world wide web at http://www.umm.uni-heidelberg.de/apps/zmf/mirwalk/index.html), a repository of experimentally validated miRNA targets curated from literature and online resources. Four target genes (DICER1, HOXA7, HOXB4, HOXD1) are targeted by miR-10b-5p, miR196a-5p, miR196b-5p, and 615-3p. miR-10b-5p shares eleven targets with miR-196a-5p (HOXB8, COX8A, HOXA10, NPC1, FLT3, AKT1, NPM1, DROSHA, AGO2, NFYC, PAX7), and one with miR-615-3p (MAPK8). miR-196a and miR-196b share 28 targets. In all, eleven of the 167 unique validated targets are Hox cluster genes (HOXA1, HOXA7, HOXA9, HOXA10, HOXB4, HOXB7, HOXB8, HOXC8, HOXD1, HOXD4, HOXD10). In some embodiments, the target gene is a gene selected from Table 9, 10 and/or 11. In some embodiments, the risk of Huntington's Disease is increased if the level of one or more genes selected from Table 11 is increased relative to a reference level.

The gene names listed in Tables 9, 10, and 11 are common names. NCBI Gene ID numbers for each of the genes listed in Tables 9, 10, and 11 can be obtained by searching the "Gene" Database of the NCBI (available on the World Wide Web at http://www.ncbi.nlm.nih.gov/) using the common name as the query and selecting the first returned Homo sapiens gene.

Accordingly, in one aspect, provided herein is an assay comprising measuring, in a sample obtained from a subject, the level of one or more genes selected from Tables 9, 10, and/or 11 and/or a miRNA selected from the group consisting of miR-10b-5p, miR196a-5p, miR196b-5p, 615-3p, and/or miR-1247-5p; determining that the subject is at increased risk of developing Huntington's Disease if the level of the gene and/or miRNA is increased relative to a reference, and determining that the subject is at decreased risk of developing Huntington's Disease if the level of is not increased relative to a reference. In some embodiments, the subject is a Huntington's Disease carrier. In some embodiments, an increased risk of developing Huntington's Disease comprises developing Huntington's Disease at a younger age, dying of Huntington's Disease at a younger age, and/or the level of CAG repeats.

In one aspect, provided herein is an assay comprising measuring, in a sample obtained from a subject, the level of one or more of miR520f-3p, miR-135b-3p, miR-4317, miR-3928-5p, miR-8082, and mir-140-5p; determining that the subject is at increased risk of developing Huntington's Disease if the level of the miRNA is increased relative to a reference, and determining that the subject is at decreased risk of developing Huntington's Disease if the level of the one or more miRNAs is not increased relative to a reference. In some embodiments, the subject is a Huntington's Disease carrier. In some embodiments, an increased risk of developing Huntington's Disease comprises developing Huntington's Disease at a younger age, dying of Huntington's Disease at a younger age, and/or the level of CAG repeats.

In one aspect, provided herein is a method comprising detecting the level of expression of at least 1 of miR520f-3p, miR-135b-3p, miR-4317, miR-3928-5p, miR-8082, mir-140-5p in a sample obtained from a subject. In some embodiments, the level of expression is detected for at least 2 of miR520f-3p, miR-135b-3p, miR-4317, miR-3928-5p, miR-8082, and mir-140-5p in a sample obtained from a subject. In some embodiments, the level of expression is detected for at least 3 of miR520f-3p, miR-135b-3p, miR-4317, miR-3928-5p, miR-8082, and mir-140-5p in a sample obtained from a subject. In some embodiments, the level of expression is detected for at least 4 of miR520f-3p, miR-135b-3p, miR-4317, miR-3928-5p, miR-8082, and mir-140-5p in a sample obtained from a subject.

In some embodiments, the level of expression is detected for at least 5 of miR520f-3p, miR-135b-3p, miR-4317, miR-3928-5p, miR-8082, and mir-140-5p in a sample obtained from a subject. In some embodiments, the level of expression is detected for miR520f-3p, miR-135b-3p, miR-4317, miR-3928-5p, miR-8082, and mir-140-5p.

In some embodiments, the subject has a htt mutation. In some embodiments, the subject has been determined to have or diagnosed as having a htt mutation. In some embodiments, the subject has not received a motor diagnosis of Huntingtons Disease. In some embodiments, the expression level of no more than 100 other expression products is detected. In some embodiments, the expression level of no more than 10 other expression products is detected. In some embodiments, the expression level of no more than 200 other expression products is detected. In some embodiments, the expression level of no more than 50 other expression products is detected. In some embodiments, the expression level of no more than 200 other expression products is detected. In some embodiments, the expression level of no more than 500 other expression products is detected.

In one aspect, described herein is an assay comprising (a) measuring, in a sample obtained from a subject, the level of one or more genes selected from Tables 9, 10, and/or 11 and/or a miRNA selected from the group consisting of miR-10b-5p, miR196a-5p, miR196b-5p, 615-3p, and/or miR-1247-5p; (b) administering a potential treatment for Huntingon's Disease; (c) measuring, in a sample obtained from a subject, the level of the gene and/or miRNA; (d) determining that the potential treatment is efficacious in reducing the risk and/or severity of Huntington's Disease if the level measured in step (c) is not increased relative to the level measured in step (a) and determining that the potential treatment is not efficacious in reducing the risk and/or severity of Huntington's Disease if the level measured in step (c) is increased relative to the level measured in step (a).

In one aspect, described herein is an assay comprising (a) measuring, in a sample obtained from a subject, the level of one or more of miR520f-3p, miR-135b-3p, miR-4317, miR-3928-5p, miR-8082, and mir-140-5p; (b) administering a potential treatment for Huntingon's Disease; (c) measuring, in a sample obtained from a subject, the level of the one or more miRNAs; (d) determining that the potential treatment is efficacious in reducing the risk and/or severity of Huntington's Disease if the level measured in step (c) is not increased relative to the level measured in step (a) and determining that the potential treatment is not efficacious in reducing the risk and/or severity of Huntington's Disease if the level measured in step (c) is increased relative to the level measured in step (a).

In some embodiments, the sample is selected from the group consisting of a blood sample and a brain sample. In some embodiments, the sample is a cerebrospinal fluid sample.

In one aspect, described herein is an assay comprising: measuring, in a sample obtained from a subject, the level of at least one miRNA selected from the group consisting of: miR-10b-5p; miR196a-5p; miR196b-5p; miR615-3p; and miR1247-5p; miR106a-5p; miR363-3p; miR-129-1-3p and miR-132-3p; and determining that the subject is at increased risk of Huntington's Disease developing or progressing if the level of an miRNA selected from the group consisting of: miR-10b-5p; miR196a-5p; miR196b-5p; miR615-3p; miR1247-5p; miR106a-5p; and miR363-3p is increased relative to a reference, and determining that the subject is at decreased risk of Huntington's Disease developing or progressing if the level of the miRNA is not increased relative to a reference; or determining that the subject is at increased risk of Huntington's Disease developing or progressing if the level of an miRNA selected from the group consisting of: miR-129-1-3p and miR-132-3p; is decreased relative to a reference, and determining that the subject is at decreased risk of Huntington's Disease developing or progressing if the level of the miRNA is not decreased relative to a reference; wherein increased risk of Huntington's Disease developing or progressing comprises developing Huntington's Disease at a younger age; death due to Huntington's Disease at a younger age, and/or becoming more severely disabled at a younger age as compared to other individuals with Huntington's Disease who do not have such a level of the miRNA.

In one aspect, described herein is an assay comprising: measuring, in a sample obtained from a subject, the level of at least one miRNA selected from the group consisting of: miR520f-3p, miR-135b-3p, miR-4317, miR-3928-5p, miR-8082, and mir-140-5p; and determining that the subject is at increased risk of Huntington's Disease developing or progressing if the level of an miRNA selected from the group consisting of: miR520f-3p, miR-135b-3p, miR-4317, miR-3928-5p, miR-8082, and mir-140-5p is increased relative to a reference, and determining that the subject is at decreased risk of Huntington's Disease developing or progressing if the level of the miRNA is not increased relative to a reference; wherein increased risk of Huntington's Disease developing or progressing comprises developing Huntington's Disease at a younger age; death due to Huntington's Disease at a younger age, and/or becoming more severely disabled at a younger age as compared to other individuals with Huntington's Disease who do not have such a level of the miRNA.

Huntington's Disease is a neurodegenerative disorder that results in a loss of muscle coordination, cognitive decline, and behavioral symptoms. Symptoms of Huntingtons' Disease can include chorea, rigidity, writhing motions, physical instability, difficulties chewing, swallowing, and speaking, sleep disturbances, cognitive disfunction, memory deficits, anxiety, depression, aggression, compulsive behavior. Physical symptoms of Huntington's Disease typically occur between 35 and 44 years of age. Life expectancy is around 20 years from the onset of physical symptoms. In some embodiments, an increased risk of Huntington's Disease developing or progressing can comprise developing Huntington's Disease symptoms by the age of 40 or earlier, e.g., 35 or earlier, 30 or earlier, 25 or earlier, 20 or earlier, or earlier. In some embodiments, an increased risk of Huntington's Disease developing or progressing can comprise developing Huntington's Disease symptoms at an age which is at least 1 standard deviation earlier than the average. In some embodiments, an increased risk of Huntington's Disease developing or progressing can comprise a life expectancy of less than 20 years from the onset of symptoms, e.g., 18 years or less, 15 years or less, or less. In some embodiments, an increased risk of Huntington's Disease developing or progressing can comprise a life expectancy from the onset of symptoms which is at least 1 standard deviation less than the average.

In one aspect, described herein is an assay comprising: measuring, in a sample obtained from a subject, the level of at least one miRNA selected from the group consisting of: miR-10b-5p; miR196a-5p; miR196b-5p; miR615-3p; and miR1247-5p; miR106a-5p; miR363-3p; miR-129-1-3p and miR-132-3p; and determining that the subject is at increased likelihood of Huntington's Disease developing at an earlier age or progressing more rapidly if the level of an miRNA selected from the group consisting of: miR-10b-5p; miR196a-5p; miR196b-5p; miR615-3p; miR1247-5p; miR106a-5p; and miR363-3p is increased relative to a reference, and determining that the subject is at decreased likelihood of Huntington's Disease developing at an earlier age or progressing more rapidly if the level of the miRNA is not increased relative to a reference; or determining that the subject is at increased likelihood of Huntington's Disease developing at an earlier age or progressing more rapidly if the level of an miRNA selected from the group consisting of: miR-129-1-3p and miR-132-3p; is decreased relative to a reference, and determining that the subject is at decreased likelihood of Huntington's Disease developing at an earlier age or progressing more rapidly if the level of the miRNA is not decreased relative to a reference; wherein increased likelihood of Huntington's Disease developing at an earlier age or progressing more rapidly comprises developing Huntington's Disease at a younger age; death due to Huntington's Disease at a younger age, and/or becoming more severely disabled at a younger age as compared to other individuals with Huntington's Disease who do not have such a level of the miRNA.

In one aspect, described herein is a method comprising: measuring, in a sample obtained from a subject, the level of at least one miRNA selected from the group consisting of: miR-10b-5p; miR196a-5p; miR196b-5p; miR615-3p; miR1247-5p; miR106a-5p; miR363-3p; miR-129-1-3p and miR-132-3p; and determining that the subject is at increased likelihood of Huntington's Disease developing at an earlier age or progressing more rapidly if the level of an miRNA selected from the group consisting of: miR-10b-5p; miR196a-5p; miR196b-5p; miR615-3p; miR1247-5p; miR106a-5p; and miR363-3p is increased relative to a reference, and determining that the subject is at decreased likelihood of Huntington's Disease developing at an earlier age or progressing more rapidly if the level of the miRNA is not increased relative to a reference; or determining that the subject is at increased likelihood of Huntington's Disease developing at an earlier age or progressing more rapidly if the level of an miRNA selected from the group consisting of: miR-129-1-3p and miR-132-3p; is decreased relative to a reference, and determining that the subject is at decreased likelihood of Huntington's disease developing at an earlier age or progressing more rapidly if the level of the miRNA is not decreased relative to a reference; and administering a treatment for Huntington's Disease if the subject is at increased likelihood of Huntington's disease developing at an earlier age or progressing more rapidly wherein increased likelihood of Huntington's disease developing at an earlier age or progressing more rapidly comprises developing Huntington's Disease at a younger age; death due to Huntington's Disease at a younger age, and/or becoming more severely disabled at a younger age, when compared to other individuals with Huntington's Disease who do not have such a level of the miRNA.

In one aspect, described herein is an assay comprising: measuring, in a sample obtained from a subject, the level of at least one miRNA selected from the group consisting of: miR520f-3p, miR-135b-3p, miR-4317, miR-3928-5p, miR-8082, and mir-140-5p; and determining that the subject is at increased likelihood of Huntington's Disease developing at an earlier age or progressing more rapidly if the level of the one or more miRNAs is increased relative to a reference, and determining that the subject is at decreased likelihood of Huntington's Disease developing at an earlier age or progressing more rapidly if the level of the miRNA is not increased relative to a reference; wherein increased likelihood of Huntington's Disease developing at an earlier age or progressing more rapidly comprises developing Huntington's Disease at a younger age; death due to Huntington's Disease at a younger age, and/or becoming more severely disabled at a younger age as compared to other individuals with Huntington's Disease who do not have such a level of the miRNA.

In one aspect, described herein is a method comprising: measuring, in a sample obtained from a subject, the level of at least one miRNA selected from the group consisting of: miR520f-3p, miR-135b-3p, miR-4317, miR-3928-5p, miR-8082, and mir-140-5p; and determining that the subject is at increased likelihood of Huntington's Disease developing at an earlier age or progressing more rapidly if the level of the at least one miRNA is increased relative to a reference, and determining that the subject is at decreased likelihood of Huntington's Disease developing at an earlier age or progressing more rapidly if the level of the miRNA is not increased relative to a reference; and administering a treatment for Huntington's Disease if the subject is at increased likelihood of Huntington's disease developing at an earlier age or progressing more rapidly wherein increased likelihood of Huntington's disease developing at an earlier age or progressing more rapidly comprises developing Huntington's Disease at a younger age; death due to Huntington's Disease at a younger age, and/or becoming more severely disabled at a younger age, when compared to other individuals with Huntington's Disease who do not have such a level of the miRNA.

In some embodiments, a treatment for Huntington's Disease can be selected from the group consisting of: regular physical exercise; regular mental exercise; improvements to the diet; or administering creatine monohydrate, coenzyme Q10, sodium phenylbutyrate. In some embodiments, a treatment for Huntington's Disease can comprise administering an agent that modulates (e.g. increases or decreases) the abnormal level or expression of at least one of the miRNAs whose abnormal levels and/or expression is described herein as indicating an increased risk or likelihood of Huntington's Disease developing or progressing.

In one aspect, described herein is an assay comprising measuring, in a sample obtained from a subject, the level of at least one miRNA selected from the group consisting of: miR-10b-5p; miR196a-5p; miR196b-5p; miR615-3p; miR1247-5p; miR106a-5p; miR363-3p; miR-129-1-3p and miR-132-3p; and administering a potential treatment for Huntington's Disease; measuring, in a sample obtained from a subject, the level of an miRNA selected from the group consisting of: miR-10b-5p; miR196a-5p; miR196b-5p; miR615-3p; miR1247-5p; miR106a-5p; miR363-3p; miR-129-1-3p and miR-132-3p; and determining that the potential treatment is efficacious in delaying age at onset and/or reducing the severity of Huntington's Disease if the level of the miRNA selected from the group consisting of: miR-10b-5p; miR196a-5p; miR196b-5p; miR615-3p; miR1247-5p; miR106a-5p; and miR363-3p measured in the second measuring step is not increased relative to the level measured in the first measuring step and determining that the potential treatment is not efficacious in delaying age at onset and/or reducing the severity of Huntington's Disease if the level of the miRNA measured in the second measuring step is increased relative to the level measured in the first measuring step; or determining that the potential treatment is efficacious in delaying age at onset and/or reducing the severity of Huntington's Disease if the level of the miRNA selected from the group consisting of: miR-129-1-3p and miR-132-3p; measured in the second measuring step is not decreased relative to the level measured in the first measuring step and determining that the potential treatment is not efficacious in delaying age at onset and/or reducing the severity of Huntington's Disease if the level of the miRNA measured in the second measuring step is decreased relative to the level measured in the first measuring step.

In one aspect, described herein is an assay comprising measuring, in a sample obtained from a subject, the level of at least one miRNA selected from the group consisting of: miR520f-3p, miR-135b-3p, miR-4317, miR-3928-5p, miR-8082, and mir-140-5p; and administering a potential treatment for Huntingon's Disease; measuring, in a sample obtained from a subject, the level of an miRNA selected from the group consisting of: miR520f-3p, miR-135b-3p, miR-4317, miR-3928-5p, miR-8082, and mir-140-5p; and determining that the potential treatment is efficacious in delaying age at onset and/or reducing the severity of Huntington's Disease if the level of the miRNA measured in the second measuring step is not increased relative to the level measured in the first measuring step and determining that the potential treatment is not efficacious in delaying age at onset and/or reducing the severity of Huntington's Disease if the level of the miRNA measured in the second measuring step is increased relative to the level measured in the first measuring step.

In one aspect, described herein is a computer system comprising a measuring module configured to measure, in a sample obtained from a subject, the level of at least one miRNA selected from the group consisting of: miR-10b-5p; miR196a-5p; miR196b-5p; miR615-3p; miR1247-5p; miR106a-5p; miR363-3p; miR-129-1-3p and miR-132-3p; a storage module configured to store data output from the measuring module; a comparison module adapted to compare the data stored on the storage module with a reference level, and to provide a retrieved content, and a display module for displaying whether the level of the miRNA in the sample obtained from the subject is greater, by a statistically significant amount, than the reference level and/or displaying the relative levels of miRNA; wherein a level of an miRNA selected from the group of: miR-10b-5p; miR196a-5p; miR196b-5p; miR615-3p; miR1247-5p; miR106a-5p; and miR363-3p in the sample of the subject which is statistically significantly greater than the reference level indicates that the subject is at increased likelihood of Huntington's disease developing at an earlier age or progressing more rapidly; and wherein a level of an miRNA selected from the group of: miR-129-1-3p and miR-132-3p; in the sample of the subject which is statistically significantly less than the reference level indicates that the subject is at increased likelihood of Huntington's disease developing at an earlier age or progressing more rapidly progressing; wherein increased likelihood of Huntington's disease developing at an earlier age or progressing more rapidly comprises developing Huntington's Disease at a younger age; death due to Huntington's Disease at a younger age, and/or becoming more severely disabled at a younger age, when compared to other individuals with Huntington's Disease who do not have such a level of the miRNA.

In one aspect, described herein is a computer system comprising a measuring module configured to measure, in a sample obtained from a subject, the level of at least one miRNA selected from the group consisting of: miR520f-3p, miR-135b-3p, miR-4317, miR-3928-5p, miR-8082, and mir-140-5p; a storage module configured to store data output from the measuring module; a comparison module adapted to compare the data stored on the storage module with a reference level, and to provide a retrieved content, and a display module for displaying whether the level of the miRNA in the sample obtained from the subject is greater, by a statistically significant amount, than the reference level and/or displaying the relative levels of miRNA(s); wherein a level of an miRNA selected from the group of: miR520f-3p, miR-135b-3p, miR-4317, miR-3928-5p, miR-8082, and mir-140-5p in the sample of the subject which is statistically significantly greater than the reference level indicates that the subject is at increased likelihood of Huntington's disease developing at an earlier age or progressing more rapidly; wherein increased likelihood of Huntington's disease developing at an earlier age or progressing more rapidly comprises developing Huntington's Disease at a younger age; death due to Huntington's Disease at a younger age, and/or becoming more severely disabled at a younger age, when compared to other individuals with Huntington's Disease who do not have such a level of the miRNA.

In some embodiments, the sample can be selected from the group consisting of: a blood sample; blood plasma; cerebrospinal fluid; and a brain sample. In some embodiments, the subject can be a Huntington's Disease carrier, e.g., a subject with expanded CAG repeats. In some embodiments, increased likelihood of Huntington's disease can developing at an earlier age or progressing more rapidly can comprise greater striatal degeneration.

Parkinson's disease is a degenerative disorder of the central nervous system characterized by shaking, rigidity, slowness of movement, difficulty walking, dementia, depression, and sensory, sleep and emotional problems. Parkinson's disease typically occurs after the age of 50, with the mean age of onset being around 60 years of age. In some embodiments, an increased risk of developing Parkinson's disease can comprise developing Parkinson's before the age of 60, e.g., before the age of 55, before the age of 50, or younger. In some embodiments, an increased risk of developing Parkinson's disease can comprise developing Parkinson's disease at an age which is at least 1 standard deviation lower than the mean and/or median age. Untreated, an average of about 8 years typically pass between onset of symptoms and loss of independent ambulation. Untreated, an average of about 10 years typically pass between onset of symptoms and being bedridden. With levodopa treatment, over 15 years can pass between the onset of symptoms and a stage of high dependency on care. With levodopa treatment, approximately 50% of individuals will develop swallowing/speech difficulties, gait/balance problems, and/or motor complications within 5 years. In some embodiments, an increased risk of Parkinson's disease progressing can reaching one or more of these symptom thresholds at least 6 months earlier than average, e.g., 6 months earlier, 1 year earlier, 2 years earlier, or earlier. In some embodiments, an increased risk of Parkinson's disease progressing can reaching one or more of these symptom thresholds at least 1 standard deviation earlier than average.

In one aspect, described herein is an assay comprising: measuring, in a sample obtained from a subject, the level of at least one miRNA selected from the group consisting of: miR-10b-5p; miR-151b; miR-29b-2-5p; miR-329-3p; miR-6511a-5p; miR-5690; miR-516b-5p; miR208b-3p; miR106a-5p; miR-363-3p; miR-4526; miR-129-1-3p; miR-129-2-3p; miR-132-3p; miR-132-5p; miR127-3p; miR212-3p; miR-1224-5p; miR16-2-3p; miR-1294; miR-30a-3p; miR-132-5p, miR-212-3p, miR-212-5p, miR-145-5p; and miR-29a-5p and determining that the subject is at increased risk of Parkinson's Disease developing or progressing if the level of an miRNA selected from the group consisting of miR-151b; miR-5690; miR-516b-5p; miR208b-3p; miR106a-5p; and miR-363-3p; miR-30a-3p; and miR-29a-5p is increased relative to a reference, and determining that the subject is at decreased risk of Parkinson's Disease developing or progressing if the level of the miRNA is not increased relative to a reference; determining that the subject is at increased risk of Parkinson's Disease developing or progressing if the level of an miRNA selected from the group consisting of: miR-10b-5p; miR-29b-2-5p; miR-329-3p; miR-6511a-5p; miR-4526; miR-129-1-3p; miR-129-2-3p; and miR-132-3p; miR-132-5p; miR127-3p; miR212-3p; miR-1224-5p; miR16-2-3p; miR-1294 miR-132-5p, miR-212-3p, miR-212-5p, and miR-145-5p; is decreased relative to a reference, and determining that the subject is at decreased risk of Parkinson's Disease developing or progressing if the level of the miRNA is not decreased relative to a reference; wherein increased risk of Parkinson's Disease developing or progressing comprises developing Parkinson's Disease at a younger age; death due to Parkinson's Disease at a younger age; development of dementia; development of dementia at an earlier age; or onset of motor symptoms at an earlier age when compared to other individuals with Parkinson's Disease who do not have such a level of the miRNA.

In one aspect, described herein is a method comprising: measuring, in a sample obtained from a subject, the level of at least one miRNA selected from the group consisting of: miR-10b-5p; miR-151b; miR-29b-2-5p; miR-329-3p; miR-6511a-5p; miR-5690; miR-516b-5p; miR208b-3p; miR106a-5p; miR-363-3p; miR-4526; miR-129-1-3p; miR-129-2-3p; miR-132-3p; miR-132-5p; miR127-3p; miR212-3p; miR-1224-5p; miR16-2-3p; miR-1294; miR-30a-3p; miR-132-5p, miR-212-3p, miR-212-5p, miR-145-5p; and miR-29a-5p and determining that the subject is at increased risk of Parkinson's Disease developing or progressing if the level of an miRNA selected from the group consisting of: miR-151b; miR-5690; miR-516b-5p; miR208b-3p; miR106a-5p; and miR-363-3p; miR-30a-3p; and miR-29a-5p is increased relative to a reference, and determining that the subject is at decreased risk of Parkinson's Disease developing or progressing if the level of the miRNA is not increased relative to a reference; determining that the subject is at increased risk of Parkinson's Disease developing or progressing if the level of an miRNA selected from the group consisting of: miR-10b-5p; miR-29b-2-5p; miR-329-3p; miR-6511a-5p; miR-4526; miR-129-1-3p; miR-129-2-3p; and miR-132-3p; miR-132-5p; miR127-3p; miR212-3p; miR-1224-5p; miR16-2-3p; miR-1294; miR-132-5p, miR-212-3p, miR-212-5p, and miR-145-5p is decreased relative to a reference, and determining that the subject is at decreased risk of Parkinson's Disease developing or progressing if the level of the miRNA is not decreased relative to a reference; and administering a treatment for Parkinson's Disease if the subject is at increased risk of Parkinson's Disease developing or progressing; wherein increased risk of Parkinson's Disease developing or progressing comprises developing Parkinson's Disease at a younger age; death due to Parkinson's Disease at a younger age; development of dementia; development of dementia at an earlier age; or onset of motor symptoms at an earlier age when compared to other individuals with Parkinson's Disease who do not have such a level of the miRNA.

In some embodiments, a treatment for Parkinson's Disease can be selected from the group consisting of: Levodopa agonists; dopamine agonists; COMT inhibitors; deep brain stimulation; MAO-B inhibitors; lesional surgery; regular physical exercise; regular mental exercise; improvements to the diet; and Lee Silverman voice treatment. In some embodiments, a treatment for Parkinson's Disease can comprise administering an agent that modulates (e.g., increases or decreases) the abnormal level or expression of at least one of the said miRNAs.

In one aspect, described herein is an assay comprising measuring, in a sample obtained from a subject, the level of at least one miRNA selected from the group consisting of: miR-10b-5p; miR-151b; miR-29b-2-5p; miR-329-3p; miR-6511a-5p; miR-5690; miR-516b-5p; miR208b-3p; miR106a-5p; miR-363-3p; miR-4526; miR-129-1-3p; miR-129-2-3p; miR-132-3p; miR-132-5p; miR127-3p; miR212-3p; miR-1224-5p; miR16-2-3p; miR-1294; miR-30a-3p; miR-132-5p, miR-212-3p, miR-212-5p, miR-145-5p; and miR-29a-5p and administering a potential treatment for Parkinson's Disease; measuring, in a sample obtained from a subject, the level of an miRNA selected from the group consisting of: miR-10b-5p; miR-151b; miR-29b-2-5p; miR-329-3p; miR-6511a-5p; miR-5690; miR-516b-5p; miR208b-3p; miR106a-5p; miR-363-3p; miR-4526; miR-129-1-3p; miR-129-2-3p; miR-132-3p; miR-132-5p;

miR127-3p; miR212-3p; miR-1224-5p; miR16-2-3p; miR-1294; miR-30a-3p; miR-132-5p, miR-212-3p, miR-212-5p, miR-145-5p; and miR-29a-5p and determining that the potential treatment is efficacious in reducing the risk of Parkinson's Disease developing or progressing if the level of the miRNA selected from the group consisting of miR-151b; miR-5690; miR-516b-5p; miR208b-3p; miR106a-5p; and miR-363-3p; miR-30a-3p; and miR-29a-5p measured in the second measuring step is not increased relative to the level measured in the first measuring step and determining that the potential treatment is not in reducing the risk of Parkinson's Disease developing or progressing if the level of the miRNA measured in the second measuring step is increased relative to the level measured in the first measuring step; or determining that the potential treatment is efficacious in reducing the risk of Parkinson's Disease developing or progressing if the level of the miRNA selected from the group consisting of: miR-10b-5p; miR-29b-2-5p; miR-329-3p; miR-6511a-5p; miR-4526; miR-129-1-3p; miR-129-2-3p; and miR-132-3p; miR-132-5p; miR127-3p; miR212-3p; miR-1224-5p; miR16-2-3p; miR-1294; miR-132-5p, miR-212-3p, miR-212-5p, and miR-145-5p measured in the second measuring step is not decreased relative to the level measured in the first measuring step and determining that the potential treatment is not efficacious in reducing the risk of Parkinson's Disease developing or progressing if the level of the miRNA measured in the second measuring step is decreased relative to the level measured in the first measuring step.

In one aspect, described herein is a computer system comprising a measuring module configured to measure, in a sample obtained from a subject, the level of at least one miRNA selected from the group consisting of: miR-10b-5p; miR-151b; miR-29b-2-5p; miR-329-3p; miR-6511a-5p; miR-5690; miR-516b-5p; miR208b-3p; miR106a-5p; miR-363-3p; miR-4526; miR-129-1-3p; miR-129-2-3p; miR-132-3p; miR-132-5p; miR127-3p; miR212-3p; miR-1224-5p; miR16-2-3p; miR-1294; miR-30a-3p; miR-132-5p, miR-212-3p, miR-212-5p, miR-145-5p; and miR-29a-5p and a storage module configured to store data output from the measuring module; a comparison module adapted to compare the data stored on the storage module with a reference level, and to provide a retrieved content, and a display module for displaying whether the level of the miRNA in the sample obtained from the subject is greater, by a statistically significant amount, than the reference level and/or displaying the relative levels of miRNA; wherein a level of an miRNA selected from the group of: miR-151b; miR-5690; miR-516b-5p; miR208b-3p; miR106a-5p; and miR-363-3p; miR-30a-3p; and miR-29a-5p in the sample of the subject which is statistically significantly greater than the reference level indicates that the subject is at increased likelihood of Parkinson's Disease developing or progressing; and wherein a level of an miRNA selected from the group of: miR-10b-5p; miR-29b-2-5p; miR-329-3p; miR-6511a-5p; miR-4526; miR-129-1-3p; miR-129-2-3p; and miR-132-3p; miR-132-5p; miR127-3p; miR212-3p; miR-1224-5p; miR16-2-3p; miR-1294; miR-132-5p, miR-212-3p, miR-212-5p, and miR-145-5p in the sample of the subject which is statistically significantly less than the reference level indicates that the subject is at increased likelihood of Parkinson's Disease developing or progressing; wherein increased risk of Parkinson's Disease developing or progressing comprises developing Parkinson's Disease at a younger age; death due to Parkinson's Disease at a younger age; development of dementia; development of dementia at an earlier age; or onset of motor symptoms at an earlier age when compared to other individuals with Parkinson's Disease who do not have such a level of the miRNA.

In some embodiments, the sample can be selected from the group consisting of: a blood sample; blood plasma; and a brain sample. In some embodiments, the subject can be a Parkinson's Disease carrier. In some embodiments, the miRNA is selected from the group consisting of: miR-10b-5p; miR-151b; miR-29b-2-5p; miR-329-3p; miR-6511a-5p; miR-5690; miR-516b-5p; and miR208b-3p; miR-30a-3p; and increased risk of Parkinson's Disease developing or progressing comprises developing Parkinson's Disease at a younger age; death due to Parkinson's Disease at a younger age; or onset of motor symptoms at an earlier age. In some embodiments, the miRNA is selected from the group consisting of miR106a-5p; miR-363-3p; miR-4526; miR-129-1-3p; miR-129-2-3p; and miR-132-3p; miR-132-5p; miR127-3p; miR212-3p; miR-1224-5p; miR16-2-3p; miR-1294; miR-132-5p, miR-212-3p, miR-212-5p, miR-145-5p; and miR-29a-5p and increased risk of Parkinson's Disease developing or progressing comprises development of dementia or development of dementia at an earlier age.

The inventors have further found that the miRNAs described herein, e.g., miR-10b-5p, promote the growth and survival of axonal projections. In one aspect, described herein is a method of increasing axonal projections, the method comprising administering an effective amount of an agonist of, e.g., miR-10b-5p expression. In one aspect, described herein is a method of treating a neuronal disease, the method comprising administering a therapeutically effective amount of an agonist of, e.g., miR-10b-5p expression. In some embodiments, the neuronal disease is selected from the group consisting of Huntington's Disease; spinal cord injury; and stroke.

In one aspect, described herein is a method of increasing axonal projections, the method comprising; administering an effective amount of an agonist or antagonist, as appropriate, of an miRNA selected from the group consisting of: miR-10b-5p; miR196a-5p; miR196b-5p; miR615-3p; and miR1247-5p; miR106a-5p; miR363-3p; miR-129-1-3p and miR-132-3p. In one aspect, described herein is a method of treating a neuronal disease, the method comprising administering a therapeutically effective amount of an agonist or antagonist, as appropriate, of an miRNA selected from the group consisting of: miR-10b-5p; miR196a-5p; miR196b-5p; miR615-3p; and miR1247-5p; miR106a-5p; miR363-3p; miR-129-1-3p and miR-132-3p. As used in this context, it is appropriate to administer an agonist to increase the level and/or activity of a miRNA and appropriate to administer an antagonist to decrease the level and/or activity of an miRNA. In some embodiments, it is appropriate to administer an agonist of a miRNA if decreased levels and/or activity of that miRNA are associated with increased risk of disease as described herein. In some embodiments, it is appropriate to administer an antagonist of a miRNA if increased levels and/or activity of that miRNA are associated with increased risk of disease as described herein.

In some embodiments of any of the aspects described herein, detection of the abnormal expression of two or more of the genes described herein (e.g., miRNAs) can indicate an increased severity, likelihood, and/or risk as compared to the detection of the abnormal expression of only one gene. In some embodiments, detection of the abnormal expression of three or more (e.g., three, four, five, six, or more) of the genes described herein (e.g., miRNAs) can indicate an increased severity, likelihood, or risk as compared to the detection of the abnormal expression of two or fewer genes.

It is contemplated herein that any combination of abnormal expression patterns as described herein can be indicative of increased severity, likelihood, and/or risk. By way of non-limiting example, and increase in the expressing of both miR-10b-5p and miR615-3p can indicate a greater risk of Huntington's Disease developing or progressing than if an increase in only miR-10b-5p or miR615-3p was detected.

As used herein, an "agonist" of the expression of an miRNA, e.g. an agonist of miR-10b-5p expression, refers to any agent that increases the expression and/or level of the miRNA, e.g. increases the expression of miR-10b-5p by at least 10%, at least 20%, at least 30%, at least 50%, at least 100%, at least 200%, at least 500% or more. In some embodiments, the agonist of, e.g., miR-10b-5p expression can be a miR-10b-5p oligonucleotide and/or a vector encoding a miR-10b-5p oligonucleotide.

As used herein, an "antagonist" of the expression of an miRNA, e.g. an antagonist of miR-10b-5p expression, refers to any agent that decreases the expression and/or level of the miRNA, e.g. decreases the expression of the miRNA by at least 10%, at least 20%, at least 30%, at least 50%, at least 100%, at least 200%, at least 500% or more. In some embodiments, the antagonist of, e.g., miR-10b-5p expression can be an oligonucleotide complementary to miR-10b-5p and/or a vector encoding a miR-10b-5p oligonucleotide.

Methods of determining levels of expression of an expression product, e.g. miR-10b-5p are well known in the art and include, by way of non-limiting example, Northern blot, PCR, RT-PCR, quantitative PCR, microarray, and/or next generation sequencing. Where the sequences of the miRNA (e.g. miR-10b-5p) is known, one of skill in the art can readily design detection reagents, e.g. nucleic acid probes and/or primers.

In one aspect, described herein is a kit comprising one or more probes for detecting the level of at least one miRNA selected from the group consisting of: miR520f-3p, miR-135b-3p, miR-4317, miR-3928-5p, miR-8082, and mir-140-5p. In some embodiments the kit can comprise one or more probes for detecting the level of at least two miRNAs selected from the group consisting of miR520f-3p, miR-135b-3p, miR-4317, miR-3928-5p, miR-8082, and mir-140-5p. In some embodiments the kit can comprise one or more probes for detecting the level of at least three miRNAs selected from the group consisting of miR520f-3p, miR-135b-3p, miR-4317, miR-3928-5p, miR-8082, and mir-140-5p. In some embodiments the kit can comprise one or more probes for detecting the level of at least four miRNAs selected from the group consisting of miR520f-3p, miR-135b-3p, miR-4317, miR-3928-5p, miR-8082, and mir-140-5p. In some embodiments the kit can comprise one or more probes for detecting the level of at least five miRNAs selected from the group consisting of miR520f-3p, miR-135b-3p, miR-4317, miR-3928-5p, miR-8082, and mir-140-5p. In some embodiments the kit can comprise one or more probes for detecting the level of miR520f-3p, miR-135b-3p, miR-4317, miR-3928-5p, miR-8082, and mir-140-5p.

In one aspect, described herein is a kit comprising one or more probes for detecting the level of at least one miRNA selected from the group consisting of: miR-10b-5p; miR196a-5p; miR196b-5p; miR615-3p; miR1247-5p; miR106a-5p; miR363-3p; miR-129-1-3p and miR-132-3p. In some embodiments the kit can comprise one or more probes for detecting the level of at least two miRNAs selected from the group consisting of miR-10b-5p; miR196a-5p; miR196b-5p; miR615-3p; miR1247-5p; miR106a-5p; miR363-3p; miR-129-1-3p and miR-132-3p. In some embodiments, the kit can comprise one or more probes for detecting the level of at least three miRNAs selected from the group consisting of miR-10b-5p; miR196a-5p; miR196b-5p; miR615-3p; miR1247-5p; miR106a-5p; miR363-3p; miR-129-1-3p and miR-132-3p. In some embodiments, the kit can comprise one or more probes for detecting the level of at least four miRNAs selected from the group consisting of: miR-10b-5p; miR196a-5p; miR196b-5p; miR615-3p; miR1247-5p; miR106a-5p; miR363-3p; miR-129-1-3p and miR-132-3p.

In one aspect, described herein is a kit comprising one or more probes for detecting the level of at least one miRNA selected from the group consisting of miR-10b-5p; miR-151b; miR-29b-2-5p; miR-329-3p; miR-6511a-5p; miR-5690; miR-516b-5p; miR208b-3p; miR106a-5p; miR-363-3p; miR-4526; miR-129-1-3p; miR-129-2-3p; miR-132-3p; miR-132-5p; miR127-3p; miR212-3p; miR-1224-5p; miR16-2-3p; miR-1294; miR-30a-3p; miR-132-5p, miR-212-3p, miR-212-5p, miR-145-5p; and miR-29a-5p. In some embodiments, the kit can comprise one or more probes for detecting the level of at least two miRNAs selected from the group consisting of: miR-10b-5p; miR-151b; miR-29b-2-5p; miR-329-3p; miR-6511a-5p; miR-5690; miR-516b-5p; miR208b-3p; miR106a-5p; miR-363-3p; miR-4526; miR-129-1-3p; miR-129-2-3p; miR-132-3p; miR-132-5p; miR127-3p; miR212-3p; miR-1224-5p; miR16-2-3p; miR-1294; miR-30a-3p; miR-132-5p, miR-212-3p, miR-212-5p, miR-145-5p; and miR-29a-5p. In some embodiments, the kit can comprise one or more probes for detecting the level of at least three miRNAs selected from the group consisting of miR-10b-5p; miR-151b; miR-29b-2-5p; miR-329-3p; miR-6511a-5p; miR-5690; miR-516b-5p; miR208b-3p; miR106a-5p; miR-363-3p; miR-4526; miR-129-1-3p; miR-129-2-3p; miR-132-3p; miR-132-5p; miR127-3p; miR212-3p; miR-1224-5p; miR16-2-3p; miR-1294; miR-30a-3p; miR-132-5p, miR-212-3p, miR-212-5p, miR-145-5p; and miR-29a-5p. In some embodiments, the kit can comprise one or more probes for detecting the level of at least four miRNAs selected from the group consisting of miR-10b-5p; miR-151b; miR-29b-2-5p; miR-329-3p; miR-6511a-5p; miR-5690; miR-516b-5p; miR208b-3p; miR106a-5p; miR-363-3p; miR-4526; miR-129-1-3p; miR-129-2-3p; miR-132-3p; miR-132-5p; miR127-3p; miR212-3p; miR-1224-5p; miR16-2-3p; miR-1294; miR-30a-3p; miR-132-5p, miR-212-3p, miR-212-5p, miR-145-5p; and miR-29a-5p.

In some embodiments, the kit can further comprise other reagent(s). The reagents include ancillary agents such as buffering agents and protein stabilizing agents, e.g., polysaccharides and the like. The diagnostic kit may further include, where necessary, other members of the signal-producing system of which system the detectable group is a member (e.g., enzyme substrates), agents for reducing background interference in a test, control reagents, apparatus for conducting a test, and the like. The test kit may be packaged in any suitable manner, typically with all elements in a single container, optionally with a sheet of printed instructions for carrying out the test. In some embodiments, the kits described herein further comprise instructions for using the kit and interpretation of results.

In some embodiments, the kits described herein further comprise at least one sample collection container for sample collection. Collection devices and container include but are not limited to syringes, lancets, BD VACUTAINER® blood collection tubes.

In some embodiments, the level of, e.g. an miRNA can be measured by transforming the target into a detectable target. As used herein, the term "transforming" or "transformation" refers to changing an object or a substance, e.g., biological sample, nucleic acid or protein, into another substance. The transformation can be physical, biological or chemical. Exemplary physical transformation includes, but not limited to, pre-treatment of a biological sample, e.g., from whole blood to a population of cells or cell groups of a particular size range by differential centrifugation or microfluidics sorting. A biological/chemical transformation can involve at least one enzyme and/or a chemical reagent in a reaction. For example, a DNA sample can be digested into fragments by one or more restriction enzyme, or an exogenous molecule can be attached to a fragmented DNA sample with a ligase. In some embodiments, a DNA sample can undergo enzymatic replication, e.g., by polymerase chain reaction (PCR).

In certain embodiments, the level of the gene expression products as described herein (e.g. the level of a miRNA) can be determined by determining the level of messenger RNA (mRNA) expression of the genes described herein. Such molecules can be isolated, derived, or amplified from a biological sample, such as a tumor biopsy. Detection of mRNA expression is known by persons skilled in the art, and comprise, for example but not limited to, PCR procedures, RT-PCR, Northern blot analysis, differential gene expression, RNA protection assay, microarray analysis, hybridization methods, next-generation sequencing etc. Non-limiting examples of next-generation sequencing technologies can include Ion Torrent, Illumina, SOLiD, 454; Massively Parallel Signature Sequencing solid-phase, reversible dye-terminator sequencing; and DNA nanoball sequencing.

In general, the PCR procedure describes a method of gene amplification which is comprised of (i) sequence-specific hybridization of primers to specific genes or sequences within a nucleic acid sample or library, (ii) subsequent amplification involving multiple rounds of annealing, elongation, and denaturation using a thermostable DNA polymerase, and (iii) screening the PCR products for a band of the correct size. The primers used are oligonucleotides of sufficient length and appropriate sequence to provide initiation of polymerization, i.e. each primer is specifically designed to be complementary to a strand of the genomic locus to be amplified. In an alternative embodiment, mRNA level of gene expression products described herein can be determined by reverse-transcription (RT) PCR and by quantitative RT-PCR (QRT-PCR) or real-time PCR methods. Methods of RT-PCR and QRT-PCR are well known in the art. The nucleic acid sequences of the marker genes described herein have been assigned NCBI accession numbers for different species such as human, mouse and rat. Accordingly, a skilled artisan can design an appropriate primer based on the known sequence for determining the mRNA level of the respective gene.

Nucleic acid and ribonucleic acid (RNA) molecules can be isolated from a particular biological sample using any of a number of procedures, which are well-known in the art, the particular isolation procedure chosen being appropriate for the particular biological sample. For example, freeze-thaw and alkaline lysis procedures can be useful for obtaining nucleic acid molecules from solid materials; heat and alkaline lysis procedures can be useful for obtaining nucleic acid molecules from urine; and proteinase K extraction can be used to obtain nucleic acid from blood (Roiff, A et al. PCR: Clinical Diagnostics and Research, Springer (1994)).

In general, the PCR procedure describes a method of gene amplification which is comprised of (i) sequence-specific hybridization of primers to specific genes within a nucleic acid sample or library, (ii) subsequent amplification involving multiple rounds of annealing, elongation, and denaturation using a DNA polymerase, and (iii) screening the PCR products for a band of the correct size. The primers used are oligonucleotides of sufficient length and appropriate sequence to provide initiation of polymerization, i.e. each primer is specifically designed to be complementary to each strand of the nucleic acid molecule to be amplified.

In an alternative embodiment, mRNA level of gene expression products described herein can be determined by reverse-transcription (RT) PCR and by quantitative RT-PCR (QRT-PCR) or real-time PCR methods. Methods of RT-PCR and QRT-PCR are well known in the art.

In some embodiments, one or more of the reagents (e.g. an antibody reagent and/or nucleic acid probe) described herein can comprise a detectable label and/or comprise the ability to generate a detectable signal (e.g. by catalyzing reaction converting a compound to a detectable product). Detectable labels can comprise, for example, a light-absorbing dye, a fluorescent dye, or a radioactive label. Detectable labels, methods of detecting them, and methods of incorporating them into reagents (e.g. antibodies and nucleic acid probes) are well known in the art.

In some embodiments, detectable labels can include labels that can be detected by spectroscopic, photochemical, biochemical, immunochemical, electromagnetic, radiochemical, or chemical means, such as fluorescence, chemifluorescence, or chemiluminescence, or any other appropriate means. The detectable labels used in the methods described herein can be primary labels (where the label comprises a moiety that is directly detectable or that produces a directly detectable moiety) or secondary labels (where the detectable label binds to another moiety to produce a detectable signal, e.g., as is common in immunological labeling using secondary and tertiary antibodies). The detectable label can be linked by covalent or non-covalent means to the reagent. Alternatively, a detectable label can be linked such as by directly labeling a molecule that achieves binding to the reagent via a ligand-receptor binding pair arrangement or other such specific recognition molecules. Detectable labels can include, but are not limited to radioisotopes, bioluminescent compounds, chromophores, antibodies, chemiluminescent compounds, fluorescent compounds, metal chelates, and enzymes.

In other embodiments, the detection reagent is label with a fluorescent compound. When the fluorescently labeled antibody is exposed to light of the proper wavelength, its presence can then be detected due to fluorescence. In some embodiments, a detectable label can be a fluorescent dye molecule, or fluorophore including, but not limited to fluorescein, phycoerythrin, phycocyanin, o-phthaldehyde, fluorescamine, Cy3™, Cy5™, allophycocyanine, Texas Red, peridenin chlorophyll, cyanine, tandem conjugates such as phycoerythrin-Cy5™, green fluorescent protein, rhodamine, fluorescein isothiocyanate (FITC) and Oregon Green™, rhodamine and derivatives (e.g., Texas red and tetrarhodimine isothiocynate (TRITC)), biotin, phycoerythrin, AMCA, CyDyes™, 6-carboxyfhiorescein (commonly known by the abbreviations FAM and F), 6-carboxy-2',4', 7',4,7-hexachlorofluorescein (HEX), 6-carboxy-4',5'-dichloro-2',7'-dimethoxyfluorescein (JOE or J), N,N,N',N'-tetramethyl-6carboxyrhodamine (TAMRA or T), 6-carboxy-X-rhodamine (ROX or R), 5-carboxyrhodamine-6G (R6G5 or G5), 6-carboxyrhodamine-6G (R6G6 or G6), and rhodamine 110; cyanine dyes, e.g. Cy3, Cy5 and Cy7 dyes; coumarins, e.g umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3, Cy5, etc; BODIPY dyes and quinoline dyes. In some embodiments, a detectable label can be a radiolabel including, but not limited to $^3$H, $^{125}$I, $^{35}$S, $^{14}$C, $^{32}$P, and $^{33}$P. In some embodiments, a detectable label can be an enzyme including, but not limited to horseradish peroxidase and alkaline phosphatase. An enzymatic label can produce, for example, a chemiluminescent signal, a color signal, or a fluorescent signal. Enzymes contemplated for use to detectably label an antibody reagent include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase. In some embodiments, a detectable label is a chemiluminescent label, including, but not limited to lucigenin, luminol, luciferin, isoluminol, theromatic acridinium ester, imidazole, acridinium salt and oxalate ester. In some embodiments, a detectable label can be a spectral colorimetric label including, but not limited to colloidal gold or colored glass or plastic (e.g., polystyrene, polypropylene, and latex) beads.

In some embodiments, detection reagents can also be labeled with a detectable tag, such as c-Myc, HA, VSV-G, HSV, FLAG, V5, HIS, or biotin. Other detection systems can also be used, for example, a biotin-streptavidin system. In this system, the antibodies immunoreactive (i. e. specific for) with the biomarker of interest is biotinylated. Quantity of biotinylated antibody bound to the biomarker is determined using a streptavidin-peroxidase conjugate and a chromagenic substrate. Such streptavidin peroxidase detection kits are commercially available, e. g. from DAKO; Carpinteria, Calif. A reagent can also be detectably labeled using fluorescence emitting metals such as $^{152}$Eu, or others of the lanthanide series. These metals can be attached to the reagent using such metal chelating groups as diethylenetriaminepentaacetic acid (DTPA) or ethylenediaminetetraacetic acid (EDTA).

In some embodiments of any of the aspects described herein, the level of expression products of more than one gene can be determined simultaneously (e.g. a multiplex assay) or in parallel. In some embodiments, the level of expression products of no more than 200 other genes is determined. In some embodiments, the level of expression products of no more than 100 other genes is determined. In some embodiments, the level of expression products of no more than 20 other genes is determined. In some embodiments, the level of expression products of no more than 10 other genes is determined.

In some embodiments, the reference level can be the level (e.g. the level of miRNA) in a population of subjects who have been demonstrated to not be at risk for HD. In some embodiments, the reference level can be the level (e.g. the level of miRNA) in a population of subjects who have been demonstrated to not have a CAG repeat mutation at the htt3 gene. In some embodiments, the reference can also be a level in a control sample, a pooled sample of control individuals or a numeric value or range of values based on the same.

The term "sample" or "test sample" as used herein denotes a sample taken or isolated from a biological organism, e.g., a blood sample from a subject. Exemplary biological samples include, but are not limited to, a biofluid sample; serum; plasma; urine; saliva; a brain or neural tissue sample and/or biopsy etc. The term also includes a mixture of the above-mentioned samples. The term "test sample" also includes untreated or pretreated (or pre-processed) biological samples. In some embodiments, a test sample can comprise cells from subject. In some embodiments, a test sample can be a blood sample. In some embodiments, the test sample can be neural cell sample, e.g. a sample comprising neural cells and/or brain cells.

The test sample can be obtained by removing a sample of cells from a subject, but can also be accomplished by using previously isolated cells (e.g. isolated at a prior timepoint and isolated by the same or another person). In addition, the test sample can be freshly collected or a previously collected sample.

In some embodiments, the test sample can be an untreated test sample. As used herein, the phrase "untreated test sample" refers to a test sample that has not had any prior sample pre-treatment except for dilution and/or suspension in a solution. Exemplary methods for treating a test sample include, but are not limited to, centrifugation, filtration, sonication, homogenization, heating, freezing and thawing, and combinations thereof. In some embodiments, the test sample can be a frozen test sample, e.g., a frozen tissue. The frozen sample can be thawed before employing methods, assays and systems described herein. After thawing, a frozen sample can be centrifuged before being subjected to methods, assays and systems described herein. In some embodiments, the test sample is a clarified test sample, for example, by centrifugation and collection of a supernatant comprising the clarified test sample. In some embodiments, a test sample can be a pre-processed test sample, for example, supernatant or filtrate resulting from a treatment selected from the group consisting of centrifugation, filtration, thawing, purification, and any combinations thereof. In some embodiments, the test sample can be treated with a chemical and/or biological reagent. Chemical and/or biological reagents can be employed to protect and/or maintain the stability of the sample, including biomolecules (e.g., nucleic acid and protein) therein, during processing. One exemplary reagent is a protease inhibitor, which is generally used to protect or maintain the stability of protein during processing. The skilled artisan is well aware of methods and processes appropriate for pre-processing of biological samples required for determination of the level of an expression product as described herein.

In some embodiments, the subject can be a human subject. In some embodiments, the subject can be a subject who is a HD carrier. In some embodiments, the subject can be a subject with a family history of HD. In some embodiments, the subject can be a subject with a mutation at the htt3 gene which indicates the subject will develop HD, e.g. a CAG repeat mutation.

In some embodiments, the methods described herein relate to treating a subject having or diagnosed as having HD. Subjects having HD can be identified by a physician using current methods of diagnosing HD. Symptoms and/or complications of HD which characterize these conditions and aid in diagnosis are well known in the art and include but are not limited to, chorea, physical instability, abnormal facial expression, difficulty chewing, speaking, and swallowing, sleep disturbances, impaired cognitive ability, memory deficits, anxiety, depression, and compulsive behavior. Tests that may aid in a diagnosis of, e.g. HD include, but are not limited to, a genetic test for CAG repeats at the htt3 gene, and/or the assays and methods described herein. A family history of HD, can also aid in determining if a subject is likely to have HD or in making a diagnosis of HD.

In some embodiments, treatment of HD can comprise advising the subject to perform regular physical exercise;

perform regular mental exercise; improve their diet; or administering coenzyme Q10 if the subject is at increased risk of developing Huntington's Disease. Although there is not presently a cure for HD, the foregoing modifications of diet and exercise can delay the onset, severity, and/or progression of symptoms.

The biomarkers described herein, due to their correlation with striatal degradation and/or age of onset of symptoms, can also permit determinations of the effectiveness of treatments, e.g. candidate agents for the treatment of HD. In some embodiments, the foregoing methods can be performed in vitro, e.g. the assay can comprise measuring, in a sample obtained from cultured cells and/or tissues (e.g. a sample of cells, e.g. a sample of cultured neurons and/or neural progenitors), the level of a biomarker described herein.

As used herein, the terms "candidate compound" or "candidate agent" refer to a compound or agent and/or compositions thereof that are to be screened for their ability to treat HD. The compounds/agents can include, but are not limited to, chemical compounds and mixtures of chemical compounds, e.g., small organic or inorganic molecules; saccharines; oligosaccharides; polysaccharides; biological macromolecules, e.g., peptides, proteins, and peptide analogs and derivatives; peptidomimetics; nucleic acids; nucleic acid analogs and derivatives; extracts made from biological materials such as bacteria, plants, fungi, or animal cells or tissues; naturally occurring or synthetic compositions; peptides; aptamers; and antibodies and intrabodies, or fragments thereof.

Generally, compounds can be tested at any concentration that can modulate exprethe activity of the target biomolecule relative to a control over an appropriate time period. In some embodiments, compounds are tested at concentration in the range of about 0.1 nM to about 1000 mM. Depending upon the particular embodiment being practiced, the test compounds can be provided free in solution, or may be attached to a carrier, or a solid support, e.g., beads. A number of suitable solid supports may be employed for immobilization of the test compounds. Examples of suitable solid supports include agarose, cellulose, dextran (commercially available as, i.e., Sephadex, Sepharose) carboxymethyl cellulose, polystyrene, polyethylene glycol (PEG), filter paper, nitrocellulose, ion exchange resins, plastic films, polyaminemethylvinylether maleic acid copolymer, glass beads, amino acid copolymer, ethylene-maleic acid copolymer, nylon, silk, etc. Additionally, for the methods described herein, test compounds may be screened individually, or in groups. Group screening is particularly useful where hit rates for effective test compounds are expected to be low such that one would not expect more than one positive result for a given group.

In one aspect, described herein is a computer system comprising a measuring module configured to measure, in a sample obtained from a subject, the level of a biomarker as described herein; a storage module configured to store data output from the measuring module; a comparison module adapted to compare the data stored on the storage module with a reference level, and to provide a retrieved content, and a display module for displaying whether the level of the biomarker in the sample obtained from the subject varies, by a statistically significant amount, from the reference level and/or displaying the relative levels of the biomarker; wherein a level of biomarker in the sample of the subject which is statistically significantly different than the reference level indicates that the subject is at increased risk of developing Huntington's Disease.

Figure 5:
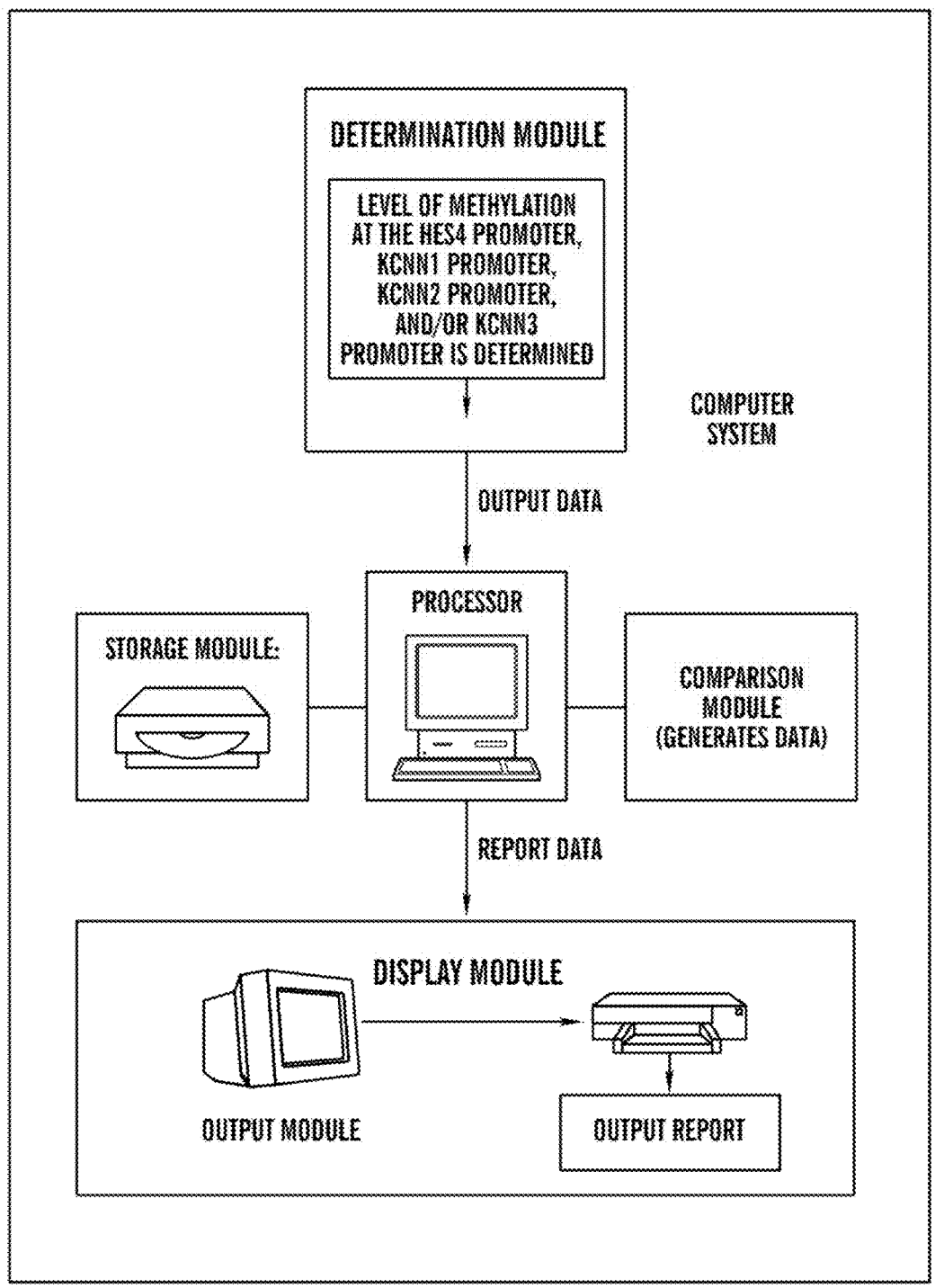
FIG. 5 is a diagram of an exemplary embodiment of a system for performing an assay for determining the level of methylation at the HES4 promoter, KCNN1 promoter, KCNN2 promoter, and/or KCNN3 promoter in sample obtained from a subject.

In one embodiment, provided herein is a system comprising: (a) at least one memory containing at least one computer program adapted to control the operation of the computer system to implement a method that includes 1) a measuring module configured to measure the level of, e.g. a miRNA in a test sample obtained from a subject, 2) a storage module configured to store output data from the measuring module, 3) a computing module adapted to identify from the output data whether the level of the miRNA in a sample obtained from a subject is statistically significantly different from a reference level, and 4) a display module for displaying a content based in part on the data output from the measuring module, wherein the content comprises a signal indicative of the level of the miRNA and (b) at least one processor for executing the computer program (see FIG. 5).

In some embodiments, the measuring module can measure the presence and/or intensity of a detectable signal from an assay indicating the level of the miRNA in the test sample. Exemplary embodiments of a measuring module can include an automated Chip assay, real-time PCR machine, etc.

The measuring module can comprise any system for detecting a signal elicited from an assay to determine the level of, e.g. a miRNA as described above herein. In some embodiments, such systems can include an instrument, e.g., a real time PCR machine (e.g. a LIGHTCYCLER™ (Roche). In one embodiment, the measuring module can be configured to perform the methods described elsewhere herein, e.g. or detection of any detectable label or signal generated by the detection of a biomolecule described herein.

The term "computer" can refer to any non-human apparatus that is capable of accepting a structured input, processing the structured input according to prescribed rules, and producing results of the processing as output. Examples of a computer include: a computer; a general purpose computer; a supercomputer; a mainframe; a super mini-computer; a mini-computer; a workstation; a micro-computer; a server; an interactive television; a hybrid combination of a computer and an interactive television; and application-specific hardware to emulate a computer and/or software. A computer can have a single processor or multiple processors, which can operate in parallel and/or not in parallel. A computer also refers to two or more computers connected together via a network for transmitting or receiving information between the computers. An example of such a computer includes a distributed computer system for processing information via computers linked by a network.

The term "computer-readable medium" may refer to any storage device used for storing data accessible by a computer, as well as any other means for providing access to data by a computer. Examples of a storage-device-type computer-readable medium include: a magnetic hard disk; a floppy disk; an optical disk, such as a CD-ROM and a DVD; a magnetic tape; a memory chip. The term a "computer system" may refer to a system having a computer, where the computer comprises a computer-readable medium embodying software to operate the computer. The term "software" is used interchangeably herein with "program" and refers to prescribed rules to operate a computer. Examples of software include: software; code segments; instructions; computer programs; and programmed logic.

The computer readable storage media can be any available tangible media that can be accessed by a computer. Computer readable storage media includes volatile and nonvolatile, removable and non-removable tangible media implemented in any method or technology for storage of information such as computer readable instructions, data structures, program modules or other data. Computer readable storage media includes, but is not limited to, RAM (random access memory), ROM (read only memory), EPROM (erasable programmable read only memory), EEPROM (electrically erasable programmable read only memory), flash memory or other memory technology, CD-ROM (compact disc read only memory), DVDs (digital versatile disks) or other optical storage media, magnetic cassettes, magnetic tape, magnetic disk storage or other magnetic storage media, other types of volatile and non-volatile memory, and any other tangible medium which can be used to store the desired information and which can accessed by a computer including and any suitable combination of the foregoing.

Computer-readable data embodied on one or more computer-readable media may define instructions, for example, as part of one or more programs that, as a result of being executed by a computer, instruct the computer to perform one or more of the functions described herein, and/or various embodiments, variations and combinations thereof. Such instructions may be written in any of a plurality of programming languages, for example, Java, J#, Visual Basic, C, C#, C++, Fortran, Pascal, Eiffel, Basic, COBOL assembly language, and the like, or any of a variety of combinations thereof. The computer-readable media on which such instructions are embodied may reside on one or more of the components of either of a system, or a computer readable storage medium described herein, may be distributed across one or more of such components.

The computer-readable media may be transportable such that the instructions stored thereon can be loaded onto any computer resource to implement the aspects of the present invention discussed herein. In addition, it should be appreciated that the instructions stored on the computer-readable medium, described above, are not limited to instructions embodied as part of an application program running on a host computer. Rather, the instructions may be embodied as any type of computer code (e.g., software or microcode) that can be employed to program a computer to implement aspects of the present invention. The computer executable instructions may be written in a suitable computer language or combination of several languages. Basic computational biology methods are known to those of ordinary skill in the art and are described in, for example, Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001).

Embodiments of the invention can be described through functional modules, which are defined by computer executable instructions recorded on computer readable media and which cause a computer to perform method steps when executed. The modules are segregated by function for the sake of clarity. However, it should be understood that the modules/systems need not correspond to discreet blocks of code and the described functions can be carried out by the execution of various code portions stored on various media and executed at various times. Furthermore, it should be appreciated that the modules can perform other functions, thus the modules are not limited to having any particular functions or set of functions.

The functional modules of certain embodiments of the invention include at minimum a measuring module, a storage module, a computing module, and a display module. The functional modules can be executed on one, or multiple, computers, or by using one, or multiple, computer networks. The measuring module has computer executable instructions to provide e.g., levels of a miRNA, etc., in computer readable form.

The information determined in the measuring system can be read by the storage module. As used herein the "storage module" is intended to include any suitable computing or processing apparatus or other device configured or adapted for storing data or information. Examples of electronic apparatus suitable for use with the present invention include stand-alone computing apparatus, data telecommunications networks, including local area networks (LAN), wide area networks (WAN), Internet, Intranet, and Extranet, and local and distributed computer processing systems. Storage modules also include, but are not limited to: magnetic storage media, such as floppy discs, hard disc storage media, magnetic tape, optical storage media such as CD-ROM, DVD, electronic storage media such as RAM, ROM, EPROM, EEPROM and the like, general hard disks and hybrids of these categories such as magnetic/optical storage media. The storage module is adapted or configured for having recorded thereon, for example, sample name, biomolecule assayed and the level of said biomolecule. Such information may be provided in digital form that can be transmitted and read electronically, e.g., via the Internet, on diskette, via USB (universal serial bus) or via any other suitable mode of communication.

As used herein, "stored" refers to a process for encoding information on the storage module. Those skilled in the art can readily adopt any of the presently known methods for recording information on known media to generate manufactures comprising expression level information.

In some embodiments of any of the systems described herein, the storage module stores the output data from the measuring module. In additional embodiments, the storage module stores reference information such as levels of, e.g. an miRNA in healthy subjects, subjects not having a HD mutation, and/or subject demonstrated to have late onset of HD symptoms.

Figure 6:
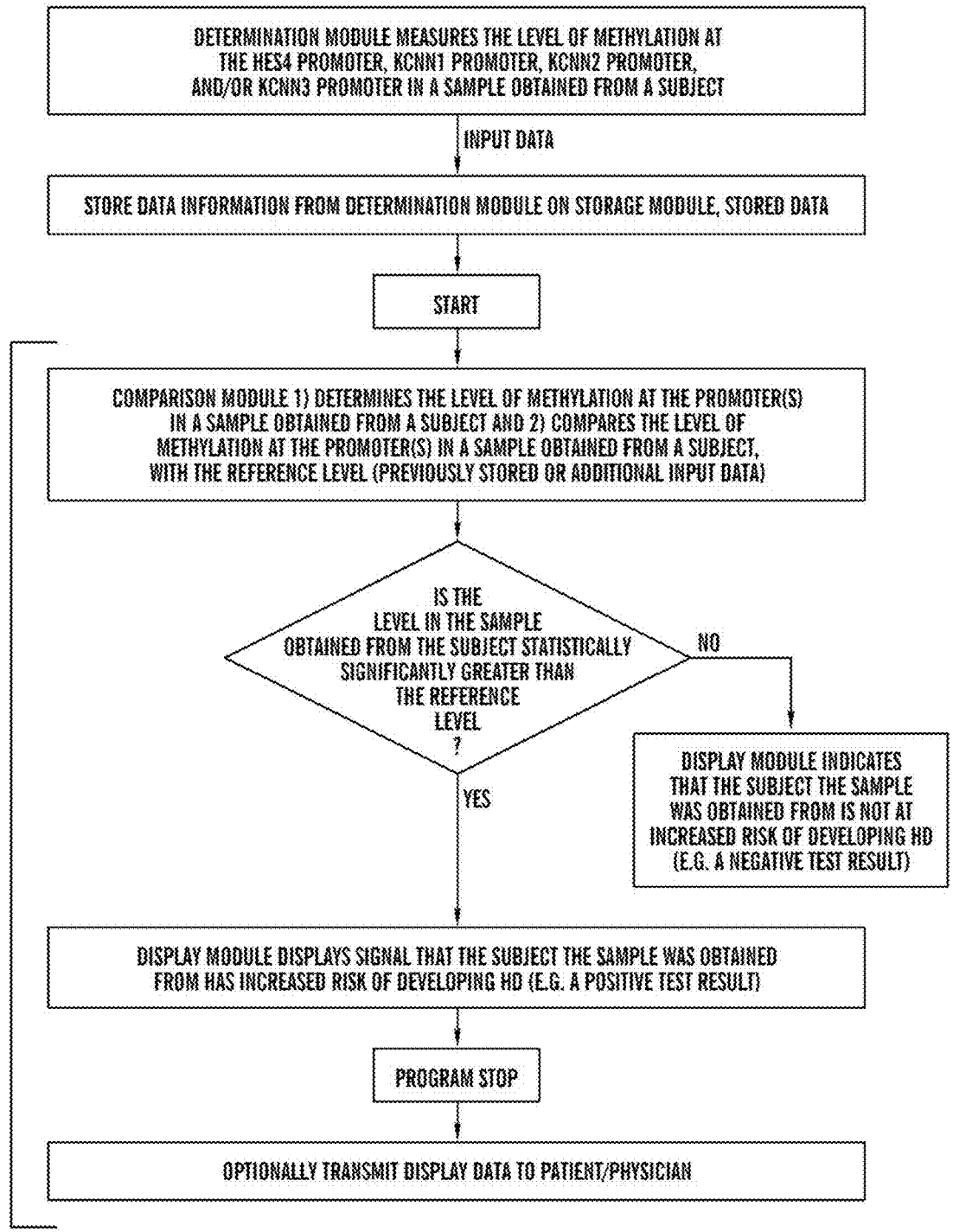
FIG. 6 is a diagram of an embodiment of a comparison module as described herein.

The "computing module" can use a variety of available software programs and formats for computing the level of, e.g. an miRNA. Such algorithms are well established in the art. A skilled artisan is readily able to determine the appropriate algorithms based on the size and quality of the sample and type of data. The data analysis tools and equations described herein can be implemented in the computing module of the invention. In some embodiments, the computing module can comprise a computer and/or a computer system. In one embodiment, the computing module further comprises a comparison module, which compares the level of, e.g., an miRNA in a sample obtained from a subject as described herein with a reference level as described herein (see, e.g. FIG. 6). By way of an example, when the level of a miRNA in a sample obtained from a subject is measured, a comparison module can compare or match the output data with the mean level of the miRNA in a population of subjects not having signs or symptoms of a HD or a population of subjects not having a HD mutation (i.e. a reference level). In certain embodiments, the mean level of, e.g. the miRNA in a population of subjects not having signs or symptoms of HD, or not having an HD mutation can be pre-stored in the storage module. During the comparison or matching process, the comparison module can determine whether the level of, e.g. the miRNA in a sample obtained from a subject is statistically significantly different from the reference level. In various embodiments, the comparison module can be configured using existing commercially-available or freely-available software for comparison purpose, and may be optimized for particular data comparisons that are conducted.

Figure 7:
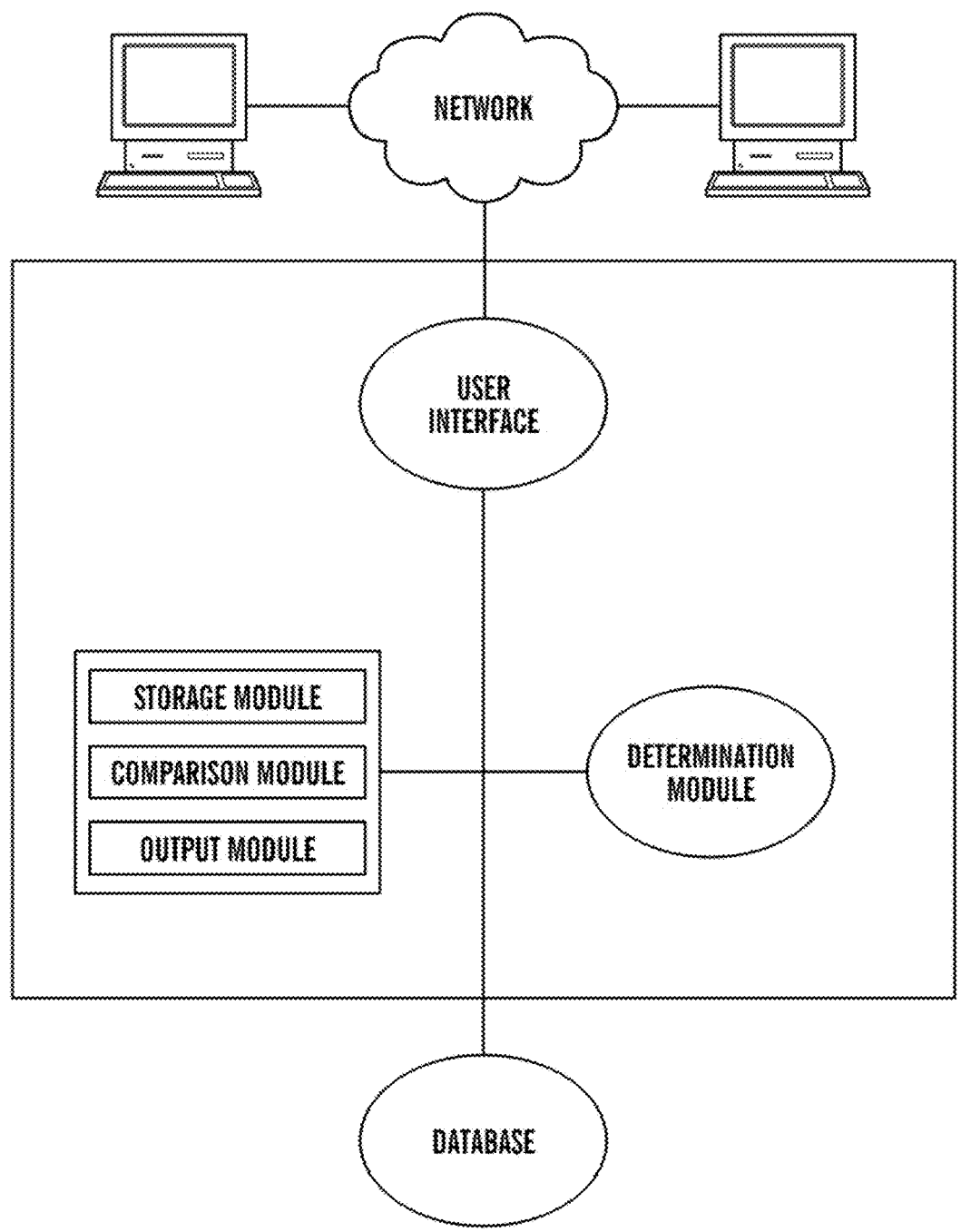
FIG. 7 is a diagram of an exemplary embodiment of an operating system and instructions for a computing system as described herein.

The computing and/or comparison module, or any other module of the invention, can include an operating system (e.g., UNIX) on which runs a relational database management system, a World Wide Web application, and a World Wide Web server. World Wide Web application includes the executable code necessary for generation of database language statements (e.g., Structured Query Language (SQL) statements). Generally, the executables will include embedded SQL statements. In addition, the World Wide Web application may include a configuration file which contains pointers and addresses to the various software entities that comprise the server as well as the various external and internal databases which must be accessed to service user requests. The Configuration file also directs requests for server resources to the appropriate hardware—as may be necessary should the server be distributed over two or more separate computers. In one embodiment, the World Wide Web server supports a TCP/IP protocol. Local networks such as this are sometimes referred to as "Intranets." An advantage of such Intranets is that they allow easy communication with public domain databases residing on the World Wide Web (e.g., the GenBank or Swiss Pro World Wide Web site). In some embodiments users can directly access data (via Hypertext links for example) residing on Internet databases using a HTML interface provided by Web browsers and Web servers (FIG. 7).

The computing and/or comparison module provides a computer readable comparison result that can be processed in computer readable form by predefined criteria, or criteria defined by a user, to provide content based in part on the comparison result that may be stored and output as requested by a user using an output module, e.g., a display module.

In some embodiments, the content displayed on the display module can be a report, e.g. the level of a miRNA in the sample obtained from a subject. In some embodiments, a report can denote the level of a miRNA. In some embodiments, the report can denote raw values of the level of the miRNA in the test sample or it indicates a percentage or fold increase in that level as compared to a reference level, and/or provides a signal that the subject is at risk of developing or not developing HD.

In some embodiments, if the computing module determines that the level of, e.g. an miRNA in the sample obtained from a subject is different by a statistically significant amount from the reference level, the display module provides a report displaying a signal indicating that the level in the sample obtained from a subject is different than that of the reference level. In some embodiments, the content displayed on the display module or report can be the relative level of miRNAr in the sample obtained from a subject as compared to the reference level. In some embodiments, the signal can indicate the degree to which the level of miRNA in the sample obtained from the subject varies from the reference level. In some embodiments, the signal can indicate that the subject is at increased risk of developing HD. In some embodiments, the signal can indicate the subject can benefit from treatment with a therapy for HD. In some embodiments, the content displayed on the display module or report can be a numerical value indicating one of these risks or probabilities. In such embodiments, the probability can be expressed in percentages or a fraction. For example, higher percentage or a fraction closer to 1 indicates a higher likelihood of a subject developing HD. In some embodiments, the content displayed on the display module or report can be single word or phrases to qualitatively indicate a risk or probability. For example, a word "unlikely" can be used to indicate a lower risk for developing HD, while "likely" can be used to indicate a high risk for developing HD.

In one embodiment of the invention, the content based on the computing and/or comparison result is displayed on a computer monitor. In one embodiment of the invention, the content based on the computing and/or comparison result is displayed through printable media. The display module can be any suitable device configured to receive from a computer and display computer readable information to a user. Non-limiting examples include, for example, general-purpose computers such as those based on Intel PENTIUM-type processor, Motorola PowerPC, Sun UltraSPARC, Hewlett-Packard PA-RISC processors, any of a variety of processors available from Advanced Micro Devices (AMD) of Sunnyvale, Calif., or any other type of processor, visual display devices such as flat panel displays, cathode ray tubes and the like, as well as computer printers of various types.

In one embodiment, a World Wide Web browser is used for providing a user interface for display of the content based on the computing/comparison result. It should be understood that other modules of the invention can be adapted to have a web browser interface. Through the Web browser, a user can construct requests for retrieving data from the computing/comparison module. Thus, the user will typically point and click to user interface elements such as buttons, pull down menus, scroll bars and the like conventionally employed in graphical user interfaces.

Systems and computer readable media described herein are merely illustrative embodiments of the invention for determining the level of, e.g. a miRNA in a sample obtained from a subject, and therefore are not intended to limit the scope of the invention. Variations of the systems and computer readable media described herein are possible and are intended to fall within the scope of the invention. The modules of the machine, or those used in the computer readable medium, may assume numerous configurations. For example, function may be provided on a single machine or distributed over multiple machines.

The compositions and methods described herein can be administered to a subject having or diagnosed as having, e.g., Huntington's Disease. In some embodiments, the methods described herein comprise administering an effective amount of compositions described herein, e.g. an agonist of miR10-b-5p to a subject in order to alleviate a symptom of Huntington's Disease. As used herein, "alleviating a symptom of Huntington's Disease" is ameliorating any condition or symptom associated with the disease. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, injection, or topical, administration. Administration can be local or systemic.

The term "effective amount" as used herein refers to the amount of a composition (e.g. an agonist of miR-10b-5p) needed to alleviate at least one or more symptom of the disease or disorder, and relates to a sufficient amount of pharmacological composition to provide the desired effect.

The term "therapeutically effective amount" therefore refers to an amount of a compound that is sufficient to provide a particular effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of a composition which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for neuronal degradation and/or growth, among others. The dosage can be determined by a physician and adjusted, as necessary, to suit observed effects of the treatment.

In some embodiments, the technology described herein relates to a pharmaceutical composition as described herein, and optionally a pharmaceutically acceptable carrier. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent as described herein.

In some embodiments, the pharmaceutical composition as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms as disclosed within are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of a composition as disclosed herein can also be incorporated into the parenteral dosage forms of the disclosure, including conventional and controlled-release parenteral dosage forms.

Pharmaceutical compositions can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia Pa. (2005).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, the composition can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

The methods described herein can further comprise administering a second agent and/or treatment to the subject, e.g. as part of a combinatorial therapy.

In certain embodiments, an effective dose of a composition as described herein can be administered to a patient once. In certain embodiments, an effective dose of a composition can be administered to a patient repeatedly. For systemic administration, subjects can be administered a therapeutic amount of a composition such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In some embodiments, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the active ingredient(s). The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition can be administered over a period of time, such as over a 5 minute, 10 minute, 15 minute, 20 minute, or 25 minute period.

The dosage ranges for the administration of a composition, according to the methods described herein depend upon, for example, the form of the active ingredient, its potency, and the extent to which symptoms, markers, or indicators of a condition described herein are desired to be reduced, for example the percentage reduction desired for neural degeneration or the extent to which, for example, neuron projection growth are desired to be induced. The dosage should not be so large as to cause adverse side effects. Generally, the dosage will vary with the age, condition, and sex of the patient and can be determined by one of skill in the art. The dosage can also be adjusted by the individual physician in the event of any complication.

The efficacy of a composition in, e.g. the treatment of a condition described herein, or to induce a response as described herein can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response, (e.g. a reduction of neuronal degeneration). It is well within the ability of one skilled in the art to monitor efficacy of administration and/or treatment by measuring any one of such parameters, or any combination of parameters. Efficacy can be assessed in animal models of a condition described herein, for example treatment of Huntington's Disease. When using an experimental animal model, efficacy of treatment is evidenced when a statistically significant change in a marker is observed, e.g. the growth and/or survival of axonal projections.

In vitro and animal model assays are provided herein which allow the assessment of a given dose of, e.g., an agonist of miR-10b-5p expression. By way of non-limiting example, the effects of a dose of an agonist of miR-10b-5p expression can be assessed by administering the composition to a mouse model of Huntington's Disease and/or monitoring the growth and/or survival of neurons in an in vitro assay.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of Huntington's Disease. A subject can be male or female.

A subject can be one who has been previously diagnosed with or identified as suffering from or having a condition in need of treatment (e.g. Huntington's Disease) or one or more complications related to such a condition, and optionally, have already undergone treatment for Huntington's Disease or the one or more complications related to Huntington's Disease. Alternatively, a subject can also be one who has not been previously diagnosed as having Huntington's Disease or one or more complications related to HD. For example, a subject can be one who exhibits one or more risk factors for HD or one or more complications related to HD or a subject who does not exhibit risk factors.

A "subject in need" of treatment for a particular condition can be a subject having that condition, diagnosed as having that condition, or at risk of developing that condition.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

In some embodiments, the RNA is chemically modified to enhance stability or other beneficial characteristics. The nucleic acids featured in the invention may be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Modifications include, for example, (a) end modifications, e.g., 5' end modifications (phosphorylation, conjugation, inverted linkages, etc.) 3' end modifications (conjugation, DNA nucleotides, inverted linkages, etc.), (b) base modifications, e.g., replacement with stabilizing bases, destabilizing bases, or bases that base pair with an expanded repertoire of partners, removal of bases (abasic nucleotides), or conjugated bases, (c) sugar modifications (e.g., at the 2' position or 4' position) or replacement of the sugar, as well as (d) backbone modifications, including modification or replacement of the phosphodiester linkages. Specific examples of RNA compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In particular embodiments, the modified RNA will have a phosphorus atom in its internucleoside backbone.

Modified RNA backbones can include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included. Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; 5,625,050; 6,028,188; 6,124,445; 6,160,109; 6,169,170; 6,172,209; 6,239,265; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; and U.S. Pat. RE39464, each of which is herein incorporated by reference Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, each of which is herein incorporated by reference.

In other RNA mimetics suitable or contemplated for use in the methods described herein, both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, each of which is herein incorporated by reference. Further teaching of PNA compounds can be found, for example, in Nielsen et al., Science, 1991, 254, 1497-1500.

Some embodiments featured in the invention include RNAs with phosphorothioate backbones and oligonucleosides with heteroatom backbones, and in particular —$CH_2$—NH—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —N($CH_3$)—$CH_2$—$CH_2$— [wherein the native phosphodiester backbone is represented as —O—P—O—$CH_2$—] of the above-referenced U.S. Pat. No. 5,489,677, and the amide backbones of the above-referenced U.S. Pat. No. 5,602,240. In some embodiments, the RNAs featured herein have morpholino backbone structures of the above-referenced U.S. Pat. No. 5,034,506.

Modified RNAs can also contain one or more substituted sugar moieties. The RNAs, e.g., dsRNAs, featured herein can include one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Exemplary suitable modifications include $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_n CH_3)]_2$, where n and m are from 1 to about 10. In other embodiments, dsRNAs include one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an iRNA, or a group for improving the pharmacodynamic properties of an iRNA, and other substituents having similar properties. In some embodiments, the modification includes a 2'-methoxyethoxy (2'-O—$CH_2CH_2OCH_3$, also known as 2'-O-(2-methoxyethyl) or 2'-MOE) (Martin et al., Helv. Chim. Acta, 1995, 78:486-504) i.e., an alkoxy-alkoxy group. Another exemplary modification is 2'-dimethylaminooxyethoxy, i.e., a $O(CH_2)_2ON(CH_3)_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—$CH_2$—O—$CH_2$—$N(CH_2)_2$, also described in examples herein below.

Other modifications include 2'-methoxy (2'-$OCH_3$), 2'-aminopropoxy (2'-$OCH_2CH_2CH_2NH_2$) and 2'-fluoro (2'-F). Similar modifications can also be made at other positions on the RNA of an iRNA, particularly the 3' position of the sugar on the 3' terminal nucleotide or in 2'-5' linked dsRNAs and the 5' position of 5' terminal nucleotide. RNAs may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application, and each of which is herein incorporated by reference.

An RNA can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, these disclosed by Englisch et al., Angewandte Chemie, International Edition, 1991, 30, 613, and those disclosed by Sanghvi, Y S., Chapter 15, dsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,30; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,681,941; 6,015,886; 6,147,200; 6,166,197; 6,222,025; 6,235,887; 6,380,368; 6,528,640; 6,639,062; 6,617,438; 7,045,610; 7,427,672; and 7,495,088, each of which is herein incorporated by reference, and U.S. Pat. No. 5,750,692, also herein incorporated by reference.

The RNA can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen, J. et al., (2005) Nucleic Acids Research 33(1):439-447; Mook, O R. et al., (2007) Mol Canc Ther 6(3):833-843; Grunweller, A. et al., (2003) Nucleic Acids Research 31(12): 3185-3193). Representative U.S. patents that teach the preparation of locked nucleic acid nucleotides include, but are not limited to, the following: U.S. Pat. Nos. 6,268,490; 6,670,461; 6,794,499; 6,998,484; 7,053,207; 7,084,125; and 7,399,845, each of which is herein incorporated by reference in its entirety.

Another modification of the RNA featured in the invention involves chemically linking to the RNA one or more ligands, moieties or conjugates that enhance the activity, cellular distribution, pharmacokinetic properties, or cellular uptake of the RNA. Such moieties include but are not limited to lipid moieties such as a cholesterol moiety (Letsinger et al., Proc. Natl. Acid. Sci. USA, 1989, 86: 6553-6556), cholic acid (Manoharan et al., Biorg. Med. Chem. Let., 1994, 4:1053-1060), a thioether, e.g., beryl-S-tritylthiol (Manoharan et al., Ann. N.Y. Acad. Sci., 1992, 660:306-309; Manoharan et al., Biorg. Med. Chem. Let., 1993, 3:2765-2770), a thiocholesterol (Oberhauser et al., Nucl. Acids Res., 1992, 20:533-538), an aliphatic chain, e.g., dodecandiol or undecyl residues (Saison-Behmoaras et al., EMBO J, 1991, 10:1111-1118; Kabanov et al., FEBS Lett., 1990, 259:327-330; Svinarchuk et al., Biochimie, 1993, 75:49-54), a phospholipid, e.g., di-hexadecyl-rac-glycerol or triethyl-ammonium 1,2-di-O-hexadecyl-rac-glycero-3-phosphonate (Manoharan et al., Tetrahedron Lett., 1995, 36:3651-3654; Shea et al., Nucl. Acids Res., 1990, 18:3777-3783), a polyamine or a polyethylene glycol chain (Manoharan et al., Nucleosides & Nucleotides, 1995, 14:969-973), or adamantane acetic acid (Manoharan et al., Tetrahedron Lett., 1995, 36:3651-3654), a palmityl moiety (Mishra et al., Biochim. Biophys. Acta, 1995, 1264:229-237), or an octadecylamine or hexylamino-carbonyloxycholesterol moiety (Crooke et al., J. Pharmacol. Exp. Ther., 1996, 277:923-937).

The KCNN (potassium intermediate/small conductance calcium-activated channel, subfamily N) proteins are calcium-activated potassium channels that control action potentials in neurons. The KCNN family includes 3 members, KCNN1 (SK1), KCNN2 (SK2), and KCNN3 (SK3). The sequences of the genes and expression products of the KCNN genes are known for a number of species, e.g. human KCNN1 (NCBI Gene ID No: 3780)(mRNA: SEQ ID NO: 4, NCBI Ref Seq: NM_002248)(polypeptide: SEQ ID NO: 5, NCBI Ref Seq: NP_002239), human KCNN2 (NCBI Gene ID No: 3781)(mRNA: SEQ ID NO: 6, NCBI Ref Seq: NM_021614)(polypeptide: SEQ ID NO: 7, NCBI Ref Seq: NP_067627), and human KCNN3 (NCBI Gene ID No: 3782)(mRNA: SEQ ID NO: 8, NCBI Ref Seq: NM_001204087)(polypeptide: SEQ ID NO: 9, NCBI Ref Seq: NP_001191016).

In some embodiments, the promoter of KCNN1 can comprise the sequence corresponding to SEQ ID NO: 16 and/or SEQ ID NO: 17, and/or SEQ ID NO: 18 (and/or the antisense strand complementary thereto). In some embodiments, methylation present at the KCNN1 promoter can be determined by measuring the level of methylation present at sequences comprising the sequences corresponding to SEQ ID NOs: 16, 17, and/or 18 (and/or the antisense strand complementary thereto). In some embodiments, methylation present at the KCNN1 promoter can be determined by measuring the level of methylation present at sequences consisting of or consisting essentially of the sequences corresponding to SEQ ID NOs: 16, 17, and/or 18 (and/or the antisense strand complementary thereto).

SEQ ID NO: 16 (designated the KCNN1-1 amplicon) is a total 163 bp within CGI44 defined by the UCSC genome database (available on the world wide web at http://www.genome.ucsc.edu) and 830 bp downstream from the 3' end of exon 1. CGI44 is located within intron 1 defined by the first exon shown by the human KCNN1 mRNA (genebank accession number of NM_002248, updated on Nov. 30, 2013). All data analyses are based on the hg19/GRCh37 human Genome Browser. SEQ ID NO: 17 (designated the KCNN1-2 amplicon) is a total 200 bp within CGT62 defined by the UCSC genome database and 3226 bp upstream of TSS (the 5' end of exon 1 of the human KCNN1 gene). CGI62 is 2893 bp upstream of the first exon shown by the human KCNN1 mRNA (genebank accession number of NM_002248, updated on Nov. 30, 2013). SEQ ID NO: 18 (designated the KCNN1-3 amplicon) is a total 259 bp within CG123 defined by the UCSC genome database and 1979 bp upstream of TSS (the 5' end of exon 1 of the human KCNN1 gene). CGI23 is 1962 bp upstream of the first exon shown by the human KCNN1 mRNA (genebank accession number of NM_002248, updated on Nov. 30, 2013).

As used herein, "MASH1," "ASCL1," or "achaete-scute family bHLH transcription factor 1" refers to a bHLH transcription factor required for neural differentiation and interacts with myocyte specific enhancer factor 2A. The sequences of the MASH1 gene and gene expression products are known for a number of species, e.g. human MASH1 (NCBI Gene ID No: 429)(mRNA: SEQ ID NO: 10, NCBI Ref Seq: NM_004316)(polypeptide: SEQ ID NO: 11, NCBI Ref Seq: NP_004307).

As used herein, "P21," "CDKN1A," or "cyclin-dependent kinase inhibitor 1A" refers a proteins that binds to and inhibits cyclin-CDK2, -CDK1, and -CDK4/6 complexes. P21 mediates cell cycle progression at G1 and S phases and is in turn regulated by p53. The sequences of the P21 gene and gene expression products are known for a number of species, e.g. human P21 (NCBI Gene ID No: 1026)(mRNA: SEQ ID NO: 12, NCBI Ref Seq: NM_000389)(polypeptide: SEQ ID NO: 13, NCBI Ref Seq: NP_000380).

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. HD. The term "treating" includes reducing or alleviating at least one adverse effect or symptom of a condition, disease or disorder associated with HD. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. An assay comprising:
    measuring, in a sample obtained from a subject, the level of at least one miRNA selected from the group consisting of:
        miR-10b-5p; miR196a-5p; miR196b-5p; miR615-3p; miR1247-5p; miR106a-5p; miR363-3p; miR-129-1-3p and miR-132-3p; and
    (a) determining that the subject is at increased likelihood of Huntington's Disease developing at an earlier age or progressing more rapidly if the level of an miRNA selected from the group consisting of:
        miR-10b-5p; miR196a-5p; miR196b-5p; miR615-3p; miR1247-5p; miR106a-5p; and miR363-3p
        is increased relative to a reference, and determining that the subject is at decreased likelihood of Huntington's Disease developing at an earlier age or progressing more rapidly if the level of the miRNA is not increased relative to a reference; or
    (b) determining that the subject is at increased likelihood of Huntington's Disease developing at an earlier age or progressing more rapidly if the level of an miRNA selected from the group consisting of:
        miR-129-1-3p and miR-132-3p;
        is decreased relative to a reference, and determining that the subject is at decreased likelihood of Huntington's Disease developing at an earlier age or progressing more rapidly if the level of the miRNA is not decreased relative to a reference;
    wherein increased likelihood of Huntington's Disease developing at an earlier age or progressing more rapidly comprises developing Huntington's Disease at a younger age; death due to Huntington's Disease at a younger age, and/or becoming more severely disabled at a younger age as compared to other individuals with Huntington's Disease who do not have such a level of the miRNA.
2. The assay of paragraph 1, wherein the sample is selected from the group consisting of:
a blood sample; blood plasma; cerebrospinal fluid; and a brain sample.
3. The assay of paragraph 1, wherein the subject is a Huntington's Disease carrier.
4. The assay of paragraph 1, wherein increased likelihood of Huntington's disease developing at an earlier age or progressing more rapidly comprises greater striatal degeneration.
5. A method comprising:
measuring, in a sample obtained from a subject, the level of at least one miRNA selected from the group consisting of:
miR-10b-5p; miR196a-5p; miR196b-5p; miR615-3p; miR1247-5p; miR106a-5p; miR363-3p; miR-129-1-3p and miR-132-3p; and
(a) determining that the subject is at increased likelihood of Huntington's Disease developing at an earlier age or progressing more rapidly if the level of an miRNA selected from the group consisting of:
miR-10b-5p; miR196a-5p; miR196b-5p; miR615-3p; miR1247-5p; miR106a-5p; and miR363-3p
is increased relative to a reference, and determining that the subject is at decreased likelihood of Huntington's Disease developing at an earlier age or progressing more rapidly if the level of the miRNA is not increased relative to a reference; or
(b) determining that the subject is at increased likelihood of Huntington's Disease developing at an earlier age or progressing more rapidly if the level of an miRNA selected from the group consisting of:
miR-129-1-3p and miR-132-3p;
is decreased relative to a reference, and determining that the subject is at decreased likelihood of Huntington's disease developing at an earlier age or progressing more rapidly if the level of the miRNA is not decreased relative to a reference; and
administering a treatment for Huntington's Disease if the subject is at increased likelihood of Huntington's disease developing at an earlier age or progressing more rapidly wherein increased likelihood of Huntington's disease developing at an earlier age or progressing more rapidly comprises developing Huntington's Disease at a younger age; death due to Huntington's Disease at a younger age, and/or becoming more severely disabled at a younger age, when compared to other individuals with Huntington's Disease who do not have such a level of the miRNA.
6. The method of paragraph 5, wherein the treatment is selected from the group consisting of:
regular physical exercise; regular mental exercise; improvements to the diet; or administering creatine monohydrate, coenzyme Q10, sodium phenylbutyrate.
7. The method of paragraph 5, wherein the treatment comprises administering an agent that modulates the abnormal level or expression of at least one of the said miRNAs.
8. The method of paragraph 5, wherein the sample is selected from the group consisting of:
a blood sample; blood plasma; cerebrospinal fluid; and a brain sample.
9. The method of paragraph 5, wherein the subject is a Huntington's Disease carrier.
10. The method of paragraph 5, wherein increased likelihood of Huntington's disease developing at an earlier age or progressing more rapidly comprises greater striatal degeneration.
11. An assay comprising:
measuring, in a sample obtained from a subject, the level of at least one miRNA selected from the group consisting of:
miR-10b-5p; miR-151b; miR-29b-2-5p; miR-329-3p; miR-6511a-5p; miR-5690; miR-516b-5p; miR208b-3p; miR106a-5p; miR-363-3p; miR-4526; miR-129-1-3p; miR-129-2-3p; miR-132-3p; miR-132-5p; miR127-3p; miR212-3p; miR-1224-5p; miR16-2-3p; miR-1294; miR-30a-3p; miR-132-5p; miR-212-3p; miR-212-5p; miR-145-5p; and miR-29a-5p; and
(a) determining that the subject is at increased risk of Parkinson's Disease developing or progressing if the level of an miRNA selected from the group consisting of:
miR-151b; miR-5690; miR-516b-5p; miR208b-3p; miR106a-5p; and miR-363-3p; miR-30a-3p; and miR-29a-5p;
is increased relative to a reference, and determining that the subject is at decreased risk of Parkinson's Disease developing or progressing if the level of the miRNA is not increased relative to a reference;
(b) determining that the subject is at increased risk of Parkinson's Disease developing or progressing if the level of an miRNA selected from the group consisting of:
miR-10b-5p; miR-29b-2-5p; miR-329-3p; miR-6511a-5p; miR-4526; miR-129-1-3p; miR-129-2-3p; and miR-132-3p; miR-132-5p; miR127-3p; miR212-3p; miR-1224-5p; miR16-2-3p; miR-1294; miR-132-5p; miR-212-3p; miR-212-5p; and miR-145-5p;
is decreased relative to a reference, and determining that the subject is at decreased risk of Parkinson's Disease developing or progressing if the level of the miRNA is not decreased relative to a reference;
wherein increased risk of Parkinson's Disease developing or progressing comprises developing Parkinson's Disease at a younger age; death due to Parkinson's Disease at a younger age; development of dementia; development of dementia at an earlier age; or onset of motor symptoms at an earlier age when compared to other individuals with Parkinson's Disease who do not have such a level of the miRNA.
12. The assay of paragraph 11, wherein the sample is selected from the group consisting of:
a blood sample; blood plasma; and a brain sample.
13. The assay of paragraph 11, wherein the subject is a Parkinson's Disease carrier.
14. The assay of paragraph 11, wherein the miRNA is selected from the group consisting of:
miR-10b-5p; miR-151b; miR-29b-2-5p; miR-329-3p; miR-6511a-5p; miR-5690; miR-516b-5p; and miR208b-3p; miR-30a-3p; and
wherein increased risk of Parkinson's Disease developing or progressing comprises developing Parkinson's Disease at a younger age; death due to Parkinson's Disease at a younger age; or onset of motor symptoms at an earlier age.

15. The assay of paragraph 11, wherein the miRNA is selected from the group consisting of:

miR106a-5p; miR-363-3p; miR-4526; miR-129-1-3p; miR-129-2-3p; and miR-132-3p; miR-132-5p; miR127-3p; miR212-3p; miR-1224-5p; miR16-2-3p; miR-1294; miR-132-5p; miR-212-3p; miR-212-5p; miR-145-5p; and miR-29a-5p;

wherein increased risk of Parkinson's Disease developing or progressing comprises development of dementia or development of dementia at an earlier age.

16. A method comprising:
    (a) measuring, in a sample obtained from a subject, the level of at least one miRNA selected from the group consisting of:
        miR-10b-5p; miR-151b; miR-29b-2-5p; miR-329-3p; miR-6511a-5p; miR-5690; miR-516b-5p; miR208b-3p; miR106a-5p; miR-363-3p; miR-4526; miR-129-1-3p; miR-129-2-3p; miR-132-3p; miR-132-5p; miR127-3p; miR212-3p; miR-1224-5p; miR16-2-3p; miR-1294; miR-30a-3p; miR-132-5p; miR-212-3p; miR-212-5p; miR-145-5p; and miR-29a-5p; and
    (b) determining that the subject is at increased risk of Parkinson's Disease developing or progressing if the level of an miRNA selected from the group consisting of:
        miR-151b; miR-5690; miR-516b-5p; miR208b-3p; miR106a-5p; and miR-363-3p; miR-30a-3p; and miR-29a-5p;
        is increased relative to a reference, and determining that the subject is at decreased risk of Parkinson's Disease developing or progressing if the level of the miRNA is not increased relative to a reference;
    (c) determining that the subject is at increased risk of Parkinson's Disease developing or progressing if the level of an miRNA selected from the group consisting of:
        miR-10b-5p; miR-29b-2-5p; miR-329-3p; miR-6511a-5p; miR-4526; miR-129-1-3p; miR-129-2-3p; and miR-132-3p; miR-132-5p; miR127-3p; miR212-3p; miR-1224-5p; miR16-2-3p; miR-1294; miR-132-5p; miR-212-3p; miR-212-5p; and miR-145-5p;
        is decreased relative to a reference, and determining that the subject is at decreased risk of Parkinson's Disease developing or progressing if the level of the miRNA is not decreased relative to a reference; and administering a treatment for Parkinson's Disease if the subject is at increased risk of Parkinson's Disease developing or progressing;
        wherein increased risk of Parkinson's Disease developing or progressing comprises developing Parkinson's Disease at a younger age; death due to Parkinson's Disease at a younger age; development of dementia; development of dementia at an earlier age; or onset of motor symptoms at an earlier age when compared to other individuals with Parkinson's Disease who do not have such a level of the miRNA.

17. The method of paragraph 16, wherein the treatment is selected from the group consisting of:
    Levodopa agonists; dopamine agonists; COMT inhibitors; deep brain stimulation; MAO-B inhibitors; lesional surgery; regular physical exercise; regular mental exercise; improvements to the diet; and Lee Silverman voice treatment.

18. The method of paragraph 16, wherein the treatment comprises administering an agent that modulates the abnormal level or expression of at least one of the said miRNAs.

19. The method of paragraph 16, wherein the sample is selected from the group consisting of:
    a blood sample; blood plasma; and a brain sample.

20. The method of paragraph 16, wherein the subject is a Parkinson's Disease carrier.

Some embodiments of the technology described herein can be defined according to any of the following numbered paragraphs:

1. An assay comprising:
    measuring, in a sample obtained from a subject, the level of a gene of Table 9, 10, or 11 and/or an miRNA selected from the group consisting of:
        miR-10b-5p; miR196a-5p; miR196b-5p; miR615-3p; and miR1247-5p;
    determining that the subject is at increased risk of developing Huntington's Disease if the level of the gene or miRNA is increased relative to a reference, and determining that the subject is at decreased risk of developing Huntington's Disease if the level of the gene or miRNA is not increased relative to a reference.

2. The assay of paragraph 1, wherein the subject is a Huntington's Disease carrier.

3. The assay of any of paragraphs 1-2, wherein increased risk of developing Huntington's Disease comprises developing Huntington's Disease at a younger age; death due to Huntington's Disease at a younger age, and/or increased CAG repeat size.

4. An assay comprising
    (a) measuring, in a sample obtained from a subject, the level of a gene of Table 9, 10, or 11 and/or an miRNA selected from the group consisting of:
        miR-10b-5p; miR196a-5p; miR196b-5p; miR615-3p; and miR1247-5p;
    (b) administering a potential treatment for Huntingon's Disease;
    (c) measuring, in a sample obtained from a subject, the level of the gene and/or miRNA;
    (d) determining that the potential treatment is efficacious in reducing the risk and/or severity of Huntington's Disease if the level of the gene and/or miRNA measured in step (c) is not decreased relative to the level measured in step (a) and determining that the potential treatment is not efficacious in reducing the risk and/or severity of Huntington's Disease if the level of the gene and/or miRNA measured in step (c) is decreased relative to the level measured in step (a).

5. The assay of any of paragraphs 1-4, wherein the sample is selected from the group consisting of:
    a blood sample and a brain sample.

6. A method of increasing axonal projections, the method comprising;
    administering an effective amount of an agonist of expression of a gene of Table 9, 10, or 11 and/or an miRNA selected from the group consisting of:
        miR-10b-5p; miR196a-5p; miR196b-5p; miR615-3p; and miR1247-5p.

7. A method of treating a neuronal disease, the method comprising;

administering a therapeutically effective amount of an agonist of expression of a gene of Table 9, 10, or 11 and/or an miRNA selected from the group consisting of:

miR-10b-5p; miR196a-5p; miR196b-5p; miR615-3p; and miR1247-5p;

8. The method of paragraph 7, wherein the neuronal disease is selected from the group consisting of: Huntington's Disease; spinal cord injury; and stroke.

Some embodiments of the technology described herein can be defined according to any of the following numbered paragraphs:

1. An assay comprising:
   measuring, in a sample obtained from a subject, the level of at least one miRNA selected from the group consisting of:
   miR-10b-5p; miR196a-5p; miR196b-5p; miR615-3p; and miR1247-5p; miR106a-5p; miR363-3p; miR-129-1-3p and miR-132-3p; and
   (a) determining that the subject is at increased likelihood of Huntington's Disease developing at an earlier age or progressing more rapidly if the level of an miRNA selected from the group consisting of:
   miR-10b-5p; miR196a-5p; miR196b-5p; miR615-3p; and miR1247-5p; miR106a-5p; and miR363-3p
   is increased relative to a reference, and determining that the subject is at decreased likelihood of Huntington's Disease developing at an earlier age or progressing more rapidly if the level of the miRNA is not increased relative to a reference; or
   (b) determining that the subject is at increased likelihood of Huntington's Disease developing at an earlier age or progressing more rapidly if the level of an miRNA selected from the group consisting of:
   miR-129-1-3p and miR-132-3p;
   is decreased relative to a reference, and determining that the subject is at decreased likelihood of Huntington's Disease developing at an earlier age or progressing more rapidly if the level of the miRNA is not decreased relative to a reference;
   wherein increased likelihood of Huntington's Disease developing at an earlier age or progressing more rapidly comprises developing Huntington's Disease at a younger age; death due to Huntington's Disease at a younger age, and/or becoming more severely disabled at a younger age as compared to other individuals with Huntington's Disease who do not have such a level of the miRNA.

2. A method comprising:
   measuring, in a sample obtained from a subject, the level of at least one miRNA selected from the group consisting of:
   miR-10b-5p; miR196a-5p; miR196b-5p; miR615-3p; and miR1247-5p; miR106a-5p; miR363-3p; miR-129-1-3p and miR-132-3p; and
   (a) determining that the subject is at increased likelihood of Huntington's Disease developing at an earlier age or progressing more rapidly if the level of an miRNA selected from the group consisting of:
   miR-10b-5p; miR196a-5p; miR196b-5p; miR615-3p; and miR1247-5p; miR106a-5p; and miR363-3p
   is increased relative to a reference, and determining that the subject is at decreased likelihood of Huntington's Disease developing at an earlier age or progressing more rapidly if the level of the miRNA is not increased relative to a reference; or
   (b) determining that the subject is at increased likelihood of Huntington's Disease developing at an earlier age or progressing more rapidly if the level of an miRNA selected from the group consisting of:
   miR-129-1-3p and miR-132-3p;
   is decreased relative to a reference, and determining that the subject is at decreased likelihood of Huntington's disease developing at an earlier age or progressing more rapidly if the level of the miRNA is not decreased relative to a reference; and
   administering a treatment for Huntington's Disease if the subject is at increased likelihood of Huntington's disease developing at an earlier age or progressing more rapidly wherein increased likelihood of Huntington's disease developing at an earlier age or progressing more rapidly comprises developing Huntington's Disease at a younger age; death due to Huntington's Disease at a younger age, and/or becoming more severely disabled at a younger age, when compared to other individuals with Huntington's Disease who do not have such a level of the miRNA.

3. The method of paragraph 2, wherein the treatment is selected from the group consisting of:
   regular physical exercise; regular mental exercise; improvements to the diet; or administering creatine monohydrate, coenzyme Q10, sodium phenylbutyrate.

4. The method of paragraph 2, wherein the treatment comprises administering an agent that modulates the abnormal level or expression of at least one of the said miRNAs.

5. An assay comprising
   (a) measuring, in a sample obtained from a subject, the level of at least one miRNA selected from the group consisting of:
   miR-10b-5p; miR196a-5p; miR196b-5p; miR615-3p; and miR1247-5p; miR106a-5p; miR363-3p; miR-129-1-3p and miR-132-3p; and
   (b) administering a potential treatment for Huntingon's Disease;
   (c) measuring, in a sample obtained from a subject, the level of an miRNA selected from the group consisting of:
   miR-10b-5p; miR196a-5p; miR196b-5p; miR615-3p; and miR1247-5p; miR106a-5p; miR363-3p; miR-129-1-3p and miR-132-3p; and
   (d) determining that the potential treatment is efficacious in delaying age at onset and/or reducing the severity of Huntington's Disease if the level of the miRNA selected from the group consisting of:
   miR-10b-5p; miR196a-5p; miR196b-5p; miR615-3p; and miR1247-5p; miR106a-5p; and miR363-3p
   measured in step (c) is not increased relative to the level measured in step (a) and determining that the potential treatment is not efficacious in delaying age at onset and/or reducing the severity of Huntington's Disease if the level of the miRNA measured in step (c) is increased relative to the level measured in step (a); or
   (e) determining that the potential treatment is efficacious in delaying age at onset and/or reducing the severity of Huntington's Disease if the level of the miRNA selected from the group consisting of:

miR-129-1-3p and miR-132-3p;
measured in step (c) is not decreased relative to the level measured in step (a) and determining that the potential treatment is not efficacious in delaying age at onset and/or reducing the severity of Huntington's Disease if the level of the miRNA measured in step (c) is decreased relative to the level measured in step (a).

6. A computer system comprising
    a measuring module configured to measure, in a sample obtained from a subject, the level of at least one miRNA selected from the group consisting of:
        miR-10b-5p; miR196a-5p; miR196b-5p; miR615-3p; and miR1247-5p; miR106a-5p; miR363-3p; miR-129-1-3p and miR-132-3p;
    a storage module configured to store data output from the measuring module;
    a comparison module adapted to compare the data stored on the storage module with a reference level, and to provide a retrieved content, and
    a display module for displaying whether the level of the miRNA in the sample obtained from the subject is greater, by a statistically significant amount, than the reference level and/or displaying the relative levels of miRNA;
    wherein a level of an miRNA selected from the group of:
        miR-10b-5p; miR196a-5p; miR196b-5p; miR615-3p; and miR1247-5p; miR106a-5p; and miR363-3p
    in the sample of the subject which is statistically significantly greater than the reference level indicates that the subject is at increased likelihood of Huntington's disease developing at an earlier age or progressing more rapidly; and
    wherein a level of an miRNA selected from the group of:
        miR-129-1-3p and miR-132-3p;
    in the sample of the subject which is statistically significantly less than the reference level indicates that the subject is at increased likelihood of Huntington's disease developing at an earlier age or progressing more rapidly progressing;
    wherein increased likelihood of Huntington's disease developing at an earlier age or progressing more rapidly comprises developing Huntington's Disease at a younger age; death due to Huntington's Disease at a younger age, and/or becoming more severely disabled at a younger age, when compared to other individuals with Huntington's Disease who do not have such a level of the miRNA.

7. The assay, method, or system of any of paragraphs 1-6, wherein the sample is selected from the group consisting of:
    a blood sample; blood plasma; cerebrospinal fluid; and a brain sample.

8. The assay, method, or system of any of paragraphs 1-7, wherein the subject is a Huntington's Disease carrier.

9. The assay, method, or system of any of paragraphs 1-8, wherein increased likelihood of Huntington's disease developing at an earlier age or progressing more rapidly comprises greater striatal degeneration.

10. A kit comprising:
    one or more probes for detecting the level of at least one miRNA selected from the group consisting of:
        miR-10b-5p; miR196a-5p; miR196b-5p; miR615-3p; and miR1247-5p; miR106a-5p; miR363-3p; miR-129-1-3p and miR-132-3p.

11. The kit of paragraph 10, comprising one or more probes for detecting the level of at least two miRNAs selected from the group consisting of:
    miR-10b-5p; miR196a-5p; miR196b-5p; miR615-3p; and miR1247-5p; miR106a-5p; miR363-3p; miR-129-1-3p and miR-132-3p.

12. The kit of paragraph 10, comprising one or more probes for detecting the level of at least three miRNAs selected from the group consisting of:
    miR-10b-5p; miR196a-5p; miR196b-5p; miR615-3p; and miR1247-5p; miR106a-5p; miR363-3p; miR-129-1-3p and miR-132-3p.

13. The kit of paragraph 10, comprising one or more probes for detecting the level of at least four miRNAs selected from the group consisting of:
    miR-10b-5p; miR196a-5p; miR196b-5p; miR615-3p; and miR1247-5p; miR106a-5p; miR363-3p; miR-129-1-3p and miR-132-3p.

14. An assay comprising:
    measuring, in a sample obtained from a subject, the level of at least one miRNA selected from the group consisting of:
        miR-10b-5p; miR-151b; miR-29b-2-5p; miR-329-3p; miR-6511a-5p; miR-5690; miR-516b-5p; miR208b-3p; miR106a-5p; miR-363-3p; miR-4526; miR-129-1-3p; miR-129-2-3p; miR-132-3p; miR-132-5p; miR127-3p; miR212-3p; miR-1224-5p; miR16-2-3p; miR-1294; and miR-30a-3p; and
    (a) determining that the subject is at increased risk of Parkinson's Disease developing or progressing if the level of an miRNA selected from the group consisting of:
        miR-151b; miR-5690; miR-516b-5p; miR208b-3p; miR106a-5p; and miR-363-3p; miR-30a-3p
    is increased relative to a reference, and determining that the subject is at decreased risk of Parkinson's Disease developing or progressing if the level of the miRNA is not increased relative to a reference;
    (b) determining that the subject is at increased risk of Parkinson's Disease developing or progressing if the level of an miRNA selected from the group consisting of:
        miR-10b-5p; miR-29b-2-5p; miR-329-3p; miR-6511a-5p; miR-4526; miR-129-1-3p; miR-129-2-3p; and miR-132-3p; miR-132-5p; miR127-3p; miR212-3p; miR-1224-5p; miR16-2-3p; miR-1294
    is decreased relative to a reference, and determining that the subject is at decreased risk of Parkinson's Disease developing or progressing if the level of the miRNA is not decreased relative to a reference;
    wherein increased risk of Parkinson's Disease developing or progressing comprises developing Parkinson's Disease at a younger age; death due to Parkinson's Disease at a younger age; development of dementia; development of dementia at an earlier age; or onset of motor symptoms at an earlier age when compared to other individuals with Parkinson's Disease who do not have such a level of the miRNA.

15. A method comprising:
    (a) measuring, in a sample obtained from a subject, the level of at least one miRNA selected from the group consisting of:

miR-10b-5p; miR-151b; miR-29b-2-5p; miR-329-3p; miR-6511a-5p; miR-5690; miR-516b-5p; miR208b-3p; miR106a-5p; miR-363-3p; miR-4526; miR-129-1-3p; miR-129-2-3p; miR-132-3p; miR-132-5p; miR127-3p; miR212-3p; miR-1224-5p; miR16-2-3p; miR-1294; and miR-30a-3p; and (b) determining that the subject is at increased risk of Parkinson's Disease developing or progressing if the level of an miRNA selected from the group consisting of:

miR-151b; miR-5690; miR-516b-5p; miR208b-3p; miR106a-5p; and miR-363-3p; miR-30a-3p is increased relative to a reference, and determining that the subject is at decreased risk of Parkinson's Disease developing or progressing if the level of the miRNA is not increased relative to a reference;

(c) determining that the subject is at increased risk of Parkinson's Disease developing or progressing if the level of an miRNA selected from the group consisting of:

miR-10b-5p; miR-29b-2-5p; miR-329-3p; miR-6511a-5p; miR-4526; miR-129-1-3p; miR-129-2-3p; and miR-132-3p; miR-132-5p; miR127-3p; miR212-3p; miR-1224-5p; miR16-2-3p; miR-1294 is decreased relative to a reference, and determining that the subject is at decreased risk of Parkinson's Disease developing or progressing if the level of the miRNA is not decreased relative to a reference; and administering a treatment for Parkinson's Disease if the subject is at increased risk of Parkinson's Disease developing or progressing;

wherein increased risk of Parkinson's Disease developing or progressing comprises developing Parkinson's Disease at a younger age; death due to Parkinson's Disease at a younger age; development of dementia; development of dementia at an earlier age; or onset of motor symptoms at an earlier age when compared to other individuals with Parkinson's Disease who do not have such a level of the miRNA.

16. The method of paragraph 15, wherein the treatment is selected from the group consisting of:

Levodopa agonists; dopamine agonists; COMT inhibitors; deep brain stimulation; MAO-B inhibitors; lesional surgery; regular physical exercise; regular mental exercise; improvements to the diet; and Lee Silverman voice treatment.

17. The method of paragraph 15, wherein the treatment comprises administering an agent that modulates the abnormal level or expression of at least one of the said miRNAs.

18. An assay comprising
   (a) measuring, in a sample obtained from a subject, the level of at least one miRNA selected from the group consisting of:
   miR-10b-5p; miR-151b; miR-29b-2-5p; miR-329-3p; miR-6511a-5p; miR-5690; miR-516b-5p; miR208b-3p; miR106a-5p; miR-363-3p; miR-4526; miR-129-1-3p; miR-129-2-3p; miR-132-3p; miR-132-5p; miR127-3p; miR212-3p; miR-1224-5p; miR16-2-3p; miR-1294; and miR-30a-3p; and
   (b) administering a potential treatment for Parkinson's Disease;
   (c) measuring, in a sample obtained from a subject, the level of an miRNA selected from the group consisting of:
   miR-10b-5p; miR-151b; miR-29b-2-5p; miR-329-3p; miR-6511a-5p; miR-5690; miR-516b-5p; miR208b-3p; miR106a-5p; miR-363-3p; miR-4526; miR-129-1-3p; miR-129-2-3p; miR-132-3p; miR-132-5p; miR127-3p; miR212-3p; miR-1224-5p; miR16-2-3p; miR-1294; and miR-30a-3p; and
   (d) determining that the potential treatment is efficacious in reducing the risk of Parkinson's Disease developing or progressing if the level of the miRNA selected from the group consisting of:
   miR-151b; miR-5690; miR-516b-5p; miR208b-3p; miR106a-5p; and miR-363-3p; miR-30a-3p
   measured in step (c) is not increased relative to the level measured in step (a) and determining that the potential treatment is not in reducing the risk of Parkinson's Disease developing or progressing if the level of the miRNA measured in step (c) is increased relative to the level measured in step (a); or
   (e) determining that the potential treatment is efficacious in reducing the risk of Parkinson's Disease developing or progressing if the level of the miRNA selected from the group consisting of:
   miR-10b-5p; miR-29b-2-5p; miR-329-3p; miR-6511a-5p; miR-4526; miR-129-1-3p; miR-129-2-3p; and miR-132-3p; miR-132-5p; miR127-3p; miR212-3p; miR-1224-5p; miR16-2-3p; and miR-1294
   measured in step (c) is not decreased relative to the level measured in step (a) and determining that the potential treatment is not efficacious in reducing the risk of Parkinson's Disease developing or progressing if the level of the miRNA measured in step (c) is decreased relative to the level measured in step (a).

19. A computer system comprising
   a measuring module configured to measure, in a sample obtained from a subject, the level of at least one miRNA selected from the group consisting of:
   miR-10b-5p; miR-151b; miR-29b-2-5p; miR-329-3p; miR-6511a-5p; miR-5690; miR-516b-5p; miR208b-3p; miR106a-5p; miR-363-3p; miR-4526; miR-129-1-3p; miR-129-2-3p; miR-132-3p; miR-132-5p; miR127-3p; miR212-3p; miR-1224-5p; miR16-2-3p; miR-1294; and miR-30a-3p; and
   a storage module configured to store data output from the measuring module;
   a comparison module adapted to compare the data stored on the storage module with a reference level, and to provide a retrieved content, and
   a display module for displaying whether the level of the miRNA in the sample obtained from the subject is greater, by a statistically significant amount, than the reference level and/or displaying the relative levels of miRNA;
   wherein a level of an miRNA selected from the group of:
   miR-151b; miR-5690; miR-516b-5p; miR208b-3p; miR106a-5p; and miR-363-3p; miR-30a-3p
   in the sample of the subject which is statistically significantly greater than the reference level indicates that the subject is at increased likelihood of Parkinson's Disease developing or progressing; and wherein a level of an miRNA selected from the group of:
  miR-10b-5p; miR-29b-2-5p; miR-329-3p; miR-6511a-5p; miR-4526; miR-129-1-3p; miR-129-2-3p; and miR-132-3p; miR-132-5p; miR127-3p; miR212-3p; miR-1224-5p; miR16-2-3p; and miR-1294
in the sample of the subject which is statistically significantly less than the reference level indicates that the subject is at increased likelihood of Parkinson's Disease developing or progressing;
wherein increased risk of Parkinson's Disease developing or progressing comprises developing Parkinson's Disease at a younger age; death due to Parkinson's Disease at a younger age; development of dementia; development of dementia at an earlier age; or onset of motor symptoms at an earlier age when compared to other individuals with Parkinson's Disease who do not have such a level of the miRNA.

20. The assay, method, or system of any of paragraphs 14-19, wherein the sample is selected from the group consisting of:
a blood sample; blood plasma; and a brain sample.

21. The assay, method, or system of any of paragraphs 14-20, wherein the subject is a Parkinson's Disease carrier.

22. The assay, method, or system of any of paragraphs 14-21, wherein the miRNA is selected from the group consisting of:
  miR-10b-5p; miR-151b; miR-29b-2-5p; miR-329-3p; miR-6511a-5p; miR-5690; miR-516b-5p; and miR208b-3p; miR-30a-3p; and
wherein increased risk of Parkinson's Disease developing or progressing comprises developing Parkinson's Disease at a younger age; death due to Parkinson's Disease at a younger age; or onset of motor symptoms at an earlier age.

23. The assay, method, or system of any of paragraphs 14-22, wherein the miRNA is selected from the group consisting of:
  miR106a-5p; miR-363-3p; miR-4526; miR-129-1-3p; miR-129-2-3p; and miR-132-3p; miR-132-5p; miR127-3p; miR212-3p; miR-1224-5p; miR16-2-3p; miR-1294; and
wherein increased risk of Parkinson's Disease developing or progressing comprises development of dementia or development of dementia at an earlier age.

24. A kit comprising:
one or more probes for detecting the level of at least one miRNA selected from the group consisting of:
  miR-10b-5p; miR-151b; miR-29b-2-5p; miR-329-3p; miR-6511a-5p; miR-5690; miR-516b-5p; miR208b-3p; miR106a-5p; miR-363-3p; miR-4526; miR-129-1-3p; miR-129-2-3p; miR-132-3p; miR-132-5p; miR127-3p; miR212-3p; miR-1224-5p; miR16-2-3p; miR-1294; and miR-30a-3p.

25. The kit of paragraph 24, comprising one or more probes for detecting the level of at least two miRNAs selected from the group consisting of:
  miR-10b-5p; miR-151b; miR-29b-2-5p; miR-329-3p; miR-6511a-5p; miR-5690; miR-516b-5p; miR208b-3p; miR106a-5p; miR-363-3p; miR-4526; miR-129-1-3p; miR-129-2-3p; miR-132-3p; miR-132-5p; miR127-3p; miR212-3p; miR-1224-5p; miR16-2-3p; miR-1294; and miR-30a-3p.

26. The kit of paragraph 24, comprising one or more probes for detecting the level of at least three miRNAs selected from the group consisting of:
  miR-10b-5p; miR-151b; miR-29b-2-5p; miR-329-3p; miR-6511a-5p; miR-5690; miR-516b-5p; miR208b-3p; miR106a-5p; miR-363-3p; miR-4526; miR-129-1-3p; miR-129-2-3p; miR-132-3p; miR-132-5p; miR127-3p; miR212-3p; miR-1224-5p; miR16-2-3p; miR-1294; and miR-30a-3p.

27. The kit of paragraph 24, comprising one or more probes for detecting the level of at least four miRNAs selected from the group consisting of:
  miR-10b-5p; miR-151b; miR-29b-2-5p; miR-329-3p; miR-6511a-5p; miR-5690; miR-516b-5p; miR208b-3p; miR106a-5p; miR-363-3p; miR-4526; miR-129-1-3p; miR-129-2-3p; miR-132-3p; miR-132-5p; miR127-3p; miR212-3p; miR-1224-5p; miR16-2-3p; miR-1294; and miR-30a-3p.

28. A method of increasing axonal projections, the method comprising;
administering an effective amount of an agonist or antagonist, as appropriate, of an miRNA selected from the group consisting of:
  miR-10b-5p; miR196a-5p; miR196b-5p; miR615-3p; and miR1247-5p; miR106a-5p; miR363-3p; miR-129-1-3p and miR-132-3p.

29. A method of treating a neuronal disease, the method comprising;
administering a therapeutically effective amount of an agonist or antagonist, as appropriate, of an miRNA selected from the group consisting of:
  miR-10b-5p; miR196a-5p; miR196b-5p; miR615-3p; and miR1247-5p; miR106a-5p; miR363-3p; miR-129-1-3p and miR-132-3p.

30. The method of paragraph 29, wherein the neuronal disease is selected from the group consisting of:
Huntington's Disease; spinal cord injury; and stroke.

Some embodiments of the technology described herein can be defined according to any of the following numbered paragraphs:

1. An assay comprising:
measuring, in a sample obtained from a subject, the level of at least three miRNAs selected from the group consisting of:
  miR-10b-5p; miR196a-5p; miR196b-5p; miR615-3p; miR1247-5p; miR106a-5p; miR363-3p; miR-129-1-3p and miR-132-3p; and
determining if the level of the miRNA varies by a statistically significant amount from a reference level.

2. The assay of paragraph 1, wherein subject is a subject having or at risk of having Huntington's Disease.

3. The assay of any of paragraphs 1-2, wherein if the level of the miRNA varies by a statistically significant amount from the reference level, the subject is at increased likelihood of Huntington's Disease developing at an earlier age or progressing more rapidly.

4. The assay of any of paragraphs 1-3, wherein the subject is at increased likelihood of Huntington's Disease developing at an earlier age or progressing more rapidly if the level of an miRNA selected from the group consisting of:
  miR-10b-5p; miR196a-5p; miR196b-5p; miR615-3p; miR1247-5p; miR106a-5p; and miR363-3p
is increased relative to a reference, and subject is at decreased likelihood of Huntington's Disease developing at an earlier age or progressing more rapidly if the level of the miRNA is not increased relative to a reference; and the subject is at increased likelihood of Huntington's Disease developing at an earlier age or progressing more rapidly if the level of an miRNA selected from the group consisting of:

miR-129-1-3p and miR-132-3p;

is decreased relative to a reference, and the subject is at decreased likelihood of Huntington's Disease developing at an earlier age or progressing more rapidly if the level of the miRNA is not decreased relative to a reference;

wherein increased likelihood of Huntington's Disease developing at an earlier age or progressing more rapidly comprises developing Huntington's Disease at a younger age; death due to Huntington's Disease at a younger age, and/or becoming more severely disabled at a younger age as compared to other individuals with Huntington's Disease who do not have such a level of the miRNA.

5. The assay of any of paragraphs 1-4, wherein the sample is selected from the group consisting of:

a blood sample; blood plasma; cerebrospinal fluid; and a brain sample.

6. The assay of any of paragraphs 1-5, wherein the subject is a Huntington's Disease carrier.

7. The assay of any of paragraphs 1-6, wherein increased likelihood of Huntington's disease developing at an earlier age or progressing more rapidly comprises greater striatal degeneration.

8. The assay of any of paragraphs 1-7, wherein the level of at least four miRNAs is measured.

9. The assay of any of paragraphs 1-7, wherein the level of at least five miRNAs is measured.

10. The assay of any of paragraphs 1-7, wherein the level of at least six miRNAs is measured.

11. The assay of any of paragraphs 1-7, wherein the level of at least seven miRNAs is measured.

12. An assay comprising:

measuring, in a sample obtained from a subject, the level of at least three miRNAs selected from the group consisting of:

miR-10b-5p; miR-151b; miR-29b-2-5p; miR-329-3p; miR-6511a-5p; miR-5690; miR-516b-5p; miR208b-3p; miR106a-5p; miR-363-3p; miR-4526; miR-129-1-3p; miR-129-2-3p; miR-132-3p; miR-132-5p; miR127-3p; miR212-3p; miR-1224-5p; miR16-2-3p; miR-1294; miR-30a-3p; miR-132-5p; miR-212-3p; miR-212-5p; miR-145-5p; and miR-29a-5p; and determining if the level of the miRNA varies by a statistically significant amount from a reference level.

13. The assay of paragraph 12, wherein subject is a subject having or at risk of having Parkinson's Disease.

14. The assay of any of paragraphs 12-13, wherein if the level of the miRNA varies by a statistically significant amount from the reference level, the subject is at increased likelihood of Parkinson's Disease developing at an earlier age or progressing more rapidly.

15. The assay of any of paragraphs 12-14, wherein the subject is at increased risk of Parkinson's Disease developing or progressing if the level of an miRNA selected from the group consisting of:

miR-151b; miR-5690; miR-516b-5p; miR208b-3p; miR106a-5p; and miR-363-3p; miR-30a-3p; and miR-29a-5p;

is increased relative to a reference, and the subject is at decreased risk of Parkinson's Disease developing or progressing if the level of the miRNA is not increased relative to a reference; and determining that the subject is at increased risk of Parkinson's Disease developing or progressing if the level of an miRNA selected from the group consisting of:

miR-10b-5p; miR-29b-2-5p; miR-329-3p; miR-6511a-5p; miR-4526; miR-129-1-3p; miR-129-2-3p; and miR-132-3p; miR-132-5p; miR127-3p; miR212-3p; miR-1224-5p; miR16-2-3p; miR-1294; miR-132-5p; miR-212-3p; miR-212-5p; and miR-145-5p;

is decreased relative to a reference, and the subject is at decreased risk of Parkinson's Disease developing or progressing if the level of the miRNA is not decreased relative to a reference;

wherein increased risk of Parkinson's Disease developing or progressing comprises developing Parkinson's Disease at a younger age; death due to Parkinson's Disease at a younger age;

development of dementia; development of dementia at an earlier age; or onset of motor symptoms at an earlier age when compared to other individuals with Parkinson's Disease who do not have such a level of the miRNA.

16. The assay of any of paragraphs 12-15, wherein the sample is selected from the group consisting of:

a blood sample; blood plasma; and a brain sample.

17. The assay of any of paragraphs 12-16, wherein the subject is a Parkinson's Disease carrier.

18. The assay of any of paragraphs 12-16, wherein the miRNA is selected from the group consisting of:

miR-10b-5p; miR-151b; miR-29b-2-5p; miR-329-3p; miR-6511a-5p; miR-5690; miR-516b-5p; and miR208b-3p; miR-30a-3p; and wherein increased risk of Parkinson's Disease developing or progressing comprises developing Parkinson's Disease at a younger age; death due to Parkinson's Disease at a younger age; or onset of motor symptoms at an earlier age.

19. The assay of any of paragraphs 12-18, wherein the miRNA is selected from the group consisting of:

miR106a-5p; miR-363-3p; miR-4526; miR-129-1-3p; miR-129-2-3p; and miR-132-3p; miR-132-5p; miR127-3p; miR212-3p; miR-1224-5p; miR16-2-3p; miR-1294; miR-132-5p; miR-212-3p; miR-212-5p; miR-145-5p; and miR-29a-5p;

wherein increased risk of Parkinson's Disease developing or progressing comprises development of dementia or development of dementia at an earlier age.

20. The assay of any of paragraphs 12-19, wherein the level of at least four miRNAs is measured.

21. The assay of any of paragraphs 12-19, wherein the level of at least five miRNAs is measured.

22. The assay of any of paragraphs 12-19, wherein the level of at least six miRNAs is measured.

23. The assay of any of paragraphs 12-19, wherein the level of at least seven miRNAs is measured.

Some embodiments of the technology described herein can be defined according to any of the following numbered paragraphs:

1. An assay comprising:
    measuring, in a sample obtained from a subject, the level of at least one miRNA selected from the group consisting of:
       miR-10b-5p; miR196a-5p; miR196b-5p; miR615-3p; miR1247-5p; miR106a-5p; miR363-3p; miR-129-1-3p and miR-132-3p; and
    (a) determining that the subject is at increased likelihood of Huntington's Disease developing at an earlier age or progressing more rapidly if the level of an miRNA selected from the group consisting of:
       miR-10b-5p; miR196a-5p; miR196b-5p; miR615-3p; miR1247-5p; miR106a-5p; and miR363-3p
    is increased relative to a reference, and determining that the subject is at decreased likelihood of Huntington's Disease developing at an earlier age or progressing more rapidly if the level of the miRNA is not increased relative to a reference; or
    (b) determining that the subject is at increased likelihood of Huntington's Disease developing at an earlier age or progressing more rapidly if the level of an miRNA selected from the group consisting of:
       miR-129-1-3p and miR-132-3p;
    is decreased relative to a reference, and determining that the subject is at decreased likelihood of Huntington's Disease developing at an earlier age or progressing more rapidly if the level of the miRNA is not decreased relative to a reference;
    wherein increased likelihood of Huntington's Disease developing at an earlier age or progressing more rapidly comprises developing Huntington's Disease at a younger age; death due to Huntington's Disease at a younger age, and/or becoming more severely disabled at a younger age as compared to other individuals with Huntington's Disease who do not have such a level of the miRNA.

2. A method comprising:
    measuring, in a sample obtained from a subject, the level of at least one miRNA selected from the group consisting of:
       miR-10b-5p; miR196a-5p; miR196b-5p; miR615-3p; miR1247-5p; miR106a-5p; miR363-3p; miR-129-1-3p and miR-132-3p; and
    (c) determining that the subject is at increased likelihood of Huntington's Disease developing at an earlier age or progressing more rapidly if the level of an miRNA selected from the group consisting of:
       miR-10b-5p; miR196a-5p; miR196b-5p; miR615-3p; miR1247-5p; miR106a-5p; and miR363-3p
    is increased relative to a reference, and determining that the subject is at decreased likelihood of Huntington's Disease developing at an earlier age or progressing more rapidly if the level of the miRNA is not increased relative to a reference; or
    (d) determining that the subject is at increased likelihood of Huntington's Disease developing at an earlier age or progressing more rapidly if the level of an miRNA selected from the group consisting of:
       miR-129-1-3p and miR-132-3p;
    is decreased relative to a reference, and determining that the subject is at decreased likelihood of Huntington's disease developing at an earlier age or progressing more rapidly if the level of the miRNA is not decreased relative to a reference; and
    administering a treatment for Huntington's Disease if the subject is at increased likelihood of Huntington's disease developing at an earlier age or progressing more rapidly wherein increased likelihood of Huntington's disease developing at an earlier age or progressing more rapidly comprises developing Huntington's Disease at a younger age; death due to Huntington's Disease at a younger age, and/or becoming more severely disabled at a younger age, when compared to other individuals with Huntington's Disease who do not have such a level of the miRNA.

3. The method of paragraph 2, wherein the treatment is selected from the group consisting of:
    regular physical exercise; regular mental exercise; improvements to the diet; or administering creatine monohydrate, coenzyme Q10, sodium phenylbutyrate.

4. The method of paragraph 2, wherein the treatment comprises administering an agent that modulates the abnormal level or expression of at least one of the said miRNAs.

5. An assay comprising
    (a) measuring, in a sample obtained from a subject, the level of at least one miRNA selected from the group consisting of:
       miR-10b-5p; miR196a-5p; miR196b-5p; miR615-3p; miR1247-5p; miR106a-5p; miR363-3p; miR-129-1-3p and miR-132-3p; and
    (b) administering a potential treatment for Huntingon's Disease;
    (c) measuring, in a sample obtained from a subject, the level of an miRNA selected from the group consisting of:
       miR-10b-5p; miR196a-5p; miR196b-5p; miR615-3p; miR1247-5p; miR106a-5p; miR363-3p; miR-129-1-3p and miR-132-3p; and
    (d) determining that the potential treatment is efficacious in delaying age at onset and/or reducing the severity of Huntington's Disease if the level of the miRNA selected from the group consisting of:
       miR-10b-5p; miR196a-5p; miR196b-5p; miR615-3p; miR1247-5p; miR106a-5p; and miR363-3p
    measured in step (c) is not increased relative to the level measured in step (a) and determining that the potential treatment is not efficacious in delaying age at onset and/or reducing the severity of Huntington's Disease if the level of the miRNA measured in step (c) is increased relative to the level measured in step (a); or
    (e) determining that the potential treatment is efficacious in delaying age at onset and/or reducing the severity of Huntington's Disease if the level of the miRNA selected from the group consisting of:
       miR-129-1-3p and miR-132-3p;
    measured in step (c) is not decreased relative to the level measured in step (a) and determining that the potential treatment is not efficacious in delaying age at onset and/or reducing the severity of Huntington's Disease if the level of the miRNA measured in step (c) is decreased relative to the level measured in step (a).

6. A computer system comprising
    a measuring module configured to measure, in a sample obtained from a subject, the level of at least one miRNA selected from the group consisting of:
       miR-10b-5p; miR196a-5p; miR196b-5p; miR615-3p; miR1247-5p; miR106a-5p; miR363-3p; miR-129-1-3p and miR-132-3p;

a storage module configured to store data output from the measuring module;
a comparison module adapted to compare the data stored on the storage module with a reference level, and to provide a retrieved content, and a display module for displaying whether the level of the miRNA in the sample obtained from the subject is greater, by a statistically significant amount, than the reference level and/or displaying the relative levels of miRNA;
wherein a level of an miRNA selected from the group of:
miR-10b-5p; miR196a-5p; miR196b-5p; miR615-3p; miR1247-5p; miR106a-5p; and miR363-3p
in the sample of the subject which is statistically significantly greater than the reference level indicates that the subject is at increased likelihood of Huntington's disease developing at an earlier age or progressing more rapidly; and
wherein a level of an miRNA selected from the group of:
miR-129-1-3p and miR-132-3p;
in the sample of the subject which is statistically significantly less than the reference level indicates that the subject is at increased likelihood of Huntington's disease developing at an earlier age or progressing more rapidly progressing;
wherein increased likelihood of Huntington's disease developing at an earlier age or progressing more rapidly comprises developing Huntington's Disease at a younger age; death due to Huntington's Disease at a younger age, and/or becoming more severely disabled at a younger age, when compared to other individuals with Huntington's Disease who do not have such a level of the miRNA.

7. The assay, method, or system of any of paragraphs 1-6, wherein the sample is selected from the group consisting of:
a blood sample; blood plasma; cerebrospinal fluid; and a brain sample.

8. The assay, method, or system of any of paragraphs 1-7, wherein the subject is a Huntington's Disease carrier.

9. The assay, method, or system of any of paragraphs 1-8, wherein increased likelihood of Huntington's disease developing at an earlier age or progressing more rapidly comprises greater striatal degeneration.

10. A kit comprising:
one or more probes for detecting the level of at least one miRNA selected from the group consisting of:
miR-10b-5p; miR196a-5p; miR196b-5p; miR615-3p; miR1247-5p; miR106a-5p; miR363-3p; miR-129-1-3p and miR-132-3p.

11. The kit of paragraph 10, comprising one or more probes for detecting the level of at least two miRNAs selected from the group consisting of:
miR-10b-5p; miR196a-5p; miR196b-5p; miR615-3p; miR1247-5p; miR106a-5p; miR363-3p; miR-129-1-3p and miR-132-3p.

12. The kit of paragraph 10, comprising one or more probes for detecting the level of at least three miRNAs selected from the group consisting of:
miR-10b-5p; miR196a-5p; miR196b-5p; miR615-3p; miR1247-5p; miR106a-5p; miR363-3p; miR-129-1-3p and miR-132-3p.

13. The kit of paragraph 10, comprising one or more probes for detecting the level of at least four miRNAs selected from the group consisting of:
miR-10b-5p; miR196a-5p; miR196b-5p; miR615-3p; miR1247-5p; miR106a-5p; miR363-3p; miR-129-1-3p and miR-132-3p.

14. An assay comprising:
measuring, in a sample obtained from a subject, the level of at least one miRNA selected from the group consisting of:
miR-10b-5p; miR-151b; miR-29b-2-5p; miR-329-3p; miR-6511a-5p; miR-5690; miR-516b-5p; miR208b-3p; miR106a-5p; miR-363-3p; miR-4526; miR-129-1-3p; miR-129-2-3p; miR-132-3p; miR-132-5p; miR127-3p; miR212-3p; miR-1224-5p; miR16-2-3p; miR-1294; miR-30a-3p; miR-132-5p; miR-212-3p; miR-212-5p; miR-145-5p; and miR-29a-5p; and
(a) determining that the subject is at increased risk of Parkinson's Disease developing or progressing if the level of an miRNA selected from the group consisting of:
miR-151b; miR-5690; miR-516b-5p; miR208b-3p; miR106a-5p; and miR-363-3p; miR-30a-3p; and miR-29a-5p;
is increased relative to a reference, and determining that the subject is at decreased risk of Parkinson's Disease developing or progressing if the level of the miRNA is not increased relative to a reference;
(b) determining that the subject is at increased risk of Parkinson's Disease developing or progressing if the level of an miRNA selected from the group consisting of:
miR-10b-5p; miR-29b-2-5p; miR-329-3p; miR-6511a-5p; miR-4526; miR-129-1-3p; miR-129-2-3p; and miR-132-3p; miR-132-5p; miR127-3p; miR212-3p; miR-1224-5p; miR16-2-3p; miR-1294; miR-132-5p; miR-212-3p; miR-212-5p; and miR-145-5p;
is decreased relative to a reference, and determining that the subject is at decreased risk of Parkinson's Disease developing or progressing if the level of the miRNA is not decreased relative to a reference;
wherein increased risk of Parkinson's Disease developing or progressing comprises developing Parkinson's Disease at a younger age; death due to Parkinson's Disease at a younger age; development of dementia; development of dementia at an earlier age; or onset of motor symptoms at an earlier age when compared to other individuals with Parkinson's Disease who do not have such a level of the miRNA.

15. A method comprising:
(a) measuring, in a sample obtained from a subject, the level of at least one miRNA selected from the group consisting of:
miR-10b-5p; miR-151b; miR-29b-2-5p; miR-329-3p; miR-6511a-5p; miR-5690; miR-516b-5p; miR208b-3p; miR106a-5p; miR-363-3p; miR-4526; miR-129-1-3p; miR-129-2-3p; miR-132-3p; miR-132-5p; miR127-3p; miR212-3p; miR-1224-5p; miR16-2-3p; miR-1294; miR-30a-3p; miR-132-5p; miR-212-3p; miR-212-5p; miR-145-5p; and miR-29a-5p; and
(b) determining that the subject is at increased risk of Parkinson's Disease developing or progressing if the level of an miRNA selected from the group consisting of:
miR-151b; miR-5690; miR-516b-5p; miR208b-3p; miR106a-5p; and miR-363-3p; miR-30a-3p; and miR-29a-5p;

is increased relative to a reference, and determining that the subject is at decreased risk of Parkinson's Disease developing or progressing if the level of the miRNA is not increased relative to a reference;

(c) determining that the subject is at increased risk of Parkinson's Disease developing or progressing if the level of an miRNA selected from the group consisting of:

miR-10b-5p; miR-29b-2-5p; miR-329-3p; miR-6511a-5p; miR-4526; miR-129-1-3p; miR-129-2-3p; and miR-132-3p; miR-132-5p; miR127-3p; miR212-3p; miR-1224-5p; miR16-2-3p; miR-1294; miR-132-5p; miR-212-3p; miR-212-5p; and miR-145-5p;

is decreased relative to a reference, and determining that the subject is at decreased risk of Parkinson's Disease developing or progressing if the level of the miRNA is not decreased relative to a reference; and administering a treatment for Parkinson's Disease if the subject is at increased risk of Parkinson's Disease developing or progressing;

wherein increased risk of Parkinson's Disease developing or progressing comprises developing Parkinson's Disease at a younger age; death due to Parkinson's Disease at a younger age; development of dementia; development of dementia at an earlier age; or onset of motor symptoms at an earlier age when compared to other individuals with Parkinson's Disease who do not have such a level of the miRNA.

16. The method of paragraph 15, wherein the treatment is selected from the group consisting of:

Levodopa agonists; dopamine agonists; COMT inhibitors; deep brain stimulation; MAO-B inhibitors; lesional surgery; regular physical exercise; regular mental exercise; improvements to the diet; and Lee Silverman voice treatment.

17. The method of paragraph 15, wherein the treatment comprises administering an agent that modulates the abnormal level or expression of at least one of the said miRNAs.

18. An assay comprising (a) measuring, in a sample obtained from a subject, the level of at least one miRNA selected from the group consisting of:

miR-10b-5p; miR-151b; miR-29b-2-5p; miR-329-3p; miR-6511a-5p; miR-5690; miR-516b-5p; miR208b-3p; miR106a-5p; miR-363-3p; miR-4526; miR-129-1-3p; miR-129-2-3p; miR-132-3p; miR-132-5p; miR127-3p; miR212-3p; miR-1224-5p; miR16-2-3p; miR-1294; miR-30a-3p; miR-132-5p; miR-212-3p; miR-212-5p; miR-145-5p; and miR-29a-5p; and (b) administering a potential treatment for Parkinson's Disease;

(c) measuring, in a sample obtained from a subject, the level of an miRNA selected from the group consisting of:

miR-10b-5p; miR-151b; miR-29b-2-5p; miR-329-3p; miR-6511a-5p; miR-5690; miR-516b-5p; miR208b-3p; miR106a-5p; miR-363-3p; miR-4526; miR-129-1-3p; miR-129-2-3p; miR-132-3p; miR-132-5p; miR127-3p; miR212-3p; miR-1224-5p; miR16-2-3p; miR-1294; miR-30a-3p; miR-132-5p; miR-212-3p; miR-212-5p; miR-145-5p; and miR-29a-5p; and (d) determining that the potential treatment is efficacious in reducing the risk of Parkinson's Disease developing or progressing if the level of the miRNA selected from the group consisting of:

miR-151b; miR-5690; miR-516b-5p; miR208b-3p; miR106a-5p; and miR-363-3p; miR-30a-3p; and miR-29a-5p;

measured in step (c) is not increased relative to the level measured in step (a) and determining that the potential treatment is not in reducing the risk of Parkinson's Disease developing or progressing if the level of the miRNA measured in step (c) is increased relative to the level measured in step (a); or (e) determining that the potential treatment is efficacious in reducing the risk of Parkinson's Disease developing or progressing if the level of the miRNA selected from the group consisting of:

miR-10b-5p; miR-29b-2-5p; miR-329-3p; miR-6511a-5p; miR-4526; miR-129-1-3p; miR-129-2-3p; and miR-132-3p; miR-132-5p; miR127-3p; miR212-3p; miR-1224-5p; miR16-2-3p; miR-1294; miR-132-5p; miR-212-3p; miR-212-5p; and miR-145-5p;

measured in step (c) is not decreased relative to the level measured in step (a) and determining that the potential treatment is not efficacious in reducing the risk of Parkinson's Disease developing or progressing if the level of the miRNA measured in step (c) is decreased relative to the level measured in step (a).

19. A computer system comprising a measuring module configured to measure, in a sample obtained from a subject, the level of at least one miRNA selected from the group consisting of:

miR-10b-5p; miR-151b; miR-29b-2-5p; miR-329-3p; miR-6511a-5p; miR-5690; miR-516b-5p; miR208b-3p; miR106a-5p; miR-363-3p; miR-4526; miR-129-1-3p; miR-129-2-3p; miR-132-3p; miR-132-5p; miR127-3p; miR212-3p; miR-1224-5p; miR16-2-3p; miR-1294; miR-30a-3p; miR-132-5p; miR-212-3p; miR-212-5p; miR-145-5p; and miR-29a-5p; and a storage module configured to store data output from the measuring module;

a comparison module adapted to compare the data stored on the storage module with a reference level, and to provide a retrieved content, and a display module for displaying whether the level of the miRNA in the sample obtained from the subject is greater, by a statistically significant amount, than the reference level and/or displaying the relative levels of miRNA;

wherein a level of an miRNA selected from the group of:

miR-151b; miR-5690; miR-516b-5p; miR208b-3p; miR106a-5p; and miR-363-3p; miR-30a-3p; and miR-29a-5p;

in the sample of the subject which is statistically significantly greater than the reference level indicates that the subject is at increased likelihood of Parkinson's Disease developing or progressing; and wherein a level of an miRNA selected from the group of:

miR-10b-5p; miR-29b-2-5p; miR-329-3p; miR-6511a-5p; miR-4526; miR-129-1-3p; miR-129-2-3p; and miR-132-3p; miR-132-5p; miR127-3p; miR212-3p; miR-1224-5p; miR16-2-3p; miR-1294; miR-132-5p; miR-212-3p; miR-212-5p; and miR-145-5p;

in the sample of the subject which is statistically significantly less than the reference level indicates that the subject is at increased likelihood of Parkinson's Disease developing or progressing;
wherein increased risk of Parkinson's Disease developing or progressing comprises developing Parkinson's Disease at a younger age; death due to Parkinson's Disease at a younger age; development of dementia; development of dementia at an earlier age; or onset of motor symptoms at an earlier age when compared to other individuals with Parkinson's Disease who do not have such a level of the miRNA.

20. The assay, method, or system of any of paragraphs 14-19, wherein the sample is selected from the group consisting of:
a blood sample; blood plasma; and a brain sample.

21. The assay, method, or system of any of paragraphs 14-20, wherein the subject is a Parkinson's Disease carrier.

22. The assay, method, or system of any of paragraphs 14-21, wherein the miRNA is selected from the group consisting of:
miR-10b-5p; miR-151b; miR-29b-2-5p; miR-329-3p; miR-6511a-5p; miR-5690; miR-516b-5p; and miR208b-3p; miR-30a-3p; and
wherein increased risk of Parkinson's Disease developing or progressing comprises developing Parkinson's Disease at a younger age; death due to Parkinson's Disease at a younger age; or onset of motor symptoms at an earlier age.

23. The assay, method, or system of any of paragraphs 14-22, wherein the miRNA is selected from the group consisting of:
miR106a-5p; miR-363-3p; miR-4526; miR-129-1-3p; miR-129-2-3p; and miR-132-3p; miR-132-5p; miR127-3p; miR212-3p; miR-1224-5p; miR16-2-3p; miR-1294; miR-132-5p; miR-212-3p; miR-212-5p; miR-145-5p; and miR-29a-5p;
wherein increased risk of Parkinson's Disease developing or progressing comprises development of dementia or development of dementia at an earlier age.

24. A kit comprising:
one or more probes for detecting the level of at least one miRNA selected from the group consisting of:
miR-10b-5p; miR-151b; miR-29b-2-5p; miR-329-3p; miR-6511a-5p; miR-5690; miR-516b-5p; miR208b-3p; miR106a-5p; miR-363-3p; miR-4526; miR-129-1-3p; miR-129-2-3p; miR-132-3p; miR-132-5p; miR127-3p; miR212-3p; miR-1224-5p; miR16-2-3p; miR-1294; miR-30a-3p; miR-132-5p; miR-212-3p; miR-212-5p; miR-145-5p; and miR-29a-5p.

25. The kit of paragraph 24, comprising one or more probes for detecting the level of at least two miRNAs selected from the group consisting of:
miR-10b-5p; miR-151b; miR-29b-2-5p; miR-329-3p; miR-6511a-5p; miR-5690; miR-516b-5p; miR208b-3p; miR106a-5p; miR-363-3p; miR-4526; miR-129-1-3p; miR-129-2-3p; miR-132-3p; miR-132-5p; miR127-3p; miR212-3p; miR-1224-5p; miR16-2-3p; miR-1294; miR-30a-3p; miR-132-5p; miR-212-3p; miR-212-5p; miR-145-5p; and miR-29a-5p.

26. The kit of paragraph 24, comprising one or more probes for detecting the level of at least three miRNAs selected from the group consisting of:
miR-10b-5p; miR-151b; miR-29b-2-5p; miR-329-3p; miR-6511a-5p; miR-5690; miR-516b-5p; miR208b-3p; miR106a-5p; miR-363-3p; miR-4526; miR-129-1-3p; miR-129-2-3p; miR-132-3p; miR-132-5p; miR127-3p; miR212-3p; miR-1224-5p; miR16-2-3p; miR-1294; miR-30a-3p; miR-132-5p; miR-212-3p; miR-212-5p; miR-145-5p; and miR-29a-5p.

27. The kit of paragraph 24, comprising one or more probes for detecting the level of at least four miRNAs selected from the group consisting of:
miR-10b-5p; miR-151b; miR-29b-2-5p; miR-329-3p; miR-6511a-5p; miR-5690; miR-516b-5p; miR208b-3p; miR106a-5p; miR-363-3p; miR-4526; miR-129-1-3p; miR-129-2-3p; miR-132-3p; miR-132-5p; miR127-3p; miR212-3p; miR-1224-5p; miR16-2-3p; miR-1294; miR-30a-3p; miR-132-5p; miR-212-3p; miR-212-5p; miR-145-5p; and miR-29a-5p.

28. A method of increasing axonal projections, the method comprising;
administering an effective amount of an agonist or antagonist, as appropriate, of an miRNA selected from the group consisting of:
miR-10b-5p; miR196a-5p; miR196b-5p; miR615-3p; and miR1247-5p; miR106a-5p; miR363-3p; miR-129-1-3p and miR-132-3p.

29. A method of treating a neuronal disease, the method comprising;
administering a therapeutically effective amount of an agonist or antagonist, as appropriate, of an miRNA selected from the group consisting of:
miR-10b-5p; miR196a-5p; miR196b-5p; miR615-3p; and miR1247-5p; miR106a-5p; miR363-3p; miR-129-1-3p and miR-132-3p.

30. The method of paragraph 29, wherein the neuronal disease is selected from the group consisting of:
Huntington's Disease; spinal cord injury; and stroke.

31. An assay comprising:
measuring, in a sample obtained from a subject, the level of a gene of Table 9, 10, or 11 and/or an miRNA selected from the group consisting of:
miR-10b-5p; miR196a-5p; miR196b-5p; miR615-3p; and miR1247-5p;
determining that the subject is at increased risk of developing Huntington's Disease if the level of the gene or miRNA is increased relative to a reference, and determining that the subject is at decreased risk of developing Huntington's Disease if the level of the gene or miRNA is not increased relative to a reference.

32. The assay of paragraph 31, wherein the subject is a Huntington's Disease carrier.

33. The assay of any of paragraphs 31-32, wherein increased risk of developing Huntington's Disease comprises developing Huntington's Disease at a younger age; death due to Huntington's Disease at a younger age, and/or increased CAG repeat size.

34. An assay comprising
(a) measuring, in a sample obtained from a subject, the level of a gene of Table 9, 10, or 11 and/or an miRNA selected from the group consisting of:
miR-10b-5p; miR196a-5p; miR196b-5p; miR615-3p; and miR1247-5p;
(b) administering a potential treatment for Huntingon's Disease;
(c) measuring, in a sample obtained from a subject, the level of the gene and/or miRNA;
(d) determining that the potential treatment is efficacious in reducing the risk and/or severity of Huntington's Disease if the level of the gene and/or miRNA measured in step (c) is not decreased relative to the level measured in step (a) and determining that the potential treatment is not efficacious in reducing the risk and/or severity of Huntington's Disease if the level of the gene and/or miRNA measured in step (c) is decreased relative to the level measured in step (a).

35. The assay of any of paragraphs 31-34, wherein the sample is selected from the group consisting of:
a blood sample and a brain sample.

36. A method of increasing axonal projections, the method comprising;
administering an effective amount of an agonist of expression of a gene of Table 9, 10, or 11 and/or an miRNA selected from the group consisting of:
miR-10b-5p; miR196a-5p; miR196b-5p; miR615-3p; and miR1247-5p.

37. A method of treating a neuronal disease, the method comprising;
administering a therapeutically effective amount of an agonist of expression of a gene of Table 9, 10, or 11 and/or an miRNA selected from the group consisting of:
miR-10b-5p; miR196a-5p; miR196b-5p; miR615-3p; and miR1247-5p;

38. The method of paragraph 37, wherein the neuronal disease is selected from the group consisting of:
Huntington's Disease; spinal cord injury; and stroke.

EXAMPLES

Example 1

It is demonstrated herein that excessive DNA methylation of HES4 promoter sequences, including a strong correlation with measures of striatal degeneration and age of onset of Huntington's disease (HD). This correlation is independent of CAG repeat number. This indicates that HES4 DNA methylation is an epigenetic biomarker to predict the degeneration of HD brain. No epigenetic biomarker has previously been shown to correlate with striatal degeneration in HD.

Huntington's disease (HD) is a devastating and progressive neurodegenerative disorder characterized by chorea, dystonia, cognitive impairment, and behavioral changes 1, 2. The CAG trinucleotide expansion in exon 1 of the huntingtin (htt) gene 3 leads to wide-spread neuronal loss and gliosis and the appearance of intranuclear inclusions of the mutant huntingtin protein (HTT) in neurons, particularly in the striatum and cerebral cortex. There is no effective treatment available. One of the main problems associated with drug development for HD is the lack of biomarker with predictive value correlating with HD pathogenesis and striatal degeneration. Lastly, while all HD patients have the same type of mutation (i.e. >35 CAG repeat repeats (SEQ ID NO: 29)) which account for ⅔ of the variance in age at motor onset, there is significant variation in their motor and cognitive symptoms and the remaining (⅓) variance of the age of onset is likely attributed to other genetic modifier factors such as epigenetic factors. In contrast to genetic change in HD, epigenetic target offer a credible avenue for postponing HD age of onset (at the epigenetic level). Previously, no epigenetic study of histone methylation H3K4me3 or DNA methylation markers of HES family in human HD brains has been described.

Despite the critical role of Notch signaling in neurodevelopment of forebrain neurons and the primary striatal pathology in HD, little is known about the involvement in HES family and the Notch signaling pathway in HD pathogenesis. As described herein, among 25 HD patients tested for DNA methylation in this study, the DNA intermediate methylation of HES4 promoter is highly correlated with severity of striatal degeneration. Interestingly, this correlation is specific for striatal degeneration, but not cortical degeneration. Moreover, it was found that there was a strong correlation between HES4 DNA intermediate methylation and age of onset of HD. Importantly, this correlation is independent of CAG repeat, indicating that HES4 may represent an epigenetic modifier of HD. Without wishing to be bound by theory, it is contemplated herein that such epigenetic modifications can in turn interact with other genetic susceptibility and facilitate HD pathogenesis.

The HES4 DNA methylation pattern described herein represents the first epigenetic mark that predicts the striatal degeneration and age of onset in HD Example 2: Epigenetic Regulation of Hairy and Enhancer of Slit 4 (HES4) and Notch Signaling are Associated with Huntington's Disease Pathogenesis To investigate epigenetic contributions to Huntington's disease (HD) pathogenesis, genome-wide mappings of histone H3 trimethylated at lysine 4 (H3K4me3) were carried out in neuronal nuclei extracted from prefrontal cortex (PFC) of HD cases and controls using chromatin immunoprecipitation followed by deep-sequencing (ChIP-seq). There was a striking enrichment for genes associated with neuronal signaling and connectivity among the 136 loci with differential H3K4me3 enrichment between HD cases and controls, confirming that cortical disease in HD involves the neuronal epigenome. Analyses reveal reverse parallel epigenetic changes (reduced H4K3me3 and increased DNA methylation) of HES4 in HD as well as a wider defect of Notch-related gene expression networks in HD, including reduced binding of nuclear proteins to the HES4 promoter in prefrontal chromatin, down-regulation of HES4 mRNA level as well as altered expression of two HES4 and Notch-related target genes, Mash1 and p21, both critically involved in striatal development. Strikingly, the hypermethylation in a CpG rich HES4 promoter sequence was significantly correlated with measures of striatal degeneration (r=0.56 p=0.006) in a cohort of 25 HD brains. These finding indicate that epigenetic dysregulation of HES4 plays a role in modifying HD disease pathogenesis and severity, by operating through the Notch signaling pathway.

Huntington's disease (HD) is a devastating neurodegenerative disorder caused by the CAG trinucleotide expansion in exon 1 of the huntingtin (htt) gene (Group, 1993) that leads to widespread neuronal loss and gliosis, particularly in the striatum and cerebral cortex. While all HD patients have the same type of mutation (i.e. >35 CAG repeat repeats (SEQ ID NO: 29)) which accounts for ⅔ of the variance in age at disease onset, it is striking that the same genetic (same CAG repeats) architecture is associated with very different age-of-onset, and up to 30 year differences have been reported (Gusella and MacDonald, 2009) (Djousse et al., 2003). It is described herein that differences in epigenetic regulation of specific promoter/regulatory sequences influence the degree of striatal degeneration and the disease age of onset. Epigenetic mechanisms, including the regulation of DNA methylation and various histone modifications, e.g., methylation and acetylation, are of particular interest, given their potential significance as novel drug targets in the treatment of HD (Vashishtha et al., 2013) and other neurodegenerative diseases (Jakovcevski and Akbarian, 2012).

To probe genome-wide changes of histone methylation markers in HD brains, the genome-wide distribution of histone H3 trimethylated at lysine K4 (H3K4me3) was mapped with next generation sequencing technology. The H3K4me3 mark correlates on a genome-wide scale broadly with gene expression activity and is sharply regulated at transcription start sites and other regulatory sequences associated with the regulation of transcription (Zhou et al., 2011) and may provide novel insights into transcriptional dysregulation in HD. To explore the epigenome in the cell type at risk in HD (cortical and striatal neurons) (Han et al., 2010), fluorescent-activated nuclei sorting was employed to isolate neuronal from non-neuronal nuclei residing in the prefrontal cortex (Cheung et al., 2010). This permitted proper comparative analyses of histone marks in neuronal elements, despite the fact that brain tissue in HD and control may have varying neurodegeneration, and thus significant shifts in neuron-to-glia ratios (Hadzi et al., 2012).

Methods

HD and Control Brain Samples.

Fifty-seven postmortem brains, (25 HD and 32 control), were obtained from the Harvard Brain Tissue Resource Center, McLean Hospital (Tables 1-3). All ChIP-sequencing, qPCR and DNA methylation studies were conducted on frozen (never fixed) tissue collected from the rostral dorsolateral portion of the frontal lobe (Brodmann 9). HD brains were selected from a restricted CAG repeat size between 40 to 54 repeats (SEQ ID NO: 30), representative of common repeat sizes in adult onset HD. To increase sample homogeneity (Petretto et al., 2006), each specimen was microdissected, avoiding the surface and layer 1 and taking as uniform a sample from the cortical grey matter (II-VI) as possible.

ChIP-Seq:

Table 1 summarizes the demographics of the six HD and five control brains used for FACS-ChIP sequencing. Postmortem intervals were within the time window in which H3 trimethylation is stable (Cheung et al., Huang et al., 2006, Huang et al., 2007, Akbarian and Huang, 2009).

DNA Methylation:

For DNA methylation analysis, genomic DNA was extracted from 25 HD (including 4 from ChIP-sequencing) and 27 control brains (Table 2).

Quantitative Reverse-Transcriptase Polymerase Chain Reaction:

For qRT-PCR, RNA was extracted from a subset of the cohort used for DNA methylation assays (14 HD and 14 control brains, Table 3).

FACS-ChIP-Seq Protocol.

Neuronal and non-neuronal nuclei were separated (Jiang et al., 2008, Matevossian and Akbarian, 2008) by fluorescence-based nuclei sorting (FACS), followed by chromatin immunoprecipitation and genome-wide histone methylation mapping via next generation sequencing (ChIP-Seq, see FIG. 1A) (Huang et al., 2007, Cheung et al., 2010). (i) Nuclei extraction and FACS: ~750 mg of tissue was homogenized in 5 mL of lysis buffer. Lysates were loaded on a sucrose solution and centrifuged at 24,400 rpm for 2.5 h at 4° C. Nuclei pellets were resuspended in 500 μL PBS and incubated in staining mix containing 1:1200 anti-NeuN (Millipore), 1:1400 Alexa488 goat anti-mouse secondary antibody (Invitrogen)] for 45 min. FACS was done on a FACSVantage™ SE flow cytometer. (ii) The sorted nuclei (3-5 million) were digested with micrococcal nuclease (4 U/mL) at 37° C. for 5 min. The reaction was stopped and nuclei were lysed and precleared by Protein G Agarose. Chromatin immunoprecipitation was carried out by incubating digested nuclei with anti-H3K4me3 (1:315; Upstate; 07-473) at 4° C. overnight. Immunoprecipitated chromatin was incubated with Protein G Agarose for 1 h, and beads were washed by a series of low and high salt buffer, lithium chloride buffer, TE buffer, and then eluted in 0.1 MNaHCO3 and 1% SDS. The eluted DNA was digested with proteinase K and then purified. (iii) ChIP-Seq Library Construction was carried out according to the Illumina protocol using Genomic Adaptor Oligo Mix™ (Illumina) by Fast-link DNA Ligation Kit™ (Epicentre) the Genomic PCR Primers (Illumina) according to the Illumina protocol. PCR product was cleaned and correct size of PCR product was confirmed by gel electrophoresis. (iv) The smaller smear was gel purified and libraries were sent for deep-sequencing on the Illumina Genome Analyzer™.

Computational Analysis of H3 Trimethylation Landscapes.

All sequencing libraries were single-end 36-basepair reads which were mapped to the gender appropriate human genome (HG19) by Bowtie (version 0.11.3), allowing up to one mismatch. Reads that mapped to multiple locations were discarded. The MACS™ software (version 1.3.5) was used to identify statistically enriched H3K4me3 regions (termed "peaks" hereafter). Each sample was contrasted against the input sample using bw=230 and tsize=36, and default values for the remaining parameters in MACS™. To identify differentially expressed H3K4me3 peaks between controls and HD cases, all peaks were combined and overlapping peaks merged, resulting in 33,148 peaks. H3K4me3 peaks that were significantly decreased in the HD samples were defined as follows: (i) minimum peak size of 1 Kb with pseudocount 0.001 for average densities; (ii) average read density in control samples greater than or equal to 0.01, (iii) the ratio of average read densities Control:HD greater than or equal to 2, and (iv) the t-test p-value less than or equal to 0.05. A Benjamini Hochberg false discovery rate was calculated. Reciprocal criteria were used to define H3K4me3 peaks significantly increased in HD.

Gene Ontology (GO) Term Enrichment Analysis.

The getEnrichedGO( ) function in the ChIPpeakAnno R™ package was used to test whether certain loci of H3K4me3 (associated with specific genes) were overrepresented than would be expected by chance (adjusted p-values<0.05, according to Benjamini & Hochberg (1995) step-up FDR controlling procedure).

Phylogenetic Analysis of HES Family Genes.

HES gene family and protein sequences were obtained from NCBI and Ensembl databases. Multiple sequence alignment of protein sequences was performed using ClustalW™ algorithm and edited in GeneDoc program using Blosum62™ as similarity scoring matrix.

DNA Methylation Detection Protocol

Genomic DNA (gDNA) was extracted from frozen brain using the Blood & Cell Culture DNA kit (Qiagen) and quantified by NanoDrop™ 2000 and 0.7% agarose gel electrophoresis for DNA integrity. Samples showing a A260/A280 ratio >1.7 and a major band around 30 kb were included in methylation analysis. DNA methylation was measured by the Methyl-Profiler PCR™ Array according to manufacturer's instructions (SABiosciences/Qiagen). This assay is based on MethylScreen™ (Brooks, 1991, Holemon et al., 2007) with combined digestion of methylation-sensitive type II enzyme (HpaII/HhaI) and methylation-dependent type IV enzyme (McrBC) (EpiTect Methyl DNA Restriction kit, Qiagen) followed by real-time PCR analysis of remaining gDNA. Primers were designed, evaluated and provided by SABiosciences/Qiagen for human HES4 (catalog# MePH00010-2A). Briefly, one microgram of gDNA from each case or control was divided among four digestion-conditions: mock, HpaII/HhaI, McrBC and HpaII/HhaI+McrBC. Overnight digestion at 37° C. with qPCR was conducted with gene-specific primers for equal quantities ($1/25^{th}$) of differentially treated genomic DNAs on an ABI Prism 7000 system. Cycle threshold (Ct) values for each condition were used to calculate un-methylated (UM), fully methylated (FM) and intermediately methylated (IM) DNA such that UM, FM and IM sum to 1.0 for a given sample. All experiments and data analyses were done in double blind.

RNA Isolation and Gene Expression Analyses (qRT-PCR)

Total RNA was extracted from frozen human HD and control brain with Trizol reagent and cleaned with an RNeasy™ micro kit (Qiagen). Total RNA was reverse transcribed to cDNA using SuperScript II™ Reverse Transcriptase Kit (Invitrogen). The qRT-PCR was performed using Taqman™ Gene Expression Assays on 7500 Real-Time PCR System. Probes and primers specific for human HES4 and 18S RNA (Hs00368353_g1 and Hs99999901_s1 respectively) were used according to the manufacturer's protocol. Averaged threshold-cycle (Ct) values of the 18S RNA were used to normalize the target gene (HES4), which then were used to determine the relative expression of the gene for HD versus control samples by the $2^{-\Delta\Delta Ct}$ method.

To analyze HES4 in Neu+ (neuronal) and Neu− (non-neuronal) cells, total RNA was extracted from 1-3 million of FACS sorted human brain nuclei using TRIzol reagent (Invitrogen) according to the manufacturer's protocol. cDNA was synthesized using Script™ cDNA Synthesis Kit (Bio-Rad #170-8891), following the manufacturer's instructions. Quantitative real-time PCR was performed in triplicate by using Power SYBR® Green PCR Master Mix (AB applied biosystem, #4367659) on LightCycler™ 96 Real-Time PCR System from Roche. The mRNA level was normalized by gene 18s rRNA. Primers used for HES4 primer set #2: forward TCAGCTCAAAACCCTCATCC (SEQ ID NO: 23), reverse TGTCTCACGGTCATCTCCAG (SEQ ID NO: 24); HES4 primer set #3: forward ATCCTGAGATGACCGTGAG (SEQ ID NO: 25), reverse CGGTACTTGCCCAGAACG (SEQ ID NO: 26); 18s rRNA forward GTTGGTGGAGCGATTTGTCT (SEQ ID NO: 27), reverse GAACGCCACTTGTCCCTCTA (SEQ ID NO: 28).

Electrophoretic Mobility Shift Assay (EA/ISA).

The promoter region of the HES4 gene was obtained by cloning the qPCR product of the HES4 DNA methylation assay into pGEM3zf at the HincII site followed by DNA sequencing. This qPCR amplicon expands a 269-bp region −387/−118 upstream of the human HES4 gene TSS. To test its binding capability under different methylation status to nuclear proteins in brain, this fragment was excised from vector using EcoR I and Hind III, and digested with BamHI sites to yield two fragments of identical size (134-135 bp) and then treated with or without SssI DNA methylase. Complementary genome DNA strands were annealed at room temperature for 30 minutes after being heated to 80° C. using the following different combinations (a)"unmethylated" probe from two strands without treatment of Sssi, (b) "methylated" probe from two strands with treatment of Sssi (c) "hemi-methylated probe" from one strand with treatment of Sssi and one strand without treatment of Sssi. The BamHI-digested, un-/hemi-/fully-methylated double-stranded DNA then were filled in with $^{32}$P-labeled dCTP as described previously (Bai and Kusiak, 1995). For binding, tissue lysates of homogenized human cortical tissue with sonication buffer were used. Approximately 5 μL (20 μg) of lysate was pre-incubated on ice for 10 min in binding buffer (15 μL volume) before 1 ng of $^{32}$P-labeled double strand probe was added. After a 10 minute incubation at 23° C. reaction mixtures were fractionated on 4% nondenaturing polyacrylamide gel in 0.25×TBE.

Statistical Analysis of the Relationship of HES4 DNA Methylation with Level of Striatal Involvement and Age of Onset in HD.

Twenty-two of the 25 HD samples studied had been evaluated previously for levels of striatal and cortical involvement (Hadzi et al., 2012). Briefly, each brain sample was reviewed by gross and microscopic examination for the level of involvement for fifty brain regions.

Cluster analysis reduced the data to two main measures of involvement: (a) striatal and (b) cortical. The striatal cluster represented a synthesis of twenty-eight brain measures and the cortical cluster constituted thirteen brain measures.

Comparisons between HD cases and controls to assess possible differences in age at death and post-mortem interval were analyzed by student t-test. The relationship of the level of UM, IM, or FM to the level of striatal involvement was studied by Spearman correlation, and by a general linear model controlling for the effect of the size of the expanded CAG repeat size and the level of cortical involvement. The t-tests, Spearman correlation, and general linear models were performed by SAS™ version 9.3.

Results

Histone H3K4Me3 Landscapes in Prefrontal Neurons of HD and Control Brains

The distribution of the H3K4me3 mark, which is sharply enriched around the 5'end of genes and on a genome-wide scale broadly correlated with gene expression activity, was mapped in neuronal chromatin from dorsolateral PFC in 6 cases and 5 controls (Table 1). All but one of the HD postmortem brains were collected more than fifteen years after onset of HD symptoms (mean=17.2 years), at which time, striatal neurons would have largely degenerated, resulting in a dramatic decline of neuronal numbers in the caudate nucleus, accompanied by extensive gliosis (Myers et al., 1991). On the other hand, the PFC of HD brains displays pathological changes similar to the striatum (including HTT aggregation), but without the severe neurodegeneration that defines HD striatum (Hadzi et al., 2012) (van Roon-Mom et al., 2006). Thus, molecular changes detected in HD PFC may be more representative for HD pathology prior to neurodegeneration.

In the cohort, 85-90% of reads of HD and 82-90% of control cohorts were mapped to one unique location in the genome. Using Poisson statistics 136 H3K4me3 peaks were identified as differentially distributed between HD and control brain (Tables 1-3), with 78 peaks maintaining significance (P<0.05) after correction for False Discovery using the Benjamini and Hochberg method (Table 4). 83 out of 136 peaks were overlapped within 2 kb of a TSS, consistent with previous studies (Cheung et al., 2010, Shulha et al., 2012). For example, there are clear dense H3K4me3 peaks around TSS of the TTTY15 gene in HD brain (FIG. 1A). Since TTTY15 is located on the Y chromosome, there is no signal at all in HD3584 because this individual was female.

Among the 136 peaks, 85 peaks were decreased and 51 peaks increased in HD, a finding that is in agreement with an overall loss of gene expression activity in HD brain by transcriptome analysis (Seredenina and Luthi-Carter, 2012). At least 45 of the 136 peaks as defined by the nearest TSS, were associated with neuronal genes important for connectivity and synaptic signaling (e.g. SHANKS, RIMS2, DLG2/PSD93) or activity-dependent neuronal transcription (ARC, RCOR2, MKL1) (Tables 1-3), supporting the view that cortical circuitry is compromised in HD due to widespread alterations in the epigenetic architecture of cortical neurons. Gene ontology analysis of the 136 peaks, when corrected for multiple comparisons, showed enrichment for 8 categories that were overwhelmingly related to neuronal compartments and synaptic signaling (data not shown). Notably, 6 out of 8 over-represented GO categories are directly related to synaptic functions, a finding consistent with the fact that neuronal nuclei were used for the ChIP-seq analysis.

Furthermore, 14 of the 136 peaks altered in HD cortical neurons are ascribed with key roles in neurodegenerative conditions (Tables 1-3). These include orphan G protein coupled receptors including GPR3 modulating gamma-secretase activity and beta-amyloid deposition (Thathiah et al., 2013) and GPR179 which, when mutated, lead to degeneration of bipolar neurons in the retina (Peachey et al., 2012). The list also includes INF2, a monogenic cause for Charcot-Marie-Tooth neuropathy (Rodriguez et al., 2013), VRK1, a monogenic cause for progressive postnatal microencephaly syndromes (Paciorkowski and Darras, 2013) and a transmembraneous protein, TMEM106B, implicated in frontotemporal dementia (Wood, 2010, Finch et al., 2011) and Alzheimer's (Rutherford et al., 2012). In addition, multiple H3K4me3 peaks altered in HD neurons located to the TSS have a key role in neuronal development and differentiation, including TNFRSF18 and TRAF7, two tumor necrosis factor (TNF) receptor-related molecules linked to the neurotrophin BDNF/TRKB signal cascade and developmental regulation of apoptosis (Xu et al., 2004, O'Keeffe et al., 2008). Notably, HES4 and JAGGED2, two components of the Notch signaling pathway implicated in the regulation of stem cells and neuronal progenitors (El Yakoubi et al., 2012, Rabadan et al., 2012) were identified.

HD Cortical Neurons Show Selective Reduction of HES4 TSS-Associated H3K4Me3.

HD pathology is characterized by striatal degeneration which has been suggested to be related to neurodevelopmental defects (Martin and Gusella, 1986, Vonsattel and DiFiglia, 1998). Given the recognized role of the HES gene family and more broadly Notch signaling in forebrain neuronal development by controlling cell-fate determination in progenitor cells and induction of terminal differentiation (Bertrand et al., 2002, Jhas et al., 2006, Kageyama et al., 2008), additional targeted analysis of H3K4me3 signals and DNA methylation of the HES4 gene and its promoter were performed. FIG. 1B shows the altered H3K4me3 pattern of HES4 gene by FACS-ChIP-seq analysis. The H3K4me3 mark of HES4 gene in cortex was increased around the TSS site, while broader regions upstream of the promoter were also involved. As shown in FIG. 1B, H3K4me3 signals of the HES4 gene were consistently reduced in all six HD brains compared to all five controls. Total tags of ChIP-seq signal were significantly reduced in HD compared to controls, and statistical analyses of tag densities in HD (0.0077) were statistically different from controls 0.0191 Log 10 (FDR corrected P=0.01).

Figure 1C:
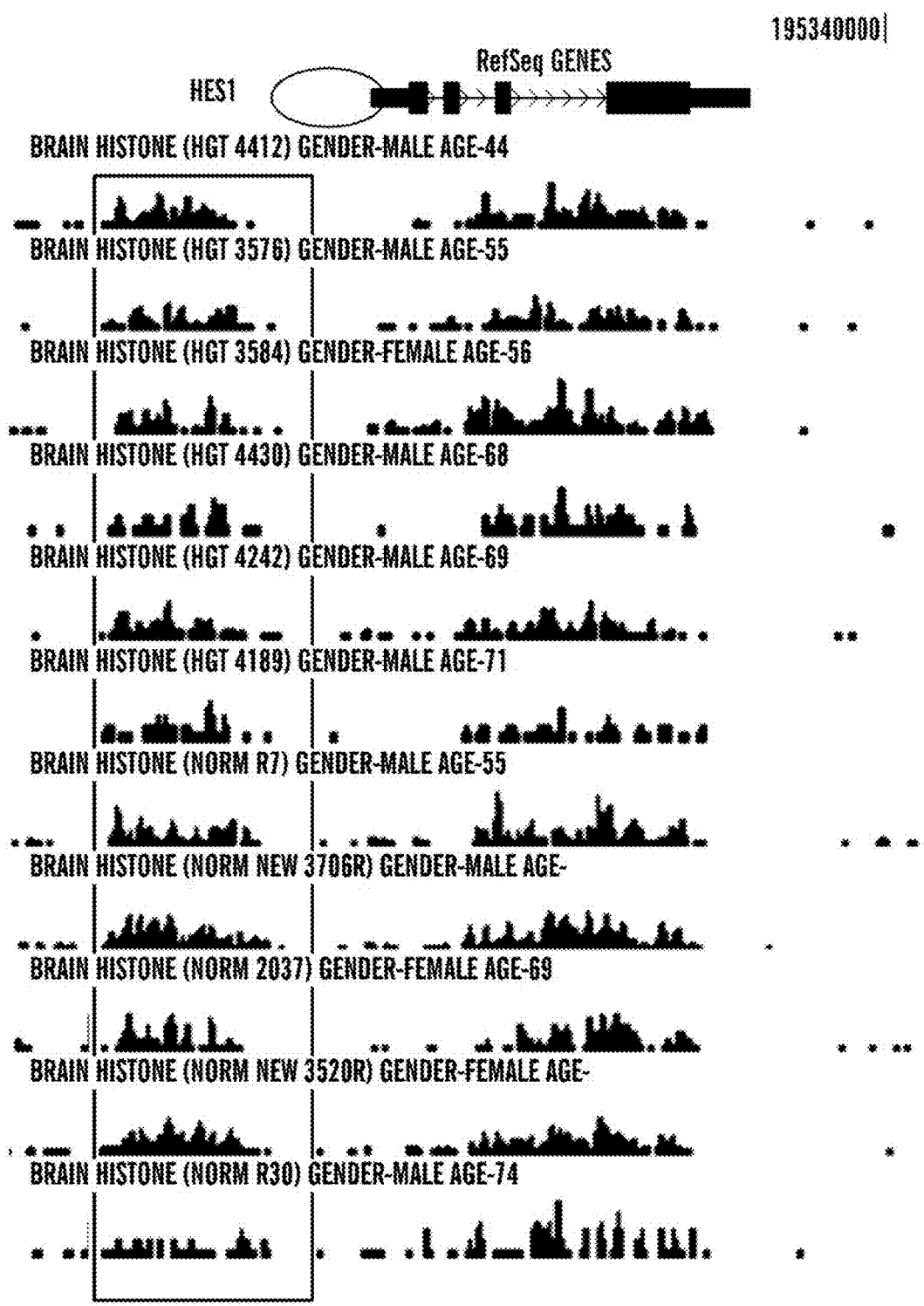

Interestingly, the reduced H3K4me3 signal is specific to HES4 since careful analysis of this histone mark for other genes of the HES family (HES1-HES7) are not affected, as illustrative by the representative example of HES1 (FIG. 1C). Recognizing that HES4 has no direct homologue in the mouse genome, further detailed phylogenetic analysis of HES4 and HES family genes were performed. The HES4 gene sequences are identified in humans and all analyzed primate species but HES4 is not specific for primates because close orthologs are found in other mammalian taxons. However, mammalian evolution is associated with occasional and independent losses of Hes4. For example, rodent Hes4 is lost in "mouse-related" Glade (*Mus musculus* and *Rattus norvegicus*), but retained in "squirrel-related" Glade (*Ictidomys tridecemlineatus*) (data not shown).

DNA Methylation Analysis Uncovered an Increase in Intermediate Methylation in the HES4 Gene in HD Brains.

Figure 2A:
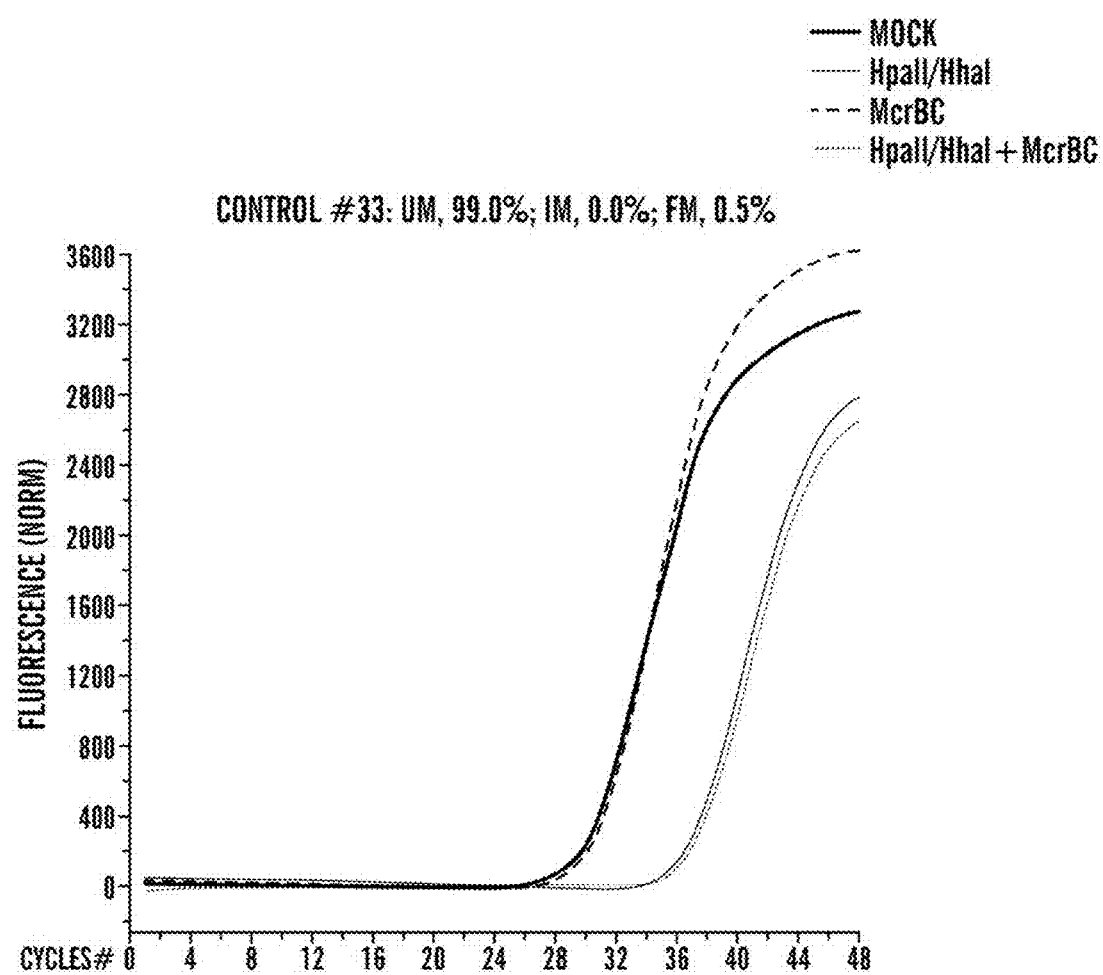
FIGS. 2A-2E demonstrate the DNA methylation of HES4 promoter of HD and control cortex. DNA methylation status of a 269 bp fragment of HES4 promoter in the PFC of 27 controls and 25 HD using Methyl-Profiler was determined as described in Example 2.
Figure 2B:
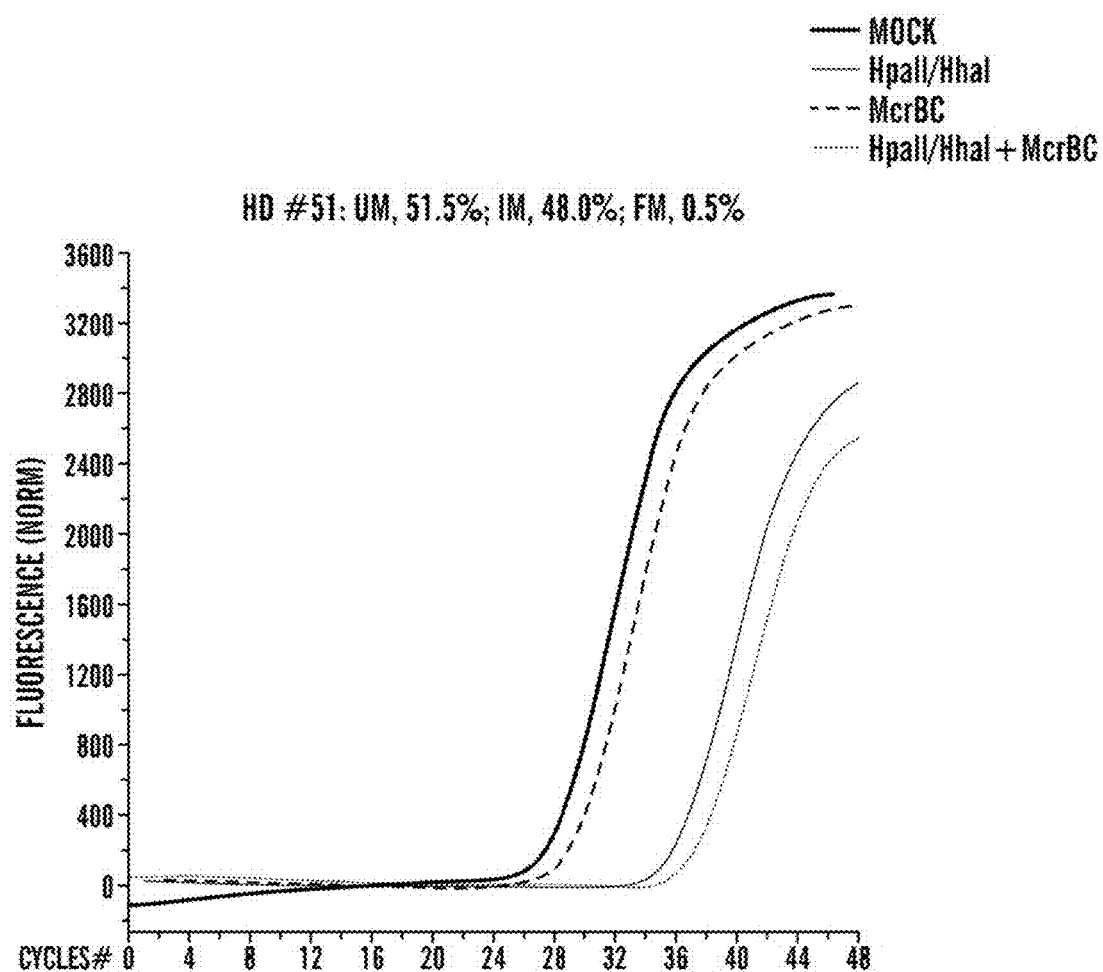
Figure 2C:
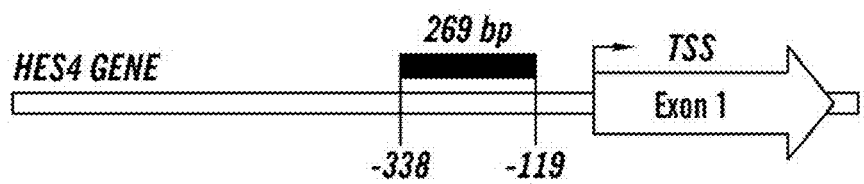
Figure 2D:
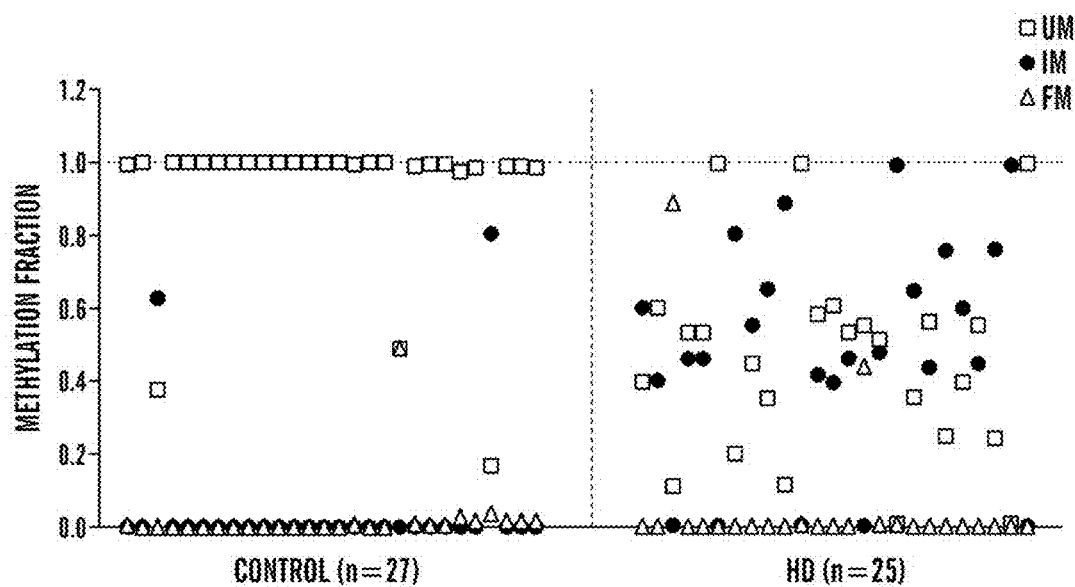
Figure 2E:
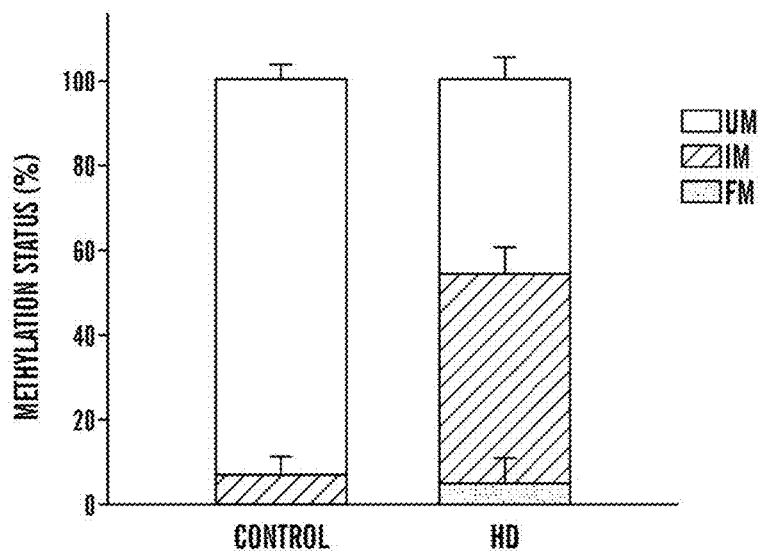

In consideration of the relationship between H3K4me3 and DNA methylation, HES4 DNA methylation was examined using the SABiosciences/Qiagen Methyl-Profiler method which assessed unmethylated (UM), fully methylated (FM) DNA and intermediately methylated (IM) DNA representing monoallelic DNA methylation as well as partial DNA methylation on one or both strands. DNA methylation status of selected CpG islands (CGIs) in the PFC of 27 controls and 25 HD was assessed (Table 2). FIGS. 2A-2B shows examples of qPCR curves of all four reactions in one control (FIG. 2A) and in one HD (FIG. 2B) for the HES4 gene. The analysis showed that in the control brain, HES4 promoter was largely unmethylated (~95%, FIG. 2D, left panel), but in HD brain, the UM fraction in HES4 gene was significantly reduced (FIGS. 2D-2E, P<0.01) and mostly converted to IM making the IM fraction significantly higher (P<0.001) in HD. Specifically, IM is robustly increased from 5% of total input DNA in control to 49% in HD (FIG. 2D, right panel), indicating that most DNA methylation occurs heterogeneously on individual molecules. In contrast, FM of the HES4 gene was not altered. After cloning the qPCR product from the DNA methylation assay, the sequence of this 269-bp fragment in the HES4 gene promoter was obtained, in which 33 CpG dinucleotides were identified on each strand and proximate to the TSS (FIG. 2C,).

Figure 3:
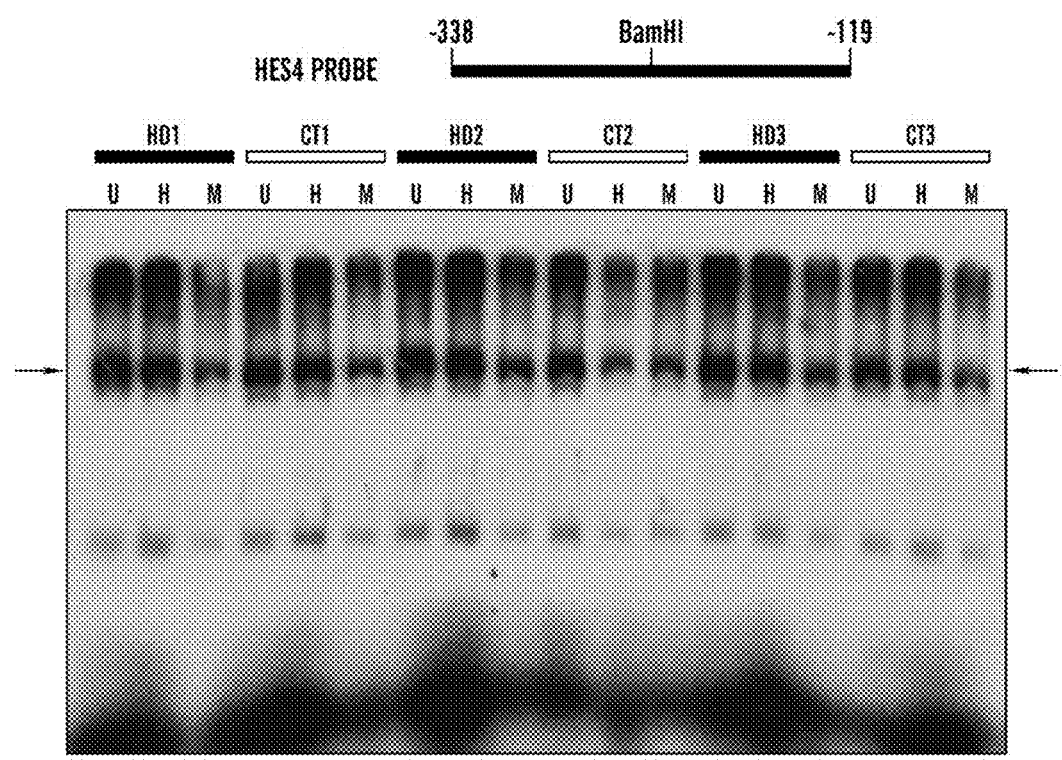
FIG. 3 demonstrates that the binding of nuclear proteins to the HES4 promoter is reduced after DNA hypermethylation in vitro. The figure depicts an image of the result of a gel shift mobility assay. Binding of nuclear proteins from HD and control cortex to the 269 bp fragment of HES4 promoter with in vitro DNA methylation by gel shift mobility assay (EMSA) as described in the Method section. This 269-bp fragment of the HES4 promoter was first digested BamHI into two identical DNA fragments and in vitro methylated and then re-annealed unmethylated (U), fully methylated (M) and hemi-methylated (H) double strand DNA probes for EMSA. Note that nuclear protein binding (indicated by arrows) was reduced and shifted to high molecular weight band at the fully methylated HES4 promoter compared to the un-methylated or hemi-methylated HES4 promoter.

Nuclear Proteins Binding to the HES4 Promoter are Reduced after DNA Hypermethylation In Vitro To explore the possible functional significance of HES4 promoter methylation, an electrophoretic mobility shift assay (EMSA) was performed to analyze the interaction of nuclear proteins with this 269-bp fragment of the HES4 promoter (−338 to −119 bp upstream of TSS) after in vitro methylation. Unmethylated (U, both strands unmethylated), hemi-methylated (H, one strand methylated and other unmethylated) and fully methylated (M, both strands methylated) DNA was tested in EMSA. Multiple bands were formed between nuclear proteins and the HES4 promoter fragment (FIG. 3). Interestingly, however, nuclear protein bindings were significantly lower on the fully methylated HES4 promoter and shifted to high molecular weight band, compared to the unmethylated or hemi-methylated HES4 promoter. Thus, these data suggest that changes in the DNA methylation status of the HES4 promoter could affect nuclear protein occupancies at the promoter.

mRNA Levels for HES4 and Two Down-Stream Target Genes, MASH1 and P21, are Reduced in HD Versus Control PFC.

Figure 4A:
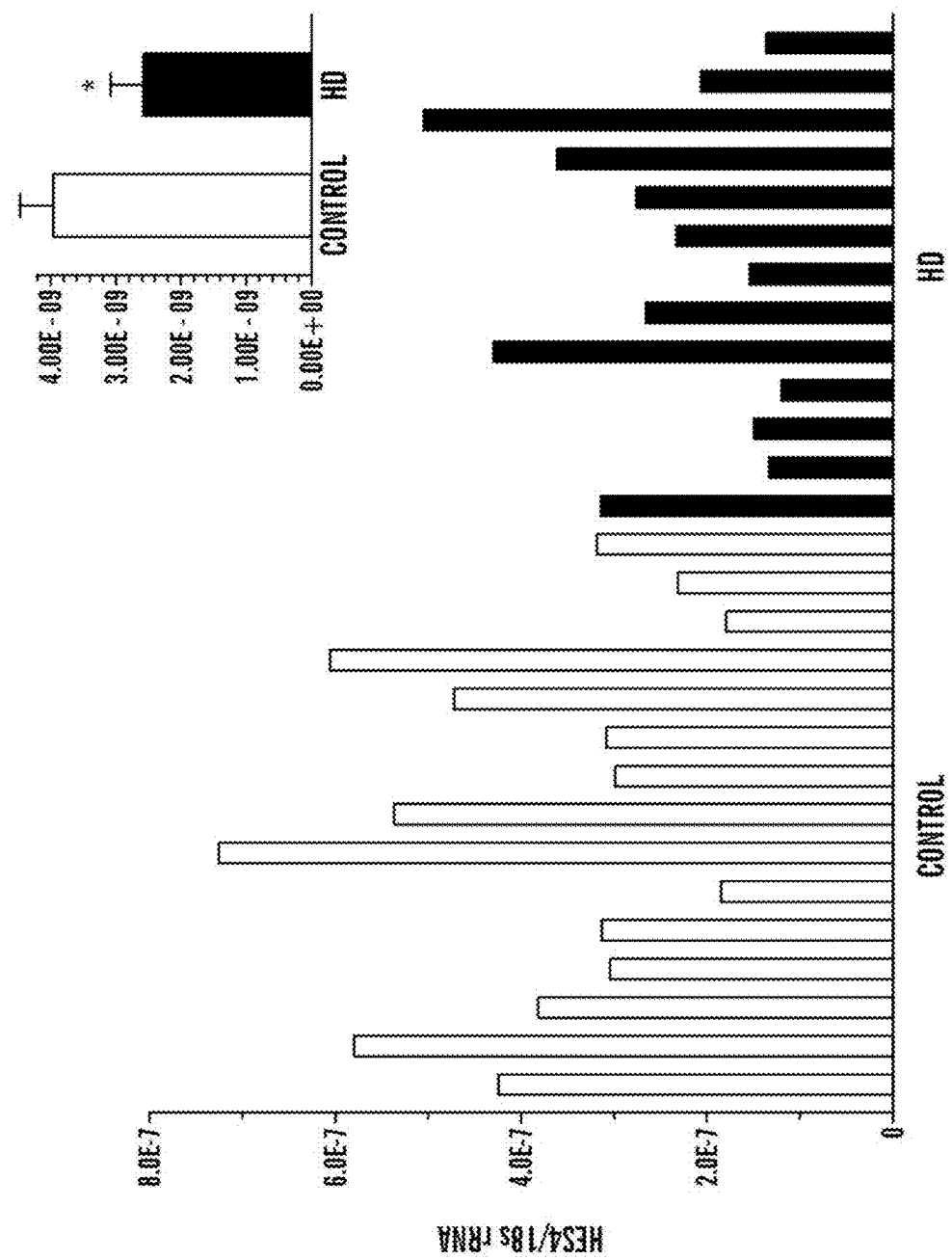
FIGS. 4A-4C demonstrate that the mRNA levels for HES4 as well as two down-stream target genes, Mash1 and p21, are reduced in the cortex of HD compared to controls.
Figure 4B:
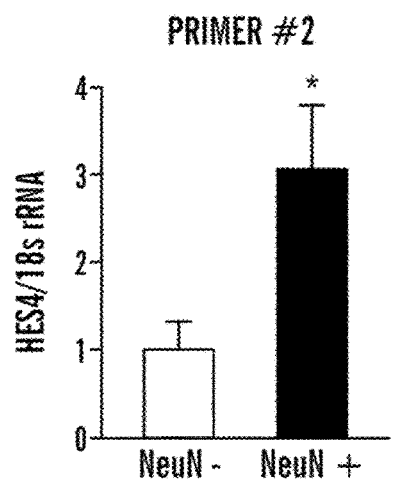
Figure 4C:
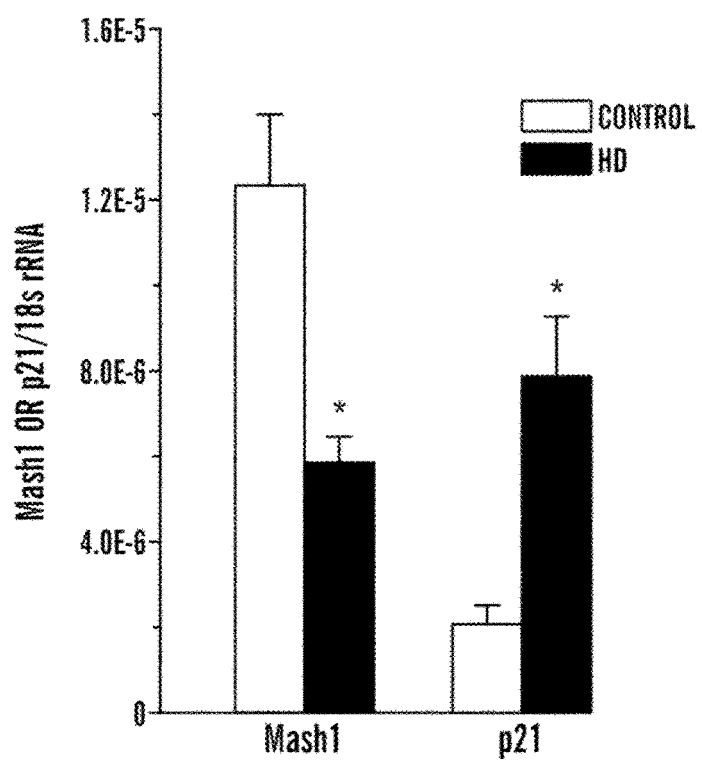

To examine the functional impact of HES4 promoter IM increase, the distribution of HES4 mRNA in neuronal (NeuN+) and non-neuronal (NeuN−) fractions was first examined by qPCR analysis of FACS sorted cells and found that HES4 mRNA is enriched in neuronal (NeuN+) nuclei compared to non-neuronal (NeuN−) nuclei in human cortex, consistent with the strong H3K4me3 associated with HES4 gene in NeuN+ nuclei (FIGS. 4A and 4B). Furthermore, it the mRNA levels for HES4 in cortex by qPCR analysis were determined in 14 HD and 14 control cortex (Table 3) and HES4 mRNA was found to be reduced ~40% in HD cortex compared to control (FIGS. 4A-4B) (t-test, p<0.05). This finding is consistent with an earlier transcriptome study in HD, with ~50% reduction of HES4 mRNA in the diseased brains (Hodges et al., 2006). This decrease in HES4 mRNA is also consistent with the reduction in nuclear protein binding to fully methylated DNA, probably due to increased IM of symmetric and incomplete methylation of the HES4 promoter in HD brain. Considering that HES1 positively regulates expression of Marshl (a proneuronal, striatum-specific transcription factor) (Casarosa et al., 1999) and negatively regulates p21 (a cell cycle suppressor) (Diguet et al., 2005, Ryman-Rasmussen et al., 2007, Katritch et al., 2013), and that HES proteins share certain structural motifs (Rajagopal et al., 2010), it was contemplated that HES4 mediates Notch signaling to affect these two Notch-sensitive genes in a manner similar to the one previously reported for HES1. Indeed, our qRT-PCR results showed that the reduced HES4 mRNA was associated with down-regulation of Mash1 mRNA in HD cortex compared to the control. By contrast, p21 mRNA was increased in the cortex of HD compared to the control. Therefore, Notch signaling may play a role in the neurodegeneration of HD.

The Extent of Intermediate DNA Methylation of the HES4 Promoter is Correlated with Striatal Degeneration and with Age of Onset in HD The correlation of levels of un-methylated, intermediate methylation, and hypermethylation to the characteristics of the HD samples is presented in Table 5. The levels of FM and UM sites were not significantly correlated with any of the HD sample characteristics. The level of intermediate methylation was correlated with the level of striatal involvement ($r=0.56$, $p=0.006$) and was also correlated with the age at death ($r=-0.47$, $p=0.02$), age at onset ($r=0.48$, $p=0.02$) and the size of the HD CAG repeat ($r=0.50$, $p=0.01$). The correlation between intermediate methylation and striatal involvement remained after removing the four samples with no intermediate methylation ($r=0.50$, $p=0.02$). No differences were seen between the HD cases and controls for age at death ($t=-0.81$, $p=0.42$) or PMI ($t=1.21$, $p=0.23$).

Because the intermediate methylation level was correlated with several different features of the HD samples, it was sought to assess the main effect of the level of striatal involvement by multivariate analysis of the relationship of the level of intermediate methylation, controlling for the age at onset, the size of the HD repeat and the level of cortical involvement. The relationship of intermediate methylation to striatal involvement remained after adjustment for these other factors. Similar results were found consistently with other models including the level of cortical involvement or when removing onset age to avoid over parameterization.

Discussion

The analysis described herein reveals that mutant HTT protein is unlikely to be associated with a generalized distortion of histone methylation landscapes in diseased neurons. Instead, HD appears to be associated with highly specific defects at (according to our estimates) 136 loci in various portions of the genome. Consistent with H3K4me3 as a fingerprint of an actively transcribed gene and a marker for transcription initiation sites (Santos-Rosa et al., 2002, Li et al., 2007, Pan et al., 2007, Guttman et al., 2009), 83 out of 136 H3K4me3 peaks were mapped to genome positions within 2 kb of a TSS, with the highest peaks around 100 base pairs downstream of the TSS in both HD or control brains. Interestingly, there was a striking enrichment for genes defining neuronal function and synaptic signaling (Table 4), confirming that the molecular pathology of HD is associated with severe defects in cortical neurons (Eidelberg and Surmeier, 2011). At some of these loci, such as the HES4 gene promoter, multiple types of epigenetic markings showed disease-associated changes, including DNA cytosine methylation which in brain generally shows an opposing and largely non-overlapping distribution with H3K4me3.

Importantly, altered H3K4me3 signaling in HD may relate to a strong inverse correlation between DNA methylation and the presence of H3K4me3 (Maunakea et al., 2010). Unmethylated CGIs have been shown to recruit the CxxC finger protein 1 (Cfp1) that associate with the H3K4 methyltransferase Setd1 (Set1/COMPASS or Set1B) (Brooks, 1991, Tai et al., 2004) to create chromatin domains rich in H3K4me3 for enhanced gene expression (Scherfler et al., 2004). This is consistent with the finding described herein that the reduced H3K4me3 signal for HES4 is associated with increased DNA methylation in the HES4 gene promoter. Furthermore, recent studies have demonstrated that normal htt function facilitates epigenetic silencer polycomb repressive complex 2 (PRC2) which regulates methylation at histone H3-lysine 27 (Seong et al.). Without wishing to be bound by theory, it is contemplated herein that since H3K4me3 demethylase, namely Rbp2 (KDM5A or JARID1A), is recruited by PRC2 (Pasini et al., 2008), mutant HTT may reduce H3K4me3 signaling by facilitating PCR2 function. Furthermore, there is evidence for physical interactions, and functional crosstalk, between histone deacetylases and histone demethylases in intact cells (Urban et al., 2007, Venkatakrishnan et al., 2013). The significance of the H3K4me3 in HD is demonstrated by a very recent study that genetic reduction of the H3K4 demethylase SMCX/Jarid1c in mice and *Drosophila* models of HD can reverse mutant Huntingtin driven pathological phenotypes (Vashishtha et al., 2013).

Despite the critical role of Notch signaling in neurodevelopment of forebrain neurons, little is known about the involvement in HES family and the Notch signaling pathway in HD pathogenesis. A recent genetic study in *Drosophila* suggests that Huntingtin-interacting protein (Hip) modulate Notch-mediated neurogenesis through a deltex-dependent pathway (Moores et al., 2008). The present finding of reduced H3K4me3 and mRNA levels for HES4 in HD cortical neurons provides evidence linking the HES transcription factor family to HD pathogenesis. However, reduced H3K4me3 is specific for HES4 since analysis of this histone mark for other HES family shows no significant changes. HES4 mRNA is also significantly enriched in human neuronal nuclei. Interestingly, the HES4 gene, while present in many vertebrate genomes, is not found in Muridae (including mouse and rat) genomes, suggesting that HES4-related HD pathophysiology cannot be easily modeled in these animals.

Moreover, it was observed herein that a signification increase in intermediate methylated DNA of the HES4 promoter region occurred in HD brain and this increase is associated with the reduced nuclear protein binding to the fully methylated HES4 promoter compared to the un-methylated or hemi-methylated HES4 promoter. It is likely that the increased intermediately methylated DNA (but not hemi-methylated DNA) can be attributed to increased asymmetric semi-methylation in HD in view of the similarity of its protein binding pattern to un-methylated and hemi-methylated DNA (FIG. 3). This type of asymmetric semi-DNA methylation is a mechanism that may be particular relevant in differentiated tissues in the context of disease (Gao et al., 2011, Verzijl and Ijzerman, 2011), in contrast to hemimethylation which commonly is linked to the process of DNA replication. Furthermore, this study implicates broadly the Notch signaling pathway in HD pathogenesis. In addition to the altered epigenetic modifications of HES4 and reduced HES4 mRNA, the present analysis uncovered that two HES4 target/down-stream genes in the Notch signaling pathway, MASH1, and P21, were dysregulated in HD cortex, albeit in opposite directions. These findings are entirely consistent with the known HES4 regulation of downstream target genes by different mechanisms: HES4 can suppress Mash1 expression by disrupting the formation of E47 with striatum-specific bHLH factors Mash1; HES4—can also interact with the Orange domain to remove the repression of transcription of the p21 WAF.

Mash1 is a forebrain-specific transcription factor and is critically involved in striatal development (Casarosa et al., 1999, Kageyama et al., 2008). p21 is the down-stream target of HES family in the Notch signaling pathway (Katritch et al., 2013); p21 has been implicated in HD pathogenesis by its direct interaction with HTT (Luo et al., 2008; Steffan et al., 2000). Moreover, blocking HES1 (the closest rodent HES family to human HES4) expression stimulates the expression of cyclin dependent kinase inhibitor p21CIP1/WAF1 to modulate differentiation of neural stem cells into GABAergic (striatal) neurons (Diguet et al., 2005). Thus, the coordinate interplay of HES family proteins and its downstream targets Mash1 and p21 play a critical role in guiding the phenotypic development of neural stem cells into striatal GABAergic neurons. Thus, epigenetic changes of HES4 (i.e. reduced H3K4me3 signal at the HES4 promoter, in conjunction with alterations in DNA methylation), leading to lower HES4 expression and dysregulation of putative HES4 target genes, including Mash1 and p21, to affect forebrain neuronal development. Given the essential role of Notch signaling in forebrain neuronal development, the finding of altered epigenetic modifications of HES4 and altered expression of Notch signaling molecules supports the increasing recognition that HD may be a lifelong disease process and suggests that abnormal neurodevelopment involving Notch signaling may contribute to HD pathogenesis (Gusella and MacDonald, 2006).

The significance of epigenetic modifications of the HES4/Notch signaling is substantiated by the finding that the degree of DNA methylation of the HES4 promoter is associated with striatal degeneration and age of onset of HD patients. The inventors found that among 523 HD patients, two classes of HD pathology with mainly striatal degeneration (class I) or cortical degeneration (class II) (Hadzi et al., 2012). Among 25 HD patients tested for DNA methylation in this study, the DNA intermediate methylation of HES4 promoter is high correlated with severity of striatal degeneration. Interestingly, this correlation is specific for striatal degeneration, but not cortical degeneration despite that the DNA methylation of HES4 was assessed in the cortex. The selective correlation between the degree of the intermediate methylation pattern for HES4 promoter and striatal degeneration is in agreement with the primary striatal degeneration in HD, and with HES4 function to control the expression of forebrain neuron-specific transcriptional factor Mash1, and consequently striatal development (Casarosa et al., 1999, Cussac et al., 2002). Thus, this finding may uncover a molecular link that contributes to selective striatal neurodegeneration and HD pathogenesis. The correlation of HES4 promoter intermediate methylation in cortex with striatal (but not cortical) degeneration indicates that alteration in HES4 is necessary but not sufficient factor in inducing neuronal degeneration. Striatum-specific factors that remain to be identified could interact with HES4 to precipitate striatal degeneration.

Moreover, it is described herein that there is a strong correlation between HES4 DNA intermediate methylation and age of onset of HD. Importantly this correlation is independent of CAG repeat, indicating that HES4 may represent an epigenetic modifier of HD. Without wishing to be bound by theory, it is contemplated herein that certain environmental exposures alter DNA methylation of the HES4 gene, leading to altered gene expression in the Notch signaling pathway in some individuals. Such epigenetic modifications can in turn interact with other genetic susceptibility and facilitate HD pathogenesis.

In summary, the results described herein indicate that genome-wide alterations in H3K4me3 methylation in HD compared to control neurons affect more than 136 loci, including HES4 and other Notch pathway regulator. Loss of the open chromatin mark, H3K4me3, is associated with a corresponding increase in (repressive) DNA cytosine methylation, resulting in down-regulated promoter activity and expression of the HES4 gene and two of its downstream targets (Mash1, and p21, both important regulators of the Notch signaling pathway and pivotal for striatal neuronal development and differentiation (Bertrand et al., 2002, Kageyama et al., 2008). Lastly, it is described herein that the degree of CGI methylation of the HES4 promoter is strongly correlated with measures of striatal involvement in HD brain samples, independent of effects of CAG repeat-size. If pharmacological and genetic manipulations of HES4 and Notch signaling in cultured human cells validate a causal role of HES4 and Notch signaling in HD pathogenesis, this finding uncovers the epigenetic modulation of the Notch signaling as a novel therapeutic target to reverse its pathogenesis process or postpone HD age of onset.

REFERENCES

Akbarian S, Huang H S. Epigenetic regulation in human brain-focus on histone lysine methylation. Biological psychiatry. 2009; 65(3):198-203.

Bai G, Kusiak J W. Functional analysis of the proximal 5'-flanking region of the N-methyl-D-aspartate receptor subunit gene, NMDAR1. J Biol Chem. 1995; 270(13): 7737-44.

Bertrand N, Castro D S, Guillemot F. Proneural genes and the specification of neural cell types. Nature reviews Neuroscience. 2002; 3(7):517-30.

Brooks D J. The clinical role of PET in cerebrovascular disease. Neurosurgical review. 1991; 14(2):91-6.

Brooks D J. Detection of preclinical Parkinson's disease with PET. Geriatrics. 1991; 46 Suppl 1:2530.

Casarosa S, Fode C, Guillemot F. Mash1 regulates neurogenesis in the ventral telencephalon. Development. 1999; 126(3):525-34.

Cheung I, Shulha H P, Jiang Y, Matevossian A, Wang J, Weng Z, et al. Developmental regulation and individual differences of neuronal H3K4me3 epigenomes in the prefrontal cortex. Proc Natl Acad Sci USA. 107(19): 8824-9.

Cheung I, Shulha H P, Jiang Y, Matevossian A, Wang J, Weng Z, et al. Developmental regulation and individual differences of neuronal H3K4me3 epigenomes in the prefrontal cortex. Proceedings of the National Academy of Sciences of the United States of America. 2010; 107(19):8824-9.

Cussac D, Newman-Tancredi A, Duqueyroix D, Pasteau V, Millan M J. Differential activation of Gq/11 and Gi(3) proteins at 5-hydroxytryptamine(2C) receptors revealed by antibody capture assays: influence of receptor reserve and relationship to agonist-directed trafficking. Molecular pharmacology. 2002; 62(3):578-89.

Diguet E, Fernagut P O, Scherfler C, Wenning G, Tison F. Effects of riluzole on combined MPTP+3-nitropropionic acid-induced mild to moderate striatonigral degeneration in mice. J Neural Transm. 2005; 112(5):613-31.

Djousse L, Knowlton B, Hayden M, Almqvist E W, Brinkman R, Ross C, et al. Interaction of normal and expanded CAG repeat sizes influences age at onset of Huntington disease. Am J Med Genet A. 2003; 119A(3):279-82.

Dompierre J P, Godin J D, Charrin B C, Cordelieres F P, King S J, Humbert S, et al. Histone deacetylase 6 inhibition compensates for the transport deficit in Huntington's disease by increasing tubulin acetylation. The Journal of neuroscience: the official journal of the Society for Neuroscience. 2007; 27(13):3571-83.

Eidelberg D, Surmeier D J. Brain networks in Huntington disease. The Journal of clinical investigation. 2011; 121(2):484-92.

El Yakoubi W, Borday C, Hamdache J, Parain K, Tran H T, Vleminckx K, et al. Hes4 controls proliferative properties of neural stem cells during retinal ontogenesis. Stem Cells. 2012; 30(12):2784-95.

Ferrante R J, Kubilus J K, Lee J, Ryu H, Beesen A, Zucker B, et al. Histone deacetylase inhibition by sodium butyrate chemotherapy ameliorates the neurodegenerative phenotype in Huntington's disease mice. The Journal of neuroscience: the official journal of the Society for Neuroscience. 2003; 23(28):9418-27.

Finch N, Carrasquillo M M, Baker M, Rutherford N J, Coppola G, Dejesus-Hernandez M, et al. TMEM106B regulates progranulin levels and the penetrance of FTLD in GRN mutation carriers. Neurology. 2011; 76(5):467-74.

Gao Z G, Verzijl D, Zweemer A, Ye K, Goblyos A, Ijzerman A P, et al. Functionally biased modulation of A(3) adenosine receptor agonist efficacy and potency by imidazoquinolinamine allosteric enhancers. Biochemical pharmacology. 2011; 82(6):658-68.

Group THsDCR. A novel gene containing a trinucleotide repeat that is expanded and unstable on Huntington's disease chromosomes. The Huntington's Disease Collaborative Research Group. Cell. 1993; 72(6):971-83.

Gusella J F, MacDonald M E. Huntington's disease: seeing the pathogenic process through a genetic lens. Trends in biochemical sciences. 2006; 31(9):533-40.

Gusella J F, MacDonald M E. Huntington's disease: the case for genetic modifiers. Genome medicine. 2009; 1(8):80.

Guttman M, Amit I, Garber M, French C, Lin M F, Feldser D, et al. Chromatin signature reveals over a thousand highly conserved large non-coding RNAs in mammals. Nature. 2009; 458(7235):223-7.

Hadzi T C, Hendricks A E, Latourelle J C, Lunetta K L, Cupples L A, Gillis T, et al. Assessment of cortical and striatal involvement in 523 Huntington disease brains. Neurology. 2012; 79(16):170815.

Han I, You Y, Kordower J H, Brady S T, Morfini G A. Differential vulnerability of neurons in Huntington's disease: the role of cell type-specific features. Journal of neurochemistry. 2010; 113(5):1073-91.

Hodges A, Strand A D, Aragaki A K, Kuhn A, Sengstag T, Hughes G, et al. Regional and cellular gene expression changes in human Huntington's disease brain. Human molecular genetics. 2006; 15(6):965-77.

Holemon H, Korshunova Y, Ordway J M, Bedell J A, Citek R W, Lakey N, et al. MethylScreen: DNA methylation density monitoring using quantitative PCR. BioTechniques. 2007; 43(5):683-93. Huang H S, Matevossian A, Jiang Y, Akbarian S. Chromatin immunoprecipitation in postmortem brain. Journal of neuroscience methods. 2006; 156(1-2):284-92.

Huang H S, Matevossian A, Whittle C, Kim S Y, Schumacher A, Baker S P, et al. Prefrontal dysfunction in schizophrenia involves mixed-lineage leukemia 1-regulated histone methylation at GABAergic gene promoters. The Journal of neuroscience: the official journal of the Society for Neuroscience. 2007; 27(42):11254-62.

Jakovcevski M, Akbarian S. Epigenetic mechanisms in neurological disease. Nature medicine. 2012; 18(8):1194-204.

Jhas S, Ciura S, Belanger-Jasmin S, Dong Z, Llamosas E, Theriault F M, et al. Hes6 inhibits astrocyte differentiation and promotes neurogenesis through different mechanisms. The Journal of neuroscience: the official journal of the Society for Neuroscience. 2006; 26(43):11061-71.

Jiang Y, Matevossian A, Huang H S, Straubhaar J, Akbarian S. Isolation of neuronal chromatin from brain tissue. BMC neuroscience. 2008; 9:42.

Kageyama R, Ohtsuka T, Kobayashi T. Roles of Hes genes in neural development. Development, growth & differentiation. 2008; 50 Suppl 1:S97-103.

Katritch V, Cherezov V, Stevens R C. Structure-function of the G protein-coupled receptor superfamily. Annual review of pharmacology and toxicology. 2013; 53:531-56.

Li B, Carey M, Workman J L. The role of chromatin during transcription. Cell. 2007; 128(4):70719.

Martin J B, Gusella J F. Huntington's disease. Pathogenesis and management. N Engl J Med. 1986; 315(20):1267-76.

Matevossian A, Akbarian S. Neuronal nuclei isolation from human postmortem brain tissue. Journal of visualized experiments: JoVE. 2008(20).

Maunakea A K, Nagarajan R P, Bilenky M, Ballinger T J, D'Souza C, Fouse S D, et al. Conserved role of intragenic DNA methylation in regulating alternative promoters. Nature. 2010; 466(7303):253-7.

Moores J N, Roy S, Nicholson D W, Staveley B E. Huntingtin interacting protein 1 can regulate neurogenesis in *Drosophila*. The European journal of neuroscience. 2008; 28(3):599-609.

Myers R H, Vonsattel J P, Paskevich P A, Kiely D K, Stevens T J, Cupples L A, et al. Decreased neuronal and increased oligodendroglial densities in Huntington's disease caudate nucleus. Journal of neuropathology and experimental neurology. 1991; 50(6):729-42.

O'Keeffe G W, Gutierrez H, Pandolfi P P, Riccardi C, Davies A M. NGF-promoted axon growth and target innervation requires GITRL-GITR signaling. Nature neuroscience. 2008; 11(2):135-42.

Paciorkowski A R, Darras B T. Making sense of genetic heterogeneity: Emergence of pathways in developmental brain disorders. Neurology. 2013; 80(5):426-7.

Pan G, Tian S, Nie J, Yang C, Ruotti V, Wei H, et al. Whole-genome analysis of histone H3 lysine 4 and lysine 27 methylation in human embryonic stem cells. Cell stem cell. 2007; 1(3):299312.

Pasini D, Hansen K H, Christensen J, Agger K, Cloos P A, Helin K. Coordinated regulation of transcriptional repression by the RBP2 H3K4 demethylase and Polycomb-Repressive Complex 2. Genes & development. 2008; 22(10):1345-55.

Peachey N S, Ray T A, Florijn R, Rowe L B, Sjoerdsma T, Contreras-Alcantara S, et al. GPR179 is required for depolarizing bipolar cell function and is mutated in autosomal-recessive complete congenital stationary night blindness. American journal of human genetics. 2012; 90(2):331-9. Petretto E, Mangion J, Dickens N J, Cook S A, Kumaran M K, Lu H, et al. Heritability and tissue specificity of expression quantitative trait loci. PLoS genetics. 2006; 2(10):e172.

Rabadan M A, Cayuso J, Le Dreau G, Cruz C, Barzi M, Pons S, et al. Jagged2 controls the generation of motor neuron and oligodendrocyte progenitors in the ventral spinal cord. Cell death and differentiation. 2012; 19(2):209-19.

Rajagopal S, Rajagopal K, Lefkowitz R J. Teaching old receptors new tricks: biasing seven-transmembrane receptors. Nature reviews Drug discovery. 2010; 9(5):373-86.

Rodriguez P Q, Lohkamp B, Celsi G, Mache C J, Auer-Grumbach M, Wernerson A, et al. Novel INF2 mutation p. L77P in a family with glomerulopathy and Charcot-Marie-Tooth neuropathy. Pediatr Nephrol. 2013; 28(2): 339-43.

Rutherford N J, Carrasquillo M M, Li M, Bisceglio G, Menke J, Josephs K A, et al. TMEM106B risk variant is implicated in the pathologic presentation of Alzheimer disease. Neurology. 2012; 79(7):717-8.

Ryman-Rasmussen J P, Griffith A, Oloff S, Vaidehi N, Brown J T, Goddard W A, 3rd, et al. Functional selectivity of dopamine D1 receptor agonists in regulating the fate of internalized receptors. Neuropharmacology. 2007; 52(2): 562-75.

Ryu H, Lee J, Hagerty S W, Soh B Y, McAlpin S E, Cormier K A, et al. ESET/SETDB1 gene expression and histone H3 (K9) trimethylation in Huntington's disease. Proceedings of the National Academy of Sciences of the United States of America. 2006; 103(50):19176-81. Ryu H, Lee J, Olofsson B A, Mwidau A, Deodeoglu A, Escudero M, et al. Histone deacetylase inhibitors prevent oxidative neuronal death independent of expanded polyglutamine repeats via an Sp1-dependent pathway. Proceedings of the National Academy of Sciences of the United States of America. 2003; 100(7):4281-6.

Santos-Rosa H, Schneider R, Bannister A J, Sherriff J, Bernstein B E, Emre N C, et al. Active genes are trimethylated at K4 of histone H3. Nature. 2002; 419(6905): 407-11.

Scherfler C, Khan N L, Pavese N, Eunson L, Graham E, Lees A J, et al. Striatal and cortical pre- and postsynaptic dopaminergic dysfunction in sporadic parkin-linked parkinsonism. Brain: a journal of neurology. 2004; 127(Pt 6):1332-42.

Seong I S, Woda J M, Song J J, Lloret A, Abeyrathne P D, Woo C J, et al. Huntingtin facilitates polycomb repressive complex 2. Hum Mol Genet. 19(4):573-83.

Seong I S, Woda J M, Song J J, Lloret A, Abeyrathne P D, Woo C J, et al. Huntingtin facilitates polycomb repressive complex 2. Human molecular genetics. 2010; 19(4):573-83.

Seredenina T, Luthi-Carter R. What have we learned from gene expression profiles in Huntington's disease? Neurobiology of disease. 2012; 45(1):83-98.

Shulha H P, Cheung I, Whittle C, Wang J, Virgil D, Lin C L, et al. Epigenetic signatures of autism: trimethylated H3K4 landscapes in prefrontal neurons. Archives of general psychiatry. 2012; 69(3):314-24.

Steffan J S, Bodai L, Pallos J, Poelman M, McCampbell A, Apostol B L, et al. Histone deacetylase inhibitors arrest polyglutamine-dependent neurodegeneration in *Drosophila*. Nature. 2001; 413(6857):739-43.

Steffan J S, Kazantsev A, Spasic-Boskovic O, Greenwald M, Zhu Y Z, Gohler H, et al. The Huntington's disease protein interacts with p53 and CREB-binding protein and represses transcription. Proceedings of the National Academy of Sciences of the United States of America. 2000; 97(12):6763-8.

Sun X J, Wei J, Wu X Y, Hu M, Wang L, Wang H H, et al. Identification and characterization of a novel human histone H3 lysine 36-specific methyltransferase. J Biol Chem. 2005; 280(42):3526171.

Tai Y F, Scherfler C, Brooks D J, Sawamoto N, Castiello U. The human premotor cortex is 'mirror' only for biological actions. Current biology: CB. 2004; 14(2):117-20.

Thathiah A, Horre K, Snellinx A, Vandewyer E, Huang Y, Ciesielska M, et al. beta-arrestin 2 regulates Abeta generation and gamma-secretase activity in Alzheimer's disease. Nature medicine. 2013; 19(1):43-9.

Thomas E A, Coppola G, Desplats P A, Tang B, Soragni E, Burnett R, et al. The HDAC inhibitor 4b ameliorates the disease phenotype and transcriptional abnormalities in Huntington's disease transgenic mice. Proc Natl Acad Sci USA. 2008; 105(40):15564-9.

Urban J D, Clarke W P, von Zastrow M, Nichols D E, Kobilka B, Weinstein H, et al. Functional selectivity and classical concepts of quantitative pharmacology. The Journal of pharmacology and experimental therapeutics. 2007; 320(1):1-13.

van Roon-Mom W M, Hogg V M, Tippett U, Faull R L. Aggregate distribution in frontal and motor cortex in Huntington's disease brain. Neuroreport. 2006; 17(6): 667-70.

Vashishtha M, Ng C W, Yildirim F, Gipson T A, Kratter I H, Bodai L, et al. Targeting H3K4 trimethylation in Huntington disease. Proceedings of the National Academy of Sciences of the United States of America. 2013; 110(32): E3027-36.

Venkatakrishnan A J, Deupi X, Lebon G, Tate C G, Schertler G F, Babu M M. Molecular signatures of G-protein-coupled receptors. Nature. 2013; 494(7436):185-94.

Verzijl D, Ijzerman A P. Functional selectivity of adenosine receptor ligands. Purinergic signalling. 2011; 7(2): 171-92.

Vonsattel J P, DiFiglia M. Huntington disease. Journal of neuropathology and experimental neurology. 1998; 57(5): 369-84.

Wood H B. TMEM106B is a susceptibility locus for Ftld. Nature reviews Neurology. 2010; 6(4): 184.

Xu L G, Li L Y, Shu H B. TRAF7 potentiates MEKK3-induced AP1 and CHOP activation and induces apoptosis. The Journal of biological chemistry. 2004; 279(17): 17278-82.

Zhou V W, Goren A, Bernstein B E. Charting histone modifications and the functional organization of mammalian genomes. Nature reviews Genetics. 2011; 12(1):7-18.

TABLE 1

Demographics of HD and control brains: Brain Samples analyzed for FACS-ChI P-sequencing. (Table 1 discloses the 'CAG Repeat' sequences as SEQ ID NOS 31, 31-34 and 33, respectively, in order of appearance).

| HD ID | Death | Onset | Duration | CAG Repeat Size | PMI (hours) | Striatal Score | Control ID | Death | PMI (hours) |
|---|---|---|---|---|---|---|---|---|---|
| HD-1 | 55 | 44 | 11 | 45 | 37 | 2.66 | C-1 | 55 | 40 |
| HD-2 | 56 | 40 | 16 | 45 | 19 | 2.66 | C-2 | 56 | 17 |
| HD-3 | 71 | 52 | 19 | 43 | 21 | 2.43 | C-3 | 71 | 24 |
| HD-4 | 69 | 50 | 19 | 42 | 19 | 2.48 | C-4 | 69 | 18 |
| HD-5 | 43 | 28 | 15 | 49 | 21 | 2.70 | C-5 | 43 | 12 |
| HD-6 | 68 | 45 | 23 | 42 | 4 | 2.67 | | | |

TABLE 2

Demographics of HD and control brains: Brain Samples analyzed for DNA methylation. (Table 2 discloses the 'CAG Repeat' sequences as SEQ ID NOS 32-34, 33, 35-38, 31, 31, 36, 39-41, 36, 32, 38, 33, 33, 33, 34, 39, 31 and 42, respectively, in order of appearance)

| HD ID | Death | Onset | Duration | CAG Repeat Size | PMI (hours) | Striatal Score | Control ID | Death | PMI (hours) |
|---|---|---|---|---|---|---|---|---|---|
| HD-3 | 71 | 52 | 19 | 43 | 21 | 2.43 | C-8 | 69 | 15 |
| HD-4 | 69 | 50 | 19 | 42 | 19 | 2.48 | C-9 | 54 | 24 |
| HD-5 | 43 | 28 | 15 | 49 | 21 | 2.70 | C-10 | 61 | 10 |
| HD-6 | 68 | 45 | 23 | 42 | 4 | 2.67 | C-12 | 44 | 28 |
| HD-7 | 89 | 70 | 19 | 40 | 57 | 3.33 | C-13 | 53 | 24 |
| HD-8 | 69 | 63 | 6 | 41 | 6 | 2.64 | C-14 | — | — |
| HD-9 | 67 | 40 | 27 | 44 | 14 | 3.33 | C-15 | 57 | 20 |
| HD-10 | 61 | 35 | 26 | 46 | 25 | 3.58 | C-16 | 43 | 15 |
| HD-11 | 63 | 40 | 23 | 45 | 21 | 2.74 | C-17 | 52 | 23 |
| HD-12 | 62 | 40 | 22 | 45 | 28 | 3.58 | C-18 | 58 | 20 |
| HD-13 | 76 | 58 | 18 | 41 | 7 | — | C-19 | 70 | 21 |
| HD-14 | 48 | 25 | 23 | 48 | 19 | 3.82 | C-20 | 46 | 30 |
| HD-15 | 49 | 34 | 6 | 51 | — | 3.52 | C-21 | 66 | 17 |
| HD-16 | 55 | 31 | 24 | 47 | 24 | — | C-23 | 36 | 21 |
| HD-17 | 72 | 55 | 17 | 41 | 8 | 2.59 | C-24 | 60 | 24 |
| HD-18 | 67 | 48 | 19 | 43 | 22 | 2.74 | C-25 | 54 | 24 |
| HD-19 | 59 | 35 | 24 | 46 | 6 | 2.62 | C-27 | 61 | 17 |
| HD-20 | 72 | 55 | 17 | 42 | 12 | 2.74 | C-28 | 62 | 18 |
| HD-21 | 78 | 62 | 16 | 42 | 18 | — | C-29 | 55 | 26 |
| HD-22 | 66 | 52 | 15 | 42 | 13 | 2.66 | C-30 | 52 | 16 |
| HD-23 | 57 | 40 | 17 | 49 | 25 | 2.91 | C-31 | 69 | 26 |
| HD-24 | 53 | 40 | 13 | 48 | 23 | 3.60 | C-32 | 61 | 25 |
| HD-25 | 48 | 38 | 10 | 45 | 11 | 3.60 | C-33 | 64 | 19 |
| HD-20 | 36 | 24 | 12 | 54 | 21 | 2.91 | C-34 | 68 | 11 |
| | | | | | | | C-35 | 71 | 40 |
| | | | | | | | C-36 | 68 | 25 |

TABLE 3

Demographics of HD and control brains: Brain Samples analyzed for VCR analysis of mRNA. (Table 3 discloses the 'CAG Repeat' sequences as SEQ ID NOS 31, 32-34, 33, 36, 41, 36, 38, 33, 33, 39, 31 and 42, respectively, in order of appearance)

| HD ID | Death | Onset | Duration | CAG Repeat Size | PMI (hours) | Striatal Score | Control ID | Death | PMI (hours) |
|---|---|---|---|---|---|---|---|---|---|
| HD-2 | 56 | 40 | 16 | 45 | 19 | 2.66 | C-10 | 61 | 10 |
| HD-3 | 71 | 52 | 19 | 43 | 21 | 2.43 | C-11 | 68 | 19 |
| HD-4 | 69 | 50 | 19 | 42 | 19 | 2.48 | C-12 | 44 | 28 |
| HD-5 | 43 | 28 | 15 | 49 | 21 | 2.7 | C-13 | 53 | 24 |
| HD-6 | 68 | 45 | 23 | 42 | 4 | 2.67 | C-15 | 57 | 20 |
| HD-8 | 69 | 63 | 6 | 41 | 6 | 2.64 | C-18 | 58 | 20 |
| HD-16 | 55 | 31 | 24 | 47 | 24 | — | C-19 | 70 | 21 |
| HD-17 | 72 | 55 | 17 | 41 | 8 | 2.59 | C-22 | 73 | 19 |
| HD-19 | 59 | 35 | 24 | 46 | 6 | 2.62 | C-24 | 60 | 24 |
| HD-21 | 78 | 62 | 16 | 42 | 18 | — | C-26 | 76 | 26 |
| HD-22 | 68 | 52 | 16 | 42 | 13 | 2.66 | C-28 | 62 | 18 |
| HD-24 | 53 | 40 | 13 | 48 | 23 | 3.6 | C-31 | 69 | 26 |

TABLE 3-continued

Demographics of HD and control brains: Brain Samples analyzed for VCR analysis of mRNA. (Table 3 discloses the 'CAG Repeat' sequences as SEQ ID NOS 31, 32-34, 33, 36, 41, 36, 38, 33, 33, 39, 31 and 42, respectively, in order of appearance)

| HD ID | Death | Onset | Duration | CAG Repeat Size | PMI (hours) | Striatal Score | Control ID | Death | PMI (hours) |
|---|---|---|---|---|---|---|---|---|---|
| HD-25 | 48 | 38 | 10 | 45 | 11 | 3.6 | C-34 | 88 | 11 |
| HD-26 | 36 | 24 | 12 | 54 | 21 | 2.91 | C-37 | 93 | 13 |

TABLE 4

H3K4me3 is altered at 78 loci in HD cortical neurons, compared to control neurons

| TSS | bp from TSS | FDR | functions |
|---|---|---|---|
| FLJ37505 | 424827 | 0.00095 | |
| KIAA1274 | 0 | 0.003032 | |
| LOC150381 | 0 | 0.007708 | |
| CLEC2L | 0 | 0.008317 | |
| N4BP3 | 0 | 0.008933 | |
| WTIP | 0 | 0.0091 | |
| LOC100128338 | 0 | 0.009306 | |
| HES4 | 0 | 0.010717 | regulator of neural stem cell proliferation |
| C6orf27 | 0 | 0.011361 | |
| NR4A1 | 10907 | 0.011401 | nuclear receptor-related transcription factor implicated in neuroprotection; |
| DSG2 | 0 | 0.011468 | |
| LGI2 | 0 | 0.011903 | |
| RCOR2 | 0 | 0.011928 | Rest Co-repressor 2, chromatin regulator in neuronal progenitor and differentiated neurons |
| GPR3 | 0 | 0.012389 | orphan GPCR modulating beta-amyloid and neurodegeneration |
| HBQ1 | 0 | 0.012418 | |
| HAGHL | 0 | 0.012435 | |
| JAG2 | 395 | 0.012692 | Notch receptor ligand Jagged 2, implicated in generation of motor neurons. |
| PPIC | 0 | 0.012768 | |
| AGRN | 19672 | 0.013164 | synaptogenesis and plasticity in CNS, key neuromuscular junction protein |
| INF2 | 0 | 0.013428 | inverted formin, a monogenic risk gene for Charcot-Marie-Tooth neuropathy |
| CYP2S1 | 0 | 0.013508 | |
| AGRN | 12379 | 0.013611 | synaptogenesis and plasticity in CNS, key neuromuscular junction protein |
| FBXL16 | 2707 | 0.014108 | |
| SBK1 | 30099 | 0.014205 | |
| COX7B | 0 | 0.017647 | |
| PDZRN3 | 62936 | 0.017812 | |
| SLC22A18 | 0 | 0.018312 | |
| VRK1 | 235498 | 0.018385 | monogenic causative gene for postnatal progressive microcephaly syndromes |
| RAMP3 | 0 | 0.019827 | |
| MIR1257 | 11074 | 0.02064 | |
| KIAA0182 | 146622 | 0.021665 | interacting with the Disrupted in Schizophrenia (DISC1) protein |
| DAB2IP | 0 | 0.022503 | a GTPase regulator involved in neuronal migration and growth |
| SUC27A5 | 1597 | 0.022839 | |
| MFSD10 | 0 | 0.023099 | |
| MIDN | 1136 | 0.024418 | nucleolar protein with uniquitin-like domain essential for midbrain development |
| NR4A1 | 0 | 0.025514 | nuclear receptor-related transcription factor implicated in neuroprotection; |
| NCR2 | 91854 | 0.026221 | |
| SCN2A | 0 | 0.027429 | sodium channel and monogenic neurodevelopmental risk gene |
| MTRF1 | 0 | 0.027521 | |
| IL1RAPL1 | 0 | 0.027891 | IL 1 receptor accessory protein-like 1, a neurodevelopmental risk gene |
| GPM6B | 0 | 0.027939 | |
| SLC26A1 | 3435 | 0.028238 | |
| PHLDA2 | 0 | 0.028441 | |
| FOS | 0 | 0.028532 | early response gene involved in activity-regulated gene expression |
| C19orf26 | 0 | 0.028861 | |
| RHBDL1 | 0 | 0.028904 | |
| TMEM200B | 0 | 0.029384 | |
| ANXA1 | 71133 | 0.029836 | |
| NFIX | 0 | 0.03029 | nuclear protein regulating neural progenitor differentiation in hippocampus |
| BHLHE40 | 3320 | 0.030664 | a bHLH transcription factor and key component of the circadian clock |
| CHRNA1 | 76396 | 0.030809 | nicotinic acetylcholine receptor important for axonal development |
| BAI1 | 46840 | 0.03169 | angiogenesis inhibitor 1, interacts with LRRK2 kinase |
| HHATL | 0 | 0.031888 | |
| HMGN4 | 13970 | 0.032202 | |
| BRSK2 | 19307 | 0.032585 | BRSK2ISAD defines neuronal polarization and axon growth in cerebral cortex |
| UNC5A | 6354 | 0.033538 | |
| GNG13 | 0 | 0.034882 | |
| NPAS4 | 0 | 0.034984 | an activity-dependent TF critical for memory and inhibitory synape formation |
| ARHGAP21 | 100221 | 0.036119 | |

TABLE 4-continued

H3K4me3 is altered at 78 loci in HD cortical neurons, compared to control neurons

| TSS | bp from TSS | FDR | functions |
|---|---|---|---|
| TRAF7 | 2580 | 0.037034 | encodes TNF receptor-associated protein that regulates apoptosis |
| KCNN1 | 0 | 0.037202 | calcium-activated potassium channel SK-1, implicated in neuroprotection |
| R3HDM1 | 54329 | 0.037236 | |
| KRT222 | 0 | 0.037633 | |
| LOXL4 | 0 | 0.038798 | |
| CRHR2 | 0 | 0.039414 | corticotropin releasing hormone receptor 2 |
| ETV4 | 0 | 0.039599 | |
| ADRA1D | 0 | 0.039638 | adrenergic receptor 1D, expressed in forebrain |
| C1orf187 | 0 | 0.041943 | neural-specific antagonist to WNT signaling and axon guidance molecule |
| RNF126 | 3401 | 0.043223 | |
| FLRT3 | 0 | 0.044157 | repulsive axon guidance cue |
| PDIA6 | 23739 | 0.04494 | a isomerase interacting with progranulin, involved in frontotemporal demenlia |
| LINGO3 | 0 | 0.045575 | |
| ARC | 1715 | 0.045616 | activity-regulated early response gene with key role in synaptic plasticity |
| SNRPN | 382 | 0.046931 | small nuclear riboprotein-associated protein N highly expressed in neurons |
| IL2RB | 16371 | 0.047114 | |
| SPRED2 | 0 | 0.047645 | |
| MIR3675 | 11662 | 0.047801 | |
| GOLT1A | 62360 | 0.049324 | |

TABLE 5

Spearman correlation of methylation levels with HD sample characteristics.

| | Hyper-Methylation | Intermediate Methylation | Un-Methylated |
|---|---|---|---|
| Striatal Involvement | −0.22 | 0.56 | −0.36 |
| (p-value) | 0.32 | 0.006 | 0.10 |
| (n) | (22) | (22) | (22) |
| Cortical Involvement | −0.33 | 0.09 | 0.06 |
| (p-value) | 0.13 | 0.69 | 0.79 |
| (n) | (22) | (22) | (22) |
| Death Age | 0.063 | −0.47 | 0.35 |
| (p-value) | 0.77 | 0.02 | 0.08 |
| (n) | (25) | (25) | (25) |
| Onset Age | −0.037 | −0.48 | 0.39 |
| (p-value) | 0.87 | 0.02 | 0.0661 |
| (n) | (23) | (23) | (23) |
| HD CAG Repeat | −0.15 | 0.50 | −0.35 |
| (p-value) | 0.47 | 0.01 | 0.08 |
| (n) | (25) | (25) | (25) |
| Duration | −0.19 | 0.24 | −0.27 |
| (p-value) | 0.38 | 0.26 | 0.21 |
| (n) | (23) | (23) | (23) |

Example 3: miR-10b-5p in Huntington's Disease

Much like the findings for the HES4 gene, the micro-RNA miR-10b-5p is found to be dramatically differentially expressed in Huntington disease brains when compared to control brain samples in studies of the prefrontal cortex. The miR-10b-5p is also very strongly associated with the extent of involvement in the striatum, and this relationship persists after adjustment for the CAG repeat size. MiR-10b-5p controls neurite outgrowth or the sprouting of axonal projections from neurons.

It is specifically contemplated herein that:
1. MiR-10b-5p may provide a method to estimate the proximity to onset for persons who carry risk factors for Huntington's Disease.
2. MiR-10b-5p can be a target for treating diseases other than HD. For example, because miR-10b-5p stimulates neurons to produce axonal projects, it can be a therapeutic target for either (a) spinal cord injury, or (b) stroke. For example, the expression of miR-10b-5p can be manipulated to treat spinal cord injury, nerve damage, or stroke. The stimulation of neurons to send projecting axons across damaged regions of the nervous system by altering the expression of microRNAs or the genes under their control can be a method of treatment. MicroRNAs have recently been targeted as candidates for therapeutic intervention in several diseases. Pencheva et al. (Cell 2012 2012 151:1068-1082) used locked nucleic acids to target microRNAs to inhibit melanoma metastases. Boon et al. (Nature 2013 495:107-10) showed that in vivo silencing of microRNAs can improve cardiac aging and health. Alternatively, genes that are regulated by microRNAs implicated in disease have been identified and these have been targeted for therapeutic intervention. For example the MED13 gene is regulated by miR-208a, and the overexpression of MED13 or the inhibition of miR-108a confer resistance to high-fat diet induced obesity (Grueter et al. Cell 2012 149:671-683.
3. MiR-10b-5p is associated with the extent of neuronal death in Huntington's disease and consequently those drugs that modify the levels of miR-10b-5p have a role in rectifying the deficits that lead to neuronal cell death. Consequently miR-10b-5p inhibitors and/or antagonists (e.g. inhibitory nucleic acids) can be treatments for Huntingon's Disease.
4. MiR-10b-5p can be, as detected in other tissues, such as blood, a biomarker for the disease. Because miR-10b-5p is associated with the extent of neuronal cell death in the striatum, it can serve as an indicator for whether drugs used in clinical trials are actually altering the toxic effects of the disease in the brain.

Example 4: microRNAs Located in the Hox Gene Clusters are Implicated in Huntington's Disease Pathogenesis Transcriptional dysregulation has long been recognized as central to the pathogenesis of Huntington's disease (HD). MicroRNAs (miRNAs) represent a major system of post-transcriptional regulation, by either preventing translational initiation or by targeting transcripts for storage or for degradation. Using next-generation miRNA sequencing in prefrontal cortex (Brodmann Area 9) of twelve HD and nine controls, five miRNAs (miR-10b-5p, miR-196a-5p, miR-196b-5p, miR-615-3p and miR-1247-5p) were identified as up-regulated in HD at genome-wide significance (FDR q-value<0.05). Three of these, miR-196a-5p, miR-196b-5p and miR-615-3p, were expressed at near zero levels in control brains. Expression was verified for all five miRNAs using reverse transcription quantitative PCR and all but miR-1247-5p were replicated in an independent sample (8HD/8C). Ectopic miR-10b-5p expression in PC12 HTT-Q73 cells increased survival by MTT assay and cell viability staining suggesting increased expression may be a protective response. All of the miRNAs but miR-1247-5p are located in intergenic regions of Hox clusters. Total mRNA sequencing in the same samples identified fifteen of 55 genes within the Hox cluster gene regions as differentially expressed in HD, and the Hox genes immediately adjacent to the four Hox cluster miRNAs as up-regulated. Pathway analysis of mRNA targets of these miRNAs implicated functions for neuronal differentiation, neurite outgrowth, cell death and survival. In regression models among the HD brains, huntingtin CAG repeat size, onset age and age at death were independently found to be inversely related to miR-10b-5p levels. CAG repeat size and onset age were independently inversely related to miR-196a-5p, onset age was inversely related to miR-196b-5p and age at death was inversely related to miR-615-3p expression. These results suggest these Hox-related miRNAs may be involved in neuroprotective response in HD. Recently, miRNAs have shown promise as biomarkers for human diseases and given their relationship to disease expression, these miRNAs are biomarker candidates in HD.

Huntington's disease (HD) is an inherited fatal neurological disorder that commonly affects people in midlife. Past studies have implicated abnormal patterns gene expression as a candidate for causing the death of the brain cells affected in HD. Micro-RNAs (miRNAs) are small molecules that regulate and target transcripts for either storage or destruction. We measured the levels of miRNAs, as well as the levels of gene expression (mRNAs) in twelve HD and nine control brain samples. We found five miRNAs that had greatly increased expression in the HD brains, including three that were not expressed in the normal samples. Four of these were related to important characteristics of the disease expression, including the age at disease onset, and the age at death of the individual. The genes that these miRNAs target for regulation were also altered in their expression with most being increased, suggesting they may have been targeted for storage. One of the miRNAs, miR-196a-5p was previously implicated in enhancing the survival of brain cells in HD. When we overexpressed miR-10b-5p in an HD cell model, the cells survived longer than untreated cells, suggesting these miRNAs may promote neuron survival and may hold new clues for treatments in HD.

Huntington's disease (HD) (OMIM: 143100) is an inherited neurodegenerative disorder characterized by involuntary movement, dementia, and changes in personality. HD is transmitted as an autosomal dominant disorder, for which an expansion of a CAG trinucleotide repeat within the coding region of the huntingtin gene (HTT) is the disease causing mutation [1]. The CAG repeat codes for a polyglutamine domain in the Htt protein and results in neuronal cell death predominantly affecting the caudate nucleus and putamen although neuronal loss is widespread in the HD brain [2,3]. While the biological processes leading to neurodegeneration in HD are poorly understood, transcriptional dysregulation has long been proposed as central to the pathogenesis of HD. Widespread alterations in gene expression have been reported [4] and several studies suggest that gene expression may be altered at one or more of the stages of RNA processing, translation, protein post-translational modification or trafficking [5,6].

MicroRNAs (miRNAs) are small non-coding RNAs that function as translational regulators of mRNA expression. miRNAs may inhibit gene expression either by repressing translation, or by targeting mRNA for either storage or degradation [7]. Recently, dysregulation of miRNAs has been linked to neurological and neurodegenerative disorders [8] and several studies have explored the role of miRNAs in HD. Marti et al [9] performed miRNA-sequencing for two pooled HD samples and two pooled control samples and reported altered expression for a large number of miRNAs. Altered expression of miRNAs, quantified using microarray technology, has been reported in cellular models of HD [10,11,12] and in mouse models of HD [12,13,14,15] but a comprehensive study of miRNA and mRNA expression obtained through next-generation sequencing technology in human HD samples has not been performed.

In order to investigate (1) the presence of altered miRNA expression and (2) the potential role of miRNAs on the altered mRNA expression seen in HD, both miRNA-sequencing and mRNA sequencing, using Illumina massively parallel sequencing in twelve HD and nine neurologically normal control brains, was performed. To our knowledge this is the first genome-wide quantification of miRNA expression comparing human HD and control brain, and the first to combine total miRNA expression with total mRNA expression obtained through massively parallel sequencing.

Results

Selection of Prefrontal Cortex and BA9.

While the striatum is the region most heavily involved neuropathologically in HD [3], 80% to 90% of the neurons in that region will have degenerated by the time of death. These changes, together with the presence of reactive astrocytosis, alter the cellular composition of the striatum. In contrast, cortical involvement in HD is well defined [2,16] and while it does not experience dramatic neuronal degeneration, cortical neurons are known to exhibit the effects of protein aggregation and nuclear inclusion bodies characteristic of the disease. Therefore, the prefrontal cortex was selected for these studies.

Five miRNAs are Up-Regulated in HD.

Figure 8:
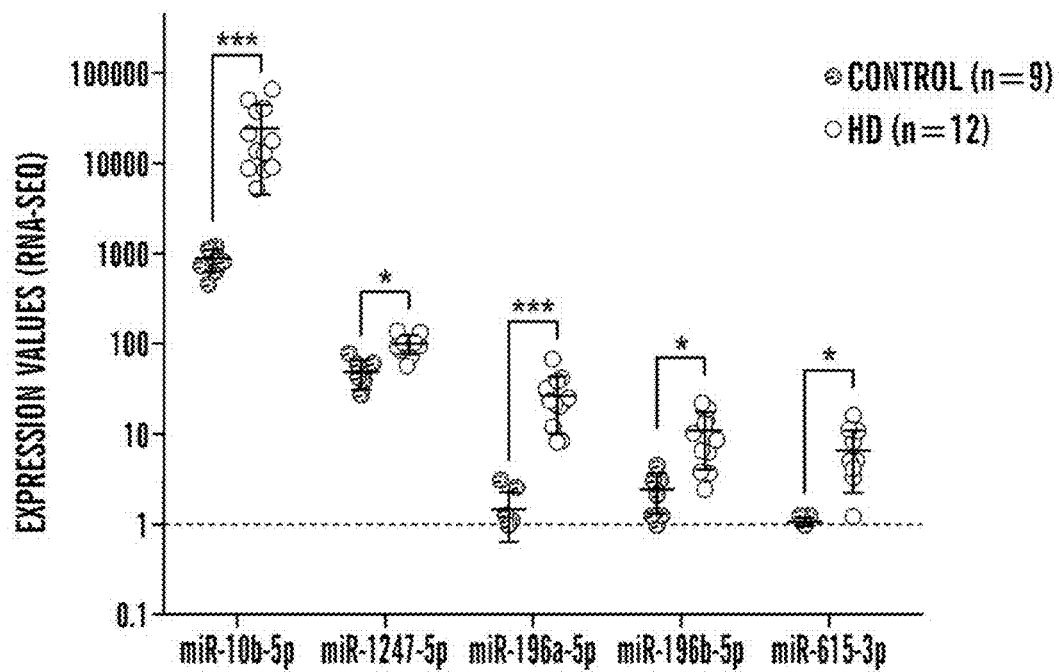
FIG. 8 demonstrates that miR-196a-5p, miR-10b-5p, and miR-615-3p were found significantly differentially expressed in Huntington's disease. miR-10b-5p, miR-1247-5p, miR-196a-5p, miR-196b-5p, and miR-615-3p were identified as differentially expressed in Huntington's disease prefrontal cortex compared to non-neurological disease controls by Illumina miRNA-sequencing. Normalized expression values quantified from DESeq analysis are shown on the y-axis. miR-196a-5p, miR-196b-5p and miR-615-3p were essentially not expressed in control samples, while the mean HD expression was 27.49, 11.01 and 6.66 respectively. miR-1247-5p was expressed at moderate levels in both control (mean=49.44) and HD brain (mean=102.01). miR-10b-5p was expressed in control (mean=915.81) and highly expressed in HD brain (mean=26,020.05). For miRNA, *p<0.05 and ***p<0.001, as determined by DESeq, followed by the Benjamini-Hochberg multiple comparison correction. (HD=Huntington's disease).

After removing sample outliers using principal component analysis filtering, five out of 1,417 detected mature miRNA species were identified as differentially expressed between twelve HD and nine control prefrontal cortex samples using the R statistical package DESeq (Tables 6, 7, and 8 and FIG. 8). All five miRNAs were significantly up-regulated in HD. The largest effect between conditions was seen for miR-10b-5p, with a 28.41 fold increased expression in HD relative to control samples (mean control expression=915.81; mean HD expression=26,020.05, FIG. 1). miR-1247-5p was expressed at moderate levels in both control (mean=49.44) and HD brain (mean=102.01). Three of the miRNAs, miR-196a-5p (mean control expression=1.47; mean HD expression=27.49), miR-196b-5p (mean control expression=2.49; mean HD expression=11.01) and miR-615-3p (mean control expression=1.09, mean HD expression=6.66), had near zero expression levels in all nine control samples.

Validation and Replication of miRNA Findings.

miRNA expression differences were orthogonally validated using the Exiqon miRCURY LNA™ technology for reverse transcription quantitative PCR (RT-qPCR) in eleven of twelve sequenced HD samples and nine control samples originally studied for miRNA-seq. All five miRNAs were confirmed to be significantly up-regulated in HD (data not shown), consistent with the miRNA-sequencing findings.

To replicate these findings in an independent sample set, RT-qPCR was performed in an additional eight control and eight HD prefrontal cortical samples (data not shown). Four out of five miRNA (miR-10b-5p, miR-196a-5p, miR-196b-5p, miR-615-3p) were confirmed as significantly increased in expression in HD (data not shown).

Similar Proportion of Neurons in HD and Control Cortical Brain Homogenate Samples.

HD is characterized by progressive cortical atrophy, with recognizable neuropathologic abnormalities in the neocortical gray matter [2,16,17,18,19,20] (Table 6). To address whether miRNA expression changes in HD may be due to altered ratios in brain cell-type abundance, such as a change in the ratio of neurons to glial cells, the number of neuronal and non-neuronal nuclei was compared across conditions. Suspensions of cell nuclei of prefrontal cortex from 28 HD cases and 19 controls were immunocytochemically labeled with anti-NeuN, a neuron-specific nuclear antigen, followed by flow cytometric analysis. The mean and range of NeuN+ ratios for controls and cases were not significantly different (t=1.67, p-value=0.10; data not shown), suggesting cortical neuron loss in the BA9 area in HD is relatively modest and does not account for the dramatic alterations in miRNA levels reported here.

Increased miR-10b-5p Expression is not Observed in Parkinson's Disease (PD).

To establish whether miR-10b-5p change is a generalized response to neurodegeneration, this miRNA was evaluated in PD prefrontal cortex. While cortical neuronal loss is variable in PD, both PD and HD are neurodegenerative and caused by protein inclusions. PD prefrontal cortex samples were selected that exhibited reported neuron loss on their neuropathological evaluation (n=6) and PD samples without reported cortical neuronal loss (n=8). From total RNA, RT-qPCR was performed for miR-10b-5p (data not shown). No difference was seen in miR-10b-5p expression when stratifying PD based on the extent of neuron loss (t=0.59, p-value=0.58). Additionally, no significant difference in HD miR-10b-5p expression from qPCR was observed when stratifying HD cases based on a measure of cortical neuron loss (f=0.28, p-value=0.76; Table 1).

Figure 9:
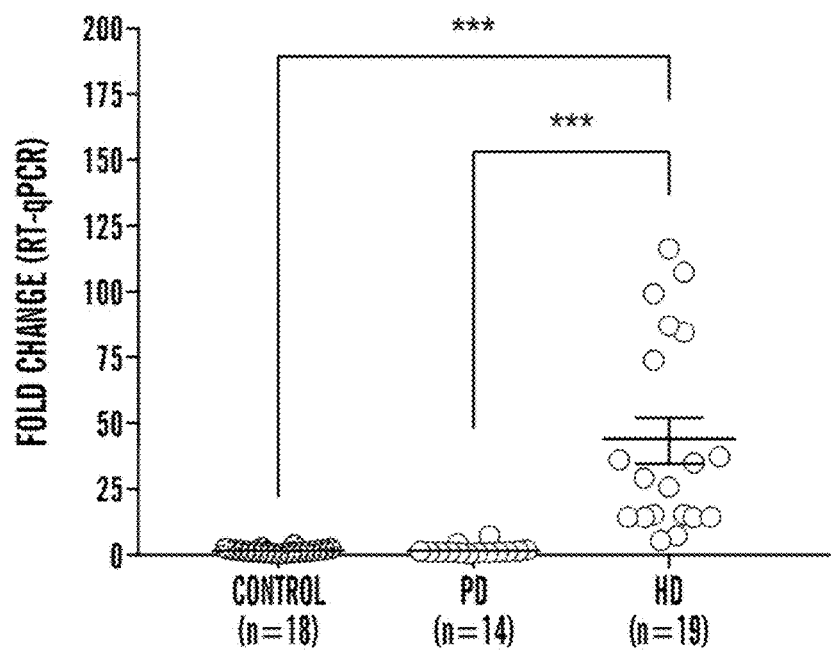
FIG. 9 demonstrates miR-10b-5p expression in control, Parkinson's disease and Huntington's disease prefrontal cortex. Up-regulation of miR-10b-5p was confirmed in HD by performing RT-qPCR, comparing nineteen Huntington's disease prefrontal cortex samples to eighteen non-neurological disease control samples (*p<0.001) or fourteen Parkinson's disease samples (*p<0.001). $\Delta\Delta C_T$ values of miR-10b-5p in PD and HD as compared to controls are shown on the y-axis. The absence of up-regulation in PD frontal cortex indicates that up-regulation of miR-10b-5p can be HD specific. ($C_T$=cycle threshold; RT-qPCR=reverse transcription quantitative PCR; PD=Parkinson's disease; HD=Huntington's disease)

Next, the relative expression of miR-10b-5p in PD was compared to all nineteen HD and eighteen control samples assayed (data not shown). While no significant difference in miR-10b-5p expression was observed between control and PD samples (q=0.05, p=0.99), a significant difference was seen in HD compared to PD (q=7.30, p<0.0001; FIG. 9), suggesting increased miR-10b-5p expression, independent of neuron loss, is not a generalized response to neurodegeneration.

Ectopic miR-10b-5p Expression Protects HD Cell Lines from Polyglutamine-Mediated Cytotoxicity.

To determine the functional importance of miR-10b-5p up-regulation in HD, miR-10b-5p was ectopically expressed in PC12 Q73 cells. These cell stably expressed huntingtin fragment derived from exon 1 (1-90), contain a pathogenic, 73 long polyglutamine repeat and a MYC epitope for protein identification. PC12 cells have been shown to terminally differentiate and form neural processes upon nerve growth factor (NGF) treatment [21], and HD models of these cells have been highly characterized, exhibiting phenotypic changes such as aggregate formation and polyglutamine-dependent cell death [22,23,24,25,26].

Figure 11:
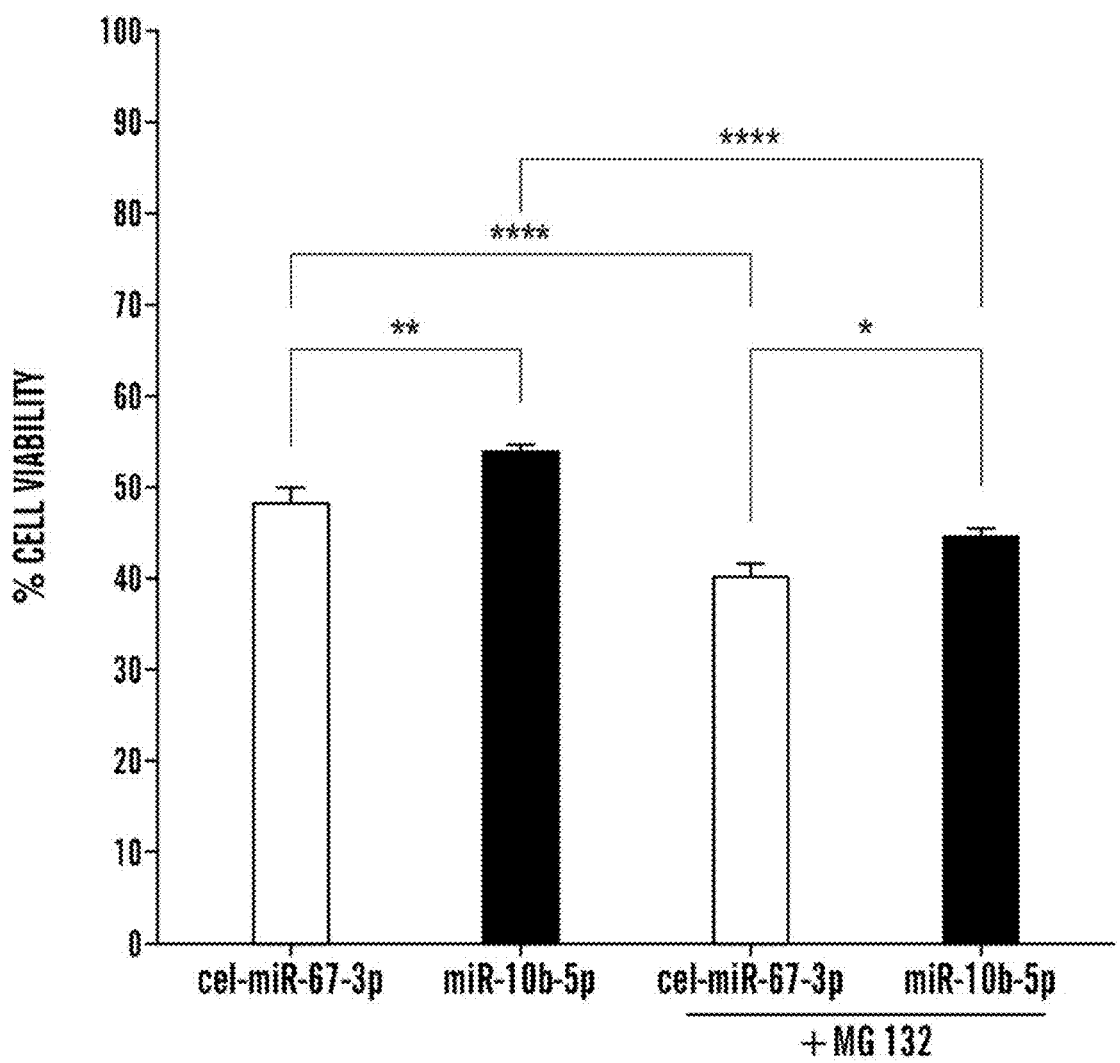
FIG. 11 demonstrates that miR-10b-5p overexpressing PC12 Q73 cells exhibit reduced cytotoxicity PC12 cells expressing huntingtin exon 1 with a polyglutamine expansion spanning 73 repeats were transfected with miR-10b-5p or cel-miR-67-3p as a negative control. On day 3 post-differentiation, a subset of cells were treated with 1 uM MG 132. A MTT assay was used to measure cell viability after four days post differentiation. On the Y-axis, the viability percentage was calculated from the initial cell count. Error bars represent SEM. (**p<0.0001; p<0.001 *p<0.05)

PC12 Q73 cells were transfected with miR-10b-5p mimic or a negative control mimic, cel-miR-67-3p, after 48 hours post-differentiation. Cell survival was quantified using a MTT cell viability assay 48 hours post-transfection. Increased survival, though modest (53.9% versus 48.2%), was statistically higher for cells transfected with miR-10b-5p compared to cells transfected with negative control miRNA (q=4.58, p-value<0.0001; FIG. 11). The enhanced survival via ectopic miR-10b-5p expression was further substantiated in experiments using viable fluorescent cell staining, where miR-10b-5p transfected cells showed increased cell viability over cells transfected with negative control miRNA (t=2.381, p-value=0.018).

Thus, miR-10b-5p may play a protective role in enhancing cell survival during stress. To model stress, miRNA transfected cells were treated with 1 uM MG 132, a potent proteasome inhibitor that increases huntingtin aggregation and cellular apoptosis in PC12 HD cell lines [27]. As expected, MG 132 treated cells had reduced cell viability as compared to untreated cells (cel-miR-67-3p, q=6.52, adjusted p-value<0.0001; miR-10b-5p, q=10.88, adjusted p-value<0.0001). However, MG 132 treated miR-10b-5p transfected PC12 Q73 cells exhibited improved survival over those transfected with negative control miRNA (q=3.728, adjusted p-value=0.045). No statistical difference was observed when comparing miR-10b-5p levels with MG 132 treatment to cel-miR-67-3p without treatment, (q=2.95, adjusted p-value=0.16), suggesting miR-10b-5p may enhance survival in times of cellular stress.

miRNA Expression is Related to Clinical Variables in HD.

RNA sequence count data may be non-normally distributed [28], and tests of normality for miRNA expression levels in HD found that miR-10b-5p was negatively skewed (see Methods). Therefore, to test the relationship of miRNA expression to clinical variables such as CAG repeat size, age at onset of motor symptoms, disease duration and age at death, as well as to the sample quality information for RIN/RQN (RNA integrity number/RNA quality number), a step-wise backwards selection, negative binomial regression model was applied.

Age at onset, duration and age at death are inter-dependent and could not be simultaneously included in the models. Furthermore, age at onset and age at death were strongly correlated with each other (Pearson r=0.85, p-value=5e-04) and both were correlated with CAG repeat size (r=−0.84, p-value=6e-04, and r=−0.89, p-value=1e-04 respectively) while duration was not correlated with age at onset, age at death or CAG repeat size in this sample. To determine which variables best modeled the relationship of the miRNAs to clinical variables, the Akaike information criterion (AIC) for each variable (onset age, death age and duration) was compared in regression analyses that adjusted for the effect of CAG repeat size. Of these three variables, duration was found to have the poorest fit with each of the five miRNAs and therefore analyses containing age at onset and age at death are reported.

Among the HD brains, CAG repeat size, age at onset and age at death were all independently found to have a negative association with miR-10b-5p (CAG, β=−0.18, p-value=2.7e-05; onset, β=−0.05, p-value=1.9e-05; death, β=−0.07, p-value=6.8e-07). CAG repeat size and age at onset were found to be independently, negatively related to miR-196a-5p (CAG, β=−0.15, p-value=1.7e-02; onset, β=−0.07, p-value=1.4e-03). Age at death was significantly related to miR-615-3p expression (β=−0.03, p-value=0.0045) and age at onset was associated with miR-196b-5p (β=−0.04, p-value=9e-04). No association to any clinical features was seen for miR-1247-5p. In order to fully evaluate whether there was any effect of disease duration on the observed relationships to the clinical features, duration was added back into final models. No substantial changes to the effect estimates were observed with the addition of duration to any of the models.

None of the miRNA levels was related to post-mortem interval in either control or HD case samples. The essentially null level of expression in controls prevented meaningful assessment of the relationship of miR-196a-5p, miR-196b-5p and miR-615-3p with clinical variables, in particular age at death, or sample variables, PMI, or RIN/RQN. Analysis of miR-10b-5p showed no association to age at death ($\beta$=−0.002, p-value=0.60), or PMI ($\beta$=−0.014, p-value=0.31), but did show association with RIN/RQN ($\beta$=0.54, p-value=7.2e-05) in controls. miR-1247-5p showed association with later age at death ($\beta$=−0.013, p-value=0.024) in controls.

Expression of miR-10b-5p, miR-196a-5p, miR-196b-5p and miR-615-3p are Correlated.

Among the twelve HD samples, the levels of four out of the five significantly differentially expressed miRNAs (miR-10b-5p, miR-196a-5p, miR-196b-5p, miR-615-3p) were strongly correlated with each other, (Spearman r range 0.71-0.88; p range 0.0002-0.01). miR-1247-5p was not significantly correlated with these miRNAs (Spearman r range 0.13-0.51; p range 0.09-0.70). Because the values of miR-615-3p and miR-196a-5p were essentially zero in the control samples, correlations among the miRNAs were not performed for controls.

mRNA Targets of miR-10b-5p, miR-196a-5p, miR-196b-5p and miR-615-3p May have Similar Functions.

Watson-Crick base-pairing between nucleotide position 2 through 8 on the mature miRNA, termed the 'seed region,' and the 3' untranslated region (3' UTR) of target mRNA determine the recognition, specificity and efficiency of miRNA silencing [29]. Seed sequences differ for miR-10b-5p (ACCCUGU), miR-615-3p (CCGAGCC) and miR-1247-5p (CCCGUCC) suggesting these miRNA have different targets, while miR-196a-5p and miR-196b-5p share a seed sequence (AGGUAGU) and only differ by a single base difference in mature miRNA sequence.

Targets of the five miRNAs were obtained from miRWalk (http://www.umm.uni-heidelberg.de/apps/zmf/mirwalk/index.html), a repository of experimentally validated miRNA targets curated from literature and online resources [30]. miRWalk targets of miR-196a, miR-196b and miR-1247 were not strand specific. The miRWalk database contained 84 unique targets for miR-10b-5p, 80 for miR-196a, 40 for miR-196b, two for miR-1247 and twelve for miR-615-3p. Since miR-1247 had just two validated targets, it was removed from analysis.

Four target genes (DICER1, HOXA7, HOXB4, HOXD1) were shared across all four miRNAs. miR-10b-5p shared eleven targets with miR-196a-5p (HOXB8, COX8A, HOXA10, NPC1, FLT3, AKT1, NPM1, DROSHA, AGO2, NFYC, PAX7), and one with miR-615-3p (MAPK8). miR-196a and miR-196b shared 28 targets. In all, eleven of the 167 unique validated targets were Hox cluster genes (HOXA1, HOXA7, HOXA9, HOXA10, HOXB4, HOXB7, HOXB8, HOXC8, HOXD1, HOXD4, HOXD10).

To understand the influence these miRNAs may be having on shared biological processes, targets of each miRNA were analyzed using IPA Core Analysis. To find overlap in biological functions and canonical pathways of each miRNA and its targets, the IPA Core Comparison Analysis tool was used. After correcting for multiple comparisons, targets of miR-10b-5p, miR-196a, miR-196b and miR-615-3p shared significant overlap in 33 biological functions; the top three functional categories were "*Cell Death and Survival*," (Benjamini-Hochberg adjusted p-value, range=3.5e-07-1.5e-04), "*Nervous System Development and Function*" (range=1.5e-07-1.5e-03) and "*Cellular Assembly and Organization*" (range=2.5e-05-1.7e-03). Twelve pathways were shared among all four sets of miRNA targets, including "*Huntington's Disease Pathway*" (range=7.6e-04-8.1e-03), (Gene set=AKT1, BAX, CAPSN1, CLTC, CREB1, EGFR, HDAC9, JUN, MAPK8).

mRNA Targets of Differentially Expressed miRNAs are Differentially Expressed.

Total mRNA-sequencing was performed in the same brain samples as miRNA-sequencing to examine whether gene expression was affected by miRNA up-regulation. Of the 169 unique gene targets for the five differentially expressed miRNAs, 167 were detected using mRNA-sequencing. 22 mRNA targets were significantly differentially expressed between the HD and control prefrontal cortex samples (FDR adjusted q-value=0.05 after adjusting for 167 comparisons). Only one gene (keratin 5, KRT5) was down-regulated in HD (see Table 9), and four of these target genes were located in the Hox clusters (HOXD4, HOXA10, HOXB7 and HOXD10).

miR-10b-5p, miR-196a-5p, miR-196b-5p and miR-615-3p Expression is Related to Hox Cluster Gene Expression.

Figure 10:
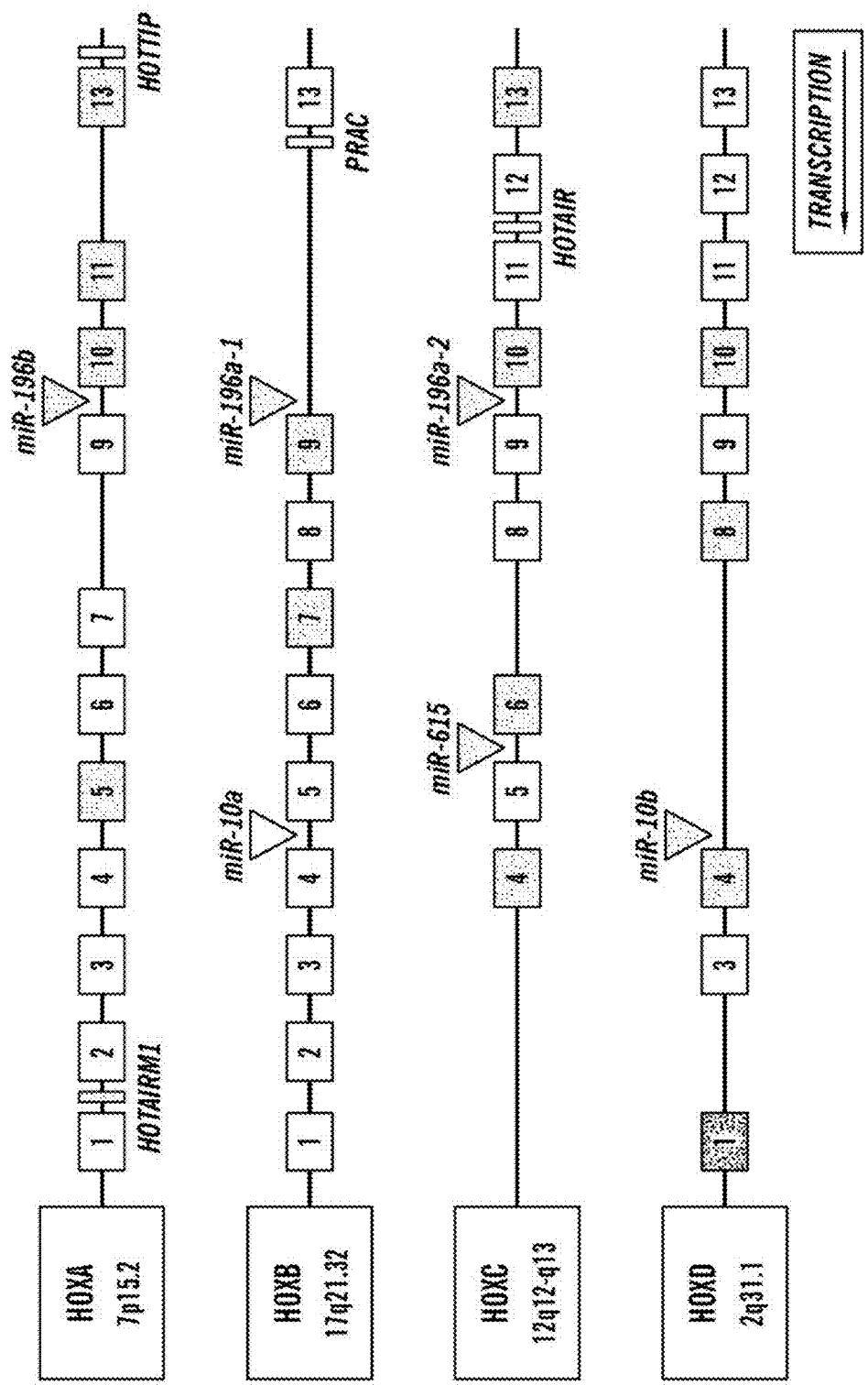
FIG. 10 demonstrates that differentially expressed miR-NAs in HD are located in Hox genes clusters. A schematic representation of Hox clusters is depicted. Hox genes are represented as numbered boxes (labeled 1-13), miRNA are represented by triangles and other genes in the regions (functional lncRNA, PRAC) are represented by rectangles. Antisense transcripts and pseudogenes are not pictured. Nineteen genes within Hox cluster regions were found significantly differentially expressed in HD prefrontal cortex using mRNA-sequencing (FDR-adjusted p-value<0.05). Four miRNAs, one lncRNA, and fourteen Hox genes were significantly up-regulated in HD (indicated by red), many of which are adjacent to differentially expressed miRNAs. A single Hox gene (HOXD1) was down-regulated in HD (indicated by blue). (HD=Huntington's disease).

Four of the five up-regulated miRNAs are located intergenic to Hox gene clusters (see FIG. 10). Because of gene duplication, miR-196a is derived from both the HOXB and HOXC clusters; miR-10b is located in the HOXD cluster and miR-615 is found in the HOXC cluster [31,32]. A total of 55 genes (40 protein-coding genes, eleven antisense transcripts, three functional lncRNAs and one pseudogene) are located in the four Hox clusters [33,34]. To evaluate evidence for a general regional up-regulation of Hox cluster genes, an expression analysis of the mRNA-sequence data was performed for all annotated genes within the Hox loci (see Table 10). Fifteen out of 55 genes within the Hox loci were differentially expressed in HD. Fourteen Hox genes were significantly up-regulated (FDR-adjust q-value<0.05, mean fold-change=6.73, range 3.02 to 16.12) and a single Hox gene was down-regulated (HOXD1, FDR-adjust q-value=3.92e-02, fold change=−2.45). The majority of differentially expressed Hox genes (13 out of 15) were essentially unexpressed in controls.

The genes adjacent to the four differentially expressed miRNAs were highly expressed. Two genes immediately adjacent to miR-10b-5p were significantly up-regulated in HD (HOXD4, FDR-adjusted q=3.22e-03; HOXD8, FDR-adjusted q=2.07e-03), (see FIG. 10). HOXB9 (FDR-adjusted q-value=3.22e-03) immediately downstream of miR-196a-1 and HOXC10 (FDR-adjusted q-value=4.14e-02) immediately upstream of miR-196a-2 were also up-regulated. Furthermore, all three Hox genes located upstream of miR-196b were significantly up-regulated in HD (HOXA10, FDR-adjusted q-value=1.11e-02; HOXA11, FDR-adjusted q-value=2.07e-03; HOXA13, FDR-adjusted q-value=2.24e-02). HOXC6 (FDR-adjusted q-value=1.27e-02) immediately upstream of miR-615 was also up-regulated.

Discussion

Up-Regulation of Expression for Five miRNAs in HD Brain.

Described herein is a next-generation sequencing study of small RNAs, identifying 1,417 mature miRNA species in the prefrontal cortex (Brodmann Area 9) of twelve HD and nine control brains. Five of these, miR-10b-5p, miR-196a-5p, miR-196b-5p, miR-615-3p and miR-1247-5p, were up-regulated in HD at genome-wide significance (FDR q-value<0.05), and three of these five, miR-196a-5p, miR-196b-5p and miR-615-3p, were expressed at near zero levels in the control brains. Up-regulation of miR-10b-5p was validated in the miRNA-sequencing samples and confirmed in an independent replication sample set. Several studies implicating a role for miRNAs in HD have been performed, although, to our knowledge this is the first genome-wide quantification of miRNA expression comparing individual human HD and control brain samples.

Packer et al. [11], studying an array of 365 mature miRNAs, had previously reported miR-196a-5p to be significantly increased by nearly six-fold in Brodmann Area 4 of HD grade 1 brains. Recently, a study by Cheng et al. [13] found increased miR-196a expression suppressed mutant HTT expression in both HD neuronal cell models and HD transgenic mouse models. These findings suggest increased expression of miR-196a may be an adaptive response, promoting neuronal survival and may have therapeutic implications for HD. Miyazaki et al. [35] studied miR-196a in spinal and bulbar muscular atrophy (SBMA), a neurodegenerative disease caused by a similar polyglutamine repeat expansion in the androgen receptor (AR) gene. They found increased miR-196a expression via adeno-associated virus vector-mediated delivery reduced AR mRNA levels leading to improved neurological function in transgenic SBMA mouse models. Together, these findings suggest a neuroprotective role for miR-196a and its targets and possible therapeutic implications across multiple polyglutamine-expansion neurodegenerative diseases. According to the miRNA search program "PubmiR," [37] miR-196b-5p, miR-1247-5p and miR-615-3p have not been previously reported in HD miRNA studies.

A number of past studies have examined miRNA levels in HD, HD transgenic mice or cellular models; however, those results are not replicated herein. Gaughwin et al. [36] reported miR-34b elevated in plasma samples in HD, but in the work described herein, neither miR-34b-3p nor miR-34b-5p were found to be altered in HD brain at genome-wide levels. We were not able to confirm any of the miRNAs reported in past microarray studies that examined targeted subsets of miRNAs, including the nine miRNAs reported as down-regulated in two mouse models of HD (YAC128 and R6/2) by Lee et al. [14] using a 567 miRNA microarray or the 38 miRNAs with altered expression in HD transgenic mice in a 382 miRNA microarray [15]. Johnson et al. [10,11,12] reported miR-29a and miR-330 to be significantly up-regulated in HD samples, neither of which was found to be altered in this study [10]. In a RT-qPCR study comparing 90 miRNAs in mouse Hdh (Q111/Q111) striatal cells to control mice [12,38], none of the 27 reported differentially expressed miRNAs was different at genome-wide levels in the present study. The most commonly reported altered miRNA in HD studies, miR-132, has been reported as both down-regulated [10,14,39] and up-regulated [11], but was not differentially expressed in the present study.

While some of the lack of concordance may be a consequence of the differences between human and animal models of HD, it is also likely that some of the differences are a consequence of the different technologies employed by these studies. Microarrays may have different levels of detection for some miRNAs from that seen by miRNA sequencing. Finally, nearly all of the studies employ microarray methods. Microarrays that study only 365 (e.g. Packer et al. [11],) to 567 miRNAs (e.g. Lee et al. [14]) are not performing as many contrasts and thus do not adjust for as many contrasts as the present genome wide analysis (e.g. 1,417 miRNAs detected) demands.

miR-10b-5p, miR-196a-5p, miR-196b-5p and miR-615-3p Implicate Hox Cluster Genes.

Four (miR-10b-5p, miR-196a-5p, miR-196b-5p and miR-615-3p) of the five differentially expressed miRNAs are related to Hox cluster genes as follows: (1) these four are located in intergenic regions of the Hox clusters, (2) eleven Hox genes are validated targets of these four miRNAs, (3) Hox genes adjoining differentially expressed miRNAs are differentially expressed and (4) multiple Hox cluster genes are differentially expressed in HD versus control brains (Table 10).

Of the eleven Hox gene targets, eight did not differ in their expression across condition. A single target, HOXD1 was seen to be down-regulated in HD (FC-2.45). HOXD1 is a reported target of four of the five miRNAs [40] which may explain its repression in HD.

Three Hox gene targets were up-regulated in HD (HOXB7, HOXD4 HOXD10). It is possible these up-regulated Hox genes share similar regulatory mechanisms, as the increased miRNA expression does not produce the expected miRNA-mediated gene silencing and suppress the observed up-regulation of the miRNA target genes. Coevolution of Hox genes and Hox-related miRNAs may further suggest that they share regulatory elements or mechanisms [41]. Furthermore, Hox genes and related miRNAs have been observed to have similar patterns of transcriptional activation and both are activated by retinoic acid [42,43,44,45,46]. Although miR-10b-5p has been validated as targeting HOXD4, they may exhibit patterns of co-expression. Specifically, Phua et al. [45] report miR-10b and HOXD4 are temporally co-expressed during neurodifferentiation. Here, a similar up-regulation and co-expression pattern in HD is observed, where miR-10b and HOXD4 are both highly expressed.

Hox genes are a family of transcription factors that contribute to major morphological changes during embryonic development and are required for anterior-posterior body axis in bilaterally developing species [47]. They are highly involved in most aspects of early development, and are prominently expressed in the developing brain [48]. Hox-related miRNAs may also follow similar spatio-temporal patterns of expression during embryogenesis [49].

Hox genes are regulated by retinoic acid but also other factors, including basic fibroblast growth factor [50], steroid hormones [51,52] and polycomb repressive complex group [53]. Polycomb group (PcG) proteins assemble into large silencing complexes and control histone-modifying activity. Hox genes are repressed by PcG complexes, specifically Polycomb Repressive Complex 2 (PRC2), which trimethylates histone H3 at lysine 27 (H3K27me3) [53].

Seong et al [54] observed knockout huntingtin mouse embryos lacked repression of HOXB1, HOXB2, and HOXB9 and showed diminished global H3K27me3, while a knock-in expanded repeat mouse exhibited increased H3K27me3 signal, suggesting mutant huntingtin may alter proper PRC2 activity. Without wishing to be limited by theory, these findings raise the possibility that the increased expression of miRNAs and Hox genes reported here are related to enhanced H3K27me3 or impaired PcG repression. However, the role of Hox in the adult, HD brain is still unclear. Increased transcriptional activity of Hox may be compensatory, helping to preserve or re-establish cell polarity, or an indirect result of impaired epigenetic regulation.

miR-10b-5p Response in HD May be Protective.

To functionally validate the miRNA-sequencing findings, miR-10b-5p was further assessed. miR-10b-5p had the highest basal expression levels and the highest fold change between conditions. Additionally, miR-10b-5p levels were not increased in PD, a comparable protein aggregate, neurodegenerative disease, nor in PD samples with pathology in the prefrontal cortex equivalent to HD.

To determine whether miR-10b-5p had a protective or deleterious effect on neuron viability, miR-10b-5p was ectopically expressed in terminally differentiated PC12 Q73 cells. Since the levels the five differentially expressed miRNA were up-regulated, we felt overexpression of miR-10b-5p best represented the phenotype observed in HD brain.

It is described herein that increased miR-10b-5p expression enhanced the survival of PC12 Q73 cells. Furthermore, it was found that increased miR-10b-5p expression enhanced survival in the presence of apoptosis-inducing compound, MG 132. In this experiment, survival in cells with increased miR-10b-5p expression was comparable to that of unchallenged cells and significantly greater than untreated cells exposed to toxin. These findings indicate that increased miR-10b-5p is a neuroprotective response to the expanded polyglutamine repeat seen in HD and speaks to the role of this microRNA in the pathology of HD.

miR-10b-5p, miR-196a-5p, miR-196b-5p and miR-615-3p have Overlapping Biological Functions.

Using pathway analysis, it was demonstrated herein that miR-10b-5p, miR-196a-5p, miR-196b-5p and miR-615-3p targeted genes are predicted to be involved in apoptosis as well as nervous system development and function. In neuroblastoma SH-SY5Y cell lines, miR-10a, miR-10b and miR-615-5p expression levels significantly increased during all-trans-retinoic-acid (ATRA) treatment, indicating miR-10a/b and miR-615-5p may have a role in neurodifferentiation [44]. SH-SY5Y cells treated with antisense miR-10a or miR-10b had impaired neurite outgrowth and morphology but did not show changes in overall cell proliferation [44]. miR-10a and miR-10b were highly expressed in SK-N-BE, LAN5 and SH-SY5Y cell lines during ATRA treatment and ectopic expression of miR-10ab mirrored the phenotype of the ATRA treatment [42]. Taken together, these studies implicate these miRNAs in neuron differentiation, migration, and outgrowth.

In our past studies [16], increased neurite outgrowth was found in HD prefrontal cortex. Relative to controls, HD pyramidal neurons had a significantly increased number of primary dendritic segments, increased total dendritic length, and more dendritic branches than control neurons. Described herein are four miRNAs that have been observed in cell models to present a similar phenotype. It is possible that increased expression of these miRNAs and related targets represent an adaptive response of neurons stressed by a toxic expanded polyglutamine protein fragment.

miR-10b-5p, miR-196a-5p, miR-196b-5p and miR-615-5p are Related to HD Pathogenesis.

Four of the five up-regulated miRNAs showed association to clinical features of HD (CAG repeat size, age of motor onset and age at death for miR-10b-5p; CAG repeat size and age at onset for miR-196a-5p, age at onset for miR-196b-5p and age at death for miR-615-3p). Due to the near zero level of expression in controls, it was not possible to assess the relationship of miR-196a-5p, mir-196b-5p and miR-615-3p to age at death, but miR-10b-5p was not correlated with age at death in controls. Thus, the increased expression of these miRNAs did not appear to be related to normal aging, but rather a component of gene regulation and transcription in the context of neurodegeneration. A growing body of literature points to the presence of toxic effects of the HD gene substantially before the onset of symptoms, perhaps from the time of conception [55,56,57].

Because age at death represents the lifetime exposure of the individual to the effects of the HD gene, it is hypothesizes that the association of miR-10b-5p and miR-615-3p with age at death may represent the lifetime exposure to the effects of the HD mutation. If the relationship of altered miRNA expression to age at death supports the view that the HD gene may have a life-long effect among expanded CAG-repeat carriers, this raises the possibility that the HD mutation may influence neuronal development in the developing brain through the action of one or more of these miRNAs and Hox cluster genes.

Target Genes of Over-Expressed miRNAs Show Increased Expression in HD.

Described herein are five miRNAs which are being highly up-regulated in HD and though the expectation was to see the mRNA targets of these miRNAs as decreased, increased expression of many of their shared mRNA targets is observed. These effects are not attributable to differences in cell populations studied, since flow cytometric analysis measuring neuron abundance found no significant difference across condition. Rather, it is hypothesized that positive miRNA-mRNA target relationships are a result of HD-specific alterations in mRNA processing.

Translation is a highly dynamic process. Cytoplasmic mRNA actively engaged in translation can cycle to a non-translated state and accumulate in stress granules or processing bodies (P-bodies). During cellular stress, mRNA can be sequestered to P-bodies or stress granules, to stall translation through translational repression machinery or miRNA silencing, until stress conditions have been resolved [7,58,59,60]. P-bodies may also serve an important role in RNA transport. Because neurons are highly polarized, cytoplasmic transport of mRNA is essential for localized translation to discrete regions of the cell. During transport, it is believed that mRNAs are silenced by miRNA, upon rapid exchange at the synapse [60,61,62].

In HD cortical neurons, excitotoxicity, oxidative damage, aberrant gene expression and energetic defects lead to stress conditions and in response, cells may sequester mRNA to P-bodies and stress granules. Among the 55 Hox locus genes studied, only one of the fifteen significantly differentially expressed genes is down regulated (Table 10). Thus, the increased levels of most of the validated gene targets of these four miRNAs may be reactionary, as they are sequestered to P-bodies for storage as part of a protective process to enhance cell viability [7].

To the best of our knowledge, no study has addressed the role of P-bodies or stress granules in HD. However, it was observed in live cortical neurons that wild-type huntingtin co-localized in P-bodies, specifically in neuronal RNA granules, along with Argonaute 2, the endonuclease required for RNA-mediated gene silencing by the RNA-induced silencing complex (RISC) [63,64]. Therefore, it is reasonable to suggest mutant huntingtin may impair miRNA-mediated mRNA degradation and/or localized translation of specific mRNAs.

There is evidence that miRNA-mRNA regulatory mechanisms may be altered in other neurodegenerative diseases as well. In a joint examination of miRNA-mRNA expression in Alzheimer's disease (AD) and control prefrontal cortex, an overwhelming number of miRNA to mRNA targets were found to be positive correlated. Genomic variants in TDP-43 and FUS, genes that encode stress granule proteins, were found to cause familial Amyotrophic lateral sclerosis [65,66] and several other stress granule proteins (TIA-1, G3BP) may also be pathogenic [67].

miRNAs as Potential Biomarkers in HD.

These studies indicate relationships of these miRNAs to CAG repeat expansion, age at onset and/or age at death. miRNA are extremely stable. The half-life of the majority miRNAs has been predicted to be on average five days and plasma miRNAs have been found to be stable after being subjected to high heat, extreme pH, long-time storage at room temperature, or multiple freeze-thaw cycles [68,69,70].

Materials and Methods

Sample Information.

Frozen brain tissue from prefrontal cortex Brodmann Area 9 (BA9) was obtained from the Harvard Brain and Tissue Resource Center (HBTRC) McLean Hospital, Belmont Mass. Twelve Huntington's disease (HD) samples and eleven neurologically-normal control samples were selected for the study (Tables 6 and 7). The HD subjects had no evidence of Alzheimer or Parkinson disease (PD) comorbidity based on neuropathology reports. For microscopic examination, 16 tissue blocks were systematically taken and histologically assessed as previously described [3]. All samples were male. HD samples and controls were not different for postmortem interval (PMI) (t=1.07, p=0.30), RNA integrity number (RIN) (t=0.83, p=0.41) or death age (t=0.40, p=0.69). CAG repeat size was known for all HD samples and onset age and disease duration was unknown for a single sample (Tables 6 and 7). Eight additional HD, nine control and fourteen PD cases were studied as part of validation and replication studies, and were obtained from the HBTRC and the Sun Health Research Institute Sun City, Ariz. (see below, (data not shown)).

RNA Extraction.

Total RNA, for all samples studied, was isolated using QIAzol Lysis Reagent and purified using miRNeasy Min-Elute Cleanup columns (Qiagen Sciences Inc, Germantown, Md.). RNA quality for sequencing was assessed using either Agilent's BioAnalyzer 2100 system and RNA 6000 Nano Kits to find RNA Integrity Number (RIN) or Agilent 2200 TapeStation and DNA ScreenTape assay RNA Quality Number (RQN; Agilent, Foster City, Calif.). Both methods calculate the area under the peak for 18S and 28S RNA as a ratio of total RNA as well as the relative height of the 18S and 28S peaks to determine RNA quality [71]. The RIN/RQN values were similar for the twelve HD and eleven control specimens studied for miRNA and mRNA (t=0.95, p=0.36).

Illumina miRNA Sequencing (miRNA-Seq).

For each brain sample, 1 ug of RNA was used to construct sequencing libraries using Illumina's TruSeq Small RNA Sample Prep Kit, according to the manufacturer's protocol (Illumina, San Diego, Calif.). In brief, small RNA molecules were adapter-ligated, reverse transcribed, PCR amplified and gel purified to generate the library. Multiplexed samples were equimolarly pooled into sets of eight samples per flowcell lane and sequenced using 1×50 bp single-end reads on Illumina's HiSeq 2000 system at Tufts University sequencing core facility (http://tucf-genomics.tufts.edu/). Demultiplexing and FASTQ file generation (raw sequence read plus quality information in Phred format) were done using Illumina's Consensus Assessment of Sequence and Variation (CASAVA) pipeline.

Primary Processing of Illumina miRNA-Seq Reads.

Sequence read quality was evaluated using the FASTQ quality filter module from the FASTX-toolkit version 0.0.13 (available on the world wide web at http://hannonlab.cshl.edu/fastx_toolkit/), and only those reads with at least 80% of the base calls above Q20 (Phred score) were retained. The 3' adapter sequence (5'-TGGAATTCTCGGGTGCCAAGG-3' (SEQ ID NO: 43)) was removed from all reads using the FASTA/Q clipper module from the FASTX-toolkit. A minimum length threshold of 15 nucleotides was set for clipped reads because miRNAs of this length will contain the seed sequence. To avoid redundancy amongst identical read species, the reads were collapsed using the FASTA/Q collapser module from FASTX-toolkit to generate a FASTA file of only the unique read species.

Alignment and Mapping of miRNA-Seq Reads.

Quality-filtered, 3' adapter-clipped reads were aligned to the UCSC human reference genome (build hg19) using Bowtie version 0.12.3 [72]. Alignment parameters were set to allow for no mismatch alignments and no limits on multiple mapping instances. Multiple-mapped identical sequences were summed for a single count for that annotated mature miRNA. The default settings were used for all other alignment options.

miRNA Abundance Estimation.

Aligned reads that overlapped with the human miRNA annotation version 19 from miRBase (available on the world wide web at http://www.mirbase.org/ftp.shtml) were identified using default BEDTools' IntersectBed functionality [73]. To select for mature miRNA reads, sequences more than 27 bases in length were removed. Only those reads for which the aligned 5' start-nucleotide matched exactly to the 5' start-nucleotide of the annotated miRNA were retained for the analysis. After filtering, collapsed read counts were summed per annotated mature miRNA (data not shown).

miRNA Differential Expression.

The R (http://www.R-project.org) package DESeq version 1.10.1 [28] was used to perform the differential expression analysis between HD and control samples using the read counts generated for each sample as described above. miRNAs with zero read counts across all case and control samples were removed from analysis. To accommodate the analysis of miRNAs with read counts of zero for some samples, a pseudo-count of one was added to all raw counts for every miRNA across all the samples, prior to performing DESeq's estimateSizeFactors and estimateDispersions functions with default options. DESeq assumes that count data follow a negative binominal distribution and factors in technical and biological variance when testing for differential gene expression between groups. DESeq's function, estimateSizeFactors, was used to obtain normalization factors for each sample and to normalize miRNA read counts.

The normalized counts were evaluated by principal component analysis (PCA) with the FactoMineR R package for all HD and control samples. The samples identified to be three or more standard deviations away from the mean on the first or second principal component were considered outliers and were removed from analysis. The first two principal components were used because they each explained more than 10% of the variance, while the remaining principal components explained less than 10% of the variance. Two control samples (C-35 and C-37) were identified as outliers based on PCA analysis.

miRNA differential expression analysis was performed with DESeq's nbinomTest function for the remaining nine control and twelve HD samples. All analyses were performed on DESeq normalized counts.

miRNA Quantitative PCR.

miRNA were assayed using Exiqon's miRCURY LNA™ Universal RT miRNA PCR following the manufacturer's protocol (Exiqon Inc, Denmark). In brief, reactions were incubated for 60 min at 42° C. followed by heat-inactivation of reverse transcription for 5 min at 95° C. and stored at 4° C. After cDNA synthesis, samples were diluted to 0.2 ng/ul in water. Brain samples were assayed using Exiqon ExiLENT SYBR Green master mix and LNA primer sets containing UniRT and miR-10b-5p, miR-196a-5p, miR-196b-5p, miR-615-3p or miR-1247. Reference primer hsa-SNORD48 PCR/UniRT was used for brain samples; U6 snRNA for cell lines. Samples were run in triplicate for each primer set in 384-well format (5 ul PCR Master mix, 1 ul PCR primer mix, 4 ul 0.2 ng cDNA). Reactions were cycled using Applied Biosystems 7900HT Fast Real-Time PCR System using manufacturer's instructions (Life Technologies, Carlsbad, Calif.). For analysis, threshold cycle ($C_T$) was generated by ABi SDS v2.4 software. $C_T$ values for triplicate wells were normalized by average RNU48 value for brain or U6 for cells. miRNA fold change was calculated using the 2-$\Delta\Delta CT$ method [74].

Neuron Abundance Quantification.

0.5-1.0 g of tissue in 5 ml of lysis buffer was homogenized using a dounce tissue grinder. Lysates were transferred to ultracentrifugation tubes, loaded on top of sucrose solution and centrifuged at 24,400 RPM for 2.5 hr at 4° C. (Beckman Coulter, Pasadena, Calif.; L8-70 M with SW80 rotor). Nuclei pellets were resuspended in 500 ul PBS and incubated at 4° C. in a staining solution containing 0.72% normal goat serum, 0.036% BSA, 1:1200 anti-NeuN (Millipore, Germany), 1:1400 Alexa488 goat anti-mouse secondary antibody (Life Technologies, Carlsbad, Calif.), for 45 min. Flow cytometry was performed at the Boston University Medical School Flow Cytometry Core Lab on a FACSVantage SE flow cytometer.

Illumina Messenger RNA Sequencing (mRNA-Seq).

For each brain sample, 1 ug of RNA was used to construct sequencing libraries using Illumina's TruSeq RNA Sample Prep Kit according to the manufacturer's protocol. In brief, mRNA molecules were polyA selected, chemically fragmented, randomly primed with hexamers, synthesized into cDNA, 3' end-repaired and adenylated, sequencing adapter ligated and PCR amplified. Each adapter-ligated library contained one of twelve TruSeq molecular barcodes. Multiplexed samples were equimolarly pooled into sets of three samples per flowcell lane and sequenced using 2×100 bp paired-end reads on Illumina's HiSeq 2000 system at Tufts University sequencing core facility (http://tucf-genomics.tufts.edu/). Demultiplexing and FASTQ file generation were accomplished using Illumina's CASAVA pipeline.

Primary Processing of Illumina mRNA-Seq Reads.

Forward and reverse sequencing reads were independently quality-filtered using the FASTQ quality filter module from the FASTX-toolkit version 0.0.13 with the same criteria as that applied for the processing of the miRNA-seq reads. Reads failing the quality threshold, as well as their corresponding mate reads, were removed.

Alignment and Mapping of mRNA-Seq Reads.

Quality-filtered paired-end reads were aligned to the UCSC human reference genome (build hg19) using TopHat version 2.0.4 [75,76]. This version of TopHat incorporates the Bowtie version 2.0.0.7 algorithm to perform the alignment [72] as well as SAMtools version 0.1.18.0 for alignment file formatting [77]. For efficient read mapping, TopHat requires the designation of the mean and standard deviation of the distance between paired-end reads, the read inner-distance. To estimate the appropriate read inner-distance, we aligned a subset of 5 million reads from four HD and four control samples to the Ensembl human reference transcriptome (release 66) using Bowtie version 2.0.0.7. Using the CollectInsertSizeMetrics function from picard-Tools version 1.76 (available on the world wide web at http://sourceforge.net/projects/picardifiles/picard-tools/), we estimated the average mean inner-distance per condition and subsequently applied these values for the TopHat alignment; 22 for HD samples 25 for controls respectively, (the current TopHat default setting is 20), (data not shown). To account for read variability, the standard deviation for inner-distance was set to 100. The number of allowed splice mismatches was set to 1. Default settings were used for all other alignment options.

mRNA Gene Abundance Estimation.

Gene expression quantification was performed using htseq-count version 0.5.3p9 (available on the world wide web at http://www-huber.embl.de/users/anders/HTSeq) and the GENCODE version 14 annotation gtf file as reference (available on the world wide web at http://www.gencode-genes.org/releases). Intersection non-empty mode and unstranded library type were specified as parameters for htseq-count. Default settings were used for all other options (data not shown).

mRNA Differential Expression Analysis.

The mRNA differential expression analysis between HD and control samples was performed using DESeq version 1.10.1 [28]; the workflow was the same as described for the miRNA differential expression analysis. No outliers were found based on the PCA of the DESeq-normalized count data. The nbinomTest function was run for eleven control samples and twelve HD samples to assess differentially expressed genes. Multiple comparison adjustment for multiple testing with the Benjamini-Hochberg correction was used to control for false discovery rate. For Hox gene differential expression analysis, 55 comparisons were used. Genes located within HOX-gene containing regions were queried through the Ensembl database (release 72), interfacing through the R package BiomaRt [78,79]. Genes that were between HOXA1-HOXA13, HOXB1-HOXB13, HOXC4-HOXC13 and HOXD1-HOXD13 start sites were regarded as "Hox genes." For miRNA target differential expression, 154 comparisons were used for Benjamini-Hochberg correction.

miRNA-mRNA Target Analysis.

Information on experimentally validated miRNA targets of miR-10b-5p, miR-196a-5p and miR-615-3p were extracted from the miRWalk "Validated Targets" module [30]. Strand specificity was preserved. Targets for miR-196a-1 and miR-196a-2 were merged for analysis. IPA Core Analysis (analysis.ingenuity.com) was run as nervous system and CNS cell line specific across all species, using target gene lists imported from miRWalk output. "Bio Functions" and "Canonical Pathway" analyses were used. Right-tailed Fisher's Exact Tests were run through IPA software and p-values with FDR-adjusted q-values (p<0.05) were considered significant. Biological functions across the 3 significant miRNA were compared using the IPA Core Comparison Analysis tool. Benjamini-Hochberg Multiple Testing Correction p-values (p<0.05) were considered significant.

Linear Modeling of miRNA Relationship to Clinical Covariates.

To account for the non-normality in the miRNA data, negative binomial general linear regressions were performed using Proc genmod in SAS. DESeq normalized counts were rounded to the nearest integer before running the model. To test the normality of gene expression data, Shapiro-Wilk tests were performed. Differentially expressed miRNA data trended as non-normally distributed in HD (miR-10b-5p, p=0.04; miR-196a-5p, p=0.05; miR-615-3p, p=0.06), but not in controls (miR-10b-5p, p=0.71; miR-196a-5p and miR-615-3p were essential zero).

Generation of Transgenic Cell Lines.

PC12 (rat adrenal gland phaeochromocytoma) cells were grown at 37° C. and 5% $CO_2$ in Dulbecco's modified Eagle's medium (DMEM; Life Technologies, Carlsbad, Calif.) with 20% fetal bovine serum (FBS; Atlanta Biologicals, Flowery Branch, Ga.), 100 units/ml penicillin and 100 units/ml streptomycin (Life Technologies, Carlsbad, Calif.). pcDNA3.1mycC expressing human huntingtin fragment (1-90) containing 73 polyglutamine repeats (Coriell Institute; CHDI-90000034) was used for stable transfection. Cells were seeded to 70% confluency and grown overnight. 15 µl of Attractene Transfection Reagent (Qiagen, Gaithersburg, Md.) was added to 4 µg plasmid DNA diluted in 300 µl Opti-MEM (Life Technologies, Carlsbad, Calif.). Cells were grown in complete media and selected for four weeks using 500 mg/ml G418 (Life Technologies, Carlsbad, Calif.). To create monoclonal cultures, single colonies were isolated using dilution cloning, picked with filter paper, grown in a 6-well plate and screened for transgenic expression by Western blot analysis using mouse Anti-c-Myc (Novex, R950-25, Life Technologies, Carlsbad, Calif.).

Cell Differentiation and miRNA Overexpression.

96-well culture plates were seeded with 10,000 cells per well. For differentiation, culture medium was replaced with medium composed of DMEM with 0.5% FBS, 100 mg/ml G418, 100 units/ml penicillin and 100 units/ml streptomycin and 100 ng/ml nerve growth factor (R&D Systems, Minneapolis, Minn.). After 48 hr, miRNA was transfected into HD cells using 0.25 ul Lipofectamine 2000 (Life Technologies, Carlsbad, Calif.) and 6.25 pmol miR-10b-5p or miRIDIAN microRNA Mimic Negative Control #1 (cel-miR-67-3p, Thermo Scientific, Waltham, Mass.) per well, following manufacturer's protocol. miR-10b-5p overexpression was verified using qPCR.

Cell Viability Assays.

For MTT assays, 1 uM MG 132 (Tocris Bioscience, United Kingdom) was added to select wells containing 10,000 cells per well at 72 hr post-differentiation. Cell viability was assessed at 96 hr post-differentiation. Following manufacturer's protocol, CellTiter 96 Non-Radioactive Cell Proliferation Assay kit (Promega; Madison, Wis.) was used to determine cell number. Cells were incubated for 1.5 hr at 37° C. and 5% $CO_2$ with MTT dye solution. Undifferentiated HD cells were serially diluted across a 96-well plate to create a standard curve for cell number calculation. Absorbance was measured using Bio-Tek Synergy H1 spectrophotometer at 540 nm for miR-10b-5p transfected wells, with MG 132 (n=44) and without MG 132 (n=35) and cel-miR-67-3p transfected wells with MG 132 (n=40) and without MG 132 (n=40). One-way ANOVA way used for statistical analysis.

For cell viability staining, miR-10b-5p and negative control mimic were transfected after 48 hours of differentiation in 12-well culture plate with 4 replicates each, 250,000 cells per well. Molecular Probes Neurite Outgrowth Staining Kit (Life Technologies, Carlsbad, Calif.) was used according to manufacturer's protocol. Using Bio-Tek Synergy H1 microplate reader, fluorescent area scans were taken at 530 nm excitation/590 nm emission with a 5×5 matrix per well.

REFERENCES

1. HDCRG (1993) A novel gene containing a trinucleotide repeat that is expanded and unstable on Huntington's disease chromosomes. Cell 72: 971-983.
2. Hadzi T C, Hendricks A E, Latourelle J C, Lunetta K L, Cupples L A, et al. (2012) Assessment of cortical and striatal involvement in 523 Huntington disease brains. Neurology 79: 1708-1715.
3. Vonsattel J P, Myers R H, Stevens T J, Ferrante R J, Bird E D, et al. (1985) Neuropathological classification of Huntington's disease. Journal of neuropathology and experimental neurology 44: 559-577.
4. Hodges A, Strand A D, Aragaki A K, Kuhn A, Sengstag T, et al. (2006) Regional and cellular gene expression changes in human Huntington's disease brain. Human molecular genetics 15: 965-977.
5. Cha J H (2000) Transcriptional dysregulation in Huntington's disease. Trends in neurosciences 23: 387-392.
6. Cha J H (2007) Transcriptional signatures in Huntington's disease. Progress in neurobiology 83: 228-248.
7. Lavut A, Raveh D (2012) Sequestration of highly expressed mRNAs in cytoplasmic granules, P-bodies, and stress granules enhances cell viability. PLoS genetics 8: e1002527.
8. Junn E, Mouradian M M (2012) MicroRNAs in neurodegenerative diseases and their therapeutic potential. Pharmacology & therapeutics 133: 142-150.
9. Marti E, Pantano L, Banez-Coronel M, Llorens F, Minones-Moyano E, et al. (2010) A myriad of miRNA variants in control and Huntington's disease brain regions detected by massively parallel sequencing. Nucleic acids research 38: 7219-7235.
10. Johnson R, Zuccato C, Belyaev N D, Guest D J, Cattaneo E, et al. (2008) A microRNA-based gene dysregulation pathway in Huntington's disease. Neurobiology of disease 29: 438-445.
11. Packer A N, Xing Y, Harper S Q, Jones L, Davidson B L (2008) The bifunctional microRNA miR-9/miR-9* regulates REST and CoREST and is downregulated in Huntington's disease. The Journal of neuroscience: the official journal of the Society for Neuroscience 28: 14341-14346.
12. Sinha M, Ghose J, Bhattarcharyya N P (2011) Micro RNA-214, -150, -146a and -125b target Huntingtin gene. RNA biology 8: 1005-1021.
13. Cheng P H, Li C L, Chang Y F, Tsai S J, Lai Y Y, et al. (2013) miR-196a Ameliorates Phenotypes of Huntington Disease in Cell, Transgenic Mouse, and Induced Pluripotent Stem Cell Models. American journal of human genetics.
14. Lee S T, Chu K, Im W S, Yoon H J, Im J Y, et al. (2011) Altered microRNA regulation in Huntington's disease models. Experimental neurology 227: 172-179.
15. Jin J, Cheng Y, Zhang Y, Wood W, Peng Q, et al. (2012) Interrogation of brain miRNA and mRNA expression profiles reveals a molecular regulatory network that is perturbed by mutant huntingtin. Journal of neurochemistry 123: 477-490.
16. Sotrel A, Williams R S, Kaufmann W E, Myers R H (1993) Evidence for neuronal degeneration and dendritic plasticity in cortical pyramidal neurons of Huntington's disease: a quantitative Golgi study. Neurology 43: 2088-2096.
17. Cudkowicz M, Kowall N W (1990) Degeneration of pyramidal projection neurons in Huntington's disease cortex. Annals of neurology 27: 200-204.

18. Gu X, Li C, Wei W, Lo V, Gong S, et al. (2005) Pathological cell-cell interactions elicited by a neuropathogenic form of mutant Huntingtin contribute to cortical pathogenesis in HD mice. Neuron 46: 433-444.
19. Rosas H D, Hevelone N D, Zaleta A K, Greve D N, Salat D H, et al. (2005) Regional cortical thinning in preclinical Huntington disease and its relationship to cognition. Neurology 65: 745-747.
20. Rosas H D, Liu A K, Hersch S, Glessner M, Ferrante R J, et al. (2002) Regional and progressive thinning of the cortical ribbon in Huntington's disease. Neurology 58: 695-701.
21. Greene L A, Tischler A S (1976) Establishment of a noradrenergic clonal line of rat adrenal pheochromocytoma cells which respond to nerve growth factor. Proceedings of the National Academy of Sciences of the United States of America 73: 2424-2428.
22. Kita H, Carmichael J, Swartz J, Muro S, Wyttenbach A, et al. (2002) Modulation of polyglutamine-induced cell death by genes identified by expression profiling. Human molecular genetics 11: 2279-2287.
23. Wyttenbach A, Swartz J, Kita H, Thykjaer T, Carmichael J, et al. (2001) Polyglutamine expansions cause decreased CRE-mediated transcription and early gene expression changes prior to cell death in an inducible cell model of Huntington's disease. Human molecular genetics 10: 1829-1845.
24. Igarashi S, Morita H, Bennett K M, Tanaka Y, Engelender S, et al. (2003) Inducible PC12 cell model of Huntington's disease shows toxicity and decreased histone acetylation. Neuroreport 14: 565-568.
25. Apostol B L, Illes K, Pallos J, Bodai L, Wu J, et al. (2006) Mutant huntingtin alters MAPK signaling pathways in PC12 and striatal cells: ERK1/2 protects against mutant huntingtin-associated toxicity. Human molecular genetics 15: 273-285.
26. Sugars K L, Brown R, Cook U, Swartz J, Rubinsztein D C (2004) Decreased cAMP response element-mediated transcription: an early event in exon 1 and full-length cell models of Huntington's disease that contributes to polyglutamine pathogenesis. The Journal of biological chemistry 279: 4988-4999.
27. Li X, Wang C E, Huang S, Xu X, Li X J, et al. (2010) Inhibiting the ubiquitin-proteasome system leads to preferential accumulation of toxic N-terminal mutant huntingtin fragments. Human molecular genetics 19: 2445-2455.
28. Anders S, Huber W (2010) Differential expression analysis for sequence count data. Genome biology 11: R106.
29. Bartel D P (2009) MicroRNAs: target recognition and regulatory functions. Cell 136: 215-233.
30. Dweep H, Sticht C, Kharkar A, Pandey P, Gretz N (2013) Parallel analysis of mRNA and microRNA microarray profiles to explore functional regulatory patterns in polycystic kidney disease: using PKD/Mhm rat model. PLoS One 8.
31. Swalla B J (2006) Building divergent body plans with similar genetic pathways. Heredity (Edinb) 97: 235-243.
32. Yekta S, Tabin C J, Bartel D P (2008) MicroRNAs in the Hox network: an apparent link to posterior prevalence. Nat Rev Genet 9: 789-796.
33. Flicek P, Ahmed I, Amode M R, Barrell D, Beal K, et al. (2013) Ensembl 2013. Nucleic acids research 41: D48-55.
34. Rinn J L, Kertesz M, Wang J K, Squazzo S L, Xu X, et al. (2007) Functional demarcation of active and silent chromatin domains in human HOX loci by noncoding RNAs. Cell 129: 1311-1323.
35. Miyazaki Y, Adachi H, Katsuno M, Minamiyama M, Jiang Y M, et al. (2012) Viral delivery of miR-196a ameliorates the SBMA phenotype via the silencing of CELF2. Nature medicine 18: 1136-1141.
36. Gaughwin P M, Ciesla M, Lahiri N, Tabrizi S J, Brundin P, et al. (2011) Hsa-miR-34b is a plasma-stable microRNA that is elevated in pre-manifest Huntington's disease. Human molecular genetics 20: 2225-2237.
37. Windemuth A S, I; Pregibon, D; Marini. D. (2012) PubmiR: A Literature Search Tool for MicroRNA Research. Firefly BioWorks, Inc.
38. Sinha M, Ghose J, Das E, Bhattarcharyya N P (2010) Altered microRNAs in STHdh(Q111)/Hdh(Q111) cells: miR-146a targets TBP. Biochemical and biophysical research communications 396: 742-747.
39. Soldati C, Bithell A, Johnston C, Wong K-Y, Stanton L W, et al. (2013) Dysregulation of REST-regulated coding and non-coding RNAs in a cellular model of Huntington's disease. J Neurochem 124: 418-430.
40. Woltering J M, Durston A J (2008) MiR-10 represses HoxB1a and HoxB3a in zebrafish. PLoS One 3.
41. Tehler D, Hoyland-Kroghsbo N M, Lund A H (2011) The miR-10 microRNA precursor family. RNA Biol 8: 728-734.
42. Foley N H, Bray I, Watters K M, Das S, Bryan K, et al. (2011) MicroRNAs 10a and 10b are potent inducers of neuroblastoma cell differentiation through targeting of nuclear receptor corepressor 2. Cell death and differentiation 18: 1089-1098.
43. Huang H, Xie C, Sun X, Ritchie R P, Zhang J, et al. (2010) miR-10a contributes to retinoid acid-induced smooth muscle cell differentiation. J Biol Chem 285: 9383-9389.
44. Meseguer S, Mudduluru G, Escamilla J M, Allgayer H, Barettino D (2011) MicroRNAs-10a and -10b contribute to retinoic acid-induced differentiation of neuroblastoma cells and target the alternative splicing regulatory factor SFRS1 (SF2/ASF). J Biol Chem 286: 4150-4164.
45. Phua S L, Sivakamasundari V, Shao Y, Cai X, Zhang L F, et al. (2011) Nuclear accumulation of an uncapped RNA produced by Drosha cleavage of a transcript encoding miR-10b and HOXD4. PloS one 6: e25689.
46. Weiss F U, Marques I J, Woltering J M, Vlecken D H, Aghdassi A, et al. (2009) Retinoic acid receptor antagonists inhibit miR-10a expression and block metastatic behavior of pancreatic cancer. Gastroenterology 137: 2136-2145 e2131-2137.
47. Lemons D, McGinnis W (2006) Genomic evolution of Hox gene clusters. Science 313: 1918-1922.
48. Pearson J C, Lemons D, McGinnis W (2005) Modulating Hox gene functions during animal body patterning. Nature reviews Genetics 6: 893-904.
49. Wienholds E, Kloosterman W P, Miska E, Alvarez-Saavedra E, Berezikov E, et al. (2005) MicroRNA expression in zebrafish embryonic development. Science 309: 310-311.
50. Diez del Corral R, Storey K G (2004) Opposing FGF and retinoid pathways: a signalling switch that controls differentiation and patterning onset in the extending vertebrate body axis. Bioessays 26: 857-869.
51. Svingen T, Tonissen K F (2006) Hox transcription factors and their elusive mammalian gene targets. Heredity (Edinb) 97: 88-96.
52. Taylor H S, Arici A, Olive D, Igarashi P (1998) HOXA10 is expressed in response to sex steroids at the time of implantation in the human endometrium. J Clin Invest 101: 1379-1384.

53. Schuettengruber B, Chourrout D, Vervoort M, Leblanc B, Cavalli G (2007) Genome regulation by polycomb and trithorax proteins. Cell 128: 735-745.
54. Seong I S, Woda J M, Song J J, Lloret A, Abeyrathne P D, et al. (2010) Huntingtin facilitates polycomb repressive complex 2. Human molecular genetics 19: 573-583.
55. Humbert S (2010) Is Huntington disease a developmental disorder? EMBO reports 11: 899.
56. Kirkwood S C, Siemers E, Hodes M E, Conneally P M, Christian J C, et al. (2000) Subtle changes among presymptomatic carriers of the Huntington's disease gene. Journal of neurology, neurosurgery, and psychiatry 69: 773-779.
57. Myers R H, Vonsattel J P, Paskevich P A, Kiely D K, Stevens T J, et al. (1991) Decreased neuronal and increased oligodendroglial densities in Huntington's disease caudate nucleus. J Neuropathol Exp Neurol 50: 729-742.
58. Liu J, Valencia-Sanchez M A, Hannon G J, Parker R (2005) MicroRNA-dependent localization of targeted mRNAs to mammalian P-bodies. Nature cell biology 7: 719-723.
59. Balagopal V, Parker R (2009) Polysomes, P bodies and stress granules: states and fates of eukaryotic mRNAs. Current opinion in cell biology 21: 403-408.
60. Bhattacharyya S N, Habermacher R, Martine U, Closs E I, Filipowicz W (2006) Relief of microRNA-mediated translational repression in human cells subjected to stress. Cell 125: 1111-1124.
61. Cougot N, Bhattacharyya S N, Tapia-Arancibia L, Bordonne R, Filipowicz W, et al. (2008) Dendrites of mammalian neurons contain specialized P-body-like structures that respond to neuronal activation. The Journal of neuroscience: the official journal of the Society for Neuroscience 28: 13793-13804.
62. Zeitelhofer M, Karra D, Macchi P, Tolino M, Thomas S, et al. (2008) Dynamic interaction between P-bodies and transport ribonucleoprotein particles in dendrites of mature hippocampal neurons. The Journal of neuroscience: the official journal of the Society for Neuroscience 28: 7555-7562.
63. Savas J N, Ma B, Deinhardt K, Culver B P, Restituito S, et al. (2010) A role for huntington disease protein in dendritic RNA granules. The Journal of biological chemistry 285: 13142-13153.
64. Savas J N, Makusky A, Ottosen S, Baillat D, Then F, et al. (2008) Huntington's disease protein contributes to RNA-mediated gene silencing through association with Argonaute and P bodies. Proceedings of the National Academy of Sciences of the United States of America 105: 10820-10825.
65. Sreedharan J, Blair I P, Tripathi V B, Hu X, Vance C, et al. (2008) TDP-43 mutations in familial and sporadic amyotrophic lateral sclerosis. Science 319: 1668-1672.
66. Kwiatkowski T J, Jr., Bosco D A, Leclerc A L, Tamrazian E, Vanderburg C R, et al. (2009) Mutations in the FUS/TLS gene on chromosome 16 cause familial amyotrophic lateral sclerosis. Science 323: 1205-1208.
67. Wolozin B (2012) Regulated protein aggregation: stress granules and neurodegeneration. Molecular neurodegeneration 7: 56.
68. Gantier M P, McCoy C E, Rusinova I, Saulep D, Wang D, et al. (2011) Analysis of microRNA turnover in mammalian cells following Dicer1 ablation. Nucleic acids research 39: 5692-5703.
69. Mitchell P S, Parkin R K, Kroh E M, Fritz B R, Wyman S K, et al. (2008) Circulating microRNAs as stable blood-based markers for cancer detection. Proceedings of the National Academy of Sciences of the United States of America 105: 10513-10518.
70. Chen X, Ba Y, Ma L, Cai X, Yin Y, et al. (2008) Characterization of microRNAs in serum: a novel class of biomarkers for diagnosis of cancer and other diseases. Cell research 18: 997-1006.
71. Schroeder A, Mueller O, Stocker S, Salowsky R, Leiber M, et al. (2006) The RIN: an RNA integrity number for assigning integrity values to RNA measurements. BMC molecular biology 7: 3.
72. Langmead B, Trapnell C, Pop M, Salzberg S L (2009) Ultrafast and memory-efficient alignment of short DNA sequences to the human genome. Genome Biol 10.
73. Quinlan A R, Hall I M (2010) BEDTools: a flexible suite of utilities for comparing genomic features. Bioinformatics 26: 841-842.
74. Livak K J, Schmittgen T D (2001) Analysis of relative gene expression data using real-time quantitative PCR and the 2(-Delta Delta C(T)) Method. Methods 25: 402-408.
75. Kim D, Pertea G, Trapnell C, Pimentel H, Kelley R, et al. (2013) TopHat2: accurate alignment of transcriptomes in the presence of insertions, deletions and gene fusions. Genome Biol 14.
76. Trapnell C, Pachter L, Salzberg S L (2009) TopHat: discovering splice junctions with RNA-Seq. Bioinformatics 25: 1105-1111.
77. Li H, Handsaker B, Wysoker A, Fennell T, Ruan J, et al. (2009) The Sequence Alignment/Map format and SAMtools. Bioinformatics 25: 2078-2079.
78. Durinck S H, W. (2013) biomaRt: Interface to BioMart databases (e.g. Ensembl, COSMIC, Wormbase and Gramene). R. 2.10.0 ed.
79. Kasprzyk A (2011) BioMart: driving a paradigm change in biological data management. Database (Oxford) 2011.

TABLE 6

HD brain samples analyzed for mRNA-seq, miRNA-seq and RT-qPCR validation of miR-10b-5p (Table 6 discloses the 'CAG Repeat' sequences as SEQ ID NOS 31, 36, 32, 39, 40, 36, 34, 33, 38, 33, 34 and 31, respectively, in order of appearance).

| Sample ID | miRNA-seq | RT-qPCR | PMI (hr.) | RIN or RQN | Death age | Onset age | Duration (yr.) | CAG repeat size | Neuron Loss in Neocortical Gray Matter |
|---|---|---|---|---|---|---|---|---|---|
| HD-01 | Passed | Y | 37 | 7.1 | 55 | 44 | 11 | 45 | 1 |
| HD-02 | Passed | Y | 6 | 7.5 | 69 | 63 | 6 | 41 | 1 |
| HD-03 | Passed | Y | 21 | 7 | 71 | 52 | 19 | 43 | 1 |
| HD-05 | Passed | Y | 19 | 6.9 | 48 | 25 | 23 | 48 | 2 |
| HD-06 | Passed | Y | NA | 6.2 | 40 | 34 | 6 | 51 | 1 |
| HD-07 | Passed | Y | 8 | 8.5 | 72 | 55 | 17 | 41 | 1 |

TABLE 6-continued

HD brain samples analyzed for mRNA-seq, miRNA-seq and RT-qPCR validation of miR-10b-5p (Table 6 discloses the 'CAG Repeat' sequences as SEQ ID NOS 31, 36, 32, 39, 40, 36, 34, 33, 38, 33, 34 and 31, respectively, in order of appearance).

| Sample ID | miRNA-seq | RT-qPCR | PMI (hr.) | RIN or RQN | Death age | Onset age | Duration (yr.) | CAG repeat size | Neuron Loss in Neocortical Gray Matter |
|---|---|---|---|---|---|---|---|---|---|
| HD-08 | Passed | Y | 21 | 7.4 | 43 | NA | NA | 49 | 1 |
| HD-09 | Passed | Y | 4 | 7.8 | 68 | 45 | 23 | 42 | 1 |
| HD-10 | Passed | Y | 6 | 8.3 | 59 | 35 | 24 | 46 | 1 |
| HD-12 | Passed | Y | 13 | 6 | 68 | 52 | 16 | 42 | 0 |
| HD-13 | Passed | N | 25 | 6.1 | 57 | 40 | 17 | 49 | 1 |
| HD-14 | Passed | Y | 11 | 7.3 | 48 | 38 | 10 | 45 | 1 |
| Mean | — | — | 15.48 | 7.18 | 58.17 | 43.91 | 15.64 | 45.17 | 0.875 |

All of the HD samples passed mRNA-seq QC.
Scale of neuron loss:
0 = absent,
1 = mild,
2 = moderate

TABLE 7

Control brain samples analyzed for mRNA-seq, miRNA-seq and RT-qPCR validation of miR-10b-5p

| Sample ID | miRNA-seq | RT-qPCR | PMI (hr.) | RIN or RQN | Death age |
|---|---|---|---|---|---|
| C-14 | Passed | Y | 21 | 8 | 79 |
| C-21 | Passed | Y | 26 | 7.3 | 76 |
| C-29 | Passed | Y | 13 | 6.4 | 93 |
| C-31 | Passed | Y | 24 | 7.3 | 53 |
| C-32 | Passed | Y | 24 | 8.3 | 57 |
| C-33 | Passed | Y | 15 | 7.5 | 43 |
| C-35 | Failed PCA | N | 21 | 7.6 | 46 |
| C-36 | Passed | Y | 17 | 7.5 | 40 |
| C-37 | Failed PCA | N | 28 | 8.3 | 44 |
| C-38 | Passed | Y | 20 | 7.7 | 57 |
| C-39 | Passed | Y | 15 | 7.3 | 80 |
| Mean | — | — | 20.36 | 7.49 | 60.73 |

All the control samples passed mRNA-seq QC.
RIN = RNA Integrity Number,
RQN = RNA Quality Number
PMI = Postmortem Interval

TABLE 8

Differentially expressed miRNAs from miRNA-seq

| miRNA | Control expression | HD expression | Fold Change | p-value | q-value* |
|---|---|---|---|---|---|
| miR-196a-5p | 1.47 | 27.49 | 18.66 | 2.05E−10 | 2.91E−07 |
| miR-10b-5p | 915.81 | 26020.05 | 28.41 | 1.99E−08 | 1.41E−05 |
| miR-615-3p | 1.09 | 6.66 | 6.09 | 2.73E−05 | 1.29E−02 |
| miR-1247-5p | 49.44 | 102.01 | 2.06 | 7.67E−05 | 2.72E−02 |
| miR-196b-5p | 2.49 | 11.01 | 4.41 | 9.77E−05 | 2.77E−02 |

*FDR-adjusted q-value

TABLE 9

22 differential expressed targets of miR-10b-5p, miR-196a, miR-196b, miR-1247 and miR-615-3p

| Target gene | miRNA | Location | Mean Control Expression (n = 9) | Mean HD Expression (n = 12) | Fold Change | p-value | q-value * |
|---|---|---|---|---|---|---|---|
| SERPINE1 | miR-10b-5p | 7q22.1 | 22.91 | 140.82 | 6.15 | 3.03E−11 | 5.06E−09 |
| CDKN1A | miR-196a | 6p21.2 | 336.73 | 841.75 | 2.5 | 1.58E−04 | 1.22E−02 |
| HOXD4 | miR-10b-5p | 2q31.1 | 1.74 | 18.33 | 10.51 | 2.38E−04 | 1.22E−02 |
| ANXA3 | miR-10b-5p | 4q21.21 | 259.93 | 553.71 | 2.13 | 2.92E−04 | 1.22E−02 |
| TWIST1 | miR-10b-5p | 7p21.2 | 43.43 | 105.16 | 2.42 | 5.63E−04 | 1.72E−02 |
| CD33 | miR-196a, miR-196b | 19q13.3 | 16.58 | 46.63 | 2.81 | 6.75E−04 | 1.72E−02 |
| DIO3 | miR-1247 | 14q32 | 10.89 | 41.93 | 3.85 | 7.29E−04 | 1.72E−02 |
| MMP2 | miR-10b-5p | 16q13-q21 | 58.67 | 137.83 | 2.35 | 8.26E−04 | 1.72E−02 |
| MMP9 | miR-10b-5p | 20q1.2-q13.1 | 5.32 | 17.33 | 3.26 | 9.33E−04 | 1.73E−02 |
| HOXA10 | miR-10b-5p, miR-196a, miR-196b | 7p15.2 | 1.06 | 17.06 | 16.12 | 1.21E−03 | 1.73E−02 |
| RHOD | miR-10b-5p | 11q14.3 | 12.71 | 37.96 | 2.99 | 1.23E−03 | 1.73E−02 |
| COL1A1 | miR-196a | 17q21.33 | 30.19 | 220.28 | 7.3 | 1.31E−03 | 1.73E−02 |
| HLA-E | miR-10b-5p | 6p21.3 | 3703.47 | 7769.76 | 2.1 | 1.34E−03 | 1.73E−02 |
| PPARA | miR-10b-5p | 22q13.31 | 444.7 | 865.02 | 1.95 | 1.53E−03 | 1.73E−02 |
| PAX6 | miR-196a | 11p13 | 693.52 | 1337.23 | 1.93 | 1.62E−03 | 1.73E−02 |
| EGFR | miR-10b-5p | 7p12 | 784.95 | 1762.88 | 2.25 | 1.66E−03 | 1.73E−02 |
| HOXB7 | miR-196a | 17q21.3 | 1.63 | 6.99 | 4.28 | 2.83E−03 | 2.78E−02 |

TABLE 9-continued 22 differential expressed targets of miR-10b-5p, miR-196a, miR-196b, miR-1247 and miR-615-3p

| Target gene | miRNA | Location | Mean Control Expression (n = 9) | Mean HD Expression (n = 12) | Fold Change | p-value | q-value * |
|---|---|---|---|---|---|---|---|
| PLAUR | miR-10b-5p | 19q13 | 56.15 | 119.67 | 2.13 | 3.65E−03 | 3.38E−02 |
| HOXD10 | miR-10b-5p | 2q31.1 | 1.25 | 9.33 | 7.45 | 4.73E−03 | 3.96E−02 |
| RUNX1 | miR-10b-5p | 21q22.3 | 87.69 | 224.88 | 2.56 | 4.74E−03 | 3.96E−02 |
| SOX2 | miR-10b-5p | 3q26.3-q27 | 1963.76 | 3492.72 | 1.78 | 5.32E−03 | 4.23E−02 |
| KRT5 | miR-196a | 12q13.13 | 113.74 | 51.99 | −2.19 | 6.00E−03 | 4.55E−02 |

* FDR-adjusted q-value for 167 targets of the five miRNAs.

TABLE 10

Differential expression of Hox cluster genes in HD

| Gene | Mean Control Expression (n = 9) | Mean HD Expression (n = 12) | Fold Change | p-value | q-value* |
|---|---|---|---|---|---|
| HOXA11 | 1.06 | 8.20 | 7.75 | 3.96e−05 | 2.07e−03 |
| HOXA5 | 1.06 | 7.63 | 7.21 | 1.03e−04 | 2.07e−03 |
| HOXD8 | 1.15 | 7.84 | 6.80 | 1.13e−04 | 2.07e−03 |
| HOXD4 | 1.74 | 18.33 | 10.51 | 2.38e−04 | 3.22e−03 |
| HOXB9 | 1.06 | 9.20 | 8.69 | 2.93e−04 | 3.22e−03 |
| HOXA10 | 1.06 | 17.06 | 16.12 | 1.21e−03 | 1.11e−02 |
| HOXC6 | 1.15 | 6.16 | 5.34 | 1.62e−03 | 1.27e−02 |
| HOXA11-AS | 1.25 | 7.39 | 5.90 | 2.49e−03 | 1.71e−02 |
| HOXB7 | 1.63 | 6.99 | 4.28 | 2.83e−03 | 1.73e−02 |
| HOXA13 | 1.45 | 8.74 | 6.03 | 4.07e−03 | 2.24e−02 |
| HOXD10 | 1.25 | 9.33 | 7.45 | 4.73e−03 | 2.36e−02 |
| HOXD1 | 55.91 | 22.80 | −2.45 | 8.55e−03 | 3.92e−02 |
| HOXC10 | 1.36 | 8.04 | 5.90 | 1.06e−02 | 4.14e−02 |
| HOXC4 | 3.57 | 10.77 | 3.02 | 1.12e−02 | 4.14e−02 |
| HOTAIRM1 | 3.52 | 12.52 | 3.56 | 1.13e−02 | 4.14e−02 |

*FDR-adjusted q-value for the 55 genes in the four Hox clusters

TABLE 11

| Gene Name |
|---|
| HOXA11 |
| HOXA5 |
| HOXD8 |
| HOXD4 |
| HOXB9 |
| HOXA10 |
| HOXC6 |
| HOXA11-AS |
| HOXB7 |
| HOXA13 |
| HOXD10 |
| HOXC10 |
| HOXC4 |
| HOTAIRM1 |
| SERPINE1 |
| CDKN1A |
| HOXD4 |
| ANXA3 |
| TWIST1 |
| CD33 |
| DIO3 |
| MMP2 |
| MMP9 |
| HOXA10 |
| RHOD |
| COL1A1 |
| HLA-E |
| PPARA |
| PAX6 |
| EGFR |
| HOXB7 |
| PLAUR |
| HOXD10 |
| RUNX1 |
| SOX2 |

Example 5: Assessment of miR-10b-5p as a Blood Biomarker of Huntington Disease (HD) Severity and Progression Study Design:

43 human blood samples were collected from nine non-HD gene carrier controls, five asymptomatic HD gene positive subjects and 29 HD subjects across various stages of the disease. HD subjects were subtyped into three groups (early stage, mid stage and late stage), by their total functional capacity (TFC) scale, as quantified during neurological examination. The levels of microRNA-10b-5p (miR-10b-5p) were quantified in plasma as it had been identified as related to age of onset and the severity of neuropathological involvement in HD brain samples (see above herein). RNA was extracted from blood plasma (as opposed to whole blood or peripheral mononuclear lymphocyte blood cells) as this is easiest blood assay for a biomarker. Studies of whole blood or lymphocytes may also prove to be effective biomarkers although we have not tested this possibility. miR-10b-5p was quantified using miRNA reverse transcriptase quantitative polymerase chain reaction (RT-qPCR).

Figure 12:
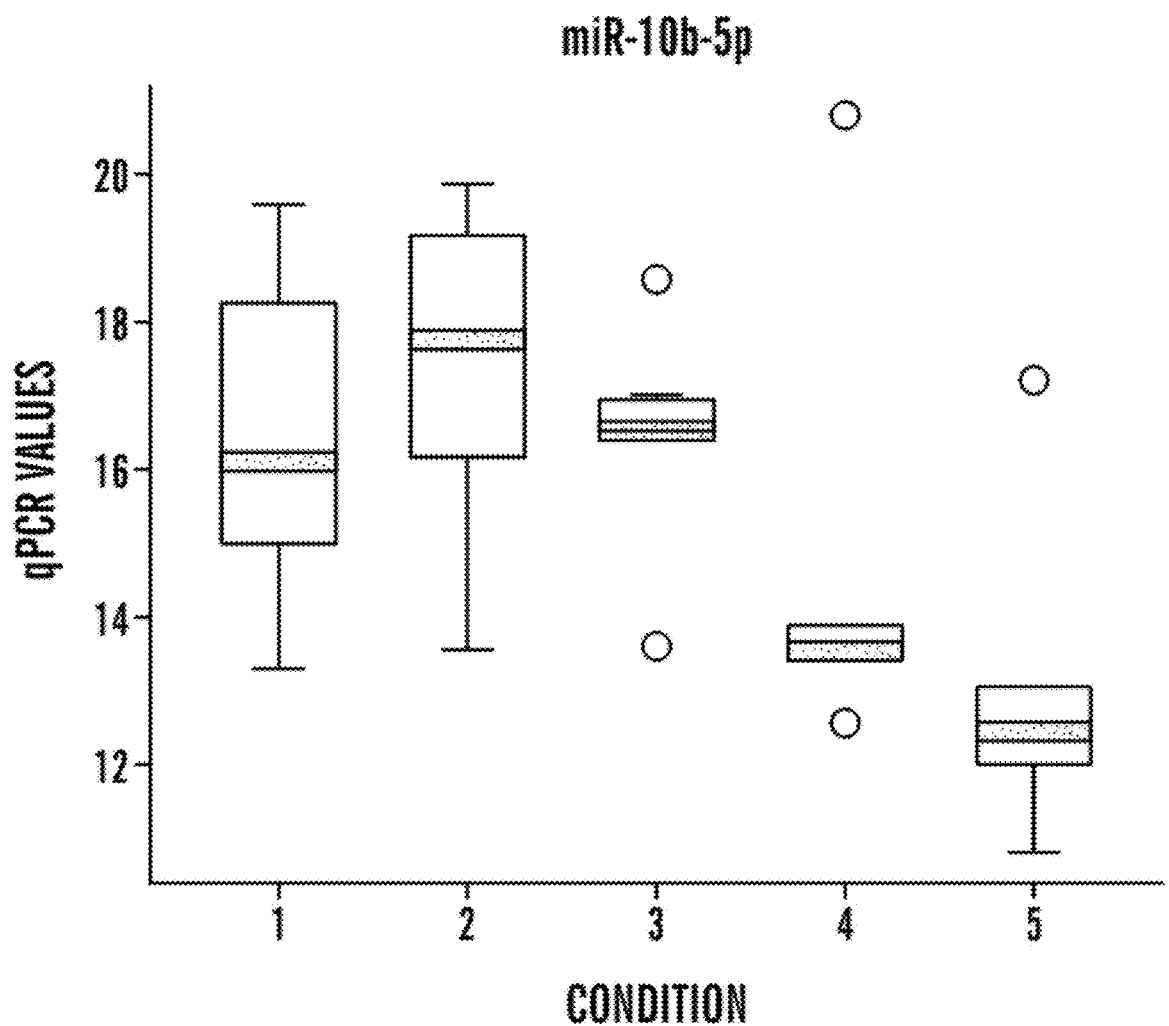
FIG. 12 depicts a graph of the relationship of miR-10b-5p expression in blood plasma to HD stages. 5=control; 4=asymptomatic HD gene carrier; 3=early stage HD; 2=mid stage HD; and 1=Late stage HD. Low qPCR values are associated with high expression. Controls had the highest level of expression. Expression was seen to decrease with increasing severity of disease in blood plasma samples.

Results:

After normalization to stably expressed miRNAs in the bloodstream (U44, miR-451), samples with high variability were removed from analysis and miR-10b-5p expression levels were statistically tested, comparing expression levels in HD to controls. A significant decrease in miR-10b-5p levels was observed in HD plasma (p=0.015). These results were found to be independent of age (data not shown). Next, using linear regression model, we compared miRNA expression across controls and disease stages. A significant, negative association of miR-10b-5p expression was found to disease stage, where controls had the most expression, followed by asymptomatic individuals, early stage and mid stage (p=6.1e-3, see FIG. 12). These experiments were repeated with the same samples and with the same, significant results.

Discussion:

miR-10b-5p plasma levels are significantly different in HD and associate with disease progression and thus miR-10b-5p can be a biomarker of disease progression and severity.

Example 6: Assessment of microRNAs in
Parkinson's Disease (PD) Brain Indicates that these
can be Biomarkers for Disease Onset and the
Likelihood for Developing Dementia Study Design:

Analysis of microRNAs was performed in prefrontal cortex (Brodmann Area 9) for 33 controls and 29 idiopathic Parkinson's disease (PD) samples. All samples were male. Clinical diagnoses were reported in medical records provided at the time at death. Twenty of the 29 PD samples had information on whether the subject was presenting symptoms of dementia, where 10 subjects had PD did not have dementia and 10 subject had PD with dementia (PDD). 21 subjects had information on the age of onset of motor symptoms. Total RNA was prepared miRNA was selected and submitted for sequencing using Illumina sequencing technology.

Differential Expression Analysis Results:

Using differential expression analysis, correcting for sequencing batch effects and the contribution of age at death on miRNA expression, 128 miRNAs were significantly altered in Parkinson's disease at a 5% false discovery rate. 66 miRNAs were down-regulated in expression and 62 were up-regulated in expression in PD relative to control samples.

Figure 13:
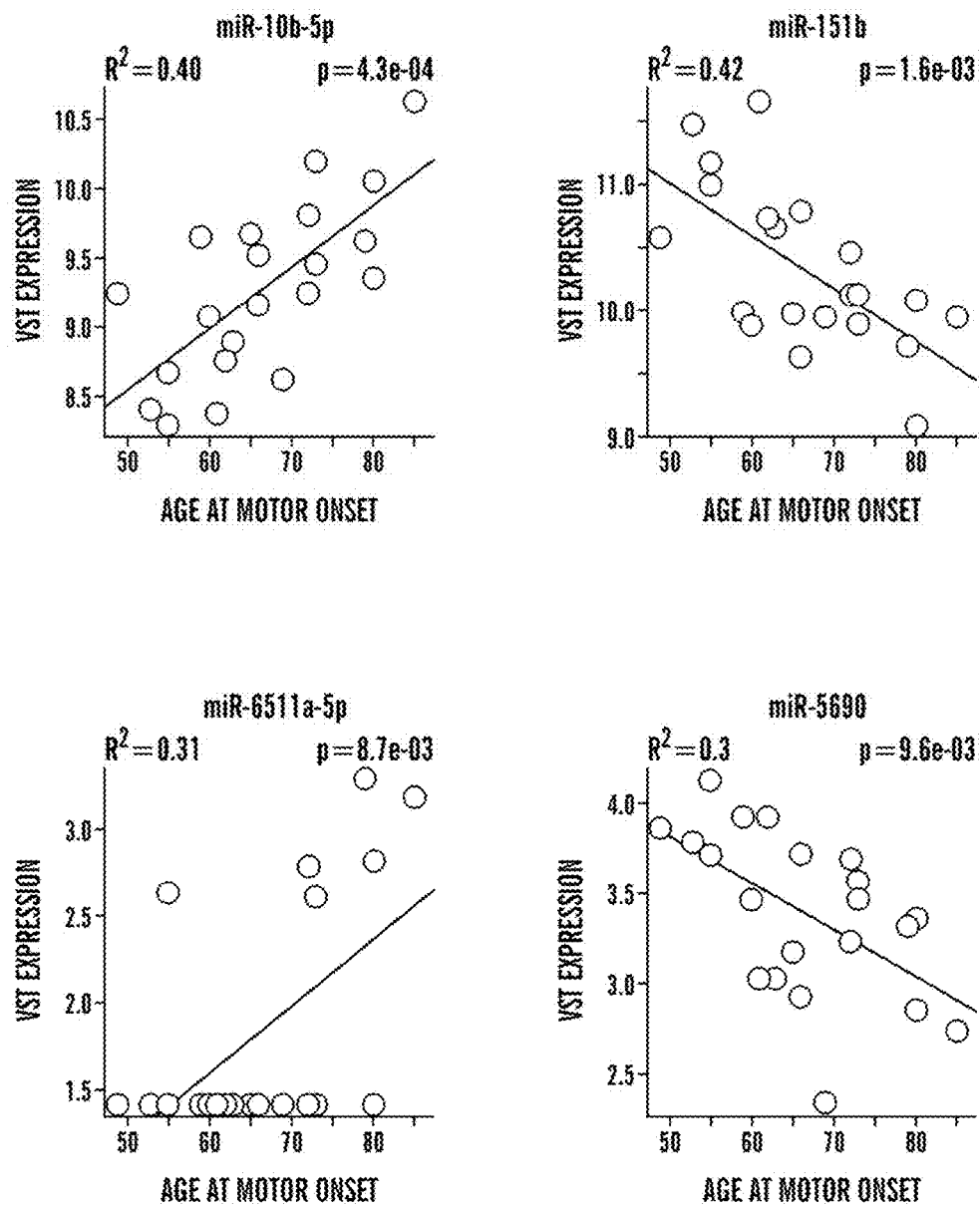
FIG. 13 demonstrates the relationship of miRNAs to PD age at motor onset

Age of Onset Analysis:

Age of onset was predicted by miRNA expression using linear regression modeling, and eight miRNAs (miR-10b-5p, miR-151b, miR-29b-2-5p, miR-329-3p, miR-6511a-5p, miR-5690, miR-516b-5p, miR-208b-3p) were found nominally significant (p<0.05) associated to motor onset (see FIG. 13). Of these eight, miR-10b-5p had the strongest relationship, exhibiting a positive association to onset ($r^2$=0.49, p=4.3e-4). miR-151b had the strongest negative association to onset ($r^2$=0.42, p=1.6e-3). These findings indicate that analyses of these microRNAs can predict the diagnosis of PD, the proximity to age at onset and disease severity.

Figure 14:
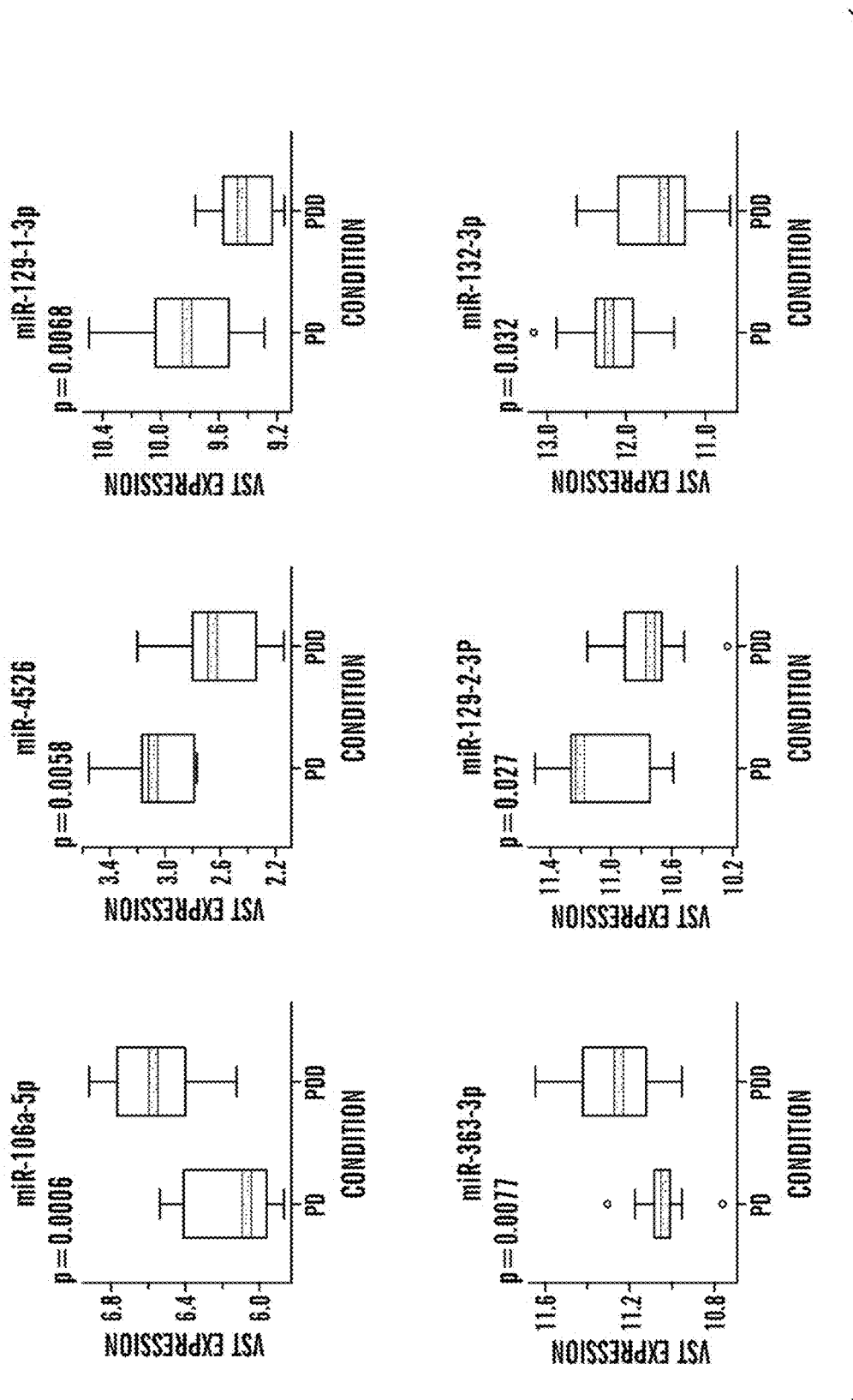
FIG. 14 demonstrates PD miRNAs that relate to dementia status (PDD=PD with dementia). These six microRNAs are associated with the presence of dementia in PD.
Figure 17:
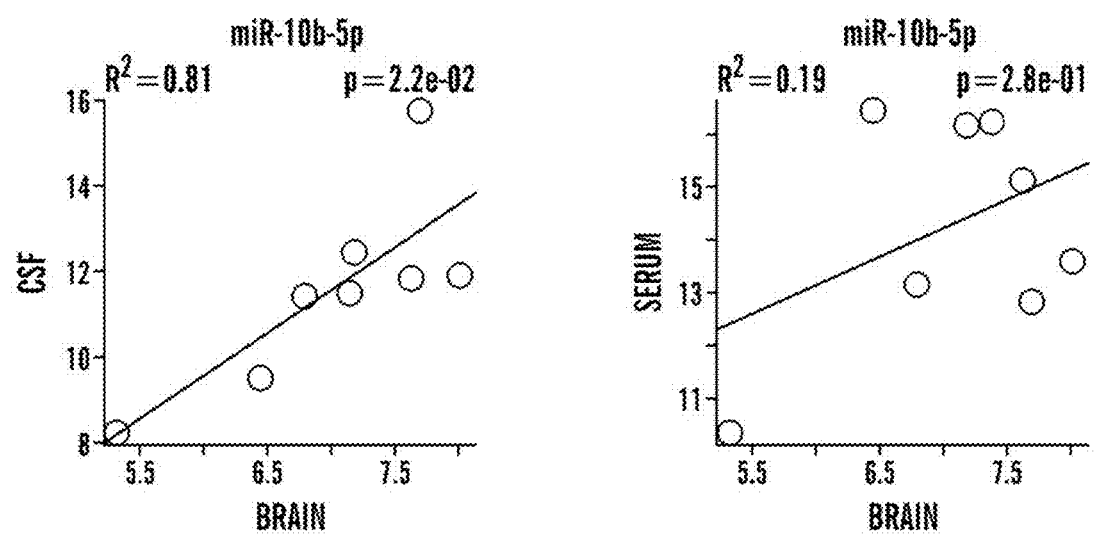
FIG. 17 depicts expression of miR-10b-5p across brain, cerebrospinal fluid and blood serum

Relationship of miRNAs to Dementia:

Six miRNAs were found to show a nominally significant relationship (p<0.05) to dementia using logistic regressions to predict dementia status (see FIG. 14). miR-106a-5p and miR-363-3p were increased in PDD as compared to PD, whereas miR-4526, miR-129-1-3p, miR-129-2-3p and miR-132-3p are decreased in PDD. These findings indicate that analyses of these microRNAs can predict which individuals are at increased risk for dementia in their manifestation of PD.

Comparison to HD miRNA Expression:

Relatively low fold changes were observed for miRNAs altered in PD, with 18% of differentially expressed miRNAs ±0.6 log fold change (LFC), as compared to 42%±0.0.6 LFC in HD. 21 miRNAs were found differentially expressed in bath PD and HD experiments. miR-10b-5p is one of the miRNAs found in both lists of dysregulated miRNAs. However, miR-10b-5p is massively increased in HD in comparison to controls whereas it is slightly decreased in PD (see FIG. 15). miR-10b-5p is found to relate to age of onset in both diseases. Again, PD and RD exhibit opposite effects, where miR-10b-5p has a strong, negative effect to age of onset in RD and a strong, positive effect in PD. Of the dementia-related miRNAs, four of the six miRNAs that relate to dementia (miR-106a-5p, miR-129-1-3p, miR-363-3p, and miR432-3p) are highly expressed, and most importantly, are differentially expressed in HD and relate to HD onset age as well as extent of degeneration in the striatum and cortex. These miRNAs have the same direction of effect when comparing PD to PDD, control to HD (see FIG. 16).

Discussion:

miRNAs expression is dysregulated in PD. A number of these altered miRNAs relate to age at motor onset or dementia status. The majority of miRNAs that relate to relevant clinical features of PD relate to relevant clinical features of HD—e.g., miR-10b-5p, miR-106a-5p, miR-129-1-3p, nail-363-3p, and miR-132-3p and these miRNAs can be representative of a generalized neurodegenerative process. microRNAs can predict the diagnosis of PD, the proximity to age at onset and disease severity and can predict which individuals are at increased risk for dementia in their manifestation of PD.

Example 7: microRNAs as Biomarkers in
Cerebrospinal Fluid and Serum: A Comparison
Study of Brain, Cerebrospinal Fluid and Serum Study Design:

In Burgos et al 2014, miRNAs from cerebrospinal fluid (CSF) and blood serum from 67 PD and 78 controls were sequenced using Illumina small RNA sequencing. First, miRNAs that were differentially expressed in each dataset were examined to see if there was any overlap in altered miRNAs across biospecimens. Here, the rationale was that differentially expressed miRNAs in the brain that are also altered significantly in CSF and/or serum are likely brain-derived and therefore potentially indicative of PD diagnosis, prognosis, or progression.

Next, of the 145 samples sequencing by Burgos et al. (2014), nine samples were from the same subjects that we had performed miRNA-sequencing from prefrontal cortex. These nine samples were analyzed, 4 controls and 5 PD, by correlating the expression of brain-specific differential expressed miRNAs to the expression of these same miRNAs in the biofluids, to discover whether these miRNAs could be potentially diagnostic of PD with dementia or age at onset.

Results:

17 miRNAs were differentially expressed in PD CSF and five were differentially expressed in PD serum. Of these 22 miRNAs, seven miRNAs were differentially expressed in brain, with four miRNAs from CSF (miR-132-5p, miR-127-3p, miR-212-3p, mild-1224-5p) and three from serum (miR-16-2-3p, miR-1294, miR-30a-3p). The log fold change (LFC) for CSF was in the same direction in brain as it was in CSF, however only one of the three serum miRNAs (miR-1294) was in the same direction in brain.

Next, the expression miRNAs in brain was correlated to CSF and serum. miR-10b-5p had the highest correlation and r-squared out of all brain differentially expressed miRNAs (r=0.88, $r^2$=0.61). miRNA that were observed as altered in both brain and CSF, were also correlated across biospecimen types (miR-212-3p, r=0.76; miR-127-3p, r=0.67; miR-1224-5p, r=0.51). These were not correlated when comparing brain to serum (miR-10b-5p, r=-0.02; miR-212-3p, r=-0.34; miR-127-3p, r=-0.04; miR-1224-5p, r=0.07).

Discussion:

miRNAs in CSF are correlated with miRNAs expressed in brain, suggesting that measures of miRNAs in CSF may be a better biomarker for disease state, severity, progression, age at onset, likelihood for dementia than similar studies in serum or plasma.

CITATION

Burgos K, Malenica I, Metpally R, Courtright A, Rakela B, et al. (2014) Profiles of Extracellular miRNA in Cerebrospinal Fluid and Serum from Patients with Alzheimer's and Parkinson's Diseases Correlate with Disease Status and Features of Pathology. PLoS ONE 9(5): e94839. doi:10.1371/journal.pone.0094839

Example 8

Huntington's disease (HD) is an inherited fatal neurological disorder that commonly affects people in midlife. Past microRNA biomarkers for Huntington disease pathogenesis studies have implicated abnormal patterns gene expression as a candidate for causing the death of the brain cells affected in HD. Currently, clinical trials in HD require a lengthy, commonly three-year protocol to evaluate efficacy of drug treatment. This process is expensive and time consuming, tying up hundreds of patients for long periods of time.

miRNAs represent a major system of post-transcriptional regulation, by either preventing translational initiation or by inducing transcript degradation. Described herein is the measurement of the levels of miRNAs, as well as the levels of gene expression (mRNAs) in twelve HD and nine control brain samples. It was found that five miRNAs (miR-10b-5p, miR-196a-5p, miR-196b-5p, miR-615-3p and miR-1247-5p) were up-regulated in HD at genome-wide significance (FDR qvalue<0.05). Three of these miRNAs, miR-196a-5p, miR-196b-5p and miR-615-3p, were expressed at near zero levels in the control brains. miR-10b-5p expression was verified and replicated with reverse transcription quantitative PCR. Four of these were related to important characteristics of the disease expression, including the age at disease onset, and the age at death of the individual. It was examined which genes these miRNAs target for regulation and many of these were also altered in their expression in the HD samples. Based upon their relationship to disease expression, these miRNAs can be HD biomarkers.

Figure 18:
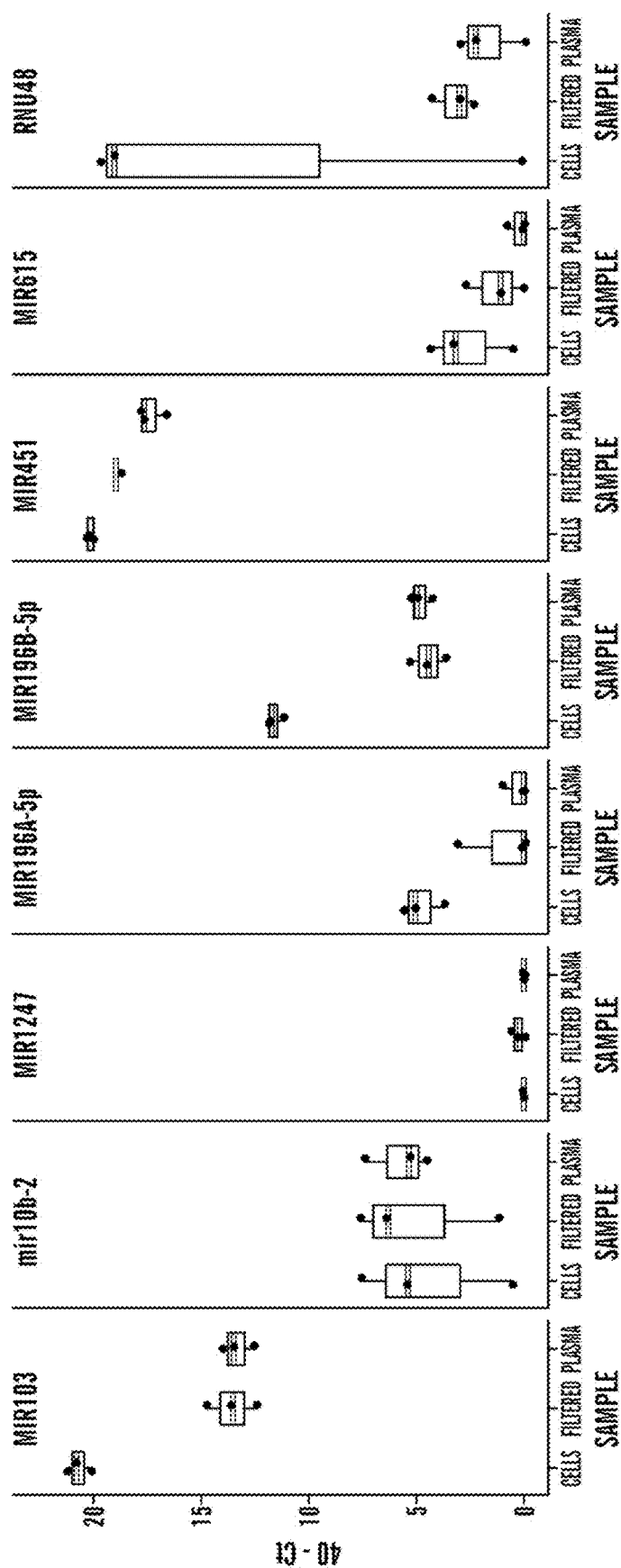
FIG. 18 depicts graphs of the levels of microRNAs detected in blood and plasma (FIG. 18). The presence of these miRNAs was evaluated in three conditions: (1) lymphocytes ("cells"), (2) "filtered plasma" where plasmids were removed by filtration, and (3) "plasma" where the plasma was centrifuged to remove plasmids.

Four of the microRNAs are detected in blood and plasma (FIG. 18). miR-10b-5p, miR-196a-5p, miR-196b-5p, and miR-615-3p are detected and miR-1247-5p is not detected (miR103 and miR451 were used as controls since they are known to be present in blood and plasma). The presence of these miRNAs was evaluated in three conditions: (1) lymphocytes ("cells"), (2) "filtered plasma" where plasmids were removed by filtration, and (3) "plasma" where the plasma was centrifuged to remove plasmids.

Five microRNAs are dramatically altered in Huntington versus control brains, as described herein. Studies of these five have been conducted in blood samples, and four of them can be detected in plasma and lymphocytes in blood. The methods described below are those used in brain samples.

RNA extraction. Total RNA, for all samples studied, was isolated using QIAzol™ Lysis Reagent and purified using miRNeasy MinElute™ Cleanup columns (Qiagen Sciences Inc, Germantown, Md.). RNA quality was assessed using either Agilent's BioAnalyzer 2100™ system and RNA 6000 Nano™ Kits to find RNA Integrity Number (RIN) or Agilent 2200 TapeStation™ and DNA ScreenTape™ assay RNA Quality Number (RQN; Agilent, Foster City, Calif.). Both methods calculate the area under the peak for 18S and 28S RNA as a ratio of total RNA as well as the relative height of the 18S and 28S peaks to determine RNA quality [47]. The RIN/RQN values were similar for the twelve HD and eleven control specimens studied for miRNA and mRNA (t=0.95, p=0.36), and for the 19 HD, 18 control and 8 PD samples, studied in RT-qPCR replication and validation studies (t=0.35, p=0.70).

Illumina™ miRNA sequencing (miRNA-seq). For each brain sample, 1 ug of RNA was used to construct sequencing libraries using Illumina's TruSeq™ Small RNA Sample Prep Kit, according to the manufacturer's protocol (Illumina, San Diego, Calif.). In brief, small RNA molecules were adapter-ligated, reverse transcribed, PCR amplified and gel purified to generate the library. Multiplexed samples were equimolarly pooled into sets of eight samples per flowcell lane and sequenced using 1×50 bp single-end reads on Illumina's HiSeq 2000™ system. Demultiplexing and FASTQ file generation (raw sequence read plus quality information in Phred format) were done using Illumina's Consensus Assessment of Sequence and Variation (CASAVA™) pipeline.

Primary processing of Illumina miRNA-seq reads. Sequence read quality was evaluated using the FASTQ quality filter module from the FASTX-toolkit version 0.0.13 (available on the world wide web at hannonlab.cshl.edu/fastx_toolkit/), and only those reads with at least 80% of the base calls above Q20 (Phred score) were retained. The 3' adapter sequence (5'-TGGAATTCTCGGGTGCCAAGG-3' (SEQ ID NO: 43)) was removed from all reads using the FASTA/Q clipper module from the FASTX-toolkit. A minimum length threshold of 15 nucleotides was set for clipped reads because miRNAs of this length will contain the seed sequence. To avoid redundancy amongst identical read species, the reads were collapsed using the FASTA/Q collapser module from FASTX-toolkit to generate a FASTA file of only the unique read species.

Alignment and mapping of miRNA-seq reads. Quality-filtered, 3' adapter-clipped reads were aligned to the UCSC human reference genome (build hg19) using Bowtie version 0.12.3 [48]. Alignment parameters were set to allow for no mismatch alignments and no limits on multiple mapping instances. Multiple-mapped identical sequences were summed for a single count for that annotated mature miRNA. The default settings were used for all other alignment options.

miRNA abundance estimation. Aligned reads that overlapped with the human miRNA annotation version 19 from miRBase (available on the world wide web at mirbase.org/ftp.shtml) were identified using default BEDTools' IntersectBed™ functionality [49]. To select for mature miRNA reads, sequences more than 27 bases in length were removed. Only those reads for which the aligned 5' start-nucleotide matched exactly to the 5' start-nucleotide of the annotated miRNA were retained for the analysis. After filtering, collapsed read counts were summed per annotated mature miRNA.

mmiRNA differential expression. The R (available on the world wide web at R-project.org) package DESeq™ version 1.10.1 [15] was used to perform the differential expression analysis between HD and control samples using the read counts generated for each sample as described above. miRNAs with zero read counts across all case and control samples were removed from analysis. To accommodate the analysis of miRNAs with read counts of zero for some samples, a pseudo-count of one was added to all raw counts for every miRNA across all the samples, prior to performing DESeq's estimateSizeFactors and estimateDispersions functions with default options. DESeq assumes that count data follow a negative binomial distribution and factors in technical and biological variance when testing for differential gene expression between groups. DESeq's function, estimateSizeFactors, was used to obtain normalization factors for each sample and to normalize miRNA read counts. The normalized counts were evaluated by principal component analysis (PCA) with the FactoMineR™ R package for all HD and control samples. The samples identified to be three or more standard deviations away from the mean on the first or second principal component were considered outliers and were removed from analysis. The first two principal components were used because they each explained more than 10% of the variance, while the remaining principal components explained less than 10% of the variance. Two control samples (C-35 and C-37) were identified as outliers based on PCA analysis.

miRNA differential expression analysis was performed with DESeq's nbinomTest™ function for the remaining nine control and twelve HD samples. All analyses were performed on DESeq normalized counts.

While there are proposals that brain imaging may provide a viable biomarker for Huntington progression, this method relies on the atrophy of brain regions to detect the efficacy of drug trials. Consequently, this approach is slow and requires several years to detect reliable effects of pharmacologic intervention. Described herein are methods and assays relating to microRNAs as, e.g., blood biomarkers of the immediate effects for drugs to correct transcriptionally altered gene expression responsible for the disease progression.

Example 9: miR-10b-5p Expression in Huntington's Disease Brain Relates to Age of Onset and the Extent of Striatal Involvement MicroRNAs (miRNAs) are small non-coding RNAs that recognize sites of complementarity of target messenger RNAs (mRNAs) resulting in transcriptional regulation and translational repression of target genes. Dysregulation of miRNA post-transcriptional machinery may impact gene expression and influence disease pathology.

Using next-generation miRNA sequence analysis in prefrontal cortex (Brodmann Area 9) of 26 HD, 2 asymptomatic HD, and 36 controls, 75 differentially expressed miRNAs were identified at genome-wide significance (FDR q-value<0.05). Among the HD brains, nine miRNAs were significantly associated with Vonsattel grade of neuropathological involvement and three of these, miR-10b-5p, miR-10b-3p, and miR-302a-3p, were significantly related (FDR q-value<0.05) to the Hadzi-Vonsattel striatal score, a continuous measure of striatal involvement, after adjustment for CAG. Five miRNAs (miR-10b-5p, miR-196a-5p, miR-196b-5p, miR-10b-3p, and miR-106a-5p) were identified as having a significant linear relationship (FDR q-value<0.05) to CAG-adjusted age of onset and of these, miR-10b-5p showed the strongest association to disease expression. Correlation of miRNAs to clinical features clustered by up- and down-regulated miRNA and the targets of these miRNAs associated with biological processes relating to nervous system development and transcriptional regulation.

These results demonstrate that measurement of miRNAs, and particularly miR-10b-5p, in cortical BA9 provides insight into the level of striatal involvement, independent of cortical involvement, and support a role for this miRNA in HD pathogenicity. The miRNAs identified in these studies of postmortem brain tissue can be detected in peripheral fluids and thus are accessible biomarkers for brain health, disease stage, rate of progression, and other important clinical characteristics of HD.

Introduction

Huntington's disease (HD) is an inherited disorder caused by a CAG trinucleotide repeat expansion within the HTT gene which leads to progressive motor and cognitive impairment due to the gradual loss of neurons within striatal and cortical brain regions [1]. Although monogenic, HD displays remarkable variation in disease expression, most readily observed by the range in age of clinical onset as determined by the manifestation of motor symptoms, varying from age 4 years to age 80 [2]. While onset age is unequivocally related to the size of the expanded CAG repeat, with longer repeats leading to earlier onset, only 50% to 70% of the variation can be attributed to repeat size [3,4]. The remaining variation is highly heritable ($h^2$=0.56), suggesting a strong role for genes that modify disease expression [3].

MicroRNAs (miRNAs) are small non-coding RNAs known to negatively regulate the expression of genes in a sequence-specific manner, binding to the 3'-untranslated region (3'UTR) to initiate cleavage or translational repression of target transcripts [5,6]. miRNAs influence a diverse range of cellular processes [7] and consequently, their impairment or altered expression may lead to or influence disease related pathological phenotypes. In the central nervous system (CNS), miRNAs are abundant, as brain-specific miRNAs assist in various neuronal processes such as synaptic development, maturation and plasticity [8,9]. Altered miRNA expression has been observed in diseases of the CNS, particularly in age-dependent neurodegenerative diseases, which suggests the expression of miRNAs may contribute to neuropathogenesis [10,11].

In HD, the dysregulation of miRNAs has been reported in HD in vitro models, transgenic HD animals and human HD brain [12-24]. Without wishing to be bound by theory, it is contemplated that post-transcriptional regulation by miRNAs can play a role in modifying the progression and severity of HD. As described above herein, a study of miRNA expression obtained through next-generation sequencing technology in human HD and control brain samples to investigate the presence of altered miRNA expression in HD and its role in transcriptional dysregulation was performed [13]. To follow-up on these findings, small RNAs have been sequenced in an additional 16 HD brains, two of which are gene positive asymptomatic HD grade 0 cases, and 27 control samples, for a combined study of 28 HD and 36 control samples. The increased sample size enables the detection of significantly altered miRNAs with lower levels of differential expression as well as more comprehensive characterization the relationship of these miRNAs to relevant clinical features of the disease including the age of motor onset of the disease, disease duration, age at death and extent of pathological involvement in the striatum and cerebral cortex. A deeper understanding of the global miRNA expression in HD can elucidate pathogenic mechanisms of disease progression in HD and indicate new therapeutic targets Results Differential Expression Analysis Highlights Disrupted miRNA Expression in HD Brain.

To evaluate the relationship of miRNA expression to salient clinical and pathological features of HD, miRNA expression was profiled using small RNA-sequencing of prefrontal cortex (Brodmanns rea 9) of 26 symptomatic HD and 36 non-neuropathological control samples (see Table 12). The HD samples consisted of Grade 2 (n=4), Grade 3 (n=15), and Grade 4 (n=7) brains as determined by Vonsattel grade, an assessment of striatal involvement classified as 0 through 4 in order of the severity of neuropathological involvement [25]. Sequenced samples were also among the 523 HD brains characterized by the recently established measure of pathological involvement termed the Hadzi-Vonsattel score (H-V score), which independently characterizes both striatal and cortical pathological involvement in each brain [26]. While Vonsattel grading and H-V striatal score are closely related, (Pearson r=0.90, measured using 346 HD brains), H-V scores are a continuous metric and therefore more amenable to adjustment of covariates such as CAG repeat size in modeling of neuropathological involvement and independently assesses striatal and cortical involvement. H-V scores ranged from 0-4, where 0 indicates no detectable neuropathological involvement and 4 indicates severe neuropathological involvement. Samples from symptomatic individuals had striatal scores ranging 1.43-3.82 and cortical scores ranging from 0.40-2.36 (see Table 12). Additionally, two Grade 0 brains (both with CAG repeat expansions of 42 repeats (SEQ ID NO: 33)) were small-RNA sequenced and analyzed separately from the 26 HD brains used in differential expression analysis. Grade 0 brains were neuropathologically normal and asymptomatic at the time of death (see Table 12).

Figure 19:
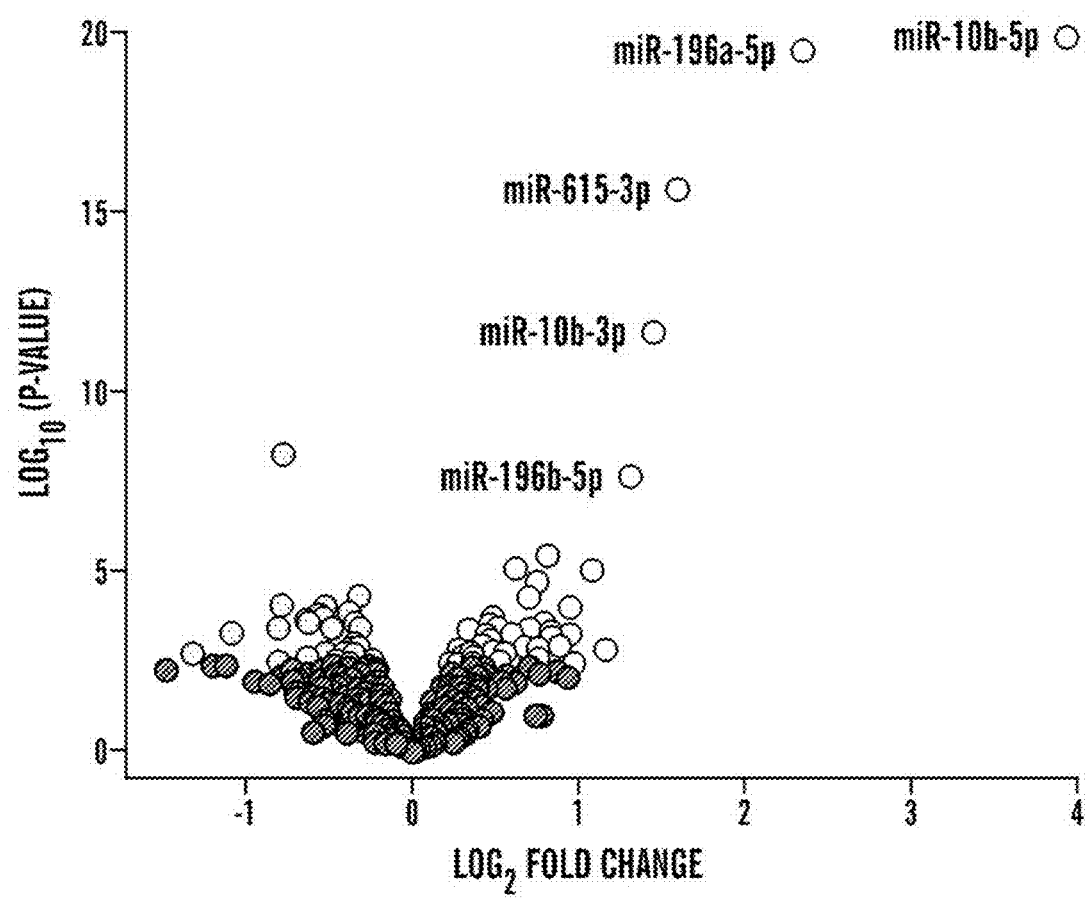
FIG. 19 depicts the characterization of miRNA in Huntington's disease brain. Volcano plot of 75 significantly differentially expressed miRNAs after FDR-adjustment for 938 comparisons. Points labeled red were up-regulated in HD and points labeled as blue were down-regulated in HD. The top five differentially expressed miRNAs (labeled in red) are all Hox-related.

After processing sequencing data to remove sequencing artifacts, normalize using variance stabilization transformation and adjust for batch effects (see Methods), 938 miRNAs were detected and 75 of these were significantly differentially expressed in HD versus control brains after adjusting for multiple comparisons (FDR q-value<0.05, see Table 13). In HD, 46 miRNAs were identified as significantly up-regulated and 29 as down-regulated in their expression. Hox-related miRNAs had the most extreme, positive fold changes, where miR-10b-5p was 3.9 log 2 fold increased, miR-196a-5p was 2.4 log 2 fold increased, miR-615-3p was 1.6 log 2 fold increased, miR-10b-3p was 1.5 log 2 fold increased, and miR-196b-5p was 1.3 log 2 fold increased (See FIG. 19, Table 13). Both the 5' and 3' mature miRNAs were DE for eight miRNA precursors (miR-10b, miR-129, miR-1298, miR-142, miR-144, miR-148a, miR-302a, and miR-486). In HD and controls, most 5'-3' miRNA pairs were positively correlated in their expression, with the exception of miR-1298 in HD and miR-10b and miR-302a in controls.

To support the DE miRNA findings in HD, the twelve HD and nine controls samples were analyzed from the original study using an updated sequence analysis pipeline (see Methods). A replication of these results was also performed using the newly sequenced consisting of fourteen HD and 27 control brains, which included grade 2 brains. Fourteen miRNAs were significantly DE (FDR q-value<0.05). Nine of the fourteen DE miRNA from the original set and thirteen of the fourteen from the replication set were significant in the combined sequence analysis (see Table 13). The fold changes of the DE miRNAs from the combined study were in all the same relative direction as the original and replication study. Hox-related miRNA, including miR-10b-5p, were among the most significantly DE across all three studies.

Firefly Bioworks™ microRNA assay, a multiplexed, particle-based technology using flow cytometry to measure miRNA levels, was used to quantify and orthogonally validate miRNA differential expression from sequencing. 16 miRNAs with moderately high expression levels were selected for testing and an additional six miRNAs were used as input normalizers (see Methods). A subset of 21 controls and 15 HD samples from the sequencing study were selected for the assay. Seven out of sixteen miRNAs assayed (miR-10b-5p, miR-194-5p, miR-223-3p, miR-132-3p, miR-144-5p, miR-148a-3p, miR-486-5p) were confirmed as being DE in HD (unadjusted p-value<0.05) (data not shown).

Nine miRNAs were Related to Vonsattel Grade

To explore the relationship of miRNA expression to principal clinical aspects of the disease, the expression of the 75 DE miRNAs was modeled to the Vonsattel grade of neuropathological involvement. Analysis of variance (ANOVA) was performed to compare the expression of the 75 DE miRNAs across Vonsattel grade in all 28 (Grade 0-4) HD and control brains. 65 miRNA were found to be significant in the ANOVA (FDR-adjusted q-value<0.05), indicating differential expression may be driven by the difference of controls to specific grades. Next, ANOVA was performed exclusively in HD brains to find whether miRNA differences exist across HD grades. Nine miRNAs were significant in both ANOVA tests after adjusting for multiple comparisons, indicating a significant difference in the expression of these miRNAs across Vonsattel grades (both FDR q-values<0.05; data not shown). Last, pairwise comparisons of each grade with the control group were performed using post-hoc Tukey's HSD tests to find specific groups that significantly differed from one another. FIGS. 20A-20I highlight the nine miRNAs that are associated with grade in order of statistical significance from the ANOVA inclusive of control brains in the test. In FIGS. 20A-20I, significant differences across grade and control groups as determined by Tukey HSD are denoted by letters (a-d) in the grey banner above each boxplot, whereby groups with different letters are significantly different from one another while those which share letters are not.

Figure 20A:
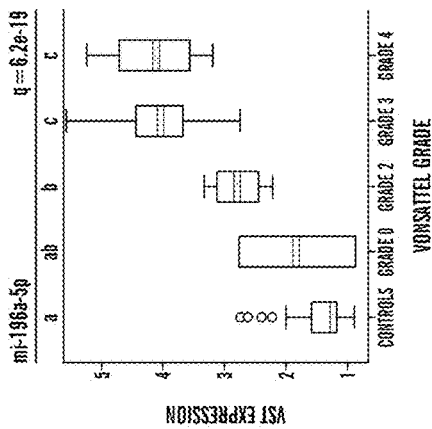
FIGS. 20A-20I demonstrate that nine miRNAs are associated with Vonsattel grade. In HD brains, expression of differentially expressed miRNA was compared across Vonsattel grades 0-4. Boxplots represent nine FDR-significant miRNAs (FDR q<0.05, adjusted for 75 contrasts) associated with Vonsattel grade by analysis of variance (ANOVA). X-axes represent Vonsattel grade, classified 0-4 in order of the severity of striatal involvement and Y-axes show the VST expression values after batch correction. Significant differences across grades and controls are denoted by letters in the grey banner above the boxplot, labeled a-d. Groups with different letters are significantly different from one another while those with the same letter are not, after correcting for multiple comparisons. For example, group "a" would be significantly different from group "b" and "c." Conditions represented by multiple letters indicate no significant difference among those groups. For example, group "ab" would not be significantly different than groups "a" and "b," but would be different group "c."
Figure 20B:
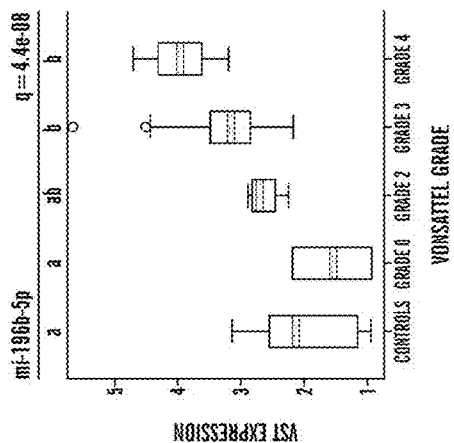
Figure 20C:
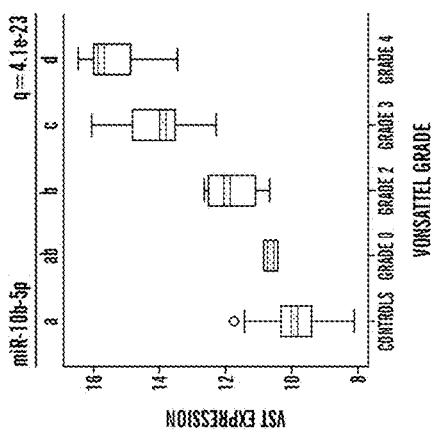
Figure 20D:
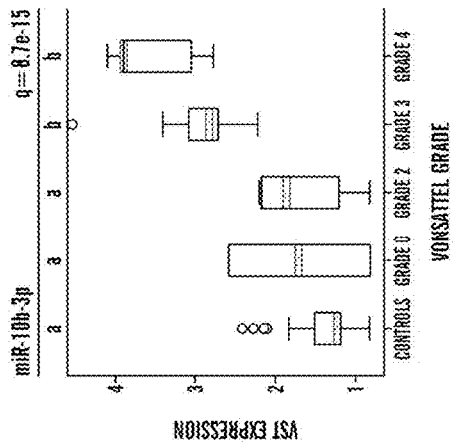
Figure 20E:
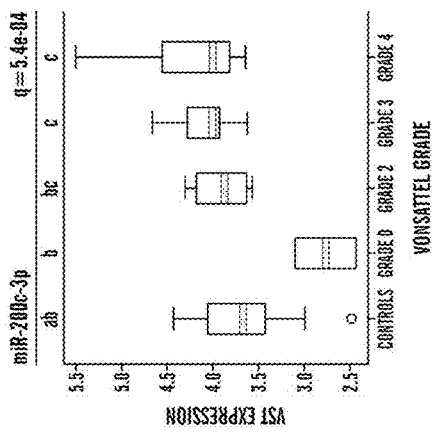
Figure 20F:
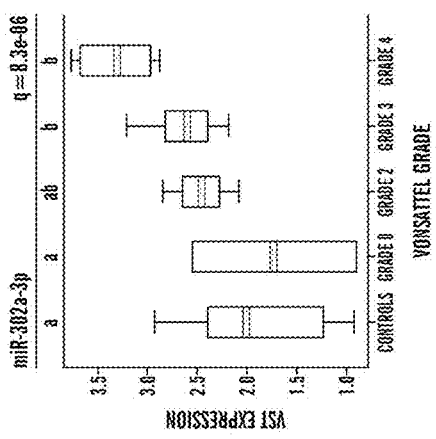
Figure 20G:
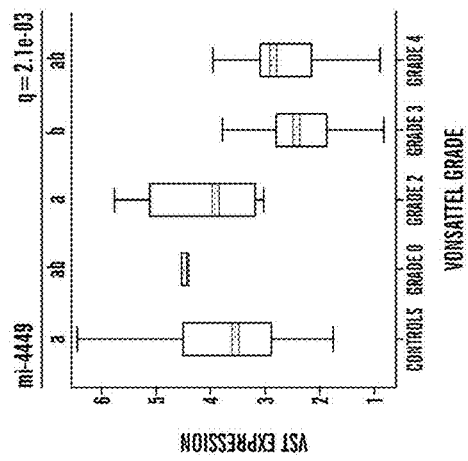
Figure 20H:
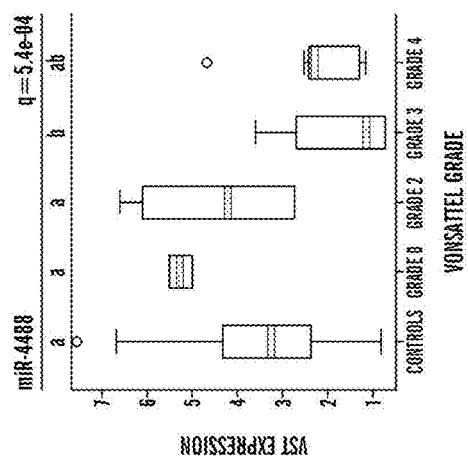
Figure 20I:
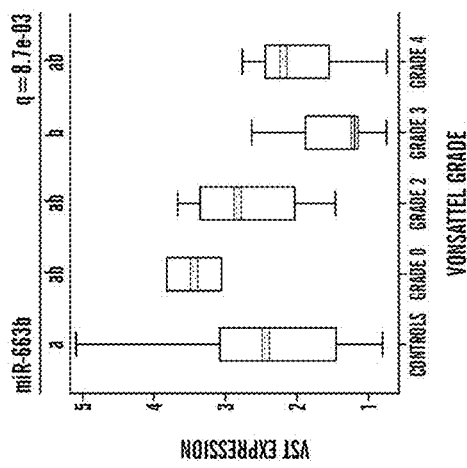
Figure 21B:
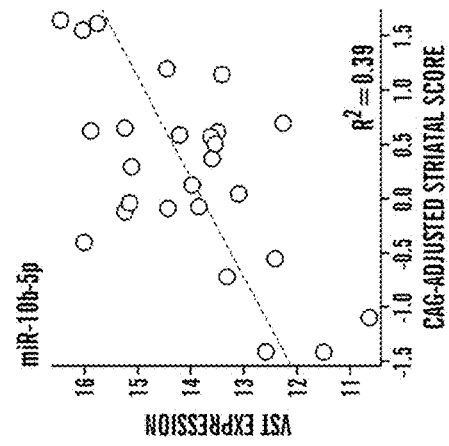
FIGS. 21A-21D demonstrate that miR-10b is associated with age of onset and striatal involvement. In 26 Vonsattel grade 2, 3 and 4 HD brains, both mature miR-10b sequences (-3p and -5p) have FDR-significant relationships to CAG-adjusted Hadzi-Vonsattel striatal score and CAG-adjusted onset age. Y-axes show the variance stabilizing transformation expression values after batch correction and shows that miR-10b-5p is expressed at much higher levels than miR-10b-3p. Grade 0 cases are not included, as they have neither onset age nor H-V striatal score.
Figure 21A:
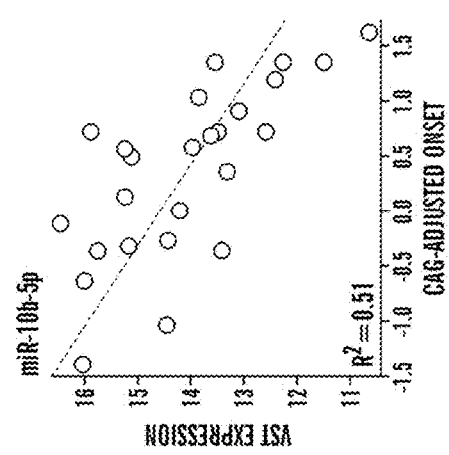
Figures 21C, 21D:
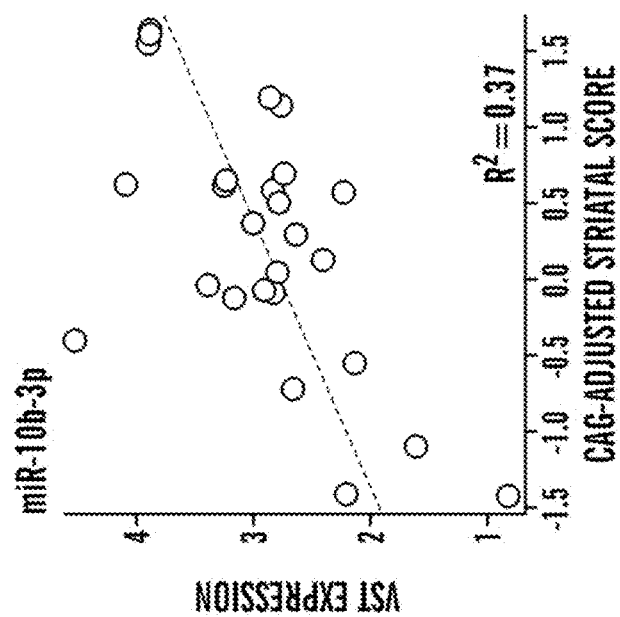

Several patterns in the relationship of grade to miRNA expression were observed. First, the expression of miR-10b-5p was significant in nearly all comparisons; pairwise contrasts between all grades as well as with the control group were different except for grade 0, although grade 0 was different than grades 2, 3 and 4 (FIG. 20A). Second, the expression of miRNAs in grade 0 brains was rarely different than controls, with the exception of miR-200c-3p, where its expression in grade 0 brains was significantly lower than both controls and grades 2-4 brains (FIG. 20G). Third, the expression of miRNAs in grade 3 and 4 brains appeared relatively similar to one another, with the exception of miR-10b-5p, as mentioned above, and miR-4488, where grade 3 brains were significantly lower than all other groups (FIG. 20D). Although not significant in the HD-only ANOVA, significant pairwise differences between grade 3 and 4 were observed for miR-1298-5p (Bonferroni q-value=0.036) and miR-615-3p (Bonferroni q-value=0.022).

miRNA Expression Relates to Striatal Involvement and Age of Onset in HD

To further investigate the association of miRNAs to HD, miRNA expression was modeled to salient features of the disease (age at motor onset, disease duration, age at death, and H-V scores of striatal and cortical involvement). To avoid confounding the analysis of these clinical features by the known, strong relationship between HTT CAG repeat size and disease pathology and onset [4,26-28], CAG-adjusted residuals were calculated for all continuous clinical traits. Residuals were created using the sample set of 346 H-V rated brains with CAG repeats less than 56 (SEQ ID NO: 44) to provide robust residual estimates for the subset of samples included in the sequencing project. (data not shown).

Using linear regression analysis, three miRNAs (miR-10b-5p, miR-10b-3p, miR-302a-3p) were observed to have a significant relationship to CAG-adjusted striatal score (all had FDR q-values=2.28e-2; data not shown). All three were significant in the analysis of miRNA expression to Vonsattel grade (see above). Additionally, five miRNAs were identified as having significant association to CAG-adjusted age of onset after adjusting for multiple comparisons (miR-10b-

5p, FDR q-value=3.49e-3; miR-196a-5p, FDR q-value=1.32e-2; miR-196b-5p, FDR q-value=1.71e-2; miR-10b-3p, FDR q-value=1.71e-2; miR-106a-5p, FDR q-value=1.71e-2; data not shown). FIGS. 21A-21D highlight the relationship of miR-10b to CAG-adjusted striatal score and onset, where both 3p and 5p mature sequences of miR-10b were the only miRNA species to have significant, linear association to these two clinical features independent of CAG effect. No FDR-significant relationships of miRNA to disease duration, death age or H-V cortical scores were observed.

No significant relationship of the expression of the 75 DE miRNA to CAG-adjusted cortical score was observed, although nominal associations were seen. In order to account for the potential impact of cortical involvement on the relationship of miRNA expression to striatal involvement, a multivariate regression analysis was performed, modeling miRNA expression to striatal H-V score while correcting for cortical H-V score. After CAG-adjusted cortical score correction, CAG-adjusted striatal score remained significant (miR-10b-5p p-value=0.04, miR-10b-3p p-value=0.01, miR-302a-3p p-value=0.005). These results indicate the relationship of miRNA expression to striatal involvement in the disease is independent of cortical involvement, which is a critical finding, because prefrontal cortex was the source of tissue profiled in these studies.

Figure 22:
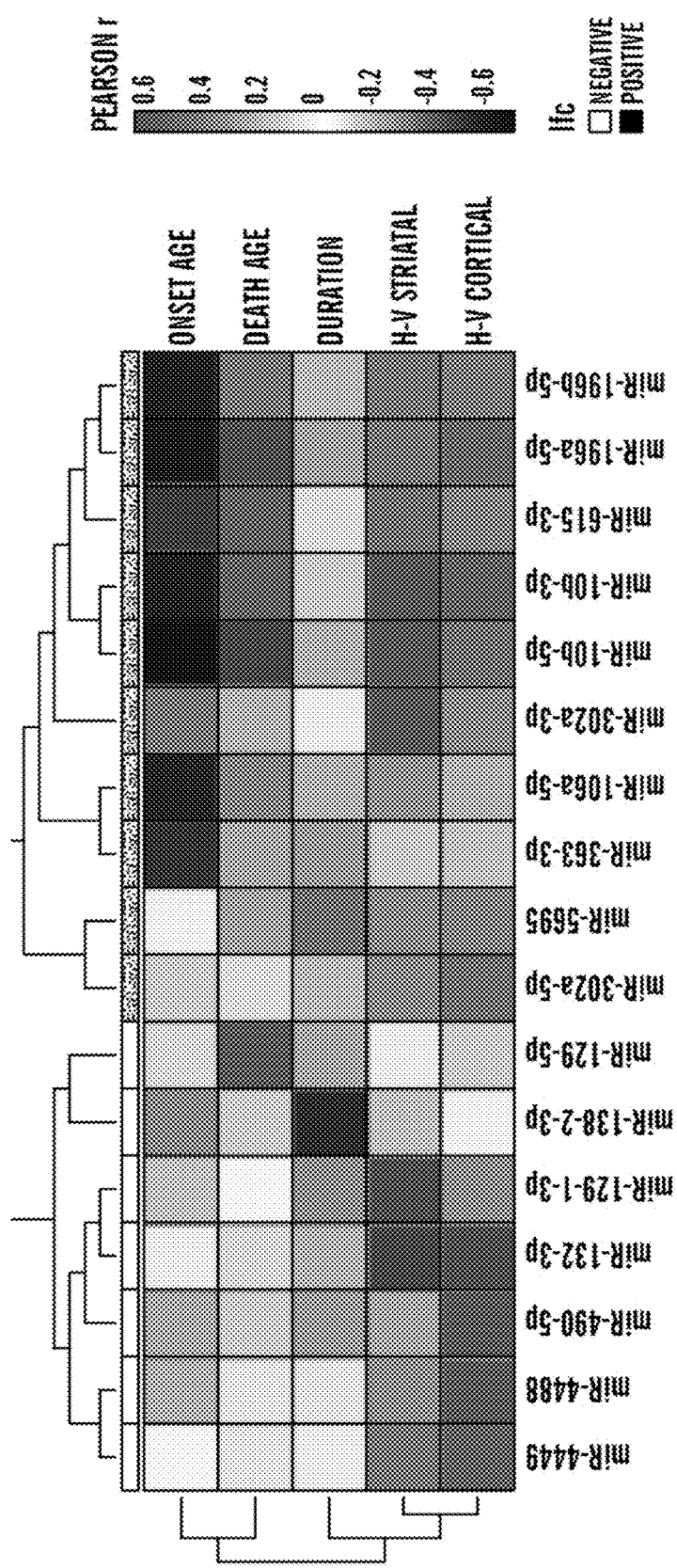
FIG. 22 demonstrates that CAG-adjusted clinical features of HD show patterns of association with miRNA expression. CAG-adjusted measures of onset age, disease duration, death age, Hadzi-Vonsattel (H-V) striatal and cortical score were correlated with DE miRNAs in HD brains. miRNAs with at least one nominal p-value<0.05 are shown. Pearson correlation coefficients and features were independently hierarchically clustered. Red boxes indicate positive correlations and blue boxes indicate negative correlations. Seven miRNAs in the left section are down-regulated in HD and the ten miRNAs in the right section are up-regulated. Unsupervised clustering separated miRNA by their direction of fold change.

Last, to characterize the patterns of association of miRNAs to clinical features, Pearson coefficients of the correlation of the expression of the DE miRNAs to five CAG-adjusted features (onset age, disease duration, death age, striatal score and cortical score) were hierarchically clustered. Correlation coefficients rather than beta coefficients were used in order to observe the direction of effect. Here, we observed DE miRNAs with correlation p-values<0.05 clustered into distinguishable patterns of association to clinical variables (FIG. 22). DE miRNAs increased in HD tended to have negative correlations with onset and death, and positive correlations with striatal and cortical score. Conversely, DE miRNAs with negative relative fold changes had positive correlations with onset and death, and negative correlations with striatal and cortical scores.

Targets of HD-Related miRNAs are Associated with Nervous System Development and Transcriptional Regulation To attempt to understand the potential functional impact of miRNA dysregulation in HD, gene ontology enrichment was performed using predicted targets for miRNAs that correlated with clinical features. 1600 unique mRNA targets for miRNAs with positive fold change in HD (miR-106a/302a, miR-196a/miR-196b, miR-363, miR-10b), and 819 mRNA targets for negative fold change in HD (miR-129-3p, miR-129-5p, miR-132) were found using Targetscan, [29] and stratified by fold change for gene ontology term (GO) enrichment analysis. Using TopGO™'s weight algorithm with Fisher's Exact Test for gene ontology term enrichment and a weighted p-value cutoff less than p<0.05, 200 GO Biological Processes, 89 GO Molecular Functions and 38 GO Cellular Component terms for mRNA for down-regulated miRNA were significant. 329 GO Biological Processes, 49 GO Molecular Functions, 38 GO Cellular Component terms for mRNA for up-regulated miRNA were significant. When comparing GO Biological Processes terms exclusively for targets of miR-10b-5p, 56% (59/106) of terms overlapped terms enriched in the full set of up-regulated miRNAs.

To make these long lists of GO terms more intelligible, terms were summarized using semantic similarity measures to remove gene-set and GO term redundancy (see Methods), reducing the number of GO Biological Processes terms by approximately 75%.

Figure 23A:
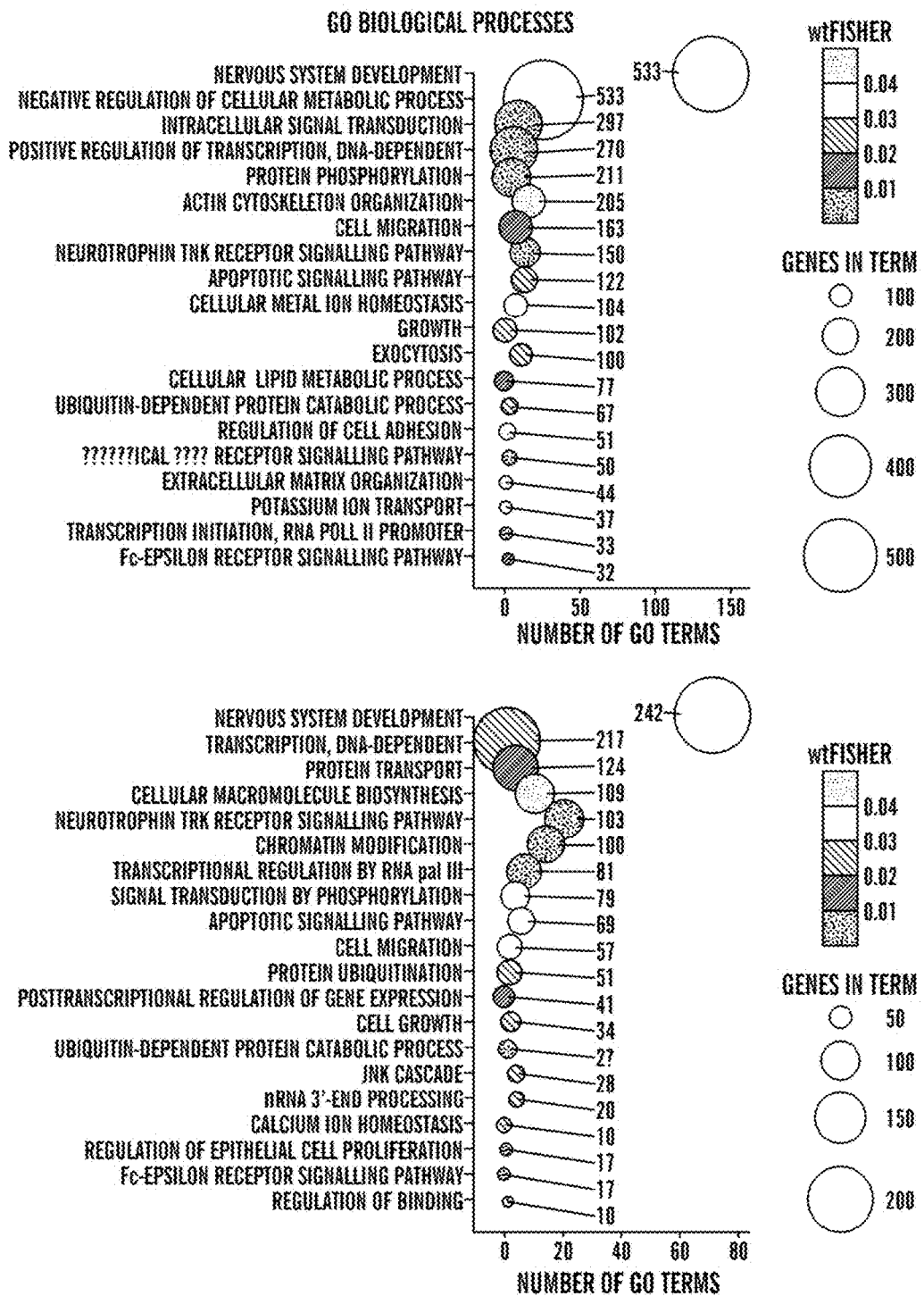
FIGS. 23A-23C demonstrate gene ontology term enrichment for mRNA targets of miRNAs that relate to HD clinical features
Figure 23B:
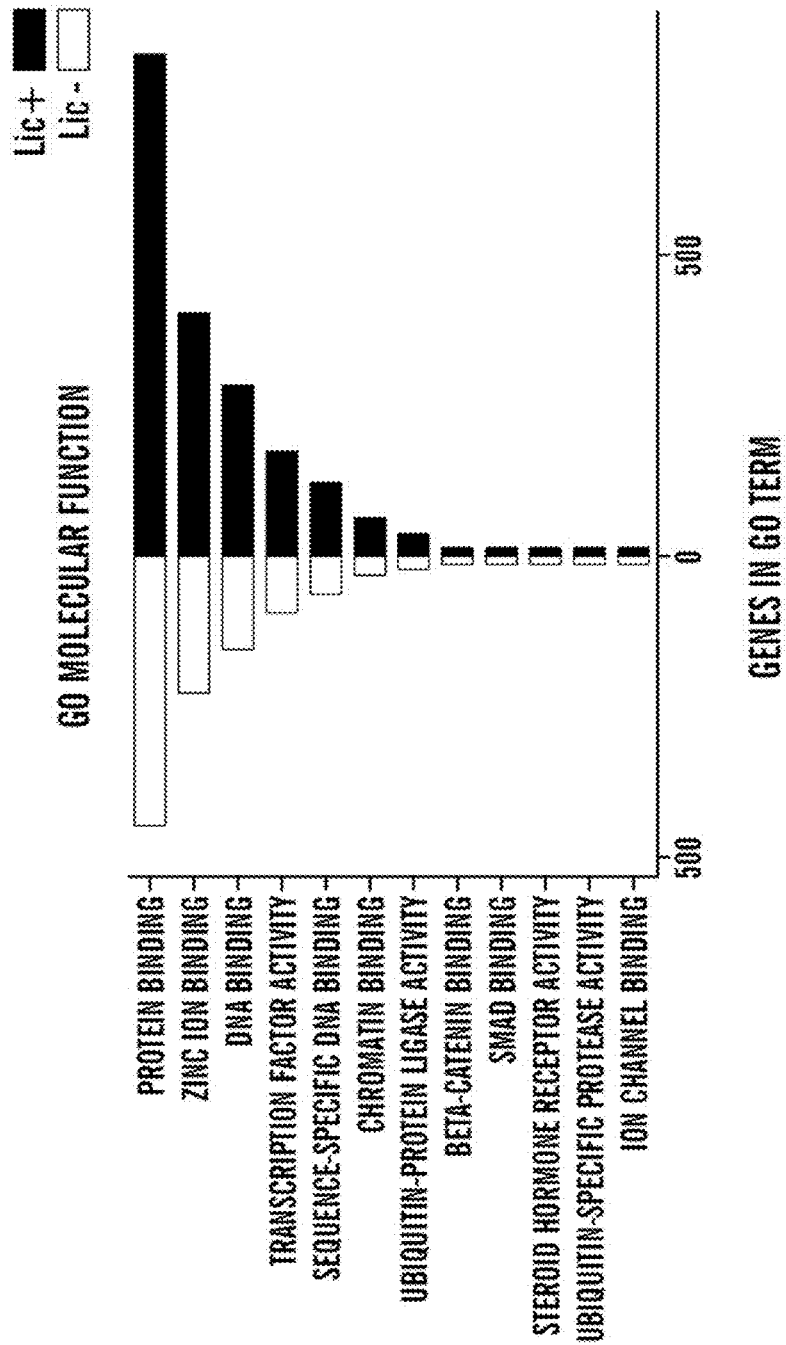
Figure 23C:
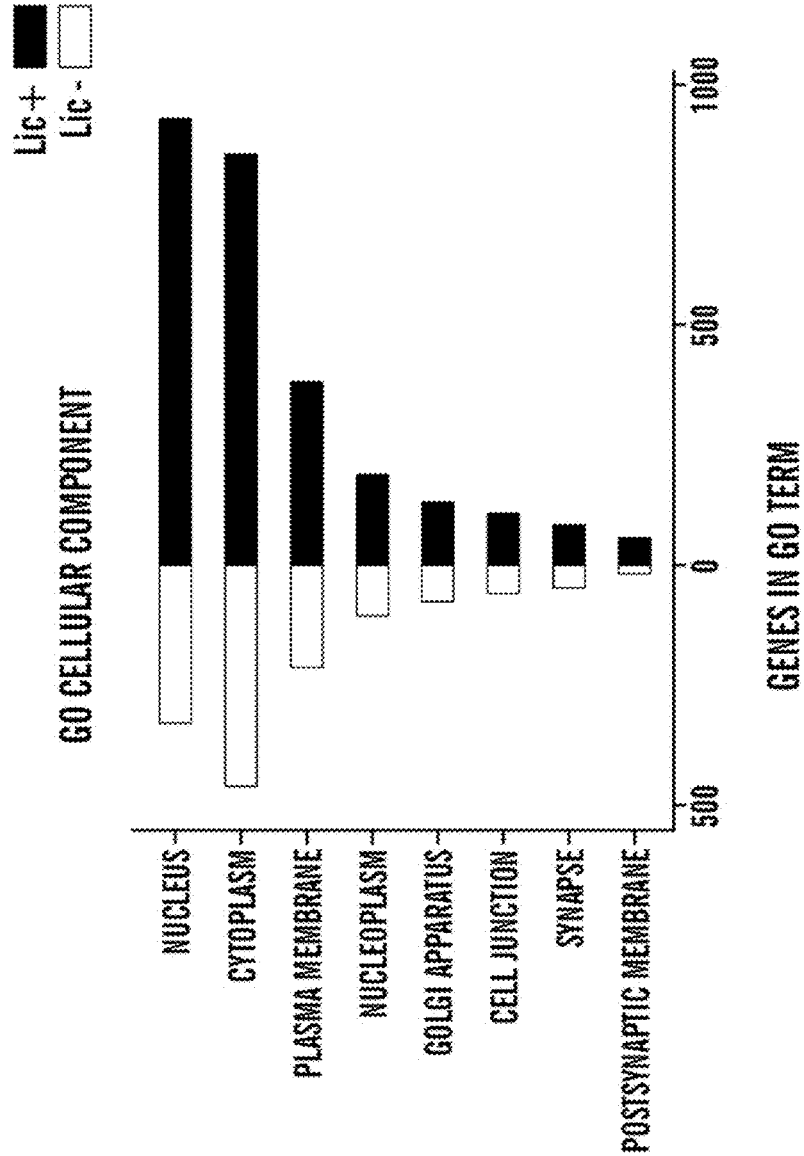

Targets of up- and down-regulated miRNAs shared significant overlap in their overall function. Six of the top twenty enriched Biological Processes terms were shared between the two sets of targets (FIG. 23A). These terms included, "nervous system development," "neurotrophin TRK receptor signaling pathway," "apoptotic signaling pathway", "cell migration", "ubiquitin-dependent protein catabolic process", and "Fc-epsilon receptor signaling pathway." Both sets had the most genes in the "nervous system development" term (Up=533, down=242). The top enriched term was "positive regulation of transcription, DNA-dependent", (N=167, p=5.3e-4) for positive gene set and "transcriptional regulation by RNA Polymerase II", (N=61, p=6.70e-06) for negative gene set. Of the 52 up-regulated Molecular Function terms and 40 down-regulated terms, twelve terms were the same (FIG. 23B). Top terms were included "protein binding", "zinc ion binding" and "transcription factor activity". For GO Cellular Component, eight terms were the same between the two gene sets. Terms included "nucleus" and "cytoplasm" as well as "synapse" and "postsynaptic membrane" (FIG. 23C).

Discussion

In a next-generation sequence analysis of small non-coding RNAs in 26 HD and 36 control brains we detected 938 miRNAs and 75 of these were differentially expressed. All five miRNAs reported as differentially expressed above herein (miR-10b-5p, miR-196a-5p, miR-196b-5p, miR-615-3p and miR-1247-5p) were significantly differentially expressed in this study [13]. These results were independently validated in the 41 (14 HD and 27 control brains) newly studied brains (Table 13), and support the presence and robust up-regulation of Hox-related miRNAs in HD brain [13]. The increased number of differentially expressed miRNAs is likely due to an increase in sample size. Increasing the sample size (from N=21 to N=62) enhanced the statistical power to detect additional miRNAs with smaller but significant changes in miRNA expression.

For eight DE miRNAs, both 5'- and 3'-arms of their miRNA precursors were DE, and the expression of the majority of these mature miRNAs were correlated in both HD and control samples. These observations are not unexpected, as the biogenesis of mature 3' and 5' strands occurs simultaneously until the final processing step. Transcription of the primary miRNA transcript (pri-miRNA) of these miRNA may be altered in HD, however it is impossible to quantify pri-miRNA from small RNA sequencing data due to the removal of large RNA species during library preparation. Although most DE 5'- and 3'-arms correlated in expression, miR-1298 did not correlate in HD samples but did so in controls. This may be driven by the strong DE effect of miR-1298-3p, which was the fifth most significant DE miRNA reported. miR-1298-3p is not well-characterized so the effect that decreased expression of this miRNA may have on HD brain remains unknown. In controls, miR-10b and miR-302a 5' and 3'-arms did not correlate in their expression. This is likely due to the low representation of miR-10b-3p and total miR-302a in controls. Without wishing to be bound by theory, the low signal from miR-10b-3p (global miRNA mean=5.0, miR-10b-3p mean=2.0), can indicate that the 3' strand is a non-functional bystander to the up-regulated 5' guide strand (miR-10b-5p mean=11.6).

Tissue homogenate was used for sequencing, so the source of miRNA signal is likely both neuronally and non-neuronally derived. To determine the miRNA cellular specificity in the brain, Jovicic et al 2013 measured miRNA expression in cultured neurons, oligodendrocytes, microglia and astrocytes to find miRNAs enriched for each cell type. Based upon this study, miRNAs found to be specifically enriched in neuronal cultures (miR-129-3p, miR-129-5p, miR-132, miR-135b, miR-431, miR-433) were all down-regulated in our study whereas miRNAs enriched in microglial cultures (miR-126-5p, miR-126-3p, miR-141, miR-142-3p, miR-142-5p, miR-150, miR-200c and miR-223) were all were up-regulated [16]. According to these enrichment categories, microglial activation miRNAs do not relate to clinical features of the disease. Conversely, three neuronal-related miRNAs, miR-129-3p/5p and miR-132, were associated with pathological involvement (see FIGS. 23A-23C).

The pattern of the expression of many of miRNAs with Vonsattel grade indicates expression changes can occur early in the disease process (FIGS. 20A-20I). Many of these miRNA changes appear present ordinal trends with an increase (miR-10b-5p, miR-10b-3p, miR-302a, miR-196a-5p, miR-196b-5p) or decrease (miR-663b, miR-4488, miR-4449) in their expression across grade. In particular, miR-10b-5p was significantly different across all groups, with the exception of the asymptomatic grade 0 brains. Only three miRNAs (miR-10b-3p/5p, miR-302a) related to CAG-adjusted striatal score. The miRNAs with association to grade but not striatal score might be an issue of power, as miR-196a/b-5p had nominal associations to striatal score. Non-linear associations were not studied with adjustment, as miR-200c was only altered in asymptomatic brains. Without wishing to be bound by theory, the association can be simply driven the effect of the CAG repeat expansion, as miR-663b and miR-4488 had nominal associations to striatal score and onset without CAG-adjustment (FIG. 22) but no associations to any CAG-adjusted features (data not shown).

Based on correlation (FIG. 22), up-regulated miRNAs clustered together based on their relationships to clinical features. Generally, these miRNAs had strong, positive associations to striatal and cortical H-V scores, weak positive association with disease duration and strong negative associations to onset and death age. Most down-regulated miRNAs were inversely associated with H-V scores and duration, opposite to up-regulated miRNAs. These patterns imply that decreasing up-regulated miRNAs and increasing down-regulated miRNA can be beneficial.

Using target analysis and GO term enrichment, targets of both up- and down-regulated miRNAs were observed to share many of the same biological processes and overall systems. For GO Biological Processes, the most genes from both up- and down-regulated miRNAs fell within "nervous system development." Both contained several transcriptional regulation in some regard (transcriptional regulation, DNA-dependent or RNA pol II, chromatin remodeling, posttranscriptional gene regulation, chromatin remodeling, etc). Both sets of genes contained terms on neurotrophins, metabolism, apoptosis, metal-binding and ubiquitin. Disruption to any of these systems can affect neuron health. Overall, these finding imply both up- and down-regulated miRNAs can be part of the same or similar biological pathways.

A large number of these miRNAs have some relation to clinical pathology and much of the signal is independent of the CAG repeat expansion. miR-10b-5p expression changes can occur pre-symptomatically. Up- and down-regulated miRNAs can target genes in similar biological systems, and these genes affect transcriptional regulation, neuronal development and other important aspects surrounding neuron function. These miRNAs are candidates for predicting onset age and overall brain health in HD.

Materials and Methods
Sample Information.

Frozen brain tissue from prefrontal cortex Brodmann Area 9 (BA9) was obtained from the Harvard Brain and Tissue Resource Center (HBTRC) McLean Hospital, Belmont Mass. and Sun Health Research Institute Sun City, Ariz. 26 Huntington's disease (HD) samples, 2 asymptomatic HD gene carriers, and 36 neurologically and neuropathologically normal control samples were selected for the study. HD subjects had no evidence of other neurological disease based on neuropathological examination. HD samples and controls were not different in postmortem interval (PMI) (t=0.41, p-value=0.69), RNA integrity number (t=−1.8, p-value=0.08) or gender (t=−0.66, p-value=0.51) but differed in ages at death (HD mean age=59.5, control mean age=68.6; t=−2.5, p-value=0.01) (see Table 12). Asymptomatic HD samples did not differ in age at death (mean age=67.5) in comparison to HD or control samples (control t=−0.1, p-value=0.92; HD t=0.86, p-value=0.40).

Total RNA was isolated using QIAzol™ Lysis Reagent and purified using miRNeasy MinElute™ Cleanup columns (Qiagen Sciences Inc, Germantown, Md.). RNA quality for sequencing was assessed using either Agilent's BioAnalyzer 2100™ system and RNA 6000™ Nano Kits to determine RNA Integrity Number (RIN) or Agilent 2200 TapeStation™ and DNA ScreenTape™ assay RNA Quality Number (RQN; Agilent, Foster City, Calif.). For each brain sample, 1 ug of RNA was used to construct sequencing libraries using Illumina's TruSeq™ Small RNA Sample Prep Kit, according to the manufacturer's protocol (Illumina, San Diego, Calif.), and sequenced using 1×51 nt single-end reads on Illumina's HiSeq 2000™ system miRNA Sequence Analysis Reads were quality filtered, removing reads below 80% Q20, using FASTX-toolkit FASTQ quality filter (version 0.0.13.2,). Adapter sequence (5'-TGGAATTCTCGGGTGC-CAAGG-3'(SEQ ID NO: 43)) was removed from the 3' end of all reads using cutadapt 1.2.1 (available on the world wide web at code.google.com/p/cutadapt/) and reads less than 15 nucleotides in length were discarded (Martin, embnet, 2011). Reads were collapsed using FASTX-toolkit FASTA/Q collapses. Reads were aligned to the UCSC human reference genome (build hg19) using Bowtie version 1.0.0, using no mismatch alignments and a limit of 200 multiple mapping instances [39]. Aligned reads that overlapped with the human miRNA annotation, miRBase version 20, (available on the world wide web at mirbase.org/ftp-.shtml) were identified using BEDTools IntersectBed [40]. Reads longer than 27 bases were removed. miRNA reads were counted if ±4 nucleotides from the mature, annotated 5' start coordinates. R version 3.1.0 and Bioconductor 2.1.4 version were used for differential expression analysis. DESeq2 version 1.40.0 was used for estimation of library size and correction, as well as variance-stabilizing transformation (VST) [41,42]. miRNAs with a mean less than 2 raw read counts across all samples were removed. Batch effect was corrected using ComBat with default options through the Bioconductor package sva 3.10 [43,44]. All samples were included in VST and batch correction. Using 36 controls and 26 HD grades 2-4, differential expression analysis was performed with LIMMA version 3.20.8 [45], adjusting for age at death in the model. Q-values were FDR-adjusted for 938 comparisons.

Firefly miRNA Assay.

A panel of 16 DE miRNAs with moderate to high expression (miR-10b-5p, miR-194-5p, miR-223-3p, miR-132-3p, miR-144-5p, miR-148a-3p, miR-486-5p, miR-363-3p, miR-199a-5p, miR-16-2-3p, miR-142-3p, miR-34c-5p, miR-129-5p, miR-433-3p, miR-885-5p, miR-346) and six stably expressed miRNAs in sequencing (miR-9-5p, miR-92a-3p, miR-98-5p, miR-101-3p, miR-151a-3p, miR-338-3p) was used for validation. In a 96-well filter plate, Firefly Multimix (Firefly BioWorks, Cambridge, Mass.) was incubated with 25 ul Hybridization Buffer and 25 ul total RNA at a concentration of 1 ng/ul at 37° C. for 60 minutes. After rinsing to removing unbound RNA, 75 ul of Labeling Buffer was added to each well, and the plate was incubated for 60 minutes at room temperature. Adapted-modified miRNAs were released from the particles using 90° C. water, and PCR amplified using a fluorescently-label primer set. PCR product was hybridized to fresh Firefly Multimix for 30 minutes at 37° C. and re-suspended in Run Buffer for readout. Particles were scanned on an EMD Millipore Guava 8HT flow cytometer. Raw output was background subtracted, normalized using the geometric mean of the six normalizer miRNAs and log-transformed. LIMMA version 3.20.8 [45] was used to calculate significance.

HD Feature Analysis/

For analysis of miRNA expression to Vonsattel grade, Tukey HSD statistics and compact letter display were generated by the multcomp R package [46]. CAG-adjusted age of onset was calculated using the logarithmic model from Djousse et al 2003 [4]. Hadzi-Vonsattel striatal and cortical scores were measured in 523 HD brain samples as previously described [26]. Samples with greater than 55 repeats or missing CAG information were excluded from analysis, leaving 346 samples. H-V striatal score, H-V cortical score, death age and disease duration features were corrected for CAG size by modeling each feature to CAG size within the HD dataset (N=346) and extracting the residuals from the model for each miRNA-profiled sample [26]. VST-batch corrected counts were used for all subsequent analyses. CAG-adjusted residuals and miRNA expression relationships were analyzed using linear regressions. Covariates (PMI, RIN, age at death) were not included in linear models, as neither PMI nor RIN were determined to have an effect on the outcome of the results. Age at death could not be included in the analysis due to the relationship of age at death and HD clinical pathology. Q-values were FDR-adjusted for 75 DE miRNA contrasts for linear regressions were reported. For the cluster analysis in FIG. 22, Pearson correlations for miRNA expression to clinical feature were performed and those miRNAs with p-values<0.05, without adjustment for multiple comparisons, were reported. Pearson correlation coefficients were hierarchically clustered using Euclidean distance and unsupervised complete clustering method through the R-package pheatmap version 0.7.7.

Target Prediction and Gene Ontology Enrichment.

Targetscan, release 6.2 [29] was used to select mRNA targets of miRNAs with at least one relationship to clinical feature. Fourteen miRNAs were available on Targetscan and twelve miRNAs had unique seed sequences. After filtering targets with total context scores ≥−0.1, miRNAs with less 200 targets were removed from the analysis. miRNAs with positive fold change in HD (miR-106a/302a, miR-196a/miR-196b, miR-363, miR-10b), and negative fold change in HD (miR-129-3p, miR-129-5p, miR-132) were stratified for gene ontology term (GO) enrichment analysis. GO term enrichment for "biological processes," "molecular function," and "cellular component," was performed using topGO [47] with the "weight01" algorithm and Fisher statistic within the R statistical environment. A weighted Fisher p-value<0.05 threshold was used to select significant GO enrichment. Significant terms were collapsed by semantic similarity using the program REVIGO [48], with the number of genes included in each term and the default settings. The union of genes from REVIGO "parent" terms was calculated using topGO's genes.in.term function.

REFERENCES

1. HDCRG (1993) A novel gene containing a trinucleotide repeat that is expanded and unstable on Huntington's disease chromosomes. Cell 72: 971-983.
2. Myers R H (2004) Huntington's disease genetics. NeuroRx: the journal of the American Society for Experimental Neuro Therapeutics 1: 255-262.
3. Li J L, Hayden M R, Almqvist E W, Brinkman R R, Dun A, et al. (2003) A genome scan for modifiers of age at onset in Huntington disease: The HD MAPS study. Am J Hum Genet 73: 682-687.
4. Djousse L, Knowlton B, Hayden M, Almqvist E W, Brinkman R, et al. (2003) Interaction of normal and expanded CAG repeat sizes influences age at onset of Huntington disease. American journal of medical genetics Part A 119A: 279-282.
5. Bartel D P (2004) MicroRNAs: genomics, biogenesis, mechanism, and function. Cell 116: 281297.
6. Bartel D P (2009) MicroRNAs: target recognition and regulatory functions. Cell 136: 215-233.
7. Alvarez-Garcia I, Miska E A (2005) MicroRNA functions in animal development and human disease. Development 132: 4653-4662.
8. Schratt G M, Tuebing F, Nigh E A, Kane C G, Sabatini M E, et al. (2006) A brain-specific microRNA regulates dendritic spine development. Nature 439: 283-289.
9. Cao X, Yeo G, Muotri A R, Kuwabara T, Gage F H (2006) Noncoding RNAs in the mammalian central nervous system. Annu Rev Neurosci 29: 77-103.
10. Gascon E, Gao F B (2012) Cause or Effect: Misregulation of microRNA Pathways in Neurodegeneration. Front Neurosci 6: 48.
11. Junn E, Mouradian M M (2012) MicroRNAs in neurodegenerative diseases and their therapeutic potential. Pharmacology & therapeutics 133: 142-150.
12. Gaughwin P M, Ciesla M, Lahiri N, Tabrizi S J, Brundin P, et al. (2011) Hsa-miR-34b is a plasma-stable microRNA that is elevated in pre-manifest Huntington's disease. Human molecular genetics 20: 2225-2237.
13. Hoss A G, Kartha V K, Dong X, Latourelle J C, Dumitriu A, et al. (2014) MicroRNAs located in the Hox gene clusters are implicated in huntington's disease pathogenesis. PLoS Genet 10: e1004188.
14. Jin J, Cheng Y, Zhang Y, Wood W, Peng Q, et al. (2012) Interrogation of brain miRNA and mRNA expression profiles reveals a molecular regulatory network that is perturbed by mutant huntingtin. Journal of neurochemistry 123: 477-490.

15. Johnson R, Zuccato C, Belyaev N D, Guest D J, Cattaneo E, et al. (2008) A microRNA-based gene dysregulation pathway in Huntington's disease. Neurobiology of disease 29: 438445.
16. Jovicic A, Roshan R, Moisoi N, Pradervand S, Moser R, et al. (2013) Comprehensive expression analyses of neural cell-type-specific miRNAs identify new determinants of the specification and maintenance of neuronal phenotypes. J Neurosci 33: 5127-5137.
17. Kocerha J, Xu Y, Prucha M S, Zhao D, Chan A W (2014) microRNA-128a dysregulation in transgenic Huntington's disease monkeys. Mol Brain 7: 46.
18. Lee S T, Chu K, Im W S, Yoon H J, Im J Y, et al. (2011) Altered microRNA regulation in Huntington's disease models. Experimental neurology 227: 172-179.
19. Marti E, Pantano L, Banez-Coronel M, Llorens F, Minones-Moyano E, et al. (2010) A myriad of miRNA variants in control and Huntington's disease brain regions detected by massively parallel sequencing. Nucleic acids research 38: 7219-7235.
20. Packer A N, Xing Y, Harper S Q, Jones L, Davidson B L (2008) The bifunctional microRNA miR-9/miR-9* regulates REST and CoREST and is downregulated in Huntington's disease. The Journal of neuroscience: the official journal of the Society for Neuroscience 28: 14341-14346.
21. Sinha M, Ghose J, Bhattarcharyya N P (2011) Micro RNA-214, -150, -146a and -125b target Huntingtin gene. RNA biology 8: 1005-1021.
22. Sinha M, Ghose J, Das E, Bhattarcharyya N P (2010) Altered microRNAs in STHdh(Q111)/Hdh(Q111) cells: miR-146a targets TBP. Biochemical and biophysical research communications 396: 742-747.
23. Soldati C, Bithell A, Johnston C, Wong K-Y, Stanton L W, et al. (2013) Dysregulation of REST-regulated coding and non-coding RNAs in a cellular model of Huntington's disease. J Neurochem 124: 418-430.
24. Cheng P H, Li C L, Chang Y F, Tsai S J, Lai Y Y, et al. (2013) miR-196a Ameliorates Phenotypes of Huntington Disease in Cell, Transgenic Mouse, and Induced Pluripotent Stem Cell Models. American journal of human genetics.
25. Vonsattel J P, Myers R H, Stevens T J, Ferrante R J, Bird E D, et al. (1985) Neuropathological classification of Huntington's disease. Journal of neuropathology and experimental neurology 44: 559-577.
26. Hadzi T C, Hendricks A E, Latourelle J C, Lunetta K L, Cupples L A, et al. (2012) Assessment of cortical and striatal involvement in 523 Huntington disease brains. Neurology 79: 1708-1715.
27. Langbehn D R, Hayden M R, Paulsen J S (2010) CAG-repeat length and the age of onset in Huntington disease (HD): a review and validation study of statistical approaches. American journal of medical genetics Part B, Neuropsychiatric genetics: the official publication of the International Society of Psychiatric Genetics 153B: 397-408.
28. Myers R H, Vonsattel J P, Stevens T J, Cupples L A, Richardson E P, et al. (1988) Clinical and neuropathologic assessment of severity in Huntington's disease. Neurology 38: 341-347.
29. Lewis B P, Burge C B, Bartel D P (2005) Conserved seed pairing, often flanked by adenosines, indicates that thousands of human genes are microRNA targets. Cell 120: 15-20.
30. Lagos-Quintana M, Rauhut R, Yalcin A, Meyer J, Lendeckel W, et al. (2002) Identification of tissue-specific microRNAs from mouse. Curr Biol 12: 735-739.
31. Miska E A, Alvarez-Saavedra E, Townsend M, Yoshii A, Sestan N, et al. (2004) Microarray analysis of microRNA expression in the developing mammalian brain. Genome Biol 5: R68.
32. Vo N, Klein M E, Varlamova O, Keller D M, Yamamoto T, et al. (2005) A cAMP-response element binding protein-induced microRNA regulates neuronal morphogenesis. Proc Natl Acad Sci USA 102: 16426-16431.
33. Kozlowska E, Krzyzosiak W J, Koscianska E (2013) Regulation of huntingtin gene expression by miRNA-137, -214, -148a, and their respective isomiRs. Int J Mol Sci 14: 16999-17016.
34. Varendi K, Kumar A, Harma M A, Andressoo J O (2014) miR-1, miR-10b, miR-155, and miR-191 are novel regulators of BDNF. Cell Mol Life Sci.
35. Li Y, Yui D, Luikart B W, McKay R M, Li Y, et al. (2012) Conditional ablation of brain-derived neurotrophic factor-TrkB signaling impairs striatal neuron development. Proc Natl Acad Sci USA 109: 15491-15496.
36. Zuccato C, Cattaneo E (2007) Role of brain-derived neurotrophic factor in Huntington's disease. Prog Neurobiol 81: 294-330.
37. Zuccato C, Ciammola A, Rigamonti D, Leavitt B R, Goffredo D, et al. (2001) Loss of huntingtin-mediated BDNF gene transcription in Huntington's disease. Science 293: 493498.
38. Meseguer S, Mudduluru G, Escamilla J M, Allgayer H, Barettino D (2011) MicroRNAs-10a and -10b contribute to retinoic acid-induced differentiation of neuroblastoma cells and target the alternative splicing regulatory factor SFRS1 (SF2/ASF). J Biol Chem 286: 4150-4164.
39. Langmead B, Trapnell C, Pop M, Salzberg S L (2009) Ultrafast and memory-efficient alignment of short DNA sequences to the human genome. Genome Biol 10.
40. Quinlan A R, Hall I M (2010) BEDTools: a flexible suite of utilities for comparing genomic features. Bioinformatics 26: 841-842.
41. Anders S, Huber W (2010) Differential expression analysis for sequence count data. Genome biology 11: R106.
42. M. I. Love W H, S. Anders (2014) Moderated estimation of fold change and dispersion for RNA-Seq data with DESeq2. bioRxiv.
43. Johnson W E, Li C, Rabinovic A (2007) Adjusting batch effects in microarray expression data using empirical Bayes methods. Biostatistics 8: 118-127.
44. Leek J, Johnson, W E, Parker, H S, Jaffe, A E, Storey, J D sva: Surrogate Variable Analysis. R package version 3.10.0.
45. Smyth G (2005) Limma: linear models for microarray data. In: Gentleman R, Carey, V, Dudoit, S, Irizarry, R, Huber, W, editor. Bioinformatics and Computational Biology Solutions Using R and Bioconductor. New York: Springer. pp. 397-420.
46. Hothorn T, Bretz F, Westfall P (2008) Simultaneous inference in general parametric models. Biom J 50: 346-363.
47. Alexa A, Rahnenfuhrer J, Lengauer T (2006) Improved scoring of functional groups from gene expression data by decorrelating GO graph structure. Bioinformatics 22: 16001607.
48. Supek F, Bosnjak M, Skunca N, Smuc T (2011) REVIGO summarizes and visualizes long lists of gene ontology terms. PLoS One 6: e21800.

TABLE 12

Sample Information

| Variable | HD, Grades 2-4 | Asymptomatic Grade 0 | Control |
|---|---|---|---|
| N | 26 | 2 | 36 |
| Age at death | 59.5 ± 10.7 | 67.5 ± 26.1 | 68.6 ± 14.3 |
| RNA integrity number | 7.3 ± 0.9 | 7.7 ± 0.6 | 7.7 ± 0.7 |
| Post mortem interval | 15.7 ± 7.7 | 28.0 ± 7.9 | 14.4 ± 8.8 |
| CAG repeat size | 44.6 ± 2.9 | 42.0 ± 0 | |
| Age of onset | 44.5 ± 11.8 | | |
| Disease duration | 15.0 ± 6.1 | | |
| Striatal score | 2.70 ± 0.65 | | |
| Cortical score | 1.25 ± 0.50 | | |

TABLE 13

Differential Expression Analysis Results

| miRNA | Average expression | Original study, N = 21 | | | Replication study, N = 41 | | | Combined study, N = 64 | | |
|---|---|---|---|---|---|---|---|---|---|---|
| | | logFC | p-value | FDR q-value | logFC | p-value | FDR q-value | logFC | p-value | FDR q-value |
| miR-10b-5p | 11.62 | 4.31 | 4.56E-11 | 4.28E-08 | 3.40 | 4.30E-12 | 1.35E-09 | 3.94 | 1.28E-20 | 1.20E-17 |
| miR-196a-5p | 2.41 | 2.18 | 1.66E-09 | 7.80E-07 | 2.13 | 3.42E-12 | 1.35E-09 | 2.35 | 2.97E-20 | 1.39E-17 |
| miR-615-3p | 1.95 | 1.28 | 1.69E-06 | 3.97E-04 | 1.73 | 2.56E-13 | 2.40E-10 | 1.59 | 2.33E-16 | 7.28E-14 |
| miR-10b-3p | 2.02 | 1.37 | 4.64E-07 | 1.45E-04 | 1.15 | 2.93E-06 | 6.88E-04 | 1.45 | 2.13E-12 | 4.98E-10 |
| miR-1298-3p | 7.05 | -0.56 | 1.72E-03 | 9.47E-02 | -0.80 | 1.09E-05 | 2.04E-03 | -0.78 | 5.52E-09 | 1.03E-06 |
| miR-196b-5p | 2.56 | 1.05 | 7.62E-05 | 1.02E-02 | 1.06 | 9.34E-05 | 5.84E-02 | 1.31 | 2.33E-08 | 3.64E-06 |
| miR-302a-3p | 2.28 | 0.64 | 6.22E-03 | 1.94E-01 | 0.84 | 3.57E-04 | 2.79E-02 | 0.81 | 3.72E-06 | 4.98E-04 |
| miR-1247-5p | 6.18 | 0.90 | 2.05E-05 | 3.84E-03 | 0.46 | 7.81E-03 | 1.63E-01 | 0.62 | 8.47E-06 | 9.55E-04 |
| miR-144-3p | 10.26 | 0.80 | 4.48E-02 | 3.73E-01 | 1.09 | 2.63E-04 | 2.47E-02 | 1.08 | 9.16E-06 | 9.55E-04 |
| miR-223-3p | 8.46 | 0.49 | 3.95E-02 | 3.54E-01 | 0.94 | 6.20E-05 | 7.33E-03 | 0.75 | 1.94E-05 | 1.82E-03 |
| miR-3200-3p | 9.75 | -0.25 | 8.48E-02 | 4.65E-01 | -0.29 | 4.20E-03 | 1.31E-01 | -0.32 | 4.85E-05 | 4.14E-03 |
| miR-302a-5p | 2.99 | 0.52 | 2.86E-03 | 1.28E-01 | 0.62 | 1.97E-02 | 2.66E-01 | 0.70 | 5.70E-05 | 4.46E-03 |
| miR-1264 | 5.00 | -0.24 | 1.09E-01 | 5.15E-01 | -0.69 | 3.87E-04 | 2.79E-02 | -0.53 | 9.49E-05 | 6.36E-03 |
| miR-6734-5p | 2.79 | -0.34 | 1.89E-01 | 6.19E-01 | -1.16 | 1.63E-05 | 2.55E-03 | -0.79 | 8.86E-05 | 6.36E-03 |
| miR-144-5p | 9.30 | 0.51 | 1.43E-01 | 5.71E-01 | 1.13 | 3.31E-04 | 2.79E-02 | 0.94 | 1.04E-04 | 6.53E-03 |
| miR-138-2-3p | 6.08 | -0.44 | 3.59E-03 | 1.41E-01 | -0.29 | 3.24E-02 | 3.01E-01 | -0.38 | 1.43E-04 | 8.38E-03 |
| miR-431-5p | 5.65 | -0.49 | 2.33E-02 | 3.09E-01 | -0.51 | 7.64E-03 | 1.63E-01 | -0.57 | 1.60E-04 | 8.84E-03 |
| miR-132-3p | 12.93 | -0.48 | 1.57E-02 | 2.60E-01 | -0.43 | 2.72E-02 | 2.89E-01 | -0.54 | 1.99E-04 | 9.31E-03 |
| miR-200c-3p | 3.84 | 0.46 | 3.97E-02 | 3.54E-01 | 0.26 | 1.12E-01 | 4.84E-01 | 0.48 | 1.97E-04 | 9.31E-03 |
| miR-23b-5p | 3.18 | -0.30 | 8.92E-02 | 4.66E-01 | -0.62 | 2.02E-03 | 9.46E-02 | -0.55 | 1.81E-04 | 9.31E-03 |
| miR-448 | 4.02 | -0.14 | 5.66E-01 | 8.91E-01 | -0.80 | 9.98E-05 | 1.04E-02 | -0.64 | 2.23E-04 | 9.96E-03 |
| miR-486-3p | 4.84 | 0.54 | 7.85E-02 | 4.57E-01 | 0.79 | 4.16E-03 | 1.31E-01 | 0.78 | 2.76E-04 | 1.04E-02 |
| miR-490-5p | 5.56 | -0.45 | 6.53E-02 | 4.34E-01 | -0.56 | 1.15E-02 | 2.12E-01 | -0.62 | 2.62E-04 | 1.04E-02 |
| miR-5695 | 3.30 | 0.38 | 3.04E-02 | 3.28E-01 | 0.48 | 4.02E-03 | 1.31E-01 | 0.47 | 2.73E-04 | 1.04E-02 |
| miR-885-5p | 10.46 | -0.31 | 5.23E-02 | 4.07E-01 | -0.27 | 3.12E-02 | 3.01E-01 | -0.35 | 2.77E-04 | 1.04E-02 |
| miR-1224-5p | 8.08 | -0.39 | 3.89E-02 | 3.54E-01 | -0.53 | 4.83E-03 | 1.39E-01 | -0.49 | 3.83E-04 | 1.20E-02 |
| miR-1298-5p | 6.43 | -0.80 | 9.80E-03 | 2.17E-01 | -0.65 | 3.24E-02 | 3.01E-01 | -0.81 | 3.84E-04 | 1.20E-02 |
| miR-142-3p | 8.13 | 0.20 | 3.09E-01 | 7.41E-01 | 0.62 | 1.70E-03 | 8.39E-02 | 0.52 | 3.84E-04 | 1.20E-02 |
| miR-346 | 8.21 | -0.31 | 6.05E-02 | 4.26E-01 | -0.27 | 1.74E-02 | 2.66E-01 | -0.32 | 3.71E-04 | 1.20E-02 |
| miR-891a-5p | 5.84 | 0.79 | 5.16E-05 | 8.07E-03 | 0.18 | 3.68E-01 | 7.04E-01 | 0.50 | 3.69E-04 | 1.20E-02 |
| miR-16-2-3p | 7.23 | 0.30 | 3.45E-01 | 7.53E-01 | 0.83 | 6.97E-04 | 4.67E-02 | 0.71 | 3.98E-04 | 1.21E-02 |
| miR-363-3p | 11.07 | 0.39 | 1.08E-02 | 2.20E-01 | 0.30 | 2.71E-02 | 2.89E-01 | 0.34 | 4.14E-04 | 1.21E-02 |
| miR-148a-3p | 13.01 | 0.69 | 1.70E-02 | 2.60E-01 | 0.47 | 7.34E-02 | 4.18E-01 | 0.69 | 4.57E-04 | 1.29E-02 |
| miR-199a-5p | 7.66 | 0.69 | 3.46E-02 | 3.35E-01 | 0.66 | 4.30E-02 | 3.45E-01 | 0.82 | 4.66E-04 | 1.29E-02 |
| miR-4449 | 3.25 | -0.96 | 1.83E-03 | 9.51E-02 | -0.86 | 5.21E-02 | 3.68E-01 | -1.09 | 5.28E-04 | 1.42E-02 |
| miR-106a-5p | 6.28 | 0.52 | 9.97E-03 | 2.17E-01 | 0.40 | 3.15E-02 | 3.01E-01 | 0.44 | 5.64E-04 | 1.43E-02 |
| miR-142-5p | 11.47 | 0.20 | 4.43E-01 | 8.36E-01 | 0.71 | 1.66E-03 | 8.39E-02 | 0.60 | 5.77E-04 | 1.43E-02 |
| miR-549a | 3.25 | 0.57 | 9.95E-02 | 4.89E-01 | 0.86 | 1.84E-02 | 2.66E-01 | 0.95 | 5.67E-04 | 1.43E-02 |
| miR-214-5p | 3.99 | 0.81 | 8.21E-03 | 2.12E-01 | 0.42 | 2.23E-01 | 5.96E-01 | 0.84 | 6.62E-04 | 1.59E-02 |
| miR-141-3p | 5.43 | 0.48 | 1.12E-01 | 5.20E-01 | 0.34 | 2.00E-02 | 2.66E-01 | 0.47 | 8.05E-04 | 1.89E-02 |
| miR-5680 | 5.39 | -0.20 | 1.92E-01 | 6.23E-01 | -0.41 | 5.42E-03 | 1.40E-01 | -0.35 | 9.93E-04 | 2.27E-02 |
| miR-3065-5p | 6.04 | 0.37 | 1.10E-02 | 5.15E-01 | 0.40 | 6.86E-03 | 1.57E-01 | 0.42 | 1.04E-03 | 2.33E-02 |
| miR-224-5p | 4.95 | 0.71 | 5.90E-02 | 4.20E-01 | 0.82 | 1.98E-02 | 2.66E-01 | 0.88 | 1.19E-03 | 2.60E-02 |
| miR-4787-3p | 5.94 | -0.25 | 1.84E-01 | 6.15E-01 | -0.30 | 1.29E-02 | 2.23E-01 | -0.33 | 1.23E-03 | 2.62E-02 |
| miR-452-5p | 4.76 | 0.32 | 2.06E-01 | 6.41E-01 | 0.68 | 2.02E-02 | 2.66E-01 | 0.67 | 1.29E-03 | 2.69E-02 |
| miR-129-1-3p | 9.79 | -0.42 | 3.13E-02 | 3.33E-01 | -0.28 | 5.47E-02 | 3.79E-01 | -0.38 | 1.36E-03 | 2.76E-02 |
| miR-4443 | 5.69 | 0.92 | 1.10E-02 | 2.20E-01 | 0.41 | 1.54E-01 | 5.39E-01 | 0.75 | 1.39E-03 | 2.77E-02 |
| miR-101-5p | 9.55 | 0.30 | 2.49E-02 | 3.11E-01 | 0.20 | 1.08E-01 | 4.74E-01 | 0.28 | 1.47E-03 | 2.88E-02 |
| miR-483-5p | 4.39 | 1.03 | 5.31E-02 | 4.07E-01 | 0.78 | 8.24E-02 | 4.31E-01 | 1.16 | 1.52E-03 | 2.91E-02 |
| miR-2114-5p | 3.41 | 0.39 | 3.34E-02 | 3.33E-01 | 0.29 | 1.85E-01 | 5.72E-01 | 0.48 | 1.65E-03 | 3.09E-02 |
| miR-1185-1-3p | 5.32 | -0.24 | 2.34E-01 | 6.71E-01 | -0.43 | 8.49E-03 | 1.67E-01 | -0.41 | 1.70E-03 | 3.12E-02 |
| miR-670-3p | 6.70 | -0.46 | 5.50E-02 | 4.13E-01 | -0.39 | 7.24E-02 | 4.18E-01 | -0.52 | 1.77E-03 | 3.19E-02 |
| miR-129-5p | 12.39 | -0.13 | 3.31E-01 | 7.47E-01 | -0.50 | 3.31E-02 | 1.20E-01 | -0.35 | 1.95E-03 | 3.22E-02 |
| miR-135b-5p | 4.45 | -0.49 | 1.70E-02 | 2.60E-01 | -0.44 | 5.58E-02 | 3.82E-01 | -0.52 | 1.97E-03 | 3.22E-02 |
| miR-194-5p | 8.77 | 0.23 | 8.25E-02 | 4.64E-01 | 0.32 | 3.68E-02 | 3.29E-01 | 0.33 | 1.99E-03 | 3.22E-02 |
| miR-208b-3p | 6.41 | 0.46 | 1.10E-02 | 2.20E-01 | 0.28 | 7.05E-02 | 4.18E-01 | 0.36 | 1.89E-03 | 3.22E-02 |
| miR-4488 | 2.97 | -1.38 | 3.79E-04 | 3.24E-02 | -0.91 | 1.35E-01 | 5.16E-01 | -1.32 | 1.96E-03 | 3.22E-02 |
| miR-888-5p | 2.83 | 0.56 | 3.39E-02 | 3.35E-01 | 0.39 | 7.20E-02 | 4.18E-01 | 0.56 | 1.91E-03 | 3.22E-02 |

TABLE 13-continued

Differential Expression Analysis Results

| miRNA | Average expression | Original study, N = 21 | | | Replication study, N = 41 | | | Combined study, N = 64 | | |
|---|---|---|---|---|---|---|---|---|---|---|
| | | logFC | p-value | FDR q-value | logFC | p-value | FDR q-value | logFC | p-value | FDR q-value |
| miR-126-5p | 15.88 | 0.41 | 2.59E−02 | 3.16E−01 | 0.23 | 6.10E−02 | 4.03E−01 | 0.29 | 2.46E−03 | 3.88E−02 |
| miR-34c-5p | 9.25 | −1.09 | 6.77E−04 | 4.75E−02 | −0.40 | 1.41E−01 | 5.26E−01 | −0.64 | 2.48E−03 | 3.88E−02 |
| miR-218-1-3p | 6.08 | 0.30 | 5.80E−02 | 4.20E−01 | 0.39 | 2.29E−02 | 2.76E−01 | 0.35 | 2.53E−03 | 3.89E−02 |
| miR-150-5p | 10.20 | 0.42 | 2.03E−02 | 2.84E−01 | 0.33 | 6.04E−02 | 4.02E−01 | 0.39 | 2.74E−03 | 4.11E−02 |
| miR-486-5p | 14.08 | 0.70 | 7.24E−02 | 4.52E−01 | 0.66 | 4.08E−02 | 3.39E−01 | 0.75 | 2.76E−03 | 4.11E−02 |
| miR-433-3p | 10.55 | −0.01 | 9.48E−01 | 9.91E−01 | −0.36 | 1.23E−03 | 7.24E−02 | −0.24 | 2.85E−03 | 4.18E−02 |
| miR-219b-3p | 3.11 | −0.46 | 1.89E−02 | 2.78E−01 | −0.24 | 3.09E−01 | 6.46E−01 | −0.47 | 3.05E−03 | 4.40E−02 |
| miR-548n | 2.82 | 0.09 | 6.44E−01 | 9.27E−01 | 0.64 | 6.41E−03 | 1.50E−01 | 0.52 | 3.14E−03 | 4.46E−02 |
| miR-663b | 2.20 | −0.73 | 1.49E−02 | 2.59E−01 | −0.59 | 9.97E−02 | 4.58E−01 | −0.81 | 3.21E−03 | 4.50E−02 |
| miR-148a-5p | 6.67 | 0.46 | 4.67E−02 | 3.81E−01 | 0.44 | 7.58E−02 | 4.18E−01 | 0.52 | 3.31E−03 | 4.57E−02 |
| miR-29a-3p | 15.37 | 0.20 | 1.33E−01 | 5.56E−01 | 0.22 | 4.17E−02 | 3.40E−01 | 0.23 | 3.46E−03 | 4.70E−02 |
| miR-320b | 5.63 | 1.13 | 1.69E−02 | 2.60E−01 | 0.56 | 1.93E−01 | 5.78E−01 | 0.97 | 3.54E−03 | 4.74E−02 |
| miR-181a-3p | 12.15 | −0.43 | 2.97E−02 | 3.26E−01 | −0.29 | 9.44E−02 | 4.51E−01 | −0.38 | 3.60E−03 | 4.75E−02 |
| miR-153-5p | 7.32 | 0.55 | 7.08E−03 | 2.05E−01 | 0.22 | 1.80E−01 | 5.72E−01 | 0.37 | 3.78E−03 | 4.79E−02 |
| miR-28-5p | 10.13 | 0.24 | 1.37E−01 | 5.65E−01 | 0.22 | 6.84E−02 | 4.14E−01 | 0.27 | 3.75E−03 | 4.79E−02 |
| miR-7-2-3p | 6.06 | 0.25 | 8.90E−01 | 4.66E−01 | 0.26 | 4.67E−02 | 3.59E−01 | 0.27 | 3.78E−03 | 4.79E−02 |

Example 10

Figure 24:
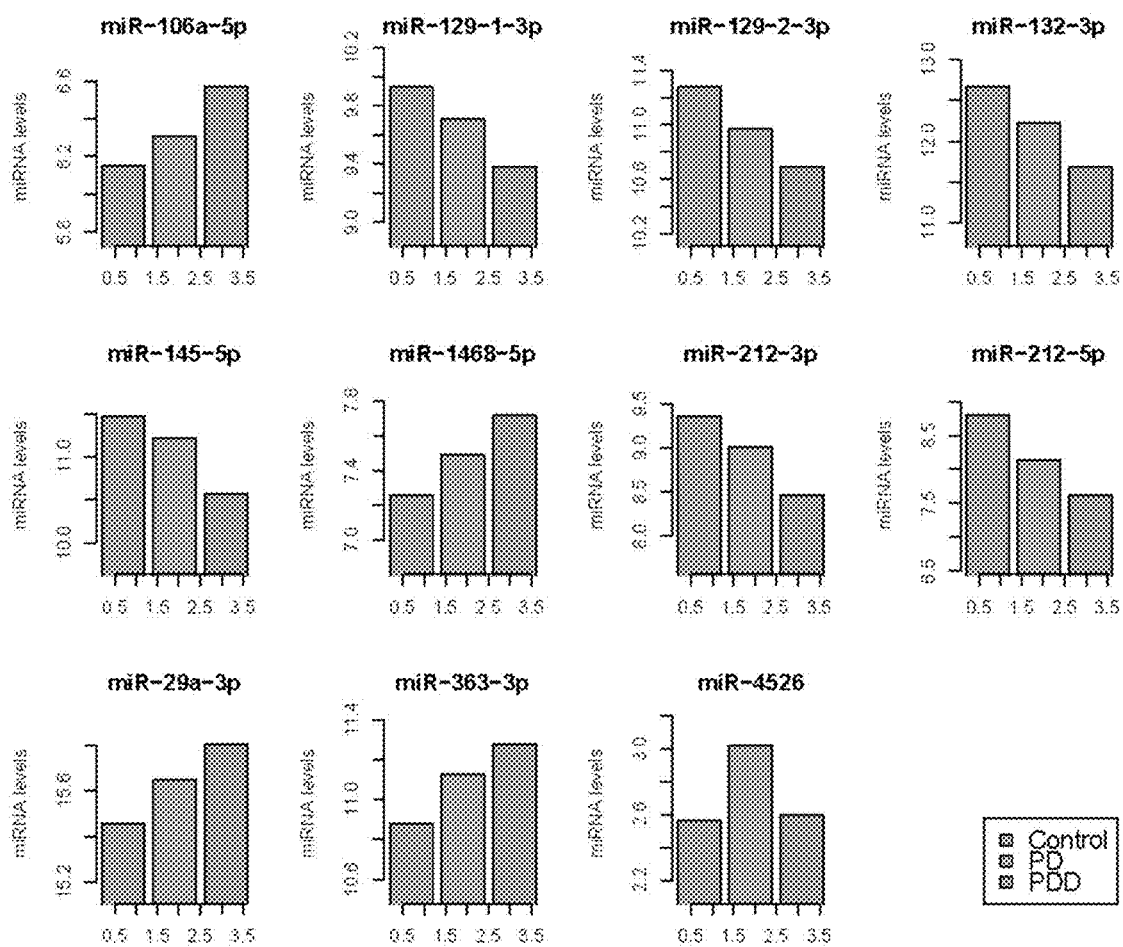
FIG. 24 depicts graphs of the levels of expression for dementia-related miRNA comparing controls (first series), PD (second series), and PDD (third series), which all differ in the levels of these miRNAs.

Illumina small RNA sequence analysis was performed in prefrontal cortex (BA9) from 36 non-neurological disease controls, 11 idiopathic Parkinson's disease (PD) and 18 Parkinson's disease with dementia (PDD). Statistical analysis, comparing miRNA levels across conditions, was performed, with and without an adjustment for age at death. The intersection of the differences observed in PD to controls and PD to PDD were reported (Table 15 and FIG. 24).

Eleven miRNAs were found to have an association to dementia (p<0.05; see table). miR-363-3p was significant after adjusting for death and is related to clinical features in both PD and HD. miR-132-5p, miR-212-3p, miR-212-5p, miR-145-5p are decreased in PD cases with dementia while miR-29a-5p is increased in PD cases with dementia.

TABLE 15

LFC = log-fold change

| miRNA | baseMean | without adjustment | | with adjustment | |
|---|---|---|---|---|---|
| | | LFC | pvalue | LFC | pvalue |
| hsa-miR-106a-5p | 88.20 | 0.22 | 2.97E−02 | 0.22 | 3.40E−02 |
| hsa-miR-129-1-3p | 791.05 | −0.31 | 7.59E−03 | −0.33 | 4.74E−03 |
| hsa-miR-129-2-3p | 2096.47 | −0.25 | 2.64E−02 | −0.27 | 2.24E−02 |
| hsa-miR-132-3p | 3338.48 | −0.42 | 9.24E−03 | −0.43 | 9.49E−03 |
| hsa-miR-145-5p | 2024.53 | −0.48 | 8.46E−04 | −0.49 | 1.01E−03 |
| hsa-miR-1468-5p | 138.34 | 0.22 | 7.29E−02 | 0.25 | 4.71E−02 |
| hsa-miR-212-3p | 392.98 | −0.35 | 3.90E−02 | −0.38 | 2.75E−02 |
| hsa-miR-212-5p | 326.17 | −0.32 | 5.01E−02 | −0.35 | 3.80E−02 |
| hsa-miR-29a-3p | 61115.38 | 0.13 | 9.28E−03 | 0.14 | 6.11E−03 |
| hsa-miR-363-3p | 2315.76 | 0.14 | 5.72E−02 | 0.16 | 4.61E−02 |
| hsa-miR-4526 | 2.84 | −0.40 | 3.90E−02 | −0.40 | 4.47E−02 |

Example 11

Huntington's disease (HD) is an inherited neurodegenerative disease with average onset age in mid-life 1. The altered gene structure responsible for HD is an expanded cytosine, adenine, guanine (CAG) trinucleotide repeat sequence in the first exon of the huntingtin gene. Neuropathological changes involving the accumulation of the huntingtin protein and the degeneration of neurons precedes motor diagnosis, with caudate volume reduced by half before diagnosis occurs in the clinic. Volumetric changes in the striatum and objective assessment of cognition are evident as early as two decades prior to diagnosis. Studies indicate that effective preventive therapeutics would need to be administered long before HD manifestation. While genetic testing can reliably detect the presence of the expanded HTT gene, the lack of validated biomarkers for onset and progression of premanifest HD precludes the evaluation of preventive therapies.

Micro ribonucleic acids (miRNAs) are small non-coding ribose molecules with a bonded nucleotide base that negatively regulate the expression of genes in a sequence-specific manner, binding to the 3'-untranslated region to initiate cleavage or translational repression of target transcripts and assist in neuronal processes including synaptic development, maturation and plasticity. Because miRNAs are resistant to degradation by ribonucleases (RNAses), it is contemplated herein that miRNA profiles can be detected in CSF and serve as effective biomarkers for several neurodegenerative diseases including Parkinson's disease and Alzheimer's disease. Having previously studied miRNA profiles in HD brain (Hoss et al., 2015), a miRNA study was performed in HD and control CSF samples: 15 controls, 10 low (far from expected onset), 10 medium (medium to expected onset), 10 high (near expected onset), and 15 HD diagnosed. 2081 miRNAs were detected and six were significantly increased in the HD subgroups versus control at FDR q<0.05 (miR520f-3p, miR-135b-3p, miR-4317, miR-3928-5p, miR-8082, mir-140-5p). Analysis of the relationship of miRNAs to estimated proximity to diagnosis revealed a pattern where levels of all six increase from control to low risk, increase again from low risk to medium risk and then plateau across the medium to high risk and HD diagnosed groups. Importantly, altered miRNA levels were detected in the prodromal HD groups furthest from diagnosis where treatments are likely to be most consequential. This proposal holds significant potential to identify effective biomarkers indicative of treatment efficacy and timing for early intervention in HD.

A cross-sectional study of miRNA levels in all existing HD-PREDICT CSF samples can be conducted. When combined with the 60 PREDICT-HD samples as described above, a total of 134 individuals can be tested with baseline CSF (36 controls, 82 premanifest, 16 diagnosed HD).

New CSF samples can be obtained concurrent with clinical and imaging data to provide clinical and biological validity for miRNAs (20 controls, 20 low, 20 medium, 20 high, 20 diagnosed). Although every effort will be made to have PREDICT-HD participants return for this study, there is no guarantee that this will occur since the parent study ended three years ago.

These results document the content validity of miRNAs in premanifest HD. Findings demonstrate significant differences between healthy controls and premanifest participants and differences among groups increase with proximity to estimated motor diagnosis (i.e., far, mid, near). The clinical concurrent validity of miRNAs in premanifest HD can be determined. Findings demonstrate significant associations with severity of clinical phenotype manifestation (motor, cognitive, psychiatric, functional). The convergent validity of miRNAs in premanifest HD can be tested. Findings show association with measures of brain volume declines assessed via magnetic resonance imaging (MRI). The discriminant validity of miRNA in premanifest HD can be investigated. Relationships between miRNA measures and blood markers of inflammation can be nonsignificant or less than associations with known HD-related imaging studies.

The first follow-up study of over 100 individuals described above can be conducted. The study can ascertain biomarker responsiveness of the miRNAs in premanifest HD. Findings can demonstrate change over 30 months and rate of change will increase in premanifest subgroups with greater proximity to manifest motor diagnosis (far, mid, near). Slopes can be compared among various significant miRNAs and their associations with worsening in clinical phenotype (motor, cognitive, psychiatric, functional). Biological correlates of miRNA responsiveness in premanifest HD can be investigated and change over time in miRNAs can be associated with change over time in brain volumes. How miRNAs are differentially associated with various brain imaging outcomes (structural volumes, diffusion weighted imaging of white matter, connectivity of corticostriatal circuitry) can be investigated and using parallel independent component analysis (pICA), aspects in brain imaging, clinical phenotype and miRNA data that are associated can be determined. Findings can indicate underlying mechanisms of early changes or targets for intervention.

Example 12: microRNAs in CSF as Prodromal Biomarkers for Huntington's Disease in the PREDICT-HD Study Experimental therapeutics to silence the mHTT gene for Huntington's disease (HD) are underway yet no biomarkers exist to determine when to intervene for those who live with certainty of the fatal neurodegenerative disease. This study was to investigate the feasibility of microRNA (miRNA) levels in cerebrospinal fluid (CSF) as biomarkers for early detection of prodromal HD.

miRNA levels were measured in CSF from 60 PREDICT-HD study participants using the HTG protocol. Using a CAG-Age Product (CAP) score, thirty prodromal HD participants were selected based on estimated probability of clinical diagnosis (i.e., low, medium, high; n=10/group). For comparison, participants with a clinical diagnosis (n=15) and healthy controls (n=15) were also selected.

2081 miRNAs were detected and six were significantly increased in the HD subgroups versus control at FDR q<0.05 (miR-520f-3p, miR-135b-3p, miR-4317, miR-3928-5p, miR-8082, mir-140-5p). In an analysis of the relationship of miRNAs to estimated risk of diagnosis, all six revealed a pattern where levels increase from control to low risk, increase again from low risk to medium risk and then plateau across the medium to high risk and HD diagnosed groups.

This study is the first to examine miRNAs as CSF biomarkers in prodromal and diagnosed HD. Importantly, miRNAs were detected in the prodromal HD groups furthest from diagnosis where treatments are likely to be most consequential and meaningful.

Huntington's disease (HD) is an inherited neurodegenerative disease most typically diagnosed in mid-life[1] although initial symptoms may appear as early as age 3 and as old as 85. The altered gene structure responsible for HD is an expanded cytosine, adenine, guanine (CAG) trinucleotide repeat sequence in the first exon of the huntingtin gene[2]. Neuropathological changes involving the accumulation of the huntingtin protein[3] and the degeneration of neurons precede motor diagnosis, with as many as half of striatal neurons lost before diagnosis occurs in the clinic[4]. Volumetric changes in the putamen and caudate are evident as early as two decades prior to predicted diagnosis[5]. These studies demonstrate that neuropathological changes occur over many years prior to clinical motor manifestation and that effective therapeutics to prevent neurodegeneration would need to be administered long before clinical symptoms are evident. While genetic testing can reliably detect the presence of the expanded CAG repeat, the lack of validated biomarkers for onset and progression of neurodegeneration prior to clinical manifestation precludes the evaluation of preventive therapies.

Micro-ribonucleic acids (miRNAs) are small non-coding ribose molecules with a bonded nucleotide base that negatively regulate the expression of genes in a sequence-specific manner, binding to the 3'-untranslated region to initiate cleavage or translational repression of target transcripts[6,7]. miRNAs are abundant in the central nervous system, and assist in various neuronal processes such as synaptic development, maturation and plasticity[8,9]. Because they are encapsulated in small vesicles (either exosomes or microvesicles)[10], and are associated with Argonaute-2 (AGO2) proteins of the RNA Induced Silencing Complex (RISC), miRNAs resist degradation by ribonuclease (RNAses). Mounting evidence suggests that disease-specific miRNA profiles can be detected in CSF for Parkinson's disease and Alzheimer's disease[11-13].

Recent studies of human HD prefrontal cortex identified 75 miRNAs significantly altered from controls[14]. Several of these were associated with age at HD diagnosis, and/or the level of neuropathology in the striatum[15], including miR-10b-5p, which was associated with both[16]. Notably, miR-10b-5p levels in brain samples of prodromal HD mHTT carriers were intermediate between those observed in controls and levels seen in diagnosed HD individuals. Although there is evidence of altered miRNA levels in plasma samples of prodromal HD, the changes were subtle and not sufficiently sensitive for an effective biomarker[17]. It was therefore sought to assess the presence of miRNAs in CSF from HD prodromal individuals as a biomarker of neurodegeneration prior to diagnosis.

Methods

Study Design and Participants. The PREDICT-HD study is a prospective observational study with 32 sites in the United States, Canada, Germany, Australia, Spain and the United Kingdom conducted from September 2002 to July 2014. All PREDICT-HD participants had genetic testing prior to study enrollment. 1078 CAG-expanded (CAG>35;

64% female) individuals who had not yet received motor diagnosis of HD were enrolled in this study. As healthy controls, 304 non-CAG-expanded siblings were also included (65% female). Annual assessments in the domains of motor, cognitive, psychiatric, functioning, and brain imaging were obtained with collection of DNA, blood, saliva and urine. The overarching goal of PREDICT-HD was to find predictive markers for motor manifestation (clinical diagnosis) of HD. All participants gave informed written consent prior to study participation, and all study procedures were approved by each site's respective institutional review board.

CSF Sample Acquisition. CSF acquisition was added to the PREDICT-HD protocol at the end of the study at a few select sites. All participants underwent screening for the lumbar puncture (LP) the day prior to sample acquisition so that biospecimens would be collected after fasting and that screening blood sample labs could be conducted. Exclusion criteria for LP were (a) use of anti-coagulant medication (i.e., warfarin, heparin) or anti-platelets (aspirin) within 14 days; (b) unable to fast for eight hours; (c) any acute or chronic infection; (d) history of any chronic inflammatory disorder; (e) unstable medical or psychiatric disorder, disease, or illness; and (f) abnormalities in any blood-based lab value from 22 results conducted in screening with an emphasis on abnormalities in increased prothrombin time, partial thromboplastin time and/or low platelets. In a sterile environment and after complete discussion of the procedure with each subject, a Sprotte 24 g atraumatic spinal needle was used after adequate local anesthesia. All samples in this study were collected by an anesthesiologist at the University of Iowa (JS) and a site coordinator recorded the time for each component of the protocol. After the LP had begun and fluid was being collected, the first 1-2 mls of CSF from the first syringe was immediately sent at room temperature to a local lab for basic CSF analyses to be conducted within four hours of collection (i.e., for cell count, erythrocytes, total protein, glucose). Remaining CSF was transferred to 15 mL conical polypropylene tubes at room temperature, mixed gently by inverting 3-4 times, and then spun down at 2000×g for 10 minutes. Micropipette was then used for transfer of 1.5 ml of supernatant directly into labeled, pre-cooled 2-ml microcentrifuge tubes, after which aliquots were immediately transferred to −80 C freezer and stored until shipment on dry ice to the NINDS biorepository until requested for biomarker research.

Samples. CSF samples for 60 participants were chosen by the PREDICT-HD Data Management Team[18,19]. All samples were shipped to the lab in a blinded fashion identified by a unique code specific for this substudy. The samples included the following study groups: 15 participants prospectively clinically diagnosed with HD according to traditional criteria using the Total Motor Score and Diagnostic Confidence Level of 4 on the Unified HD Rating Scale20; 30 participants determined to be prodromal gene-expansion carriers for HD and 15 healthy controls. Disease burden in the prodromal participants was determined by calculation of the CAG-Age Product (CAP=Age×[CAG-33•66])[21], developed to reflect age-adjusted cumulative exposure to the effects of mutant huntingtin.

miRNA Pre-Processing and Quantification. 15 ul of CSF was processed for miRNA levels using the HTG molecular diagnostics "miRNA whole transcriptome" protocol HTG EdgeSeg™ system (available on the world wide web at htgmolecular.com/products/htg-edg-system-edgeseq). This process includes specific probes for 2,083 miRNAs, producing both raw small-RNA sequencing files and pre-quantified data. A maximum of 24 samples can be processed in a single run and samples were randomly assigned to each of three batches. The HTG EdgeSeg™ assay was performed by the Biopolymers Facility at Harvard Medical School. Raw sequencing files were processed and eventually used for differential analyses. Initial checks for sample quality, as well as adapter sequence identification was performed using FastQC (version 0.11.3, available on the world wide web at bioinformatics.babraham.ac.uk/projects/fastqc/). For each sample, low quality reads were removed using FastX (version 0.0.14, available at hannonlab.cshl.edu/fastx_toolkit/) FASTQ Quality Filter, using a quality score of 80%. TruSeq Adapter Index 2 adapter sequence 9, (5'-GATCGGAAGAG-CACACGTCTGAACTCCAGTCACCGATGTATCTCG-TATGCCGTCTTCTGCTT G-3' (SEQ ID NO: 51), was removed from each read using Cutadapt™ (version 1.7.1), removing reads with fewer than 15 remaining nucleotides. Reads with the same sequence were combined using FastX™ (version 0.0.14) Collapser, reporting the number of duplicated reads per sequence[22]. Reads were aligned to human genome version hg19 using Bowtie™ (version 1.1.1), allowing for 0 mismatches[23]. The resulting bam files were converted to bed files using Bedtools™ (version 2.25.0) bamToBed24. miRNAs were defined as reads aligning within +/−4 bases from the start coordinate of annotated miRNAs from mirBase (version 20), filtered for the 2,083 probes reported by HTG[25]. miRNA reads were counted using GenomicRanges™ (version 1.22.4) R package, removing reads greater than 27 bases[26].

Statistical Analysis. All statistical analysis was carried out using R (version 3.2.2). After removing two lowly expressed miRNAs with mean raw counts <2, counts were normalized using the DESeq2/variance stabilization transformation in DESeg2™ (version 1.10.1)[27]. These values were then adjusted for batch effects from their sequencing run, using ComBat™ (version 3.18.0)[28]. Unless otherwise stated, expression values reported in this manuscript are count values, after transformation on a log 2 scale. Sample-level quality control was conducted across all samples. All differential expression analyses were carried out with linear models using miRNA expression as the outcome variable. FDR q-values were calculated from nominal p-values using the Benjamini-Hochberg procedure.

Sample-Level Quality Control. Outlier samples were detected via qualitative assessment of plots of the first two principal components of expression values across all samples. After initial outlier samples were removed, the first two principal components of the remaining samples were re-plotted and the remaining samples were re-evaluated for outliers. After two iterations of this process, no additional samples were removed.

Diagnosed HD vs. Controls. Differential expression analysis between diagnosed HD and controls was performed using both the complete set of miRNAs, as well as a subset of 16 miRNAs previously reported by Hoss et al.[16] as highly expressed in prefrontal cortex and differentially expressed between postmortem HD and control subjects. In each model, age was included as a covariate.

Ordinal Scales of prodromal HD progression. In order to explore the relationship of miRNA expression with estimated risk of clinical HD diagnosis, ordinal values were assigned to each clinical group. The following values were assigned: 0 to control, 1 to low risk, 2 to medium risk, 3 to high risk, and 4 to diagnosed manifest HD participants. Age was not included as a covariate in these models because it is a factor in assigning HD prodromal staging.

Hierarchical Clustering of diagnosed HD and Controls. Hierarchical clustering was carried out on diagnosed HD and controls, using a subset of miRNAs determined to be significantly differentially expressed (FDR q-value<0.1) between the two groups. Euclidean distance with Ward's Agglomerative method was used to cluster both the samples and miRNAs.

Results

Differential analysis of miRNA expression in CSF between diagnosed HD and Controls. In order to evaluate the level to which miRNA expression disruption in the diagnosed HD brain could be measured in CSF, differential expression was performed using a set that included 2,082 miRNA probes, quantified from small-RNA sequencing using the HTG EdgeSeq system. Of the 60 samples processed, 56 passed quality control filtering (see Methods), including 14 Controls, 10 low risk, 8 medium risk, 10 high risk and 14 diagnosed HD (See Table 14).

Figure 25:
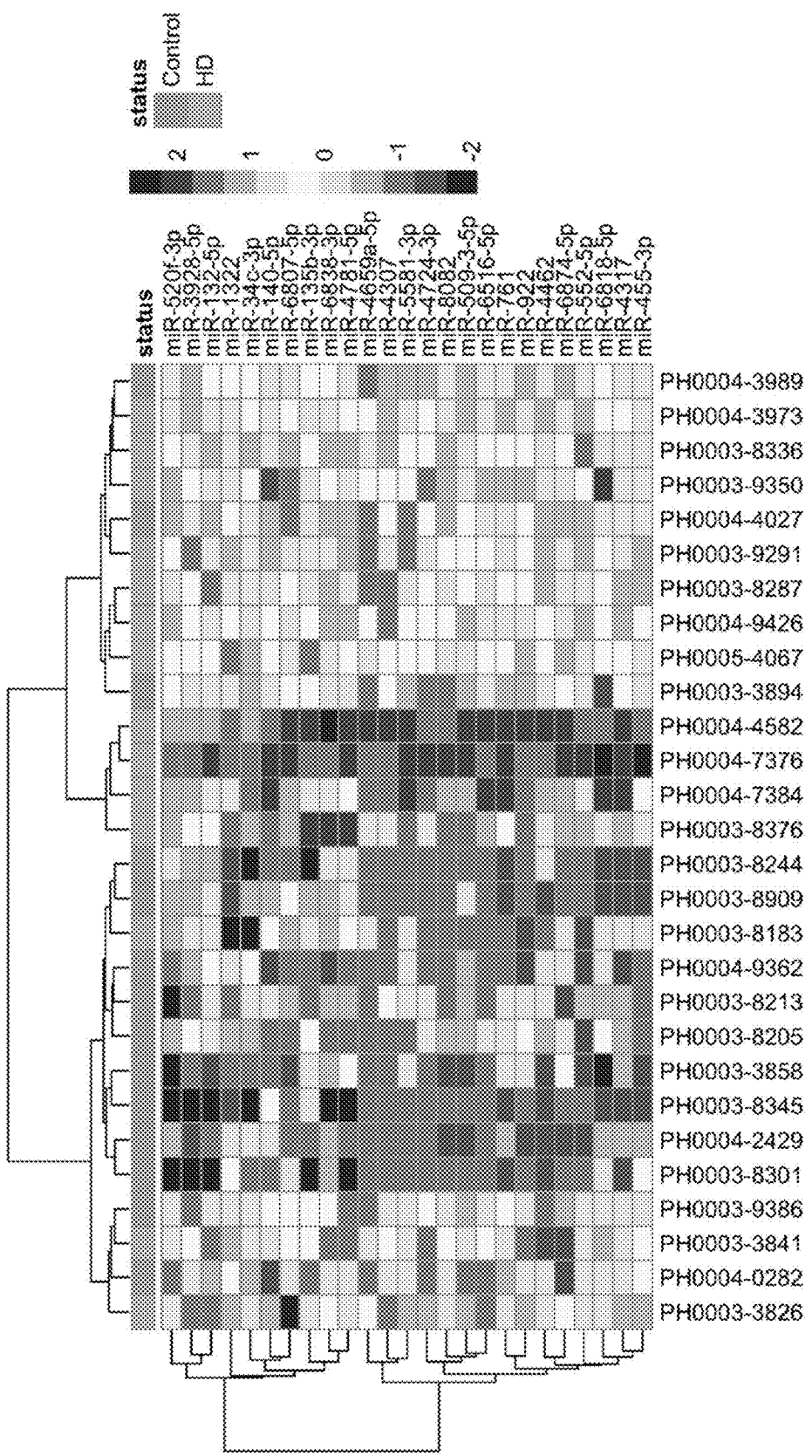
FIG. 25 depicts the hierarchal clustering of differentially expressed miRNAs. Hierarchal clustering of 14 diagnosed HD and 14 controls, using the top 25 most differentially expressed miRNAs (See Table 15). Samples and miRNAs have been clustered based on their normalized expression. Colors in this heatmap reflect miRNA-wise z-score transformation of normalized expression.

The initial analysis compared diagnosed HD to controls. After removal of two lowly expressed transcripts, normalization and batch correction, miRNAs were tested independently using multivariate linear modeling, adjusting for age. Of the 2081 expressed miRNAs, 25 reached FDR significance q-value<0.1, and six reached FDR significance q-value<0.05. In all 25 of these miRNAs, expression was up-regulated in HD and 14 had fold-change greater than (log 2FC>1) in HD compared to control participants (See Table 15). The extent to which these 25 miRNAs separated HD cases from controls was further explored via hierarchical clustering. This revealed a clear partition between cases and controls, with all but three HD samples and three control samples clustering within their group (See FIG. 25).

In the subset of 16 miRNAs reported by Hoss et al.[16] to be highly and differentially expressed between post-mortem HD and control brains, none reached statistical significance when performing FDR corrections for either the full set 2081 miRNA or the Hoss et al. candidate set of just the 16 miRNAs, though four miRNAs reached nominal significance (p-value<0.05).

Figure 26:
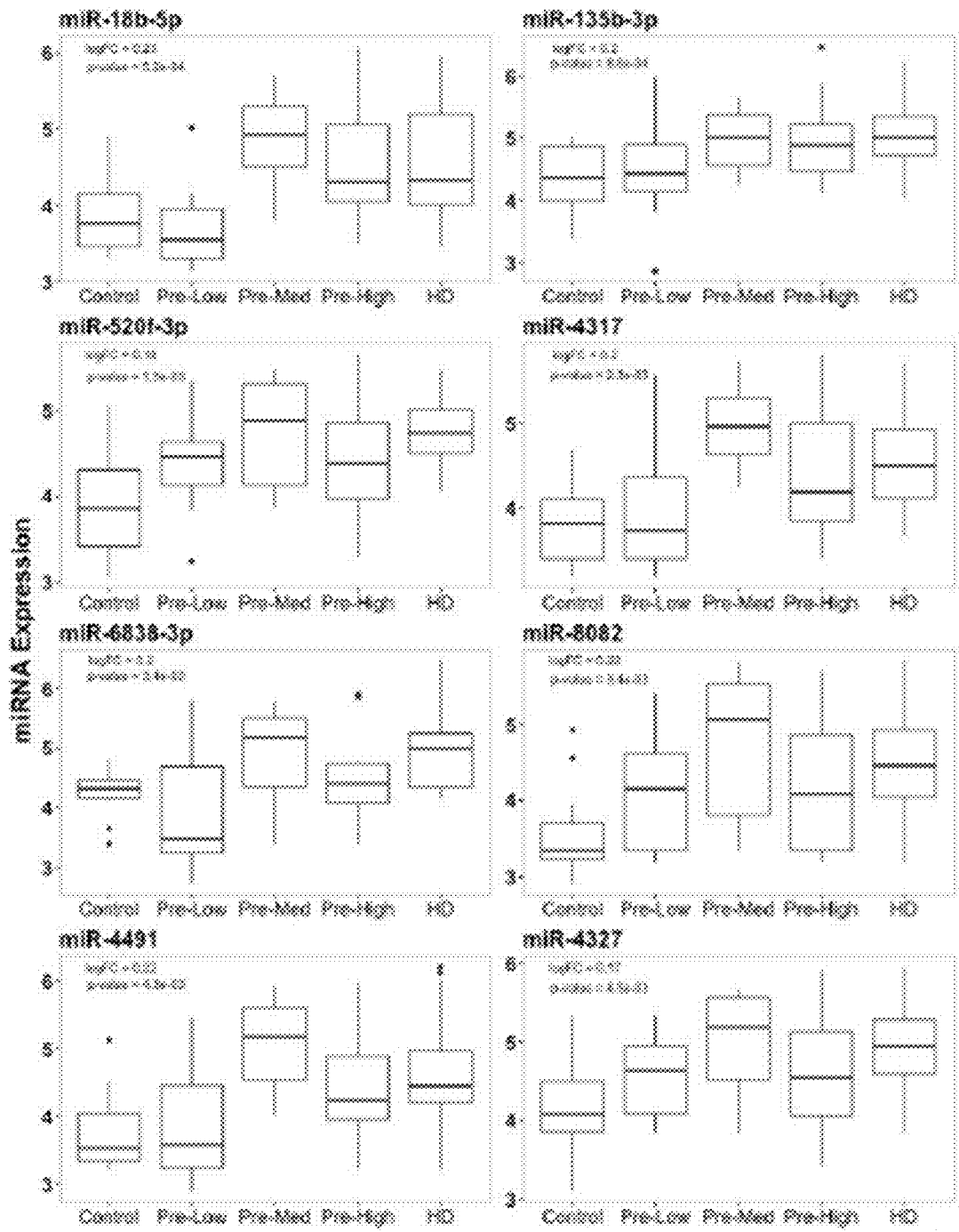
FIG. 26 depicts plots of miRNAs across categories of control, prodromal and diagnosed HD. Boxplots of the distribution of DESeq2/variance stabilized and batch corrected expression between the five ordinal groups (risk of diagnosis of HD) for each of the top 16 miRNAs. P-values and log FC values are that same as in Table 16. The low risk, medium risk, high risk and diagnosed HD groups are synonymous with the "far-from-onset", "middlefrom-onset", "near-onset", and "symptomatic HD" groups.
Figure 26:
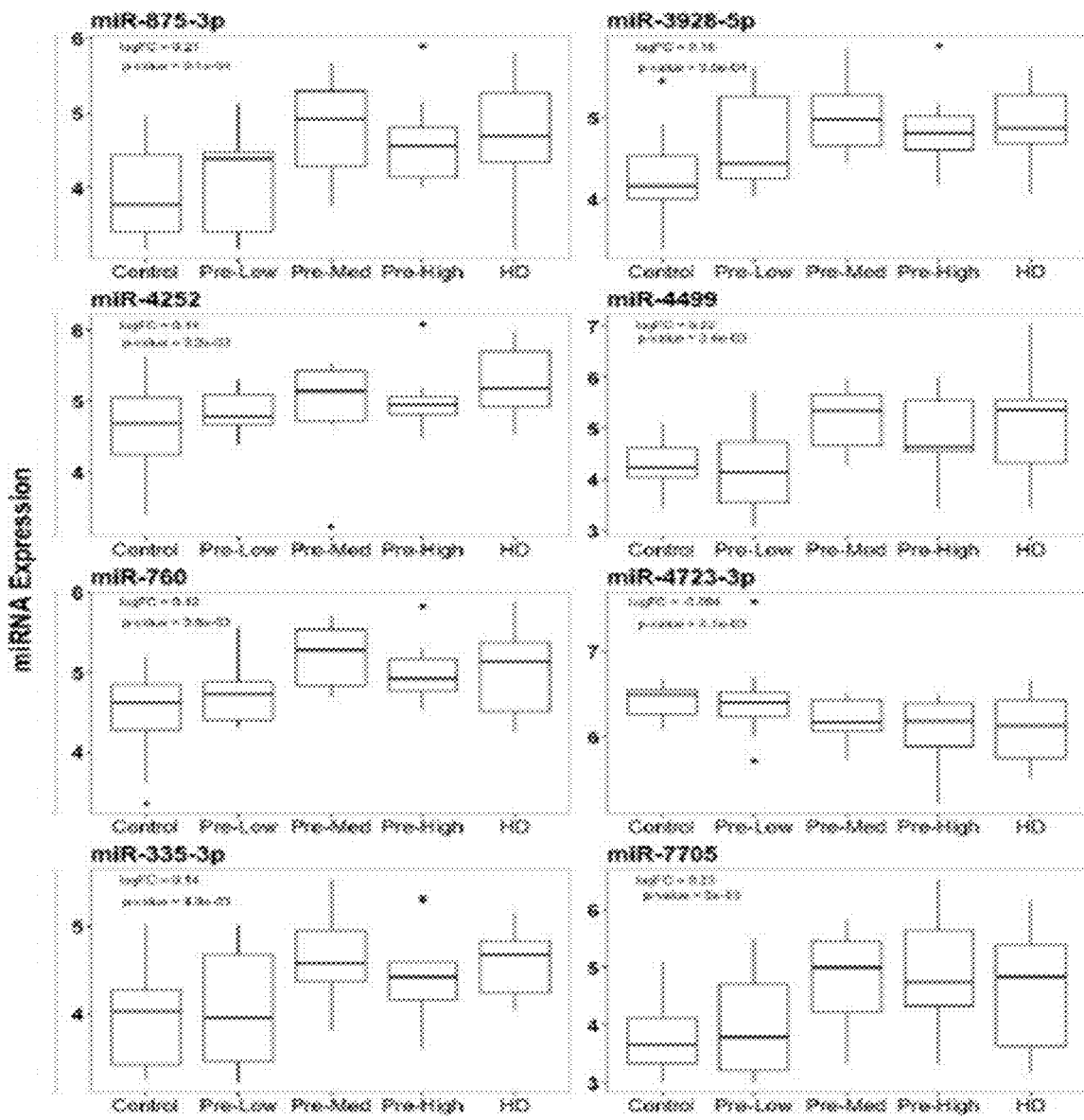

Analysis of miRNA expression and estimated risk of HD diagnosis. In order to evaluate the association between miRNA expression and progression in prodromal to diagnosed HD, each group was assigned an ordinal variable, 0 to 4, where 0 was assigned to controls, 4 to diagnosed HD participants, and 1-3 to each of the prodromal groups. Linear modeling of the 2081 expressed miRNAs across the 56 samples revealed no miRNAs that reached FDR significance although 16 had nominal p-values<0.005 (Table 316). These 16 miRNAs included the top five significantly differentially expressed (q<0.05) in the HD versus Control analysis: miR-520f-3p, miR-135b-3p, miR-4317, miR-3928-5p, miR-8082, and one at q<0.1, miR-6838-3p. Boxplots of the distribution of expression across each group in these 16 miRNAs are shown in FIG. 26. For each of these miRNAs, the direction of the log 2FC between adjacent nominal groups is consistent with the direction of altered expression seen between HD versus controls. None of the candidate miRNAs reported by Hoss et al.[16] as differentially expressed in HD versus control prefrontal cortex reached FDR q<0.1, and only two reached nominal significance (miR-132-3p, p<0.017, miR-5695, p<0.05).

Discussion

This analysis reports the first assessment of miRNAs in HD CSF as a biomarker for HD. The differential levels of miRNAs were evaluated for both diagnosed HD individuals (n=14) versus controls (n=14) as well as the relationship of miRNA levels among gene-expansion positive prodromal individuals (n=28) with varying estimated risk of diagnosis (Table 14). It was first sought to distinguish miRNAs which characterize diagnosed HD, using a discovery set of ~2,000 miRNAs. Six miRNAs were differentially found in diagnosed HD versus control CSF (FDR q<0.05) and an additional 19 at FDR q<0.1 (Table 15). All of the miRNAs were up-regulated in HD CSF. However, none of the miRNAs that were previously identified with differential levels in diagnosed HD versus control prefrontal cortex brain samples (Hoss et al. 2015) were found to be different in these early diagnosed HD CSF samples.

When examining the association of miRNA expression to an ordinal scale of diagnosis risk, or time-to-diagnosis, where 0 was assigned to controls, 4 to diagnosed HD subjects, and 1-3 to each prodromal group with decreasing proximity to (or risk of) diagnosis, 16 miRNAs had nominal p<0.005 (FDR<0.326), including the top five differentially expressed in diagnosed HD versus controls FDR q<0.05 (Table 16). When the 16 miRNAs with lowest p-values were plotted, a consistent pattern of association between miRNA expression across prodromal groups was observed. Specifically, expression of 15 of these 16 miRNAs increases from control to low risk and increases again from low risk to medium risk but then appears to plateau and remain stable across the medium risk to high risk and HD diagnosed groups (FIG. 26).

In our analysis, miR-132-5p was differentially expressed in diagnosed HD versus control (Table 15), as well as nominally associated with ordinal categorization prodromal HD progression (p=0.035, FDR=0.33). miR-132-3p was included in the set of candidate miRNAs that were highly expressed and differentially regulated in HD brain[16]. Of these 16 miRNAs, miR-132-3p had the second lowest nominal p-value when comparing diagnosed HD versus control CSF (p=0.025, FDR=0.15), as well as the lowest nominal p-value for the ordinal relationship (p=0.020, FDR=0.27). miR-760 was one of top 16 miRNAs in the ordinal analysis (p=0.0038, FDR=0.36; Table 16; FIG. 26).

A strong relationship between miRNA levels that distinguish HD from control in brain with the miRNA levels that distinguish HD from control in CSF was not observed. Without wishing to be bound by theory, the process by which miRNAs are released into CSF is still not well understood, and it is contemplated herein that that those miRNAs released into CSF are derived from the degeneration of neurons as the integrity of the neuronal cell membrane is lost while the predominant differential miRNA levels seen in HD brain may instead reflect miRNAs found in non-neuronal cell types (microglia, astrocytes and oligodendrocytes), which may explain a lack of concordance.

Of critical interest, the pattern for miRNA incremental increase present for the earliest prodromal stages of HD is very important for future clinical trials as those miRNAs may nonetheless reflect changes occurring in the brain which echo effects of the initial neurodegeneration seen in HD, even before clinical diagnoses are reported in the clinic. In clinical trials that seek to prevent the earliest damaging effects of the HTT gene on the integrity of the brain, a panel of these miRNAs can provide insight into whether treatments are preventing the initiation of the degenerative process in HD. These findings show particular promise since very few baseline/cross-sectional measures have detected differences between the low risk/far from diagnosis prodromal group and controls. Emotion recognition[32] and striatal volumes[33] from magnetic resonance imaging are the only reported cross-sectional differences between controls and those prodromal subjects who are furthest from HD diagnosis. Given that preventive therapeutics are currently being planned for Phase III human clinical trials, biomarkers to detect and track the earliest measures of disease will become of prominent importance in the near future.

TABLE 14

Sample information before and after sample-level quality control. Four samples, one control, one HD diagnosed and 1 prodromal (both medium risk) which did not meet QC standards and were removed from the study.

|  |  |  | Control | Prodromal HD Low Risk | Prodromal HD Medium Risk | Prodromal HD High Risk | Diagnosed HD |
|---|---|---|---|---|---|---|---|
| Before Sample Quality Control | | | | | | | |
| N | | | 15 | 10 | 10 | 10 | 15 |
| Age | | Mean (SD) | 45.91 (13.98) | 31.21 (9.89) | 38.93 (9.33) | 51.22 (15.89) | 55.94 (8.69) |
| CAG | | Mean (SD) | 20.53 (4.1) | 41.6 (1.78) | 42.4 (1.84) | 43 (4.08) | 42 (1.46) |
| Gender | Male | N (%) | 7 (46.67) | 5 (50.00) | 5 (50.00) | 5 (50.00) | 5 (33.33) |
|  | Female |  | 8 (53.33) | 5 (50.00) | 5 (50.00) | 5 (50.00) | 10 (66.67) |
| Batch | 1 | N (%) | 6 (40.00) | 4 (40.00) | 4 (40.00) | 5 (50.00) | 5 (33.33) |
|  | 2 |  | 6 (40.00) | 4 (40.00) | 4 (40.00) | 4 (40.00) | 6 (40.00) |
|  | 3 |  | 3 (20.00) | 2 (20.00) | 2 (20.00) | 1 (10.00) | 4 (26.67) |
| After Sample Quality Control | | | | | | | |
| N | | | 14 | 10 | 8 | 10 | 14 |
| Age | | Mean (SD) | 45.36 (14.33) | 31.21 (9.89) | 39.85 (10.13) | 51.22 (15.89) | 55.51 (8.85) |
| CAG | | Mean (SD) | 20.71 (4.2) | 41.6 (1.78) | 42.38 (2.07) | 43 (4.08) | 42.14 (1.41) |
| Gender | Male | N (%) | 6 (42.86) | 5 (50.00) | 4 (50.00) | 5 (50.00) | 5 (35.71) |
|  | Female |  | 8 (57.14) | 5 (50.00) | 4 (50.00) | 5 (50.00) | 9 (64.29) |
| Batch | 1 | N (%) | 6 (42.86) | 4 (40.00) | 4 (50.00) | 5 (50.00) | 4 (28.57) |
|  | 2 |  | 5 (35.71) | 4 (40.00) | 4 (50.00) | 4 (40.00) | 6 (42.86) |
|  | 3 |  | 3 (21.43) | 2 (20.00) | 0 (0.00) | 1 (10.00) | 4 (28.57) |

TABLE 15

Differentially expressed miRNAs between diagnosed HD and controls. Results of differential expression of miRNAs between 14 diagnosed HD and 14 Control participants. Shown are the 6 miRNAs with FDR q-values < 0.05, and an additional 19 with q < 0.1, ordered by nominal p-value. These p-values reflect the coefficient for HD status, adjusted for participant age in a multivariate linear model. FDR q-values are calculated using the Benjamini-Hochberg procedure for the set of 2081 miRNAs tested. The mean expression values are calculated from the DESeq2/variance stabilized and batch corrected values across all 28 participants.

| microRNA | Mean Expression | logFC | p-value | FDR q-value |
|---|---|---|---|---|
| miR-520f-3p | 4.47 | 1.24 | 4.93E−05 | 4.05E−02 |
| miR-135b-3p | 3.53 | 1.16 | 7.45E−05 | 4.05E−02 |
| miR-4317 | 6.03 | 1.20 | 7.60E−05 | 4.05E−02 |
| miR-3928-5p | 6.37 | 0.98 | 7.78E−05 | 4.05E−02 |
| miR-8082 | 3.30 | 1.42 | 1.28E−04 | 4.92E−02 |
| miR-140-5p | 6.19 | 0.65 | 1.42E−04 | 4.92E−02 |
| miR-509-3-5p | 5.04 | 1.36 | 2.04E−04 | 5.52E−02 |
| miR-6516-5p | 4.06 | 1.50 | 2.12E−04 | 5.52E−02 |
| miR-455-3p | 3.76 | 0.95 | 2.97E−04 | 5.92E−02 |
| miR-6838-3p | 4.31 | 1.05 | 2.98E−04 | 5.92E−02 |
| miR-552-5p | 3.64 | 1.21 | 3.29E−04 | 5.92E−02 |
| miR-761 | 3.47 | 0.95 | 3.68E−04 | 5.92E−02 |
| miR-4659a-5p | 4.87 | 1.18 | 3.70E−04 | 5.92E−02 |
| miR-4781-5p | 6.15 | 0.92 | 4.09E−04 | 6.08E−02 |
| miR-4462 | 4.73 | 1.05 | 5.30E−04 | 7.35E−02 |
| miR-132-5p | 5.34 | 0.90 | 5.83E−04 | 7.36E−02 |
| miR-6818-5p | 3.81 | 1.03 | 6.01E−04 | 7.36E−02 |
| miR-34c-3p | 3.05 | 0.86 | 7.25E−04 | 8.34E−02 |
| miR-4724-3p | 6.87 | 1.08 | 7.62E−04 | 8.34E−02 |
| miR-4307 | 5.97 | 0.95 | 8.87E−04 | 9.00E−02 |
| miR-6874-5p | 3.98 | 1.10 | 9.08E−04 | 9.00E−02 |
| miR-5581-3p | 3.76 | 0.95 | 1.01E−03 | 9.38E−02 |
| miR-6807-5p | 5.09 | 0.90 | 1.04E−03 | 9.38E−02 |
| miR-922 | 3.13 | 1.28 | 1.12E−03 | 9.38E−02 |
| miR-1322 | 3.73 | 1.33 | 1.13E−03 | 9.38E−02 |

TABLE 16 miRNAs expression association with ordinal categories of prodromal and diagnosed HD. Results of univariate linear modeling of miRNAs expression versus ordinal categories of risk of diagnosis. Shown are the 16 miRNAs with the lowest nominal p-values. These pvalues reflect the coefficient for ordinal group membership. FDR q-values are calculated using the Benjamini-Hochberg procedure for the set of 2081 miRNAs tested. The mean expression values are calculated from the DESeq2/variance stabilized and batch corrected values across all 56 subjects. The logFC values represent the estimated change in miRNA expression between two adjacent ordinal groups

|  | Mean Expression | logFC | p-value | FDR q-value |
|---|---|---|---|---|
| miR-18b-5p | 4.95 | 0.23 | 5.21E−04 | 3.26E−01 |
| miR-135b-3p | 4.34 | 0.20 | 8.64E−04 | 3.26E−01 |
| miR-875-3p | 6.28 | 0.21 | 9.07E−04 | 3.26E−01 |
| miR-3928-5p | 6.40 | 0.16 | 9.52E−04 | 3.26E−01 |
| miR-520f-3p | 4.14 | 0.18 | 1.46E−03 | 3.26E−01 |
| miR-4317 | 6.30 | 0.20 | 2.29E−03 | 3.26E−01 |
| miR-4252 | 5.48 | 0.14 | 3.17E−03 | 3.26E−01 |
| miR-4499 | 4.75 | 0.22 | 3.36E−03 | 3.26E−01 |
| miR-6838-3p | 4.51 | 0.20 | 3.37E−03 | 3.26E−01 |
| miR-8082 | 4.86 | 0.22 | 3.41E−03 | 3.26E−01 |
| miR-760 | 4.48 | 0.12 | 3.79E−03 | 3.26E−01 |
| miR-4723-3p | 4.25 | −0.09 | 4.09E−03 | 3.26E−01 |
| miR-4491 | 5.41 | 0.22 | 4.33E−03 | 3.26E−01 |
| miR-4327 | 6.33 | 0.17 | 4.52E−03 | 3.26E−01 |
| miR-335-3p | 5.20 | 0.14 | 4.88E−03 | 3.26E−01 |
| miR-7705 | 5.69 | 0.23 | 4.97E−03 | 3.26E−01 |

REFERENCES

1. Myers R H. Huntington's Disease Genetics. NeuroRx. 2004; 1(2):255-262.
2. MacDonald M E, Ambrose C M, Duyao M P, Myers R H, et al. A novel gene containing a trinucleotide repeat that is expanded and unstable on Huntington's disease chromosomes A Novel Gene Containing a Trinucleotide That Is Expanded and Unstable on Huntington's Disease Chromosomes. Cell. 2016; 72(6):971-983.

3. Gómez-Tortosa E, Macdonald M E, Friend J C, Taylor S A M, et al. Quantitative Neuropathological Changes in Presymptomatic Huntington's Disease. Ann Neurol. 2001; 49(1):29-34.
4. Vonsattel J P, Myers R H, Stevens T J, Ferrante R J, Bird E D, Richardson E P. Neuropathological Classification of Huntington's Disease. J Neuropathol Exp Neurol. 1985; 44(6):559-577.
5. Aylward E H, Sparks B F, Field K M, Yallapragada V, Shpritz B D, Rosenblatt A, Brandt J, Gourley L M, Liang K, Zhou H, et a. Onset and rate of striatal atrophy in preclinical Huntington disease. Neurology. 2004; 63(1): 66-72.
6. Bartel D P. MicroRNAs: Genomics, Biogenesis, Mechanism, and Function Genomics: The miRNA Genes. Cell. 2004; 116(2):281-297.
7. Bartel D P. Review MicroRNAs: Target Recognition and Regulatory Functions. Cell. 2009; 136(2):215-233.
8. Schratt G M, Tuebing F, Nigh E A, Kane C G, Sabatini M E, et al. A brain-specific microRNA regulates dendritic spine development. Nature. 2006; 439(7074):283-289.
9. Cao X, Yeo G, Muotri A R, Kuwabara T, Gage F H. Noncoding RNAs in the Mammalian Central Nervous System. Annu Rev Neurosci. 2006; 29:77-103.
10. Arroyo J D, Chevillet J R, Kroh E M, Ruf I K, Pritchard C C, Gibson D F, et al. Argonaute2 complexes carry a population of circulating microRNAs independent of vesicles in human plasma. PNAS. 2011; 108(12):5003-5008.
11. Burgos K, Malenica I, Metpally R, Courtright A, et al. Profiles of Extracellular miRNA in Cerebrospinal Fluid and Serum from Patients with Alzheimer's and Parkinson's Diseases Correlate with Disease Status and Features of Pathology. PLoS One. 2014; 9(5).
12. Kumar S, Reddy P H. Are circulating microRNAs peripheral biomarkers for Alzheimer's disease? Biochim Biophys Acta. 2016; 1862(9):1617-1627.
13. Gui Y, Liu H, Zhang L, Lv W, Hu X. Altered microRNA profiles in cerebrospinal fluid exosome in Parkinson disease and Alzheimer disease. Oncotarget. 2015; 6(35): 37043-37053.
14. Hoss A G, Kartha V K, Dong X, Latourelle J C, et al. MicroRNAs Located in the Hox Gene Clusters Are Implicated in Huntington's Disease Pathogenesis. PLoS Genet. 2014 Feb. 27; 10(2):e1004188.
15. Hadzi T C, Hendricks A E, Latourelle J C, Lunetta K L, et al. Assessment of cortical and striatal involvement in 523 Huntington disease brains. Neurology. 2012; 79(16): 1708-1715.
16. Hoss A G, Labadorf A, Latourelle J C, Kartha V K, et al. miR-10b-5p expression in Huntington's disease brain relates to age of onset and the extent of striatal involvement. BMC Med Genomics. 2015; 8(1):10.
17. Hoss A G, Lagomarsino V N, Frank S, Hadzi T C, Myers R H, Latourelle J C. Study of Plasma-Derived miRNAs Mimic Differences in Huntington's Disease Brain. Mov Disord. 2015; 30(14):1961-1964.
18. Paulsen J S, Hayden M, Stout J C, Langbehn D R, et al. Preparing for preventive clinical trials: the Predict-HD study. Arch Neurol. 2006; 63(6):883-890.
19. Paulsen J S, Long J D, Ross C A, Harrington D L, et al. Prediction of manifest Huntington disease with clinical and imaging measures: A 12-year prospective observational study. Lancet Neurol. 2014; 13(12):1193-1201.
20. Huntington Study Group. Unified Huntington's Disease Rating Scale: Reliability and Consistency. Mov Disord. 1996; 11(2):136-142.
21. Zhang Y, Long J D, Mills J A, Warner J H, Lu W, Paulsen J S. Indexing Disease Progression at Study Entry with Individuals At Risk for Huntington Disease. Am J Med Genet B Neuropsychiatr Genet. 2011; 156(7):751-763.
22. Martin M. Cutadapt removes adapter sequences from high-throughput sequencing reads. EMBnet.journal. 2011; 17(1):10.
23. Langmead B, Trapnell C, Pop M, Salzberg S L. Ultrafast and memory-efficient alignment of short DNA sequences to the human genome. Genome Biol. 2009; 10(3):R25.
24. Quinlan A R, Hall I M. BEDTools: A flexible suite of utilities for comparing genomic features. Bioinformatics. 2010; 26(6):841-842.
25. Kozomara A, Griffiths-Jones S. MiRBase: Annotating high confidence microRNAs using deep sequencing data. Nucleic Acids Res. 2014; 42(D1):68-73.
26. Lawrence M, Huber W, Pagès H, Aboyoun P, et al. Software for Computing and Annotating Genomic Ranges. PLoS Comput Biol. 2013; 9(8):e1003118.
27. Love M I, Huber W, Anders S. Moderated estimation of fold change and dispersion for RNA-seq data with DESeq2. Genome Biol. 2014; 15(12):550.
28. Johnson W E, Li C, Rabinovic A. Adjusting batch effects in microarray expression data using empirical Bayes methods. Biostatistics. 2007; 8(1):118-127.
29. Lau P, Bossers K, Janky R, Salta E, et al. Alteration of the microRNA network during the progression of Alzheimer's disease. EMBO Mol Med. 2013; 5(10):1613-1634.
30. Kim S Y, Lee Y H, Bae Y S. miR-186, miR-216b, miR-337-3p, and miR-760 cooperatively induce cellular senescence by targeting a subunit of protein kinase CKII in human colorectal cancer cells. Biochem Biophys Res Commun. 2012; 429(3-4):173-179.
31. Yin L, Sun Y, Wu J, Yan S, et al. Discovering novel microRNAs and age-related nonlinear changes in rat brains using deep sequencing. Neurobiol Aging. 2015; 36(2):1037-1044.
32. Stout J C, Paulsen J S, Queller S, Solomon A C, et al. Neurocognitive Signs in Prodromal Huntington Disease. Neuropsychology. 2011; 25(1):1-14.
33. Paulsen J S, Nopoulos P C, Aylward E, Ross C A, et al. Striatal and white matter predictors of estimated diagnosis for Huntington disease. Brain Res Bull. 2010; 82(3-4): 201-207.

What is claimed herein is:

1. A method comprising detecting the level of expression of at least 1 of miR520f-3p, miR-135b-3p, miR-4317, miR-3928-5p, miR-8082, mir-140-5p in a sample obtained from a subject having an htt mutation.

2. The method of claim 1, wherein the level of expression is detected for at least 2 of miR520f-3p, miR-135b-3p, miR-4317, miR-3928-5p, miR-8082, and mir-140-5p in the sample obtained from the subject.

3. The method of claim 1, wherein the level of expression is detected for at least 3 of miR520f-3p, miR-135b-3p, miR-4317, miR-3928-5p, miR-8082, and mir-140-5p in the sample obtained from the subject.

4. The method of claim 1, wherein the level of expression is detected for at least 4 of miR520f-3p, miR-135b-3p, miR-4317, miR-3928-5p, miR-8082, and mir-140-5p in the sample obtained from the subject.

5. The method of claim 1, wherein the level of expression is detected for at least 5 of miR520f-3p, miR-135b-3p, miR-4317, miR-3928-5p, miR-8082, and mir-140-5p in the sample obtained from the subject.

6. The method of claim 1, wherein the level of expression is detected for miR520f-3p, miR-135b-3p, miR-4317, miR-3928-5p, miR-8082, and mir-140-5p in the sample obtained from the subject.

7. The method of claim 1, wherein the subject is a mammal.

8. The method of claim 7, wherein the subject is a human.

9. The method of claim 1, wherein the subject has been determined to have or diagnosed as having a htt mutation.

10. The method of claim 1, wherein the subject has not received a motor diagnosis of Huntington's Disease.

11. The method of claim 1, wherein the sample is a cerebrospinal fluid sample.

12. The method of claim 1, wherein the expression level of no more than 100 other expression products is detected.

13. The method of claim 1, wherein the detecting step comprises performing next-generation sequencing.

14. A method comprising:
 obtaining a sample from a subject having an htt mutation; and
 detecting the level of at least 1 of miR520f-3p, miR-135b-3p, miR-4317, miR-3928-5p, miR-8082, mir-140-5p in the sample.

* * * * *

SEQUENCE LISTING

```
<160> NUMBER OF SEQ ID NOS: 51

<210> SEQ ID NO 1
<211> LENGTH: 269
<212> TYPE: DNA
<213> ORGANISM: Homo sapiens
```

<400> SEQUENCE: 1

```
gagaccgagg ctcgcccacc cctcggcgcc gccggaccct gcgccactgg gggaatttcc      60
ttcccgactt cccgcgcggc cacagcccca gctccgtcca gccccggctc ccggccccct    120
gggcgggaga gtgagcccg agactccgcc cagccccggg ggtcccggc cccgttcgcc      180
cccagcggcc cctcccggcg cgttgctcgg ccccggctgc atcggggagc gcgggatcac    240
ccggccctgt ccccagcggt gtcggaggg                                      269
```

<210> SEQ ID NO 2
<211> LENGTH: 1053
<212> TYPE: DNA
<213> ORGANISM: Homo sapiens

<400> SEQUENCE: 2

```
gggaaagaat gcggagccgg gttcacacac cccgcggcgg cgaggcctta aatagggaaa      60
cggcctgagg cgcgcgcggg cctggagccg ggatccgccc taggggctcg gatcgccgcg    120
cgctcgccgc tcgcccgcca gcccgcccgt ggtccgtggc ggcgcgctcc acccggcacg    180
gggaggcgcg gggcgcacca tggccgcaga cacgccgggg aaaccgagcg cctcgccgat    240
ggcaggagcg ccggccagcg ccagccggac cccagacaag ccccggagcg cggccgagca    300
ccgcaaggtg gggtcccggc cgggcgtgag ggggcgacc ggggggcggg agggacgcgg    360
gactcagccg gtgcccgacc cgcagtcctc caagccggtc atggagaagc ggcgccgagc    420
gcgtattaac gagagcctcg ctcagctcaa aaccctcatc ctggacgccc tcagaaaaga    480
gagctcccgc cactcgaagc tggagaaggc ggacatcctg gagatgaccg tgagacacct    540
gcggagcctg cgtcgcgtgc aggtgacggc cgcgctcagc gccgaccccg ccgttctggg    600
caagtaccgc gccggcttcc acgagtgtct ggcggaggtg aaccgcttcc tggccggctg    660
cgagggcgtc ccggccgacg tgcgctcccg cctgctgggc cacctggcag cctgcctgcg    720
ccagctggga ccctccccgcc gcccggcctc gctgtccccg gctgccccg cagaggcccc    780
agcgcccgag gtctacgcgg gccgcccgct gctgccatcg ctcggcggcc ccttccctct    840
gctcgcgccg ccgctgctgc cgggtctgac ccgggcgctg cccgccgccc caggggcggg    900
gccgcagggc ccgggtgggc cctggaggcc gtggctgcgc tgaggctgtg gccctgagac    960
tgcatcggag gcggcgcccc gttctagggc cgtggccttt gccgagactg tagcagagaa   1020
aacgtattta ttattccaaa aaaaaaaaaa aaa                                 1053
```

<210> SEQ ID NO 3
<211> LENGTH: 247
<212> TYPE: PRT
<213> ORGANISM: Homo sapiens

<400> SEQUENCE: 3

```
Met Ala Ala Asp Thr Pro Gly Lys Pro Ser Ala Ser Pro Met Ala Gly
1               5                   10                  15

Ala Pro Ala Ser Ala Ser Arg Thr Pro Asp Lys Pro Arg Ser Ala Ala
                20                  25                  30

Glu His Arg Lys Val Gly Ser Arg Pro Gly Val Arg Gly Ala Thr Gly
            35                  40                  45

Gly Arg Glu Gly Arg Gly Thr Gln Pro Val Pro Asp Pro Gln Ser Ser
        50                  55                  60

Lys Pro Val Met Glu Lys Arg Arg Ala Arg Ile Asn Glu Ser Leu
65                  70                  75                  80
```

Ala Gln Leu Lys Thr Leu Ile Leu Asp Ala Leu Arg Lys Glu Ser Ser
            85                  90                  95

Arg His Ser Lys Leu Glu Lys Ala Asp Ile Leu Glu Met Thr Val Arg
        100                 105                 110

His Leu Arg Ser Leu Arg Arg Val Gln Val Thr Ala Ala Leu Ser Ala
        115                 120                 125

Asp Pro Ala Val Leu Gly Lys Tyr Arg Ala Gly Phe His Glu Cys Leu
130                 135                 140

Ala Glu Val Asn Arg Phe Leu Ala Gly Cys Glu Gly Val Pro Ala Asp
145                 150                 155                 160

Val Arg Ser Arg Leu Leu Gly His Leu Ala Ala Cys Leu Arg Gln Leu
                165                 170                 175

Gly Pro Ser Arg Arg Pro Ala Ser Leu Ser Pro Ala Ala Pro Ala Glu
            180                 185                 190

Ala Pro Ala Pro Glu Val Tyr Ala Gly Arg Pro Leu Leu Pro Ser Leu
        195                 200                 205

Gly Gly Pro Phe Pro Leu Leu Ala Pro Pro Leu Leu Pro Gly Leu Thr
    210                 215                 220

Arg Ala Leu Pro Ala Ala Pro Arg Ala Gly Pro Gln Gly Pro Gly Gly
225                 230                 235                 240

Pro Trp Arg Pro Trp Leu Arg
            245

<210> SEQ ID NO 4
<211> LENGTH: 2662
<212> TYPE: DNA
<213> ORGANISM: Homo sapiens

<400> SEQUENCE: 4

```
ggtggtctga gctggagcca cgctttctgt tggaggggggc agctgaagga gaacagcaag      60
acatatccgg cggccctacg gactcggaga gctggaggga ccccggagat ctcaaaggga     120
caggaaaggc agcagcagcc accctctctc ccagtcaagt ggtcaccagc aggactgaag     180
gggacagccc ctttgcagtg gctcggcgag gagaccccctg caccctaggg tcagtgcagg     240
agcccagccg ctgagccatg ccgggccccg ggcggcctgc agcgagccca accctgcac      300
ccaggtagtc atgaacagcc acagctacaa tggcagcgtg gggcggccgc tgggcagcgg     360
gccgggcgcc ctgggacgag accctccgga ccctgaggcc ggccacccc cacaaccccc     420
gcacagcccg ggcctccagg tggtagtggc aagagtgag ccagcccggc cctcacccgg      480
cagcccccgg gggcagcccc aggaccagga cgatgacgag gatgatgagg aagatgaggc     540
cggcaggcag agagcctcgg ggaaaccctc aaatgtgggc caccgcctgg ccaccggcg      600
ggcgctcttc gagaagcgga agcgcctcag cgactatgcc ctcattttcg gcatgtttgg     660
catcgtcgtc atggtgacgg agaccgagct gtcctggggg gtgtacacca aggagtctct     720
gtactcattc gcactcaaat gcctcatcag cctctccacg gccatcctgc tgggtctcgt     780
tgtcctctac catgcccggg agatccagct gttcatggtg gacaacgggg ctgatgactg     840
gcgcatcgcc atgaccctgc agcgcgtgtt cctcatctcg ctagagctgg cagtgtgcgc     900
cattcacccg gtgcccggcc actaccgctt cacgtggacg cgcgcggctgg ccttcacgta     960
cgcgccctcg gtggccgagg ccgacgtgga cgtgctgctg tccatcccca tgttcctgcg    1020
cctctacctg ctgggccggg tgatgctact gcacagcaaa atcttcacgg acgcctcgag    1080
ccgcagcatc ggggcccctca acaagatcac cttcaacacg cgcttcgtca tgaagacact    1140
```

-continued

```
catgaccatc tgccccggca ccgtgctgct ggtcttcagc atctcctcct ggatcatcgc    1200
agcctggacc gtgcgcgtct gcagagggta ccacgacaag caggaagtga ccagcaactt    1260
cctgggggcc atgtggctga tttccatcac cttcctctcc attggctacg cgacatggt    1320 gccccacacc tactgcggga agggtgtgtg cctgctcact ggcatcatgg gagctggctg    1380
taccgcgctc gtggtggctg tggtggctcg gaagctggag ctcaccaagg ctgagaagca    1440
cgtgcacaac ttcatgatgg acactcagct caccaagcgg gtaaaaaacg ccgctgctaa    1500
cgttctcagg gagacgtggc tcatctacaa acataccagg ctggtgaaga agccagacca    1560
agcccgggtt cggaaacacc agcgtaagtt cctccaagcc atccatcagg ctcagaagct    1620
ccggagtgtg aagatcgagc aagggaagct gaacgaccag gctaacacgc ttaccgacct    1680
agccaagacc cagaccgtca tgtacgacct tgtatcggag ctgcacgctc agcacgagga    1740
gctggaggcc cgcctggcca ccctggaaag ccgcttggat gcgctgggtg cctctctaca    1800
ggccctgcct ggcctcatcg cccaagccat acgcccaccc ccgcctcccc tgcctcccag    1860
gcccggcccc ggccccaag accaggcagc ccggagctcc cctgccggt ggacgcccgt     1920 ggcccctcg gactgcgggt gacggccctg cccgccacca ccccctaaa tcttggccat      1980 cgtgtggccg ccacctccgg gaagccttgt acagtggcgc ctcttggagt tcaagaagcc    2040
aacgctgagt caggctgagt ggactgaggc ctgccccgcc cagactgccc aggcagaggg    2100
cagggctgga ccatgggtga gggcagggga gcccggagct tcctctggtc acctggtccc    2160
ccgactctcc ccaggccccc ggtgggcatg gagcagcccg gggaggggtc cgtgctggtt    2220
ctgaataaag caggacccgc ctagtggctg cctgtgtgca tggctggaag gcactggtga    2280
tgtcccagga ggtagacctc cagccctggg taccaagatg aatgtgggaa tcagaaaaac    2340
ctgttcccat caccggccta gcctagaatc ctagcctaga agccctctct ccctctgggc    2400
tggagctcag tgagggacaa ctctctaggg acacctgtac cagccccacc tggcgctgag    2460
atccctcaga cagcatggcc cagccctggc cagaagcatc gctcccctcc aaccaaccgc    2520
gttgatggac acccactgtg tgccaggccc cagcggggcc catggggag gtgacctggg     2580 tgaggaaggt catttggggtt tttgtgagat ttgtattgag cacctgctgt ctacagagaa    2640
tgtgatgatg tcaattaaaa aa                                             2662
```

<210> SEQ ID NO 5
<211> LENGTH: 543
<212> TYPE: PRT
<213> ORGANISM: Homo sapiens

<400> SEQUENCE: 5

```
Met Asn Ser His Ser Tyr Asn Gly Ser Val Gly Arg Pro Leu Gly Ser
1               5                   10                  15

Gly Pro Gly Ala Leu Gly Arg Asp Pro Pro Asp Pro Glu Ala Gly His
            20                  25                  30

Pro Pro Gln Pro Pro His Ser Pro Gly Leu Gln Val Val Val Ala Lys
        35                  40                  45

Ser Glu Pro Ala Arg Pro Ser Pro Gly Ser Pro Arg Gly Gln Pro Gln
    50                  55                  60

Asp Gln Asp Asp Asp Glu Asp Asp Glu Glu Glu Ala Gly Arg Gln
65                  70                  75                  80

Arg Ala Ser Gly Lys Pro Ser Asn Val Gly His Arg Leu Gly His Arg
                85                  90                  95

Arg Ala Leu Phe Glu Lys Arg Lys Arg Leu Ser Asp Tyr Ala Leu Ile
```

```
                100                 105                 110
Phe Gly Met Phe Gly Ile Val Val Met Val Thr Glu Thr Glu Leu Ser
            115                 120                 125
Trp Gly Val Tyr Thr Lys Glu Ser Leu Tyr Ser Phe Ala Leu Lys Cys
            130                 135             140
Leu Ile Ser Leu Ser Thr Ala Ile Leu Leu Gly Leu Val Val Leu Tyr
145                 150                 155                 160
His Ala Arg Glu Ile Gln Leu Phe Met Val Asp Asn Gly Ala Asp Asp
                165                 170                 175
Trp Arg Ile Ala Met Thr Cys Glu Arg Val Phe Leu Ile Ser Leu Glu
            180                 185                 190
Leu Ala Val Cys Ala Ile His Pro Val Pro Gly His Tyr Arg Phe Thr
            195                 200                 205
Trp Thr Ala Arg Leu Ala Phe Thr Tyr Ala Pro Ser Val Ala Glu Ala
            210                 215                 220
Asp Val Asp Val Leu Leu Ser Ile Pro Met Phe Leu Arg Leu Tyr Leu
225                 230                 235                 240
Leu Gly Arg Val Met Leu Leu His Ser Lys Ile Phe Thr Asp Ala Ser
                245                 250                 255
Ser Arg Ser Ile Gly Ala Leu Asn Lys Ile Thr Phe Asn Thr Arg Phe
            260                 265                 270
Val Met Lys Thr Leu Met Thr Ile Cys Pro Gly Thr Val Leu Leu Val
            275                 280                 285
Phe Ser Ile Ser Ser Trp Ile Ile Ala Ala Trp Thr Val Arg Val Cys
            290                 295                 300
Glu Arg Tyr His Asp Lys Gln Glu Val Thr Ser Asn Phe Leu Gly Ala
305                 310                 315                 320
Met Trp Leu Ile Ser Ile Thr Phe Leu Ser Ile Gly Tyr Gly Asp Met
                325                 330                 335
Val Pro His Thr Tyr Cys Gly Lys Gly Val Cys Leu Leu Thr Gly Ile
            340                 345                 350
Met Gly Ala Gly Cys Thr Ala Leu Val Val Ala Val Val Ala Arg Lys
            355                 360                 365
Leu Glu Leu Thr Lys Ala Glu Lys His Val His Asn Phe Met Met Asp
            370                 375                 380
Thr Gln Leu Thr Lys Arg Val Lys Asn Ala Ala Ala Asn Val Leu Arg
385                 390                 395                 400
Glu Thr Trp Leu Ile Tyr Lys His Thr Arg Leu Val Lys Lys Pro Asp
                405                 410                 415
Gln Ala Arg Val Arg Lys His Gln Arg Lys Phe Leu Gln Ala Ile His
            420                 425                 430
Gln Ala Gln Lys Leu Arg Ser Val Lys Ile Glu Gln Gly Lys Leu Asn
            435                 440                 445
Asp Gln Ala Asn Thr Leu Thr Asp Leu Ala Lys Thr Gln Thr Val Met
            450                 455                 460
Tyr Asp Leu Val Ser Glu Leu His Ala Gln His Glu Glu Leu Glu Ala
465                 470                 475                 480
Arg Leu Ala Thr Leu Glu Ser Arg Leu Asp Ala Leu Gly Ala Ser Leu
                485                 490                 495
Gln Ala Leu Pro Gly Leu Ile Ala Gln Ala Ile Arg Pro Pro Pro
            500                 505                 510
Pro Leu Pro Pro Arg Pro Gly Pro Gly Pro Gln Asp Gln Ala Ala Arg
            515                 520                 525
```

Ser Ser Pro Cys Arg Trp Thr Pro Val Ala Pro Ser Asp Cys Gly
530                 535                 540

<210> SEQ ID NO 6
<211> LENGTH: 2531
<212> TYPE: DNA
<213> ORGANISM: Homo sapiens

<400> SEQUENCE: 6

| | | | | | |
|---|---|---|---|---|---|
| cggcggcagc | agcccatgcc | tccggtgcaa | cagctgcgcc | tcctccggtg | ccccggcggc | 60 |
| gggggcggga | gataacctgt | ccctgctgct | ccgcacctcc | tcgcccggcg | cgcccttccg | 120 |
| gacccgcacc | tcctcgccgc | tgtcgggctc | gtcctgctgc | tgctgctgct | gctcgtcgcg | 180 |
| ccggggcagc | cagctcaatg | tgagcgagct | gacgccgtcc | agccatgcca | gtgcgctccg | 240 |
| gcagcagtac | gcgcagcagt | ccgcgcagca | gtcggcgtcc | gcctcccagt | accaccagtg | 300 |
| ccacagcctg | cagcccgccg | ccagccccac | gggcagcctc | ggcagtctgg | gctccgggcc | 360 |
| cccgctctcg | caccaccacc | accacccgca | cccggcgcac | caccagccac | accagcccca | 420 |
| ggcgcgccgc | gagagcaacc | ccttcaccga | aatagccatg | agcagctgca | ggtacaacgg | 480 |
| gggcgtcatg | cggccgctca | gcaacttgag | cgcgtcccgc | cggaacctgc | acgagatgga | 540 |
| ctcagaggcg | cagcccctgc | agccccccgc | gtctgtcgga | ggaggtggcg | gcgcgtcctc | 600 |
| cccgtctgca | gccgctgccg | ccgccgccgc | tgtttcgtcc | tcagccccccg | agatcgtggt | 660 |
| gtctaagccc | gagcacaaca | actccaacaa | cctggcgctc | tatggaaccg | gcggcggagg | 720 |
| cagcactgga | ggaggcggcg | gcggtggcgg | gagcgggcac | ggcagcagca | gtggcaccaa | 780 |
| gtccagcaaa | aagaaaaacc | agaacatcgg | ctacaagctg | ggccaccggc | gcgccctgtt | 840 |
| cgaaaagcgc | aagcggctca | cgactacgc | gctcatcttc | ggcatgttcg | gcatcgtggt | 900 |
| catggtcatc | gagaccgagc | tgtcgtgggg | cgcctacgac | aaggcgtcgc | tgtattcctt | 960 |
| agctctgaaa | tgccttatca | gtctctccac | gatcatcctg | ctcggtctga | tcatcgtgta | 1020 |
| ccacgccagg | gaaatacagt | tgttcatggt | ggacaatgga | gcagatgact | ggagaatagc | 1080 |
| catgacttat | gagcgtattt | tcttcatctg | cttggaaata | ctggtgtgtg | ctattcatcc | 1140 |
| catacctggg | aattatacat | tcacatggac | ggcccggctt | gccttctcct | atgccccatc | 1200 |
| cacaaccacc | gctgatgtgg | atattatttt | atctataccca | atgttcttaa | gactctatct | 1260 |
| gattgccaga | gtcatgcttt | tacatagcaa | acttttcact | gatgcctcct | ctagaagcat | 1320 |
| tggagcactt | aataagataa | acttcaatac | acgttttgtt | atgaagactt | taatgactat | 1380 |
| atgcccagga | actgtactct | tggtttttag | tatctcatta | tggataattg | ccgcatggac | 1440 |
| tgtccgagct | tgtgaaaggt | accatgatca | acaggatgtt | actagcaact | tccttggagc | 1500 |
| gatgtggttg | atatcaataa | cttttctctc | cattggttat | ggtgacatgg | tacctaacac | 1560 |
| atactgtgga | aaaggagtct | gcttacttac | tggaattatg | ggtgctggtt | gcacagccct | 1620 |
| ggtggtagct | gtagtggcaa | ggaagctaga | acttaccaaa | gcagaaaaac | acgtgcacaa | 1680 |
| tttcatgatg | gatactcagc | tgactaaaag | agtaaaaaat | gcagctgcca | atgtactcag | 1740 |
| ggaaacatgg | ctaatttaca | aaatacaaa | gctagtgaaa | aagatagatc | atgcaaaagt | 1800 |
| aagaaaacat | caacgaaaat | tcctgcaagc | tattcatcaa | ttaagaagtg | taaaaatgga | 1860 |
| gcagaggaaa | ctgaatgacc | aagcaaacac | tttggtggac | ttggcaaaga | cccagaacat | 1920 |
| catgtatgat | atgatttctg | acttaaacga | aaggagtgaa | gacttcgaga | gaggattgt | 1980 |
| taccctggaa | acaaaactag | agactttgat | tggtagcatc | cacgccctcc | ctgggctcat | 2040 |

-continued

```
aagccagacc atcaggcagc agcagagaga tttcattgag gctcagatgg agagctacga    2100
caagcacgtc acttacaatg ctgagcggtc ccggtcctcg tccaggaggc ggcggtcctc    2160
ttccacagca ccaccaactt catcagagag tagctagaag agaataagtt aaccacaaaa    2220
taagactttt tgccatcata tggtcaatat tttagctttt attgtaaagc ccctatggtt    2280
ctaatcagcg ttatccgggt tctgatgtca gaatcctggg aacctgaaca ctaagtttta    2340
ggccaaaatg agtgaaaact ctttttttt cttttcagatg cacagggaat gcacctatta    2400
ttgctatata gattgttcct cctgtaattt cactaacttt ttattcatgc acttcaaaca    2460
aactttacta ctacattata tgatatataa taaaaaaagt taatttctgc acataaaaaa    2520
aaaaaaaaaa a                                                        2531
```

<210> SEQ ID NO 7
<211> LENGTH: 579
<212> TYPE: PRT
<213> ORGANISM: Homo sapiens

<400> SEQUENCE: 7

```
Met Ser Ser Cys Arg Tyr Asn Gly Gly Val Met Arg Pro Leu Ser Asn
1               5                   10                  15

Leu Ser Ala Ser Arg Arg Asn Leu His Glu Met Asp Ser Glu Ala Gln
            20                  25                  30

Pro Leu Gln Pro Pro Ala Ser Val Gly Gly Gly Gly Ala Ser Ser
        35                  40                  45

Pro Ser Ala Ala Ala Ala Ala Ala Ala Val Ser Ser Ser Ala Pro
    50                  55                  60

Glu Ile Val Val Ser Lys Pro Glu His Asn Asn Ser Asn Asn Leu Ala
65                  70                  75                  80

Leu Tyr Gly Thr Gly Gly Gly Ser Thr Gly Gly Gly Gly Gly
            85                  90                  95

Gly Gly Ser Gly His Gly Ser Ser Gly Thr Lys Ser Ser Lys Lys
            100                 105                 110

Lys Asn Gln Asn Ile Gly Tyr Lys Leu Gly His Arg Arg Ala Leu Phe
        115                 120                 125

Glu Lys Arg Lys Arg Leu Ser Asp Tyr Ala Leu Ile Phe Gly Met Phe
    130                 135                 140

Gly Ile Val Val Met Val Ile Glu Thr Glu Leu Ser Trp Gly Ala Tyr
145                 150                 155                 160

Asp Lys Ala Ser Leu Tyr Ser Leu Ala Leu Lys Cys Leu Ile Ser Leu
            165                 170                 175

Ser Thr Ile Ile Leu Leu Gly Leu Ile Ile Val Tyr His Ala Arg Glu
            180                 185                 190

Ile Gln Leu Phe Met Val Asp Asn Gly Ala Asp Asp Trp Arg Ile Ala
        195                 200                 205

Met Thr Tyr Glu Arg Ile Phe Phe Ile Cys Leu Glu Ile Leu Val Cys
    210                 215                 220

Ala Ile His Pro Ile Pro Gly Asn Tyr Thr Phe Thr Trp Thr Ala Arg
225                 230                 235                 240

Leu Ala Phe Ser Tyr Ala Pro Ser Thr Thr Thr Ala Asp Val Asp Ile
            245                 250                 255

Ile Leu Ser Ile Pro Met Phe Leu Arg Leu Tyr Leu Ile Ala Arg Val
            260                 265                 270

Met Leu Leu His Ser Lys Leu Phe Thr Asp Ala Ser Ser Arg Ser Ile
```

```
            275                 280                 285
Gly Ala Leu Asn Lys Ile Asn Phe Asn Thr Arg Phe Val Met Lys Thr
290                 295                 300

Leu Met Thr Ile Cys Pro Gly Thr Val Leu Leu Val Phe Ser Ile Ser
305                 310                 315                 320

Leu Trp Ile Ile Ala Ala Trp Thr Val Arg Ala Cys Glu Arg Tyr His
            325                 330                 335

Asp Gln Gln Asp Val Thr Ser Asn Phe Leu Gly Ala Met Trp Leu Ile
            340                 345                 350

Ser Ile Thr Phe Leu Ser Ile Gly Tyr Gly Asp Met Val Pro Asn Thr
            355                 360                 365

Tyr Cys Gly Lys Gly Val Cys Leu Leu Thr Gly Ile Met Gly Ala Gly
        370                 375                 380

Cys Thr Ala Leu Val Val Ala Val Val Ala Arg Lys Leu Glu Leu Thr
385                 390                 395                 400

Lys Ala Glu Lys His Val His Asn Phe Met Met Asp Thr Gln Leu Thr
            405                 410                 415

Lys Arg Val Lys Asn Ala Ala Asn Val Leu Arg Glu Thr Trp Leu
            420                 425                 430

Ile Tyr Lys Asn Thr Lys Leu Val Lys Lys Ile Asp His Ala Lys Val
            435                 440                 445

Arg Lys His Gln Arg Lys Phe Leu Gln Ala Ile His Gln Leu Arg Ser
        450                 455                 460

Val Lys Met Glu Gln Arg Lys Leu Asn Asp Gln Ala Asn Thr Leu Val
465                 470                 475                 480

Asp Leu Ala Lys Thr Gln Asn Ile Met Tyr Asp Met Ile Ser Asp Leu
            485                 490                 495

Asn Glu Arg Ser Glu Asp Phe Glu Lys Arg Ile Val Thr Leu Glu Thr
            500                 505                 510

Lys Leu Glu Thr Leu Ile Gly Ser Ile His Ala Leu Pro Gly Leu Ile
            515                 520                 525

Ser Gln Thr Ile Arg Gln Gln Arg Asp Phe Ile Glu Ala Gln Met
        530                 535                 540

Glu Ser Tyr Asp Lys His Val Thr Tyr Asn Ala Glu Arg Ser Arg Ser
545                 550                 555                 560

Ser Ser Arg Arg Arg Ser Ser Thr Ala Pro Pro Thr Ser Ser
            565                 570                 575

Glu Ser Ser

<210> SEQ ID NO 8
<211> LENGTH: 13080
<212> TYPE: DNA
<213> ORGANISM: Homo sapiens

<400> SEQUENCE: 8
gagccagcga ggagtgaagc tgagcctggc ctcacacgct cctagaggac cacctcctga     60
gagagttctt tcaccccctc ttctttctcc aagctcccct cctgctctcc ctccctgccc    120
aatacaatgc attcttgagt ggcagcgtct ggactccagg cagccccaga gaaccgaagc    180
aagccaaaga gaggactgga gccaagatac tggtggggga gattggatgc ctggctttct    240
ttgaggacat ctttggagcg agggtggctt tggggtgggg gcttgtgctg cagggaatac    300
agccaggccc caagatggac acttctgggc acttccatga ctcggggggtg ggggacttgg    360 atgaagaccc caagtgcccc tgtccatcct ctggggatga gcagcagcag cagcagcagc    420
```

```
agcaacagca gcagcagcca ccaccgccag cgccaccagc agccccccag cagcccctgg      480
gaccctcgct gcagcctcag cctccgcagc ttcagcagca gcagcagcag cagcagcagc      540
agcagcagca gcagccaccg catcccctgt ctcagctcgc ccaactccag agccagcccg      600
tccaccctgg cctgctgcac tcctctccca ccgctttcag gccccccct tcgtccaact       660 ccaccgccat cctccaccct tcctccaggc aaggcagcca gctcaatctc aatgaccact      720
tgcttggcca ctctccaagt tccacagcta caagtgggcc tggcggaggc agccggcacc      780
gacaggccag cccctggtg caccggcggg acagcaaccc cttcacggag atcgccatga       840
gctcctgcaa gtatagcggt ggggtcatga agccctcag ccgcctcagc gcctcccgga       900
ggaacctcat cgaggccgag actgagggcc aaccctcca gcttttcagc cctagcaacc       960
ccccggagat cgtcatctcc tcccgggagg acaaccatgc ccaccagacc ctgctccatc      1020
accctaatgc cacccacaac caccagcatg ccggcaccac cgccagcagc accaccttcc      1080
ccaaagccaa caagcggaaa aaccaaaaca ttggctataa gctgggacac aggagggccc      1140
tgtttgaaaa gagaaagcga ctgagtgact atgctctgat ttttgggatg tttggaattg      1200
ttgttatggt gatagagacc gagctctctt ggggtttgta ctcaaaggac tccatgtttt      1260
cgttggccct gaaatgcctt atcagtctgt ccaccatcat ccttttgggc ttgatcatcg      1320
cctaccacac acgtgaagtc cagctcttcg tgatcgacaa tggcgcggat gactggcgga      1380
tagccatgac ctacgagcgc atcctgtaca tcagcctgga gatgctggtg tgcgccatcc      1440
accccattcc tggcgagtac aagttcttct ggacggcacg cctggccttc tcctacacac      1500
cctcccgggc ggaggccgat gtggacatca tcctgtctat ccccatgttc ctgcgcctgt      1560
acctgatcgc ccgagtcatg ctgctgcaca gcaagctctt caccgatgcc tcgtcccgca      1620
gcatcggggc cctcaacaag atcaacttca caccccgctt tgtcatgaag acgctcatga      1680
ccatctgccc tggcactgtg ctgctcgtgt tcagcatctc tctgtggatc attgctgcct      1740
ggaccgtccg tgtctgtgaa agtcctgaat caccagccca gccttctggc tcatcacttc      1800
ctgcttggta ccatgaccag caggacgtaa ctagtaactt tctgggtgcc atgtggctca      1860
tctccatcac attcctttcc attggttatg gggacatggt gccccacaca tactgtggga      1920
aaggtgtctg tctcctcact ggcatcatgg gtgcaggctg cactgccctt gtggtggccg      1980
tggtggcccg aaagctggaa ctcaccaaag cggagaagca cgttcataac ttcatgatgg      2040
acactcagct caccaagcgg atcaagaatg ctgcagccaa tgtccttcgg gaaacatggt      2100
taatctataa acacacaaag ctgctaaaga agattgacca tgccaaagtg aggaaacacc      2160
agaggaagtt cctccaagct atccaccagt tgaggagcgt caagatggaa cagaggaagc      2220
tgagtgacca agccaacact ctggtggacc tttccaagat gcagaatgtc atgtatgact      2280
taatcacaga actcaatgac cggagcgaag acctggagaa gcagattggc agcctggagt      2340
cgaagctgga gcatctcacc gccagcttca actccctgcc gctgctcatc gccgacaccc      2400
tgcgccagca gcagcagcag ctcctgtctg ccatcatcga ggcccggggt gtcagcgtgg      2460
cagtgggcac caccacacc ccaatctccg atagccccat tggggtcagc tccacctcct       2520
tcccgacccc gtacacaagt tcaagcagtt gctaaataaa tctccccact ccagaagcat      2580
tacccatagg tcttaagatg caaatcaact ctctcctggt cgctttgcca tcaagaaaca      2640
ttcagaccag ggaacggaaa gaagagagac cgagctaatt aactaactca tgttcattca      2700
gcgtgcttgg tccgacatgc cttgaaacca gaaatctaat ctctgtttag gtgcctctac      2760
```

```
ttgggagcgg gaagaggaga tgacaggaag cgacgcctct ggcagggccc ttgctgcaga    2820
gttggtggag aacagaaatc cacgctcaat ctcaggtctt cacgcggggg gtgggggtca    2880
gatgcactga agtagccaac agcgaagcca gtccagaaga ggggtccgct gggagggagg    2940
gttgtgtcag gcttggggga tgggctcttc gccatggggg tctttgaaca cacctctctc    3000
cttttccttt gtctacggaa gcctctgggt gacaaaagta aaagagagct gcccacaact    3060
tgccaaaaca gatatactcg aatcagactg aaaaaaaaaa aaaagacac agacaaataa    3120
aaagccagat tttccactcg atattaatac ccacataaac ctgtgtgttt gcaaacgtgt    3180
acatgtacac acatacacat cccacgttcg cttcaggtcc tttcttattt gagcttaatc    3240
caaataaaaa gggacttgac accttaccct gcatacaata ggcaccccttt acatgtgttt    3300
tgagttggtc tgaatctgaa catggggtgc tttcagttca ggtagttagc tagttctggc    3360
cacattctga gtttcactga agatgtggat cccttcagac ataatgcaca ttgctttgtc    3420
ctggatatgc accttgcttg atttgaaatg gatgccaagc caaaattgtt ggcattcagg    3480
agggataagc aggcttctaa aaataacagc atctgcagag ttttcttctt ccatccaaac    3540
aagttgtgtt tcgatggtcc acatgaccag gtgtatgtct gtaagtgtgg agggagagga    3600
caagaaattg tgcatgtgtg tgcagacatg cacaaacagg agcaatccaa taacacctta    3660
gtgaatagaa atatggttgg ggatttgctg agctgtattt atccagcaac aggtttccag    3720
ccccagatgt tagtagtgca aagggccaa gtgcctcaat tgtgagcctc tgagctagga    3780
ggagaagtga tgaagagtgg cctatgtggt cccttctacc tgaccttaag tcatctcaaa    3840
atgaaatatt gtgagaatga agggaaccct tagggaacct tgtgggtaag gtaagtggac    3900
atggatttgt cagtagcctg ttcctactgt gccatgttaa tcttggtgcg aaaaactatt    3960
ccaatacatc tcaaactcca agagacttca gaaacatcaa gatttagtgt aatgagcggc    4020
gcagaaaaat gttttcattg ctccataatc tgaccacacg taacatttgt gacgtgaaaa    4080
ccatgacttt ctcattctga ggtctttggt ttctgcctgt gggaaattga atggcactgt    4140
atggactatt tcatctgttg atggtaaaac aaaagggtga tttttttgct tgtggttgtc    4200
atcttgggtt tacctttgta agaagacatc atcaccattc tgaaggcagt ggcttggcat    4260
ggagattttt attctgtagc actgggcctg ttcttctaag gacagcacaa ggtagacaat    4320
tgtagagcca aggccacttt ttcaggaaga tctagtctct tgctaaccct cttctttctc    4380
tcttgctatt gctgctgctc ttttgatggt ttatagtctt aatggcctgc cttgataatt    4440
cctttgaaca cttccattag ttgttttgca taccagagat gccgcacctg ctgttggctt    4500
atttttttac ttgttctatt aactgttgat tatctgaatg tttcccctcc tccttgtttc    4560
atgtcccaag aatggtgctc ctgttttcag tgacagttca gctgaacata taagcagatg    4620
tgtaaacaga tgaagtaacc atgcagtttc cttgtggcat tagttccatt tcacaaagtg    4680
aagaccactg gtgggctgat ctgagtgtgc caatcctgat catttaaacc tacagccttc    4740
aactggtgat tcctacccac cgttttcatt ctgctataac cctgtgatat gtgtgcgtgt    4800
gggtgtgagt gtgggtgtgt gcacatatag agatttagtc ttaatttcaa ccaaatgaca    4860
tgcaagattc cactgccact cttcctggcc aaaagtgtgc acagactgtg atttattcat    4920
tgtggtctgt gactttaacc catcattgat gctctcactt aggtaaaccc taaagaccaa    4980
actagcaaca ctagtcaagg gagtgactgg agttatttct ggtagcagta gccactggca    5040
tcctagaaac acatggacat ttgtagcatg aattgaccta ttggtagtgc aatagctata    5100
catgattttt attcttggca aaagaaaatg cttcaaaaaa aaagtgatca aacctgcaca    5160
```

```
ttgatcctgt aatagcaaat ggaaggctat ttctctgtac tagcatttca gctttatgtg   5220
ggaaagttac ccgttctcct gcaagtacaa tcaacccttg atgacttaag tattaattat   5280
tctgggtgta gctcacccaa gttttcttcc tacatctttt ggctaattcc accacacctc   5340
agcatcacag tcagatggga aaaggggcag gtggattctc atgtcatgcc ttcttgtacc   5400
ttattttcaa gttttgtggt ggaggaggtt taattatctg ctcaagaatc tggtatatat   5460
agccaggtgc ggtggctcat gcctgtaatc ccaggacttt gggcaaggcg agaggatcac   5520
ctgaggtcag gagttcaaga ccagcctggc caacatggca aaacccccatc tctactaaaa   5580 atacaaaaat tagctgggtt tggtggtgga cacctgtagt cccagctact tgggaggctg   5640
cggcaggaga atcacttgaa ccccggaagt ggaggttgca gtgagccaag atcgtgccat   5700
tgcactccag cttgggtgac cgagcaagac tccgtctcaa aaaaaaaaaa aaaatcggct   5760
atatgtaaaa actattaatt atgtaacctc actccaatac tgtactgatc aagatctgcc   5820
cactcctaga ggactgaccc aatggcagat cccctactat aatctttctg acaactcagt   5880
gacaggtaaa atcactctaa tattcctaaa atatctagac acttgaatta gaaatacaga   5940
accaccccca cccctgccat tgcttaagcc atattaaagc ttcatgtact gtaaagtcag   6000
ggatgtactg tgatacttta agaccactaa tctcagtgga atttcaggac atagcattag   6060
ttggtaaatt acaccagact aggggctcac tcctccttag attgaagtcc aaataaaagt   6120
cttcaccttt ggatcaaagg ccacatatat atgatcatca tcaataaatt gtcataaagt   6180
gtctatgaac tgctcttgcc atcttcctaa tacgtaactt catgacatca tgtctctaga   6240
agtgcttaat acaatccaaa agaacaaggg gggaaggccc caagtcacca ctgaccgacc   6300
tcagcagggg ccagtggtag aacaacaatc ttgtgaatta ggagacatag aaaatgtacg   6360
caaaagtaaa ttccaagcgc tgagcatgta caagctattt ttattattaa aagccaagaa   6420
ggaagagcat tgaagaagta atgattttaa tatagtgggg gatttccccc ttaaattttt   6480
ataatttcct tgtgaataaa caatcatgga aaagaagaaa cctagtcata caaaatcaga   6540
ataaataaaa atcttaagac tggatccaca tctttggcca attcatataa gcacctaata   6600
catcaatttc tctgtactta aaatgaagag aataattaat attcttaagt acaatgtttt   6660
caatagagaa caaatgaaat cacctttgtc atcaacagca gcccagactg actgtatcta   6720
gatcacacct tgatgttacg tttgaatgca gtcagtagtt accaaaaagt aattagtgca   6780
cattaaatag tggtaaaatc agcagggaga aatatgggat tagcacgtag ttccagaacc   6840
ttcctcctcc tccagagtgc aactcaacaa acagtacact ccaaattaag aatcaatgtt   6900
tcatcccagg acaaacggtg ttgctcccat cacagtacca caactgagat actgtgaagt   6960
cattgcacta ccagtaggtt actactcttt tgaagttact gttttttaaat cctaaaatat   7020 gtccccagtt ttctacattc attcttcttc ccctaagagt tgctagaagc agatgaagga   7080
tccctattga ctctgcaggg tttgatttca gtaccttaga cagctatctg gtgacttccc   7140
agtaggcacg aacaaccccct tctctcccct tgcagtcggt gggcttgatg acgccccaga   7200
cagtatcctt tccttctcta ctgccgccaa aataaacatt agggaaatgg gatcattaac   7260
accactgaga aaggagttta cagggatcgc aatagtaact gtctgcttgt ggtagtagaa   7320
agcttgtgcc aggctgcatg aatagaaatt aatgttaaac tcctgttaga cgagtaatat   7380
gtagattttt attgaaacag accacagctt attaaaagt actcagtgca atggtatata   7440
catatataca gatagaaaaa aatataactg tgatcttttt gtcttacgcc attactggaa   7500
```

```
acacccaaac gtgaactgga gttccctctg aacaaaacca ttgtcaaatc ttcaacatat    7560
gacctccaaa tctaggtgcc aagtgccctg tgacagttgt ttacacacct gaaaaatgta    7620
tcctggaagc tgtaatcttg ggcctgggct atgtgttgaa acaagcaaaa gagacacatc    7680
gtgaccaacc aagctggtgg aggaaaagca caaaattcaa ctccaacctg cagttaggat    7740
cccaaagaga tgttgacatt tatagccaaa agaaaaagt acatatatat atatatatat    7800
atatatatat atatatatat atatatatat ctgaatcaga tcgaagcagc caacgtccag    7860
cttcactcaa gaaggacaag gaataaacaa cattctctag ctgtgtcatg ttgtctcagt    7920
ttttgaatct caaccaggac tgatccacct tcatcagata cgttttttaa tggcgcaaca    7980
actcaatttt ggtcccagac tctccattct gcactggcca cgagaacaac aagagaatga    8040
caggatgtta atggaggaaa cattttcatg gcaagctcag aaactgaagt gtttatattc    8100
agaatcagat gagctttaat atgaatttgc atcttgcctc tgtactgctt gctattttt     8160 aatgatagga gaaagcataa cagtttattt taaatatgaa atatattgat atattataaa    8220
atatattgta actttcaatt aacattttgt atcaaactag tgtttagcag gtccactgtc    8280
agcctgctct cccaatgact gtttctgagt acacatcact gttagtgatt gccgggcacc    8340
cagaaaaagg gtcctcctac cacagcctac tgaactgcca tattctaatt ctccaaggcc    8400
tgggtattag agacaaaaga acattattcc aagagtagag gaataattct accctaaatt    8460
ctatcaagcc atttcagaag agattttaaa agccatcact cctttagtag ctctgcaaag    8520
ccagtttaat aaaagttcag gctctttcta tataaattca aaggcctcat tacataaatt    8580
atataagtct caaacctagc caaccagttt tcctttgaca atgtcagaat tggacataag    8640
aaagagtcct gttttcctgt aacttaaaat actcaaaatc ctaggcattc tgagtttctc    8700
catgtacgtg aaaccggggt cggctttcca aactacacaa ggcccaacaa gagtccagtg    8760
tgcagatgtg cttttctaaa ttggcaatac ccttgaggga gcaaggttcc cacatgttta    8820
tcaaggacat ggagcccagc tcctaaggga gtgatgggag gagccggcag gacatgaaca    8880
gccagagcca gcaaagagcc gggctgcctt ttctgctagc ttcctctagc tgggaggaaa    8940
taaagggttc ccgttgagat attgtccttt atagcaaaat taagcaactc atggaatcta    9000 caccccctctt tctctacaga gcagctgaga catacatgta gaagttctca gttccctcct    9060
tcatatggct aaggcactac ttctagatga aaacaggatg tgttcggtta cagaataaag    9120
attttctaga atcagtgagc ctcttctcac ctgggaccct cacttgctgt tgttgctttg    9180
gtgcaatatt gtacaggtgc aaaccaggtt gcatcgggc agattaactg agcctatgtg     9240
tctcttccct tcccaagccc tgaaaattca catagattta cagatagtgc aaaacaacaa    9300
gttttctcct gggaaaaggc tggaatcctt caaatttcaa tttatatgag cttaaaggta    9360
tataagtcat ggggctcact gacattaggt attcatgctg tttgaaagag aaatgtctaa    9420
atgcccgttt tcagtctgtt tgtgtagctg agccctaact tgtacacaag ttttcttgtt    9480
atggagctaa attctctcag tgcctgtatt actcctcagt tatatgttag gccgagctcc    9540
actaaagcca tctgaactcc agggcacttg ttttatcag gttacttact caccggataa      9600
tggaaattgg cttattttca attttacaat tgactgatga atgtattggt ggtaattgat    9660
ttatttcttc acttttttt gctactaaat gattttttct tttttaaaat tattattatt     9720
attattttga gatggagtct cactctgtcg cccaggctgg agtgcagtgg cgccatctca    9780
gctcactgca agctctgcct cctgggttca tgcaattctc ctgcctcagc ctcccgagta    9840
gctgggatta caggtgcgtg ccaccacgac cagctaattt ttttgtattt ttagtagaga    9900
```

```
cagggtttca tcatgttaac caggatggtc tcgatctcct gacctcgtga tccacctgcc   9960
tgggcctccc aaagtgagcc actgtgcctg gcccagtaag tgcttttttc ttttggtttt  10020
tccttctaac actgctcaga ccaagactta catttataaa gagcaaatat attctgacct  10080
ttcccctcaa agttgtattc catctagaat caaggaaaca aatgcaaatt catcatttgg  10140
ggaaagcaga cctcttgaca gtaattcaag tccatggcta tatgctaacc cttgctactc  10200
aaagtgtggt ccacagacca gcagcgttag catcatctgt aagcttgtta gaaatgcaga  10260
atctcaggcc ccacatcaaa ccttcttcat cagaattggc cttttaacaa atccccaggt  10320
gacctgtatg caccagaaat attgataagc actggcctca cctcaccgta gtgataacta  10380
acctcgttaa taattagaga atgaagctat ctcttccttg agtctcattt acagaattat  10440
ttgaagatgt gaaggtcctg aatgatcata aggattaaaa aaatgcatct ttaaattcca  10500
cttgaggtta tataacttgg atggtctaca tcaaacataa taaagtcaat aagagatagt  10560
cttttttccgg tcttacctaa atagcactcc atatccttga gccacctcaa agcccccatt  10620
tttaagtttt agtcttttttt tttttagacc agactagcaa agccatcaga atatcaggtg  10680
gaacctcagg gcaggtcctc tggaaggcta caggagtctc tgcttagcat agtacagaaa  10740
ttgttgtgtt tctcgatcct tgtgttcttc ccttgaggaa ctcagcatct caccagtaag  10800
aactccccctc ccctagagga aaatagcaag agaagttagt ttaaccatct agaaacattg  10860
ctaatctcct tgaaagccaa ttctcttact cattgcacca acaagaaaca ctccaaggtg  10920
ggcaaggaaa gacgtgaatt ctgatattgg cgccataact cgatatgtac ccagaaacag  10980
ttatgttcta aattaatggc tttaacctgt tcattgtaaa aagtgccttg gacttcaatc  11040
taaagaggtc agtataaata tgtatgtgtg tgtgtgacgt gtatgtaggc aaatatttac  11100
agatttatac atacataggt gcacacacat atacccgcac attcatatat aatatataca  11160
tacatatata aatgcttcat aatatatcat attgctattc acagctccat ttcttttgtc  11220
tggtcctatg tttatttgtt tagtgagacc tttacataga gaggttctat tcggaacatt  11280
gatgtatttt ttgtttgttt tttactttttt attaaaaagg taaggatat taaaaaaaaa  11340
aaaaaaagtc aagtgcctga aggttttgaa tggagttacg gtaaacttttc tcaggtcacc  11400
aaagaggaaa catttttcct ttggaaaaca tttttctgtt tcagtgactt tgttttccct  11460
tggtggtaat gcataaataa gagtggttaa agtgattttg taagttttat ttcaatccat  11520
ttctgtggtt cccataaggc aatagctaaa aatttgttca gtctagtgcc cagttttctc  11580
cacacatcag catcagaagg gcccggtctt cacatgctct gtgtggtttt gttcgcgttg  11640
ttactgtgtt ccttactaag gaaaggcaaa tgaaattgca ggggctggag cttagaccag  11700
ctccaaatat ggcttccttt tggtaacaca cacagaaggt ggactagtgg gaagtctctc  11760
tccctgaagc aggtgggaac ctgtgtctta aaggcagag gagtcccagt gaactctcca  11820
cagctccatg ggccctgcct gtctacagtt atacaactgc ctgtatgagt cagcttttct  11880
ctaccttagc caaaggtctt ctctttctgt ggtgtgacag cttgtaatga accaacttgc  11940
tctggttaga agtccctaga gctccaggaa gagtcgccag gtttccattg ctgtgctcaa  12000
agctcaagga cacattatac ttcttttaaac caactaaatc tctctagctc cctgccccca  12060
tggtgacact ttcataatag gcagggccaa gtcagagagg tcatgccctg tatacagtgt  12120
caatcagaag agacactgca aaatgtcaga ggtgaccaga aagacaacag atctctccag  12180
ctgtcctcac agctgcaggc acatttgtgg aattgtgagt aggaaggctt ggcagccagg  12240
```

-continued

```
ggatgggaaa tgaatttccc caagttgaaa accctgtacc cttactttcc ttcccataaa    12300 ttttctgta gttctaggta aataataata ataataaaaa tgcaaattag gtgctttaga    12360
aggagtatgt aatatctggg acttttcta agttggtaga cctaaaaaat gttttcaaaa    12420
atatatctag ctgcatttct actgctgtca ttccttaaag ctcttcctcc aaaaactcca    12480
tatgaatgaa tacatttacc aactcagtga ttactaaata atagtacttt atacttatac    12540
acagtaatac ctttcatcta aggatctcaa atgccaatat attagtcatc accctgtaag    12600
gtggatgaca tattattccc attattccaa tgggaaaatt gggccataga aaactgagga    12660
gcaaatgact catctacagg aattaaatgg aaaaaacagg ctaggatttc tcagcacact    12720
ttaggagtga atgaaaactt acaggcttca gttctactgc tggccaccat tggatttgta    12780
agatccagga tgtgtattga ccacatgtgt ccagacccag gcttagggca tctggaatga    12840
gagtggtggg ctggtgtgtg ggtctgagga tctggatggg agactgcatt tcttctctg    12900 tgcaaaatat ggaagtgtga ccttgaaggt gggcttagtc tatggccttc cccactcctg    12960
cttgaactga agctggagag aatgggcatt tttaaatgtt acggcatatg ctaatataat    13020
attatggcat taaataaaaa caagaagaga actgactaaa accaaaaaaa aaaaaaaaa    13080
```

<210> SEQ ID NO 9
<211> LENGTH: 746
<212> TYPE: PRT
<213> ORGANISM: Homo sapiens

<400> SEQUENCE: 9

```
Met Asp Thr Ser Gly His Phe His Asp Ser Gly Val Gly Asp Leu Asp
1               5                   10                  15

Glu Asp Pro Lys Cys Pro Cys Pro Ser Ser Gly Asp Glu Gln Gln Gln
            20                  25                  30

Gln Gln Gln Gln Gln Gln Gln Gln Gln Pro Pro Pro Ala Pro Pro
        35                  40                  45

Ala Ala Pro Gln Gln Pro Leu Gly Pro Ser Leu Gln Pro Gln Pro Pro
    50                  55                  60

Gln Leu Gln Gln Gln Gln Gln Gln Gln Gln Gln Gln Gln Gln Gln Gln
65                  70                  75                  80

Pro Pro His Pro Leu Ser Gln Leu Ala Gln Leu Gln Ser Gln Pro Val
                85                  90                  95

His Pro Gly Leu Leu His Ser Ser Pro Thr Ala Phe Arg Ala Pro Pro
            100                 105                 110

Ser Ser Asn Ser Thr Ala Ile Leu His Pro Ser Arg Gln Gly Ser
        115                 120                 125

Gln Leu Asn Leu Asn Asp His Leu Leu Gly His Ser Pro Ser Ser Thr
    130                 135                 140

Ala Thr Ser Gly Pro Gly Gly Ser Arg His Arg Gln Ala Ser Pro
145                 150                 155                 160

Leu Val His Arg Arg Asp Ser Asn Pro Phe Thr Glu Ile Ala Met Ser
                165                 170                 175

Ser Cys Lys Tyr Ser Gly Gly Val Met Lys Pro Leu Ser Arg Leu Ser
            180                 185                 190

Ala Ser Arg Arg Asn Leu Ile Glu Ala Glu Thr Glu Gly Gln Pro Leu
        195                 200                 205

Gln Leu Phe Ser Pro Ser Asn Pro Pro Glu Ile Val Ile Ser Ser Arg
    210                 215                 220

Glu Asp Asn His Ala His Gln Thr Leu Leu His His Pro Asn Ala Thr
```

```
              225                 230                 235                 240
        His Asn His Gln His Ala Gly Thr Thr Ala Ser Ser Thr Thr Phe Pro
                        245                 250                 255
        Lys Ala Asn Lys Arg Lys Asn Gln Asn Ile Gly Tyr Lys Leu Gly His
                        260                 265                 270
        Arg Arg Ala Leu Phe Glu Lys Arg Lys Arg Leu Ser Asp Tyr Ala Leu
                        275                 280                 285
        Ile Phe Gly Met Phe Gly Ile Val Val Met Val Ile Glu Thr Glu Leu
                        290                 295                 300
        Ser Trp Gly Leu Tyr Ser Lys Asp Ser Met Phe Ser Leu Ala Leu Lys
        305                 310                 315                 320
        Cys Leu Ile Ser Leu Ser Thr Ile Ile Leu Leu Gly Leu Ile Ile Ala
                        325                 330                 335
        Tyr His Thr Arg Glu Val Gln Leu Phe Val Ile Asp Asn Gly Ala Asp
                        340                 345                 350
        Asp Trp Arg Ile Ala Met Thr Tyr Glu Arg Ile Leu Tyr Ile Ser Leu
                        355                 360                 365
        Glu Met Leu Val Cys Ala Ile His Pro Ile Pro Gly Glu Tyr Lys Phe
                        370                 375                 380
        Phe Trp Thr Ala Arg Leu Ala Phe Ser Tyr Thr Pro Ser Arg Ala Glu
        385                 390                 395                 400
        Ala Asp Val Asp Ile Ile Leu Ser Ile Pro Met Phe Leu Arg Leu Tyr
                        405                 410                 415
        Leu Ile Ala Arg Val Met Leu Leu His Ser Lys Leu Phe Thr Asp Ala
                        420                 425                 430
        Ser Ser Arg Ser Ile Gly Ala Leu Asn Lys Ile Asn Phe Asn Thr Arg
                        435                 440                 445
        Phe Val Met Lys Thr Leu Met Thr Ile Cys Pro Gly Thr Val Leu Leu
                        450                 455                 460
        Val Phe Ser Ile Ser Leu Trp Ile Ile Ala Ala Trp Thr Val Arg Val
        465                 470                 475                 480
        Cys Glu Ser Pro Glu Ser Pro Ala Gln Pro Ser Gly Ser Ser Leu Pro
                        485                 490                 495
        Ala Trp Tyr His Asp Gln Gln Asp Val Thr Ser Asn Phe Leu Gly Ala
                        500                 505                 510
        Met Trp Leu Ile Ser Ile Thr Phe Leu Ser Ile Gly Tyr Gly Asp Met
                        515                 520                 525
        Val Pro His Thr Tyr Cys Gly Lys Gly Val Cys Leu Leu Thr Gly Ile
                        530                 535                 540
        Met Gly Ala Gly Cys Thr Ala Leu Val Val Ala Val Val Ala Arg Lys
        545                 550                 555                 560
        Leu Glu Leu Thr Lys Ala Glu Lys His Val His Asn Phe Met Met Asp
                        565                 570                 575
        Thr Gln Leu Thr Lys Arg Ile Lys Asn Ala Ala Ala Asn Val Leu Arg
                        580                 585                 590
        Glu Thr Trp Leu Ile Tyr Lys His Thr Lys Leu Leu Lys Lys Ile Asp
                        595                 600                 605
        His Ala Lys Val Arg Lys His Gln Arg Lys Phe Leu Gln Ala Ile His
                        610                 615                 620
        Gln Leu Arg Ser Val Lys Met Glu Gln Arg Lys Leu Ser Asp Gln Ala
        625                 630                 635                 640
        Asn Thr Leu Val Asp Leu Ser Lys Met Gln Asn Val Met Tyr Asp Leu
                        645                 650                 655
```

```
Ile Thr Glu Leu Asn Asp Arg Ser Glu Asp Leu Glu Lys Gln Ile Gly
            660                 665                 670

Ser Leu Glu Ser Lys Leu Glu His Leu Thr Ala Ser Phe Asn Ser Leu
        675                 680                 685

Pro Leu Leu Ile Ala Asp Thr Leu Arg Gln Gln Gln Gln Gln Leu Leu
    690                 695                 700

Ser Ala Ile Ile Glu Ala Arg Gly Val Ser Val Ala Val Gly Thr Thr
705                 710                 715                 720

His Thr Pro Ile Ser Asp Ser Pro Ile Gly Val Ser Ser Thr Ser Phe
                725                 730                 735

Pro Thr Pro Tyr Thr Ser Ser Ser Ser Cys
            740                 745

<210> SEQ ID NO 10
<211> LENGTH: 2490
<212> TYPE: DNA
<213> ORGANISM: Homo sapiens

<400> SEQUENCE: 10
```

| | | | | | |
|---|---|---|---|---|---|
| agcactctct | cacttctggc | cagggaacgt | ggaaggcgca | ccgacaggga | tccggccagg | 60
| gagggcgagt | gaaagaagga | aatcagaaag | gaagggagtt | aacaaaataa | taaaaacagc | 120
| ctgagccacg | gctggagaga | ccgagacccg | gcgcaagaga | gcgcagcctt | agtaggagag | 180
| gaacgcgaga | cgcggcagag | cgcgttcagc | actgactttt | gctgctgctt | ctgctttttt | 240
| ttttcttaga | aacaagaagg | cgccagcggc | agcctcacac | gcgagcgcca | cgcgaggctc | 300
| ccgaagccaa | cccgcgaagg | gaggagggga | gggaggagga | ggcggcgtgc | agggaggaga | 360
| aaaagcattt | tcacttttttt | tgctcccact | ctaagaagtc | tcccggggat | tttgtatata | 420
| ttttttaact | tccgtcaggg | ctcccgcttc | atatttcctt | ttctttccct | ctctgttcct | 480
| gcacccaagt | tctctctgtg | tccccctcgc | gggccccgca | cctcgcgtcc | cggatcgctc | 540
| tgattccgcg | actccttggc | cgccgctgcg | catggaaagc | tctgccaaga | tggagagcgg | 600
| cggcgccggc | cagcagcccc | agccgcagcc | ccagcagccc | ttcctgccgc | ccgcagcctg | 660
| tttctttgcc | acggccgcag | ccgcggcggc | cgcagccgcc | gcagcggcag | cgcagagcgc | 720
| gcagcagcag | cagcagcagc | agcagcagca | gcagcaggcg | ccgcagctga | ccggcggc | 780
| cgacggccag | ccctcagggg | gcggtcacaa | gtcagcgccc | aagcaagtca | agcgacagcg | 840
| ctcgtcttcg | cccgaactga | tgcgctgcaa | acgccggctc | aacttcagcg | gctttggcta | 900
| cagcctgccg | cagcagcagc | cggccgccgt | ggcgcgccgc | aacgagcgcg | agcgcaaccg | 960
| cgtcaagttg | gtcaacctgg | gctttgccac | ccttcgggag | cacgtcccca | acggcgcggc | 1020
| caacaagaag | atgagtaagg | tggagacact | gcgctcggcg | gtcgagtaca | tccgcgcgct | 1080
| gcagcagctg | ctggacgagc | atgacgcggt | gagcgccgcc | ttccaggcag | gcgtcctgtc | 1140
| gcccaccatc | tcccccaact | actccaacga | cttgaactcc | atggccggct | cgccggtctc | 1200
| atcctactcg | tcggacgagg | gctcttacga | cccgctcagc | cccgaggagc | aggagcttct | 1260
| cgacttcacc | aactggttct | gaggggctcg | gcctggtcag | gccctggtgc | gaatggactt | 1320
| tggaagcagg | gtgatcgcac | aacctgcatc | tttagtgctt | tcttgtcagt | ggcgttggga | 1380
| gggggagaaa | aggaaaagaa | aaaaaaaaga | agaagaagaa | gaaagagaaa | gaagaaaaaa | 1440
| acgaaaacag | tcaaccaacc | ccatcgccaa | ctaagcgagg | catgcctgag | agacatggct | 1500
| ttcagaaaac | gggaagcgct | cagaacagta | tctttgcact | ccaatcattc | acggagatat | 1560

```
gaagagcaac tgggacctga gtcaatgcgc aaaatgcagc ttgtgtgcaa aagcagtggg    1620
ctcctggcag aagggagcag cacacgcgtt atagtaactc ccatcacctc taacacgcac    1680
agctgaaagt tcttgctcgg gtcccttcac ctcctcgccc tttcttaaag tgcagttctt    1740
agccctctag aaacgagttg gtgtctttcg tctcagtagc ccccacccca ataagctgta    1800
gacattggtt tacagtgaaa ctatgctatt ctcagccctt tgaaactctg cttctcctcc    1860
agggcccgat tcccaaaccc catggcttcc ctcacactgt cttttctacc attttcatta    1920
tagaatgctt ccaatctttt gtgaattttt tattataaaa aatctatttg tatctatcct    1980
aaccagttcg gggatatatt aagatatttt tgtacataag agagaaagag agagaaaaat    2040
ttatagaagt tttgtacaaa tggtttaaaa tgtgtatatc ttgatactttt aacatgtaat   2100 gctattacct ctgcatattt tagatgtgta gttcaccttta caactgcaat tttccctatg   2160
tggttttgta aagaactctc ctcataggtg agatcaagag gccaccagtt gtacttcagc    2220
accaatgtgt cttactttat agaaatgttg ttaatgtatt aatgatgtta ttaaatactg    2280
ttcaagaaga acaaagttta tgcagctact gtccaaactc aaagtggcag ccagttggtt    2340
ttgataggtt gccttttgga gatttctatt actgcctttt ttttcttac tgttttatta    2400 caaacttaca aaaatatgta taaccctgtt ttatacaaac tagtttcgta ataaaacttt    2460
ttcctttttt taaaatgaaa ataaaaaaaa                                     2490

<210> SEQ ID NO 11
<211> LENGTH: 236
<212> TYPE: PRT
<213> ORGANISM: Homo sapiens

<400> SEQUENCE: 11

Met Glu Ser Ser Ala Lys Met Glu Ser Gly Gly Ala Gly Gln Gln Pro
1               5                   10                  15

Gln Pro Gln Pro Gln Gln Pro Phe Leu Pro Pro Ala Ala Cys Phe Phe
            20                  25                  30

Ala Thr Ala Ala Ala Ala Ala Ala Ala Ala Ala Ala Ala Ala Ala Gln
        35                  40                  45

Ser Ala Gln Gln Gln Gln Gln Gln Gln Gln Gln Gln Gln Gln Ala Pro
    50                  55                  60

Gln Leu Arg Pro Ala Ala Asp Gly Gln Pro Ser Gly Gly Gly His Lys
65                  70                  75                  80

Ser Ala Pro Lys Gln Val Lys Arg Gln Arg Ser Ser Pro Glu Leu
                85                  90                  95

Met Arg Cys Lys Arg Arg Leu Asn Phe Ser Gly Phe Gly Tyr Ser Leu
            100                 105                 110

Pro Gln Gln Gln Pro Ala Ala Val Ala Arg Arg Asn Glu Arg Glu Arg
        115                 120                 125

Asn Arg Val Lys Leu Val Asn Leu Gly Phe Ala Thr Leu Arg Glu His
    130                 135                 140

Val Pro Asn Gly Ala Ala Asn Lys Lys Met Ser Lys Val Glu Thr Leu
145                 150                 155                 160

Arg Ser Ala Val Glu Tyr Ile Arg Ala Leu Gln Gln Leu Leu Asp Glu
                165                 170                 175

His Asp Ala Val Ser Ala Ala Phe Gln Ala Gly Val Leu Ser Pro Thr
            180                 185                 190

Ile Ser Pro Asn Tyr Ser Asn Asp Leu Asn Ser Met Ala Gly Ser Pro
        195                 200                 205
```

| Val | Ser | Ser | Tyr | Ser | Ser | Asp | Glu | Gly | Ser | Tyr | Asp | Pro | Leu | Ser | Pro |
|||||||||||||||||
| | 210 | | | | 215 | | | | | 220 | | | | | |

| Glu | Glu | Gln | Glu | Leu | Leu | Asp | Phe | Thr | Asn | Trp | Phe |
||||||||||||
| 225 | | | | | 230 | | | | 235 | | |

<210> SEQ ID NO 12
<211> LENGTH: 2175
<212> TYPE: DNA
<213> ORGANISM: Homo sapiens

<400> SEQUENCE: 12

| | | | | | |
|---|---|---|---|---|---|
| gttgtatatc | agggccgcgc | tgagctgcgc | cagctgaggt | gtgagcagct | gccgaagtca | 60 |
| gttccttgtg | gagccggagc | tgggcgcgga | ttcgccgagg | caccgaggca | ctcagaggag | 120 |
| gcgccatgtc | agaaccggct | ggggatgtcc | gtcagaaccc | atgcggcagc | aaggcctgcc | 180 |
| gccgcctctt | cggcccagtg | gacagcgagc | agctgagccg | cgactgtgat | gcgctaatgg | 240 |
| cgggctgcat | ccaggaggcc | cgtgagcgat | ggaacttcga | cttttgtcacc | gagacaccac | 300 |
| tggagggtga | cttcgcctgg | gagcgtgtgc | ggggccttgg | cctgcccaag | ctctaccttc | 360 |
| ccacggggcc | ccggcgaggc | cgggatgagt | tgggaggagg | caggcggcct | ggcacctcac | 420 |
| ctgctctgct | gcagggcaca | gcagaggaag | accatgtgga | cctgtcactg | tcttgtaccc | 480 |
| ttgtgcctcg | ctcaggggag | caggctgaag | ggtccccagg | tggacctgga | gactctcagg | 540 |
| gtcgaaaacg | gcggcagacc | agcatgcacg | atttctacca | ctccaaacgc | cggctgatct | 600 |
| tctccaagag | gaagccctaa | tccgcccaca | ggaagcctgc | agtcctggaa | gcgcgagggc | 660 |
| ctcaaaggcc | cgctctacat | cttctgcctt | agtctcagtt | tgtgtgtctt | aattattatt | 720 |
| tgtgttttaa | tttaaacacc | tcctcatgta | cataccctgg | ccgcccctg | cccccagcc | 780 |
| tctggcatta | gaattattta | aacaaaaact | aggcggttga | atgagaggtt | cctaagagtg | 840 |
| ctgggcatt | ttattttatg | aaatactatt | taaagcctcc | tcatcccgtg | ttctccttt | 900 |
| cctctctccc | ggaggttggg | tgggccggct | tcatgccagc | tacttcctcc | tccccacttg | 960 |
| tccgctgggt | ggtaccctct | ggaggggtgt | ggctccttcc | catcgctgtc | acaggcggtt | 1020 |
| atgaaattca | ccccctttcc | tggacactca | gacctgaatt | cttttcatt | tgagaagtaa | 1080 |
| acagatggca | ctttgaaggg | gcctcaccga | gtggggcat | catcaaaaac | tttggagtcc | 1140 |
| cctcacctcc | tctaaggttg | gcagggtga | ccctgaagtg | agcacagcct | agggctgagc | 1200 |
| tggggacctg | gtaccctcct | ggctcttgat | accccctct | gtcttgtgaa | ggcagggga | 1260 |
| aggtggggtc | ctggagcaga | ccaccccgcc | tgccctcatg | gcccctctga | cctgcactgg | 1320 |
| ggagcccgtc | tcagtgttga | gccttttccc | tctttggctc | ccctgtacct | tttgaggagc | 1380 |
| cccagctacc | cttcttctcc | agctgggctc | tgcaattccc | ctctgctgct | gtccctcccc | 1440 |
| cttgtccttt | cccttcagta | ccctctcagc | tccaggtggc | tctgaggtgc | ctgtcccacc | 1500 |
| cccacccca | gctcaatgga | ctggaagggg | aagggacaca | caagaagaag | ggcaccctag | 1560 |
| ttctacctca | ggcagctcaa | gcagcgaccg | cccctcctc | tagctgtggg | ggtgagggtc | 1620 |
| ccatgtggtg | gcacaggccc | ccttgagtgg | ggttatctct | gtgttagggg | tatatgatgg | 1680 |
| gggagtagat | ctttctagga | gggagacact | ggccctcaa | atcgtccagc | gaccttcctc | 1740 |
| atccacccca | tccctcccca | gttcattgca | ctttgattag | cagcggaaca | aggagtcaga | 1800 |
| cattttaaga | tggtggcagt | agaggctatg | gacagggcat | gccacgtggg | ctcatatggg | 1860 |
| gctgggagta | gttgtctttc | ctggcactaa | cgttgagccc | ctggaggcac | tgaagtgctt | 1920 |
| agtgtacttg | gagtattggg | gtctgacccc | aaacaccttc | cagctcctgt | aacatactgg | 1980 |

```
cctggactgt tttctctcgg ctccccatgt gtcctggttc ccgtttctcc acctagactg    2040
taaacctctc gagggcaggg accacaccct gtactgttct gtgtctttca cagctcctcc    2100
cacaatgctg aatatacagc aggtgctcaa taaatgattc ttagtgactt tacttgtaaa    2160
aaaaaaaaaa aaaaa                                                      2175
```

<210> SEQ ID NO 13
<211> LENGTH: 164
<212> TYPE: PRT
<213> ORGANISM: Homo sapiens

<400> SEQUENCE: 13

```
Met Ser Glu Pro Ala Gly Asp Val Arg Gln Asn Pro Cys Gly Ser Lys
1               5                   10                  15

Ala Cys Arg Arg Leu Phe Gly Pro Val Asp Ser Glu Gln Leu Ser Arg
            20                  25                  30

Asp Cys Asp Ala Leu Met Ala Gly Cys Ile Gln Glu Ala Arg Glu Arg
        35                  40                  45

Trp Asn Phe Asp Phe Val Thr Glu Thr Pro Leu Glu Gly Asp Phe Ala
    50                  55                  60

Trp Glu Arg Val Arg Gly Leu Gly Leu Pro Lys Leu Tyr Leu Pro Thr
65                  70                  75                  80

Gly Pro Arg Arg Gly Arg Asp Glu Leu Gly Gly Gly Arg Arg Pro Gly
                85                  90                  95

Thr Ser Pro Ala Leu Leu Gln Gly Thr Ala Glu Glu Asp His Val Asp
            100                 105                 110

Leu Ser Leu Ser Cys Thr Leu Val Pro Arg Ser Gly Glu Gln Ala Glu
        115                 120                 125

Gly Ser Pro Gly Gly Pro Gly Asp Ser Gln Gly Arg Lys Arg Arg Gln
    130                 135                 140

Thr Ser Met Thr Asp Phe Tyr His Ser Lys Arg Arg Leu Ile Phe Ser
145                 150                 155                 160

Lys Arg Lys Pro
```

<210> SEQ ID NO 14
<211> LENGTH: 110
<212> TYPE: DNA
<213> ORGANISM: Homo sapiens

<400> SEQUENCE: 14

```
ccagaggttg taacgttgtc tatatatacc ctgtagaacc gaatttgtgt ggtatccgta     60
tagtcacaga ttcgattcta ggggaatata tggtcgatgc aaaaacttca                110
```

<210> SEQ ID NO 15
<211> LENGTH: 23
<212> TYPE: RNA
<213> ORGANISM: Homo sapiens

<400> SEQUENCE: 15

```
uacccuguag aaccgaauuu gug                                             23
```

<210> SEQ ID NO 16
<211> LENGTH: 163
<212> TYPE: DNA
<213> ORGANISM: Homo sapiens

<400> SEQUENCE: 16

```
cgcacaccct cccggctcac acgcccttgc ccggccgtgc acttgtcttc gcgctcgggc      60
agggcgcagg gactccggct gcggcggccg actccggccg gtgagtggca gtgggggggca   120 cggcggggag cgttcggtcc cggcggcggt ccccttctct ttg                       163

<210> SEQ ID NO 17
<211> LENGTH: 200
<212> TYPE: DNA
<213> ORGANISM: Homo sapiens

<400> SEQUENCE: 17
agggaatccc cagctccgcc gcagagagcg ggaggggggcg tgagagggga gttccgtgcg      60
cgcccagccg gccccgcgtg cgttgccagg acgaccgggc ggggccgcgg ggccgccggt     120
cgctcactgc gcctgcgcgg gggtgctcgc catttgcgcc ggggctttcc cgtcgcgcgc     180
cagcagaaga ggggatgccg                                                 200

<210> SEQ ID NO 18
<211> LENGTH: 259
<212> TYPE: DNA
<213> ORGANISM: Homo sapiens

<400> SEQUENCE: 18
gaagacgcct ttgtctcccg cctgcctagc gccccacagc ccggcatgtg gggtgtaccc      60
ccgggccccg tcatcccctc ccccagccat ctgccgtcct cctggccttg aacaacagcc    120
tgaagtcgag tccgggctag caggggaaa gcgcaaaggt gcagcacgca ccctcgggga     180
ttttctcagc gctcctcacc ccccacgacc tccaaaccct ccgctatggg cctggccctg    240
ccaaggccac atcgccccg                                                  259

<210> SEQ ID NO 19
<211> LENGTH: 22
<212> TYPE: RNA
<213> ORGANISM: Homo sapiens

<400> SEQUENCE: 19
uagguaguuu cauguuguug gg                                               22

<210> SEQ ID NO 20
<211> LENGTH: 22
<212> TYPE: RNA
<213> ORGANISM: Homo sapiens

<400> SEQUENCE: 20
uagguaguuu ccuguuguug gg                                               22

<210> SEQ ID NO 21
<211> LENGTH: 22
<212> TYPE: RNA
<213> ORGANISM: Homo sapiens

<400> SEQUENCE: 21
uccgagccug ggucucccuc uu                                               22

<210> SEQ ID NO 22
<211> LENGTH: 22
<212> TYPE: RNA
<213> ORGANISM: Homo sapiens

<400> SEQUENCE: 22
acccgucccg uucgucccg ga                                                22
```

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tcagctcaaa accctcatcc                                              20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tgtctcacgg tcatctccag                                              20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
atcctggaga tgaccgtgag                                              20

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cggtacttgc ccagaacg                                                18

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gttggtggag cgatttgtct                                              20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gaacgccact tgtccctcta                                              20

<210> SEQ ID NO 29
<211> LENGTH: 105
<212> TYPE: DNA
<213> ORGANISM: Homo sapiens

<400> SEQUENCE: 29
cagcagcagc agcagcagca gcagcagcag cagcagcagc agcagcagca gcagcagcag    60
cagcagcagc agcagcagca gcagcagcag cagcagcagc agcag                   105

<210> SEQ ID NO 30
<211> LENGTH: 162
<212> TYPE: DNA
<213> ORGANISM: Homo sapiens
<220> FEATURE:
<221> NAME/KEY: misc_feature
<222> LOCATION: (1)..(162)
<223> OTHER INFORMATION: This sequence encompasses 40-54 'CAG' repeating
      units

<400> SEQUENCE: 30
cagcagcagc agcagcagca gcagcagcag cagcagcagc agcagcagca gcagcagcag    60
cagcagcagc agcagcagca gcagcagcag cagcagcagc agcagcagca gcagcagcag   120
cagcagcagc agcagcagca gcagcagcag cagcagcagc ag                     162

<210> SEQ ID NO 31
<211> LENGTH: 135
<212> TYPE: DNA
<213> ORGANISM: Homo sapiens

<400> SEQUENCE: 31
cagcagcagc agcagcagca gcagcagcag cagcagcagc agcagcagca gcagcagcag    60
cagcagcagc agcagcagca gcagcagcag cagcagcagc agcagcagca gcagcagcag   120
cagcagcagc agcag                                                   135

<210> SEQ ID NO 32
<211> LENGTH: 129
<212> TYPE: DNA
<213> ORGANISM: Homo sapiens

<400> SEQUENCE: 32
cagcagcagc agcagcagca gcagcagcag cagcagcagc agcagcagca gcagcagcag    60
cagcagcagc agcagcagca gcagcagcag cagcagcagc agcagcagca gcagcagcag   120
cagcagcag                                                          129

<210> SEQ ID NO 33
<211> LENGTH: 126
<212> TYPE: DNA
<213> ORGANISM: Homo sapiens

<400> SEQUENCE: 33
cagcagcagc agcagcagca gcagcagcag cagcagcagc agcagcagca gcagcagcag    60
cagcagcagc agcagcagca gcagcagcag cagcagcagc agcagcagca gcagcagcag   120
cagcag                                                             126

<210> SEQ ID NO 34
<211> LENGTH: 147
<212> TYPE: DNA
<213> ORGANISM: Homo sapiens

```
<400> SEQUENCE: 34
cagcagcagc agcagcagca gcagcagcag cagcagcagc agcagcagca gcagcagcag    60
cagcagcagc agcagcagca gcagcagcag cagcagcagc agcagcagca gcagcagcag   120
cagcagcagc agcagcagca gcagcag                                       147

<210> SEQ ID NO 35
<211> LENGTH: 120
<212> TYPE: DNA
<213> ORGANISM: Homo sapiens

<400> SEQUENCE: 35
cagcagcagc agcagcagca gcagcagcag cagcagcagc agcagcagca gcagcagcag    60
cagcagcagc agcagcagca gcagcagcag cagcagcagc agcagcagca gcagcagcag   120

<210> SEQ ID NO 36
<211> LENGTH: 123
<212> TYPE: DNA
<213> ORGANISM: Homo sapiens

<400> SEQUENCE: 36
cagcagcagc agcagcagca gcagcagcag cagcagcagc agcagcagca gcagcagcag    60
cagcagcagc agcagcagca gcagcagcag cagcagcagc agcagcagca gcagcagcag   120
cag                                                                 123

<210> SEQ ID NO 37
<211> LENGTH: 132
<212> TYPE: DNA
<213> ORGANISM: Homo sapiens

<400> SEQUENCE: 37
cagcagcagc agcagcagca gcagcagcag cagcagcagc agcagcagca gcagcagcag    60
cagcagcagc agcagcagca gcagcagcag cagcagcagc agcagcagca gcagcagcag   120
cagcagcagc ag                                                       132

<210> SEQ ID NO 38
<211> LENGTH: 138
<212> TYPE: DNA
<213> ORGANISM: Homo sapiens

<400> SEQUENCE: 38
cagcagcagc agcagcagca gcagcagcag cagcagcagc agcagcagca gcagcagcag    60
cagcagcagc agcagcagca gcagcagcag cagcagcagc agcagcagca gcagcagcag   120
cagcagcagc agcagcag                                                 138

<210> SEQ ID NO 39
<211> LENGTH: 144
<212> TYPE: DNA
<213> ORGANISM: Homo sapiens

<400> SEQUENCE: 39
cagcagcagc agcagcagca gcagcagcag cagcagcagc agcagcagca gcagcagcag    60
cagcagcagc agcagcagca gcagcagcag cagcagcagc agcagcagca gcagcagcag   120
cagcagcagc agcagcagca gcag                                          144

<210> SEQ ID NO 40
<211> LENGTH: 153
```

```
<212> TYPE: DNA
<213> ORGANISM: Homo sapiens

<400> SEQUENCE: 40
cagcagcagc agcagcagca gcagcagcag cagcagcagc agcagcagca gcagcagcag    60
cagcagcagc agcagcagca gcagcagcag cagcagcagc agcagcagca gcagcagcag   120
cagcagcagc agcagcagca gcagcagcag cag                                153

<210> SEQ ID NO 41
<211> LENGTH: 141
<212> TYPE: DNA
<213> ORGANISM: Homo sapiens

<400> SEQUENCE: 41
cagcagcagc agcagcagca gcagcagcag cagcagcagc agcagcagca gcagcagcag    60
cagcagcagc agcagcagca gcagcagcag cagcagcagc agcagcagca gcagcagcag   120
cagcagcagc agcagcagca g                                             141

<210> SEQ ID NO 42
<211> LENGTH: 162
<212> TYPE: DNA
<213> ORGANISM: Homo sapiens

<400> SEQUENCE: 42
cagcagcagc agcagcagca gcagcagcag cagcagcagc agcagcagca gcagcagcag    60
cagcagcagc agcagcagca gcagcagcag cagcagcagc agcagcagca gcagcagcag   120
cagcagcagc agcagcagca gcagcagcag cagcagcagc ag                      162

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
tggaattctc gggtgccaag g                                              21

<210> SEQ ID NO 44
<211> LENGTH: 168
<212> TYPE: DNA
<213> ORGANISM: Homo sapiens

<400> SEQUENCE: 44
cagcagcagc agcagcagca gcagcagcag cagcagcagc agcagcagca gcagcagcag    60
cagcagcagc agcagcagca gcagcagcag cagcagcagc agcagcagca gcagcagcag   120
cagcagcagc agcagcagca gcagcagcag cagcagcagc agcagcag                168

<210> SEQ ID NO 45
<211> LENGTH: 22
<212> TYPE: RNA
<213> ORGANISM: Homo sapiens

<400> SEQUENCE: 45
aagugcuucc uuuuagaggg uu                                             22

<210> SEQ ID NO 46
<211> LENGTH: 22
```

```
<212> TYPE: RNA
<213> ORGANISM: Homo sapiens

<400> SEQUENCE: 46
auguagggcu aaaagccaug gg                                              22

<210> SEQ ID NO 47
<211> LENGTH: 23
<212> TYPE: RNA
<213> ORGANISM: Homo sapiens

<400> SEQUENCE: 47
ugaagcucua agguuccgcc ugc                                             23

<210> SEQ ID NO 48
<211> LENGTH: 22
<212> TYPE: RNA
<213> ORGANISM: Homo sapiens

<400> SEQUENCE: 48
cagugguuuu acccuauggu ag                                              22

<210> SEQ ID NO 49
<211> LENGTH: 17
<212> TYPE: RNA
<213> ORGANISM: Homo sapiens

<400> SEQUENCE: 49
acauugccag ggaguuu                                                    17

<210> SEQ ID NO 50
<211> LENGTH: 22
<212> TYPE: RNA
<213> ORGANISM: Homo sapiens

<400> SEQUENCE: 50
ugauggagcu gggaauacuc ug                                              22

<210> SEQ ID NO 51
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
gatcggaaga gcacacgtct gaactccagt caccgatgta tctcgtatgc cgtcttctgc     60
ttg                                                                   63
```